US011345741B2

(12) United States Patent
Crowe, Jr. et al.

(10) Patent No.: US 11,345,741 B2
(45) Date of Patent: May 31, 2022

(54) HUMAN MONOCLONAL ANTIBODIES TO SEVERE ACUTE RESPIRATORY SYNDROME CORONAVIRUS 2 (SARS-COV-2)

(71) Applicant: Vanderbilt University, Nashville, TN (US)

(72) Inventors: James E. Crowe, Jr., Nashville, TN (US); Seth Zost, Nashville, TN (US); Robert Carnahan, Nashville, TN (US); Pavlo Gilchuk, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 17/212,949

(22) Filed: Mar. 25, 2021

(65) Prior Publication Data
US 2021/0300999 A1 Sep. 30, 2021

Related U.S. Application Data

(60) Provisional application No. 63/000,299, filed on Mar. 26, 2020, provisional application No. 63/002,896, filed on Mar. 31, 2020, provisional application No. 63/003,716, filed on Apr. 1, 2020, provisional application No. 63/023,545, filed on May 12, 2020, provisional application No. 63/024,204, filed on May 13, 2020, provisional application No. 63/024,248, filed on May 13, 2020, provisional application No. 63/027,173, filed on May 19, 2020, provisional application No. 63/037,984, filed on Jun. 11, 2020, provisional application No. 63/040,224, filed on Jun. 17, 2020, provisional application No. 63/040,246, filed on Jun. 17, 2020, provisional application No. 63/142,196, filed on Jan. 27, 2021, provisional application No. 63/161,890, filed on Mar. 16, 2021.

(51) Int. Cl.
*C07K 16/10* (2006.01)
*A61P 31/14* (2006.01)
*G01N 33/569* (2006.01)
*A61K 39/00* (2006.01)

(52) U.S. Cl.
CPC .............. *C07K 16/10* (2013.01); *A61P 31/14* (2018.01); *G01N 33/56983* (2013.01); *A61K 2039/505* (2013.01); *A61K 2039/507* (2013.01); *C07K 2317/52* (2013.01); *C07K 2317/55* (2013.01); *C07K 2317/565* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| 11,053,304 B1 * | 7/2021 | Glanville ................ A61P 31/14 |
| 2021/0261650 A1 * | 8/2021 | Corti ...................... A61P 31/14 |

FOREIGN PATENT DOCUMENTS

WO WO2021158521 A1 * 8/2021 ............. C07K 16/10

OTHER PUBLICATIONS

Tian et al., Emerg Microbes Infect. Feb. 17, 2020;9(1):382-385. doi: 10.1080/22221751.2020.1729069. eCollection 2020.*
Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Adams, P.D., et al., "Phenix: A Comprehensive Python-based System for Macromolecular Structure Solution," Acta Crystallographica. Section D, Biological Crystallography 66(Pt 2):213-221, Wiley-Blackwell, United States (2010).
Algaissi. A., et al., "SARS-CoV-2 S1 and N-based Serological Assays Reveal Rapid Seroconversion and Induction of Specific Antibody Response in COVID-19 Patients," Scientific Reports 10(1):16561, Nature Publishing Group, England (Oct. 2020).
Andreano, E., et al., "SARS-CoV-2 Escape in Vitro from a Highly Neutralizing COVID-19 Convalescent Plasma," bioRxiv 2020.12.28.424451, Cold Spring Harbor Laboratory, United States (Dec. 2020).
Bailey, J. R., et al., "Broadly Neutralizing Antibodies With Few Somatic Mutations and Hepatitis C Virus Clearance," JCI Insight 2(9):e92872, American Society for Clinical Investigation, United States (May 2017).
Barzon, L., et al., "Infection Dynamics in a Traveller With Persistent Shedding of Zika Virus RNA in Semen for Six Months After Returning From Haiti to Italy, Jan. 2016," Euro Surveillance 21(32):30316, European Centre for Disease Prevention and Control (ECDC), Sweden (Aug. 2016).
Baum, A., et al., "REGN-COV2 Antibodies Prevent and Treat SARS-CoV-2 Infection in Rhesus Macaques and Hamsters," Science 370(6520):1110-1115, American Association for the Advancement of Science, United States (Nov. 2020).

(Continued)

*Primary Examiner* — Michael Szperka
(74) *Attorney, Agent, or Firm* — Sterne, Kessler, Goldstein & Fox P.L.L.C.

(57) ABSTRACT

The present disclosure is directed to antibodies binding to and neutralizing the coronavirus designated SARS-CoV-2 and methods for use thereof.

26 Claims, 46 Drawing Sheets
(17 of 46 Drawing Sheet(s) Filed in Color)
Specification includes a Sequence Listing.

(56) References Cited

OTHER PUBLICATIONS

Benton, D. J., et al., "Receptor Binding and Priming of the Spike Protein of SARS-CoV-2 for Membrane Fusion," Nature 588(7837):327-330, Nature Publishing Group, England (Sep. 2020).
Bepler, T., et al., "Topaz-Denoise: General Deep Denoising Models for cryoEM and cryoET," Nature Communications 11(1):5208, Nature Pub. Group, England (Oct. 2020).
Brouwer, P. J. M., et al., "Potent Neutralizing Antibodies From COVID-19 Patients Define Multiple Targets of Vulnerability," Science 369(6504):643-650, American Association for the Advancement of Science, United States (Aug. 2020).
Cao, Y., et al., "Potent Neutralizing Antibodies against SARS-CoV-2 Identified by High-Throughput Single-Cell Sequencing of Convalescent Patients' B Cells," Cell 182(1):73-84.e16, Cell Press, United States (Jul. 2020).
Case, J. B., et al., "Neutralizing Antibody and Soluble ACE2 Inhibition of a Replication-Competent VSV-SARS-CoV-2 and a clinical isolate of SARS-CoV-2," Cell Host & Microbe 28(3):475-485, Cell Press, United States (Sep. 2020).
Chen, Z., et al., "Human Neutralizing Monoclonal Antibody Inhibition of Middle East Respiratory Syndrome Coronavirus Replication in the Common Marmoset," The Journal of Infectious Diseases 215(12):1807-1815, Oxford University Press, United States (Jun. 2017).
Chng, J., et al., "Cleavage Efficient 2A Peptides for High Level Monoclonal Antibody Expression in CHO Cells," mAbs 7(2):403-12, Taylor & Francis, United States (2015).
Choi, J.H., et al., "Characterization of a Human Monoclonal Antibody Generated from a B-cell Specific for a Prefusion-stabilized Spike Protein of Middle East Respiratory Syndrome Coronavirus," PloS One 15(5):e0232757, Public Library of Science, United States (May 2020).
Cornwell, O., et al., "Comparing Hydrogen Deuterium Exchange and Fast Photochemical Oxidation of Proteins: a Structural Characterisation of Wild-Type and DeltaN6 Beta2-Microglobulin," Journal of the American Society for Mass Spectrometry 29(12):2413-2426, ACS Publications, United States (Dec. 2018).
Corti, D., et al., "Prophylactic and Postexposure Efficacy of a Potent Human Monoclonal Antibody Against MERS Coronavirus," Proceedings of the National Academy of Sciences of the United States of America 112(33):10473-10478, National Academy of Sciences, United States (Aug. 2015).
Dinnon, K.H., et al., "A Mouse-adapted SARS-CoV-2 Model for the Evaluation of COVID-19 Medical Countermeasures," bioRxiv 2020.05.06.081497, Cold Spring Harbor Laboratory, United States (May 2020).
Duffy, M.R., et al., "Zika Virus Outbreak on Yap Island, Federated States of Micronesia," The New England Journal of Medicine 360(24):2536-2543, Massachusetts Medical Society, United States (Jun. 2009).
Emsley, P. and Cowtan, K., "Coot: Model-building Tools for Molecular Graphics," Acta crystallographica. Section D, Biological Crystallography 60(Pt 12 Pt 1):2126-2132, Wiley-Blackwell, United States (Dec. 2004).
Galloway, S. E., et al., "Emergence of SARS-CoV-2 B.1.1.7 Lineage—United States, Dec. 29, 2020-Jan. 12, 2021," Morbidity and Mortality Weekly Report 70(3):95-99, Centers for Disease Control, United States (Jan. 2021).
Giang, E., et al., "Human Broadly Neutralizing Antibodies to the Envelope Glycoprotein Complex of Hepatitis C Virus," Proceedings of the National Academy of Sciences of the United States of America 109(16):6205-6210, National Academy of Sciences, United States (Apr. 2012).
Gornet, M.E., et al., "Zika Virus in Semen: What We Know and What We Need to Know," Seminars in Reproductive Medicine 34(5):285-292, Thieme Medical Publishers, United States (Sep. 2016).
Greaney, A. J., et al., "Complete Mapping of Mutations to the SARS-CoV-2 Spike Receptor-Binding Domain that Escape Antibody Recognition," Cell Host & Microbe 29(1):44-57, Cell Press, United States (Jan. 2021).
Greaney, A. J., et al., "Comprehensive Mapping of Mutations to the SARS-CoV-2 Receptor-binding Domain That Affect Recognition by Polyclonal Human Serum Antibodies," bioRxiv 2020.12.2031.425021 29(3):463-476 (Jan. 2021).
Halfon, P., et al., "Semen May Harbor HIV Despite Effective HAART: Another Piece in the Puzzle," PloS one 5(5):e10569, Public Library of Science, United States (May 2010).
Hansen, J., et al., "Studies in Humanized Mice and Convalescent Humans Yield a SARS-CoV-2 Antibody Cocktail," Science 369(6506):1010-1014, American Association for the Advancement of Science, United States (Aug. 2020).
Hoffmann, M., et al., "SARS-CoV-2 Cell Entry Depends on ACE2 and TMPRSS2 and Is Blocked by a Clinically Proven Protease Inhibitor," Cell 181(2):271-280, Cell Press, United States (Apr. 2020).
Huang, C. C., et al., "Structural Basis of Tyrosine Sulfation and VH-gene Usage in Antibodies That Recognize the HIV Type 1 Coreceptor-binding Site on gp120," Proceedings of the National Academy of Sciences of the United States of America 101(9):2706-2711, National Academy of Sciences, United States (Mar. 2004).
Huo, J. et al., "Neutralization of SARS-CoV-2 by Destruction of the Prefusion Spike," Cell Host & Microbe 28(3):445-454, Cell Press, United States (Sep. 2020).
Ianevski, A., et al., "Synergyfinder: A Web Application for Analyzing Drug Combination Dose-response Matrix Data," Bioinformatics 33(15):2413-2415, Oxford University Press, England (Aug. 2017).
Jiang, L., et al., "Neutralizing Antibodies against SARS-CoV-2 and Other Human Coronaviruses," Trends in Immunology 41(5):355-359, Elsevier Science Ltd., England (May 2020).
Jiang, L., et al., "Potent Neutralization of MERS-CoV by Human Neutralizing Monoclonal Antibodies to the Viral Spike Glycoprotein," Science Translational Medicine 6(234):234ra59, American Association for the Advancement of Science, United States (Apr. 2014).
Joyce, M. G., et al., "Vaccine-Induced Antibodies that Neutralize Group 1 and Group 2 Influenza A Viruses," Cell 166(3):609-623, Cell Press, United States (Jul. 2016).
Ju, B et al., "Human Neutralizing Antibodies Elicited by SARS-CoV-2 Infection," Nature 584(7819):115-119, Nature Publishing Group, England (May 2020).
Kabsch, W., "XDS," Acta Crystallographica. Section D, Biological Crystallography 66(Pt 2):125-132, Wiley-Blackwell, United States (Feb. 2010).
Klimstra, W. B., et al., "SARS-CoV-2 Growth, Furin-cleavage-site Adaptation and Neutralization Using Serum From Acutely Infected Hospitalized COVID-19 Patients," The Journal of General Virology 101(11):1156-1169, Microbiology Society, England (Aug. 2020).
Kreer, C., et al., "Longitudinal Isolation of Potent Near-Germline SARS-CoV-2-Neutralizing Antibodies from COVID-19 Patients," Cell 182(4):843-854, Cell Press, United States (Aug. 2020).
Laha, S., et al., "Characterizations of SARS-CoV-2 Mutational Profile, Spike Protein Stability and Viral Transmission," Infection, Genetics and Evolution 85:104445, Elsevier Science, Netherlands (Jun. 2020).
Lan, J., et al., "Structure of the SARS-CoV-2 Spike Receptor-binding Domain Bound to the ACE2 Receptor," Nature 581(7807):215-220, Nature Publishing Group, England (Mar. 2020).
Letko, M., et al., "Functional Assessment of Cell Entry and Receptor Usage for SARS-CoV-2 and Other Lineage B Betacoronaviruses," Nature Microbiology 5(4):562-569, Nature Publishing Group, England (Mar. 2020).
Leung, K., et al., "Early Transmissibility Assessment of the N501Y Mutant Strains of SARS-CoV-2 in the United Kingdom, Oct. to Nov. 2020," Euro Surveillance 26(1):2002106, European Centre for Disease Prevention and Control (ECDC), Sweden (Jan. 2021).
Li, Q., et al., "The Impact of Mutations in SARS-CoV-2 Spike on Viral Infectivity and Antigenicity," Cell 182(5):1284-1294, Cell Press, United States (Sep. 2020).
Li, W., et al., "Angiotensin-converting Enzyme 2 Is a Functional Receptor for the SARS Coronavirus," Nature 426(6965):450-454, Nature Publishing Group, England (Nov. 2003).

(56) References Cited

OTHER PUBLICATIONS

Liu, L., et al., "Potent Neutralizing Antibodies Against Multiple Epitopes on SARS-CoV-2 Spike," Nature 584(7821):450-456, Nature Publishing Group, England (Jul. 2020).
Liu, Z., et al., "Landscape Analysis of Escape Variants Identifies SARS-CoV-2 Spike Mutations That Attenuate Monoclonal and Serum Antibody Neutralization," bioRxiv 2020.11.06.372037, Cold Spring Harbor Laboratory, United States (Nov. 2020).
Long, Q. X., et al., "Antibody Responses to SARS-CoV-2 in Patients With COVID-19," Nature Medicine 26(6):845-848, Nature Publishing Company, United States (Jun. 2020).
McCoy, A. J., et al., "Phaser Crystallographic Software," Journal of Applied Crystallography 40(Pt 4):658-674, Wiley Online Library, United States (Aug. 2007).
Mukherjee, S., et al., "Enhancing Dengue Virus Maturation Using a Stable Furin Over-expressing Cell Line," Virology 497:33-40, Academic Press, United States (Oct. 2016).
Nielsen, S. C. A., et al., "Human B Cell Clonal Expansion and Convergent Antibody Responses to SARS-CoV-2," Cell Host & Microbe 28(4):516-525, Cell Press, United States (Oct. 2020).
Niu, P., et al., "Ultrapotent Human Neutralizing Antibody Repertoires Against Middle East Respiratory Syndrome Coronavirus From a Recovered Patient," The Journal of Infectious Diseases 218(8):1249-1260, Oxford University Press, United States (Sep. 2018).
Otwinowski, J., et al., "Inferring the Shape of Global Epistasis," Proceedings of the National Academy of Sciences of the United States of America 115(32):E7550-E7558, National Academy of Sciences, United States (Aug. 2018).
Pappas, L., et al., "Rapid Development of Broadly Influenza Neutralizing Antibodies Through Redundant Mutations," Nature 516(7531):418-422, Nature Publishing Group, England (Dec. 2014).
Piccoli, L., et al., "Mapping Neutralizing and Immunodominant Sites on the SARS-CoV-2 Spike Receptor-Binding Domain by Structure-Guided High-Resolution Serology," Cell 183(4):1024-1042, Cell Press, United States (Nov. 2020).
Pillay, T.S., "Gene of the Month: the 2019-nCoV/SARS-CoV-2 Novel Coronavirus Spike Protein," Journal of Clinical Pathology 73(7):366-369, BMJ Pub. Group, England (May 2020).
Plante, J. A., et al., "Spike Mutation D614G Alters SARS-CoV-2 Fitness," Nature 592(7852):116-121, Nature Publishing Group, England (Oct. 2020).
Purpura, L.J., et al., "Zika Virus in Semen: Lessons From Ebola," The Lancet. Infectious Diseases 16(10):1107-1108, The Lancet Pub., United States (Oct. 2016).
Rappuoli, R., et al., "Reverse Vaccinology 2.0: Human Immunology Instructs Vaccine Antigen Design," The Journal of Experimental Medicine 213(4):469-481, Rockefeller University Press, United States (Apr. 2016).
Robbiani, D. F., et al., "Convergent Antibody Responses to SARS-CoV-2 in Convalescent Individuals," Nature 584(7821):437-442, Nature Publishing Group, England (Jun. 2020).
Robbiani, D. F., et al., "Convergent Antibody Responses to SARS-CoV-2 Infection in Convalescent Individuals," bioRxiv 2020.05.13.092619, Cold Spring Harbor Laboratory, United States (May 2020).
Rockx, B., et al., "Structural Basis for Potent Cross-neutralizing Human Monoclonal Antibody Protection Against Lethal Human and Zoonotic Severe Acute Respiratory Syndrome Coronavirus Challenge," Journal of Virology 82(7):3220-3235, American Society For Microbiology, United States (Apr. 2008).
Rogers, T. F., et al., "Isolation of Potent SARS-CoV-2 Neutralizing Antibodies and Protection From Disease in a Small Animal Model," Science 369(6506):956-963, American Association for the Advancement of Science, United States (Aug. 2020).
Sawatzki, K., et al., "Ferrets Not Infected by SARS-CoV-2 in a High-exposure Domestic Setting," bioRxiv, 14 pages, 2020.2008.2021.254995 (Aug. 2020).
Sheehan, K. C. F., et al., "Blocking Monoclonal Antibodies Specific for Mouse IFN-alpha/beta Receptor Subunit 1 (IFNAR-1) From Mice Immunized by in Vivo Hydrodynamic Transfection," Journal of Interferon & Cytokine Research 26(11):804-819, Mary Ann Liebert, United States (Nov. 2006).
Shi, R., et al., "A Human Neutralizing Antibody Targets the Receptor-binding Site of SARS-CoV-2," Nature 584(7819):120-124, Nature Publishing Group, England (May 2020).
Soto, C., et al., "High Frequency of Shared Clonotypes in Human B Cell Receptor Repertoires," Nature 566(7744):398-402, Nature Publishing Group, England (Jul. 2020).
Starr, T. N., et al., "Deep Mutational Scanning of SARS-CoV-2 Receptor Binding Domain Reveals Constraints on Folding and ACE2 Binding," Cell 182(5):1295-1310, Cell Press, United States (Sep. 2020).
Starr, T. N., et al., "Prospective Mapping of Viral Mutations That Escape Antibodies Used to Treat COVID-19," bioRxiv 2020.11.30.405472, Cold Spring Harbor Laboratory, United States (Jan. 2021).
Sui, J., et al., "Potent Neutralization of Severe Acute Respiratory Syndrome (SARS) Coronavirus by a Human mAb to S1 Protein That Blocks Receptor Association," Proceedings of the National Academy of Sciences of the United States of America 101(8):2536-2541, National Academy of Sciences, United States (Feb. 2004).
Sui, J., et al., "Structural and Functional Bases for Broad-spectrum Neutralization of Avian and Human Influenza a Viruses," Nature Structural & Molecular Biology 16(3):265-273, Nature Pub. Group, United States (Mar. 2009).
Tang, X.C., et al., "Identification of Human Neutralizing Antibodies Against MERS-CoV and Their Role in Virus Adaptive Evolution," Proceedings of the National Academy of Sciences of the United States of America 111(19):E2018-E2026, National Academy of Sciences, United States (May 2014).
Tegally, H., et al., "Emergence and Rapid Spread of a New Severe Acute Respiratory Syndrome-related Coronavirus 2 (SARS-CoV-2) Lineage With Multiple Spike Mutations in South Africa," medRxiv, 2020.2012.2021.20248640 (Dec. 2020).
Ter Meulen, J., et al., "Human Monoclonal Antibody as Prophylaxis for SARS Coronavirus Infection in Ferrets," Lancet 363(9427):2139-2141, Elsevier, England (Jun. 2004).
Ter Meulen, J., et al., "Human Monoclonal Antibody Combination Against Sars Coronavirus: Synergy and Coverage of Escape Mutants," PLoS Medicine 3(7):e237, Public Library of Science, United States (Jul. 2006).
Tian, C., et al., "Immunodominance of the VH1-46 Antibody Gene Segment in the Primary Repertoire of Human Rotavirus-specific B Cells Is Reduced in the Memory Compartment Through Somatic Mutation of Nondominant Clones," Journal of Immunology 180(5):3279-3288, American Association of Immunologists, United States (Mar. 2008).
Tortorici, M. A., et al., "Ultrapotent Human Antibodies Protect Against SARS-CoV-2 Challenge via Multiple Mechanisms," Science 370(6519):950-957, American Association for the Advancement of Science, United States (Sep. 2020).
Chai, K.L., et al., "Convalescent Plasma or Hyperimmune Immunoglobulin for People With COVID-19: A Rapid Review," The Cochrane Database of Systematic Reviews 5(5):CD013600, Wiley, England (May 2020).
Voloch, C. M., et al., "Genomic Characterization of a Novel SARS-CoV-2 Lineage From Rio De Janeiro, Brazil," medRxiv, 2020.2012.2023.20248598 (Mar. 2021).
Wahba, L., et al., "An Extensive Meta-Metagenomic Search Identifies SARS-CoV-2-Homologous Sequences in Pangolin Lung Viromes," mSphere 5(3):e00160-20, American Society for Microbiology, United States (May 2020).
Walls, A. C., et al., "Tectonic Conformational Changes of a Coronavirus Spike Glycoprotein Promote Membrane Fusion," Proceedings of the National Academy of Sciences of the United States of America 114(42):11157-11162, National Academy of Sciences, United States (Oct. 2017).
Wan, Y., et al., "Receptor Recognition by the Novel Coronavirus from Wuhan: an Analysis Based on Decade-Long Structural Studies of SARS Coronavirus," Journal of Virology 94(7):e00127-20, American Society For Microbiology, United States (Jan. 2020).
Wang, L., et al., "Importance of Neutralizing Monoclonal Antibodies Targeting Multiple Antigenic Sites on the Middle East Respiratory Syndrome Coronavirus Spike Glycoprotein To Avoid Neu-

(56) References Cited

OTHER PUBLICATIONS tralization Escape," Journal of Virology 92(10):e02002-17, American Society For Microbiology, United States (Mar. 2018).

Wang, N., et al., "Structural Definition of a Neutralization-Sensitive Epitope on the MERS-CoV S1-NTD," Cell Reports 28(13):3395-3405, Cell Press, United States (Sep. 2019).

Weisblum, Y., et al., "Escape From Neutralizing Antibodies by SARS-CoV-2 Spike Protein Variants," eLife (Oct. 2020).

Weitkamp, J. H., et al., "Infant and Adult Human B Cell Responses to Rotavirus Share Common Immunodominant Variable Gene Repertoires," Journal of Immunology 171(9):4680-4688, American Association of Immunologists, United States (Nov. 2003).

Wheatley, A. K., et al., "H5N1 Vaccine-Elicited Memory B Cells Are Genetically Constrained by the IGHV Locus in the Recognition of a Neutralizing Epitope in the Hemagglutinin Stem," Journal of Immunology 195(2):602-610, American Association of Immunologists, United States (Jul. 2015).

Wibmer, C. K., et al., "SARS-CoV-2 501Y.V2 Escapes Neutralization by South African COVID-19 Donor Plasma," bioRxiv 2021.01.18.427166, Cold Spring Harbor Laboratory, United States (Mar. 2021).

Williams, W. B., et al., "HIV-1 Vaccines. Diversion of HIV-1 Vaccine-induced Immunity by gp41-microbiota Cross-reactive Antibodies," Science 349(6249):aab1253, American Association for the Advancement of Science, United States (Aug. 2015).

Winn, M. D., et al., "Overview of the CCP4 Suite and Current Developments," Acta crystallographica. Section D, Biological crystallography 67(Pt 4):235-242, Wiley-Blackwell, United States (Apr. 2011).

Wrapp, D., et al., "Cryo-EM Structure of the 2019-nCoV Spike in the Prefusion Conformation," Science 367(6483):1260-1263, American Association for the Advancement of Science, United States (Feb. 2020).

Wrobel, A. G., et al., "SARS-CoV-2 and Bat RaTG13 Spike Glycoprotein Structures Inform on Virus Evolution and Furin-cleavage Effects," Nature Structural & Molecular Biology 27(8):763-767, Nature Pub. Group, United States (Jul. 2020).

Wu, X., et al., "Focused Evolution of HIV-1 Neutralizing Antibodies Revealed by Structures and Deep Sequencing," Science 333(6049):1593-1602, American Association for the Advancement of Science, United States (Sep. 2011).

Xie, X., et al., "An Infectious cDNA Clone of SARS-CoV-2," Cell Host & Microbe 27(5):841-848, Cell Press, United States (Apr. 2020).

Ying, T., et al., "Exceptionally Potent Neutralization of Middle East Respiratory Syndrome Coronavirus by Human Monoclonal Antibodies," Journal of Virology 88(14):7796-7805, American Society For Microbiology, United States (Jul. 2014).

Yuan, M., et al., "A Highly Conserved Cryptic Epitope in the Receptor Binding Domains of SARS-CoV-2 and SARS-CoV," Science 368(6491):630-633, American Association for the Advancement of Science, United States (Apr. 2020).

Yuan, M., et al., "Structural Basis of a Shared Antibody Response to SARS-CoV-2," Science 369(6507):1119-1123, American Association for the Advancement of Science, United States (Jul. 2020).

Zhang, S., et al., "Structural Definition of a Unique Neutralization Epitope on the Receptor-Binding Domain of MERS-CoV Spike Glycoprotein," Cell Reports 24(2):441-452, Cell Press, United States (Jul. 2018).

Zhou, P., et al., "A Pneumonia Outbreak Associated With a New Coronavirus of Probable Bat Origin," Nature 579(7798):270-273, Nature Publishing Group, England (Feb. 2020).

Zhou, T., et al., "Structural Repertoire of HIV-1-Neutralizing Antibodies Targeting the CD4 Supersite in 14 Donors," Cell 161(6):1280-1292, Cell Press, United States (Jun. 2015).

Zhu, N., et al., "A Novel Coronavirus from Patients with Pneumonia in China, 2019," The New England Journal of Medicine 382(8):727-733, Massachusetts Medical Society, United States (Feb. 2020).

Zhu, Z., et al., "Potent Cross-reactive Neutralization of SARS Coronavirus Isolates by Human Monoclonal Antibodies," Proceedings of the National Academy of Sciences of the United States of America 104(29):12123-12128, National Academy of Sciences, United States (Jul. 2007).

Zost, S. J., et al., "Potently Neutralizing and Protective Human Antibodies Against SARS-CoV-2," Nature 584(7821):443-449, Nature Publishing Group, England (Jul. 2020).

Zost, S. J., et al., "Rapid Isolation and Profiling of a Diverse Panel of Human Monoclonal Antibodies Targeting the SARS-CoV-2 Spike Protein," Nature Medicine 26(9):1422-1427, Nature Publishing Company, United States (Sep. 2020).

Dong, J. et al., "Genetic and Structural Basis for Recognition of SARS-CoV-2 Spike Protein by a Two-Antibody Cocktail." bioRxiv 2021.01.27.428529, Cold Spring Harbor Laboratory, United States (Mar. 2021).

* cited by examiner

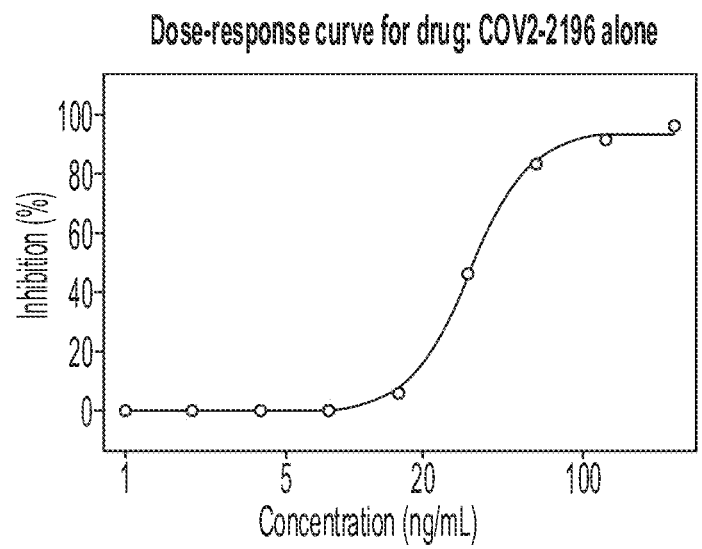
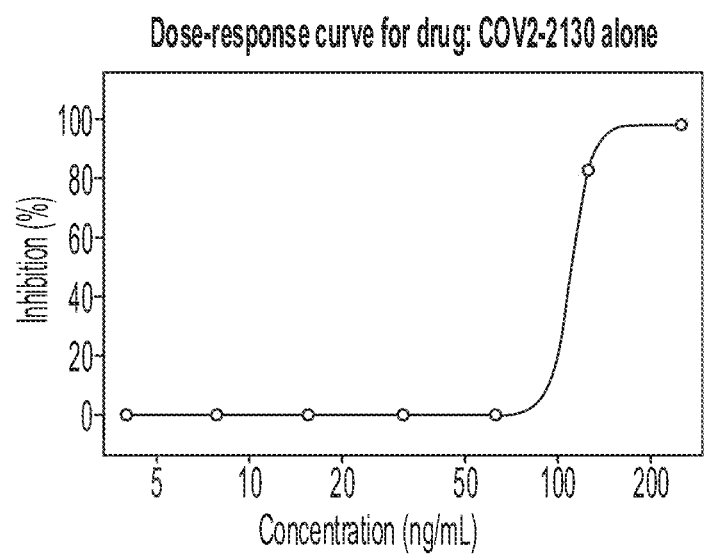
FIG. 2B

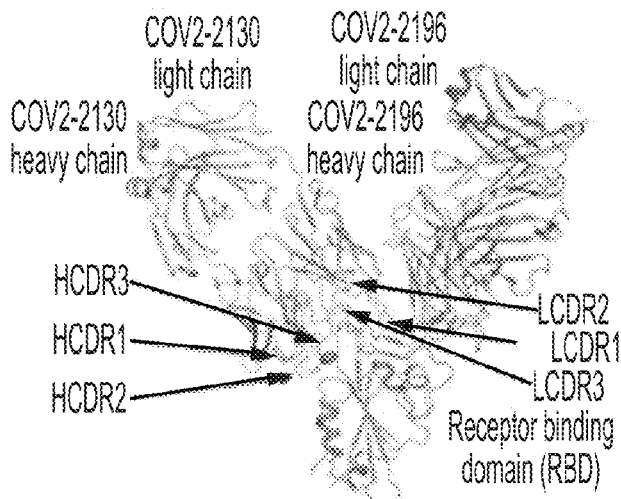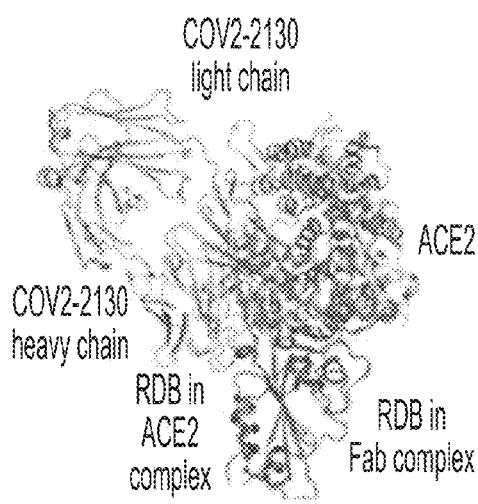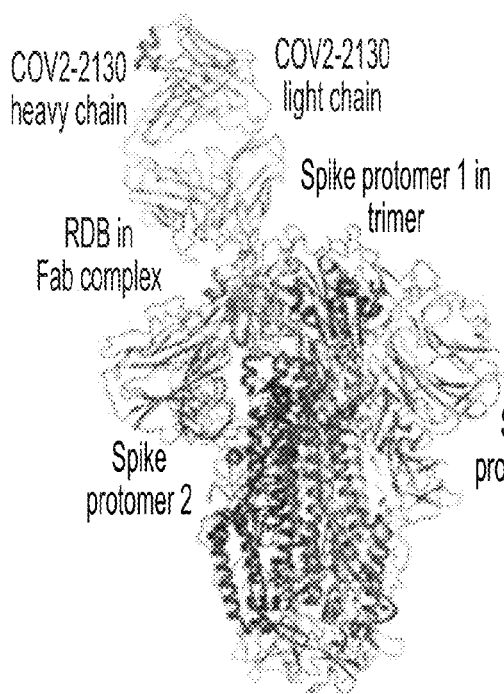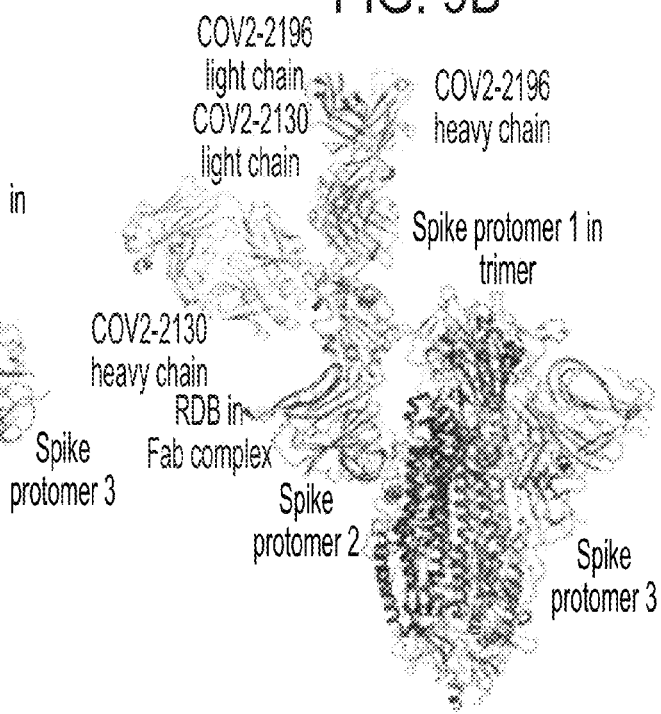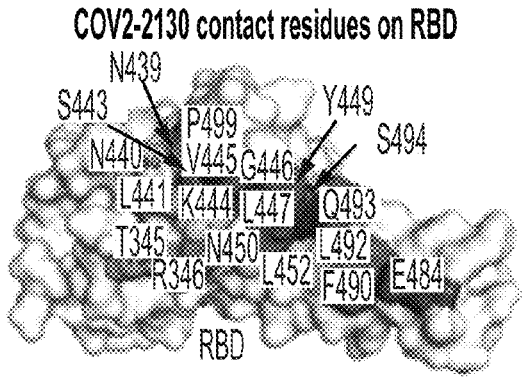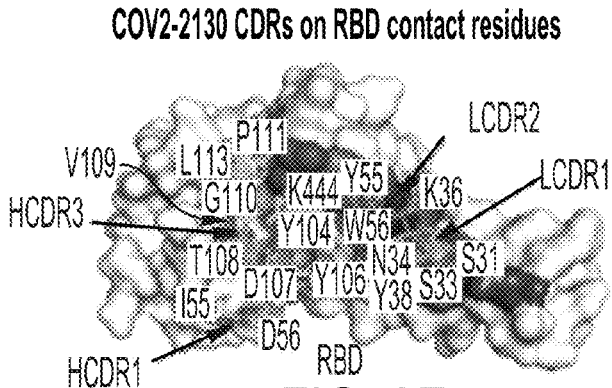

| gene | Heavy chain | | | Light chain | | | Reference |
|---|---|---|---|---|---|---|---|
| | FR2-HCDR2 | HCDR3-FR4 | | LCDR1-FR2 | LCDR3-FR4 | | |
| IGHV1-58 | IGWIV | CAA......... | | | | | |
| IGHD2-2 | | ...GYCSSTSCYA.... | | | | | |
| IGHD2-8 | | ...GYCTNGVCYA.... | | | | | |
| IGHD2-15 | | ...GYCSGGSCYS... | | | | | |
| IGHJ3*02 | | ..........DAFDIW | | | | | |
| IGKV3-20 | | | | SSYLAW..... | QYGSSP...... | | |
| IGKJ1*01 | | | | | ........WTFG | | |

| mAb | | | | | | | |
|---|---|---|---|---|---|---|---|
| | 4A | 9A | | 31 | 91 | | |
| COV2-2196 | IGWIV | CAAPYCSSISCNDGFDIW | | SSYLAW | HYGSSRGWTFG | | Zost et al., 2020 |
| COV2-2381 | IGWIA | CAAPYCSRTSCHDAFDIW | | SSYLAW | HFGSSSQWTFG | | |
| COV2-2072 | IGWIV | CAAPHCNRTSCYDAFDLW | | SSYLGW | QYGSSP.WTTG | | |
| MnC5t2p1_G1 | IGWIV | CAAPRCSQQSCYDGFDIW | | SSYLAW | QYGSSP.WTFG | | Kreer et al., 2020 |
| HbnC3t1p2_C6 | IGWIV | CAAPYCSSTRCYDAFDIW | | SSYLAW | QYGRSP.WTFG | | |
| HbnC3t1p1_C6 | IGWIV | CAAPHCSSTICYDGFDIW | | SSYLAW | QYGSSP.WTFG | | |
| S2E12 | VGWIV | CASPYCSGGSCDGFDIW | | SSYLAW | QYVGLTGWTFG | | Tortorici et al., 2020 |
| COV107_1 | IGWIV | CAAPHCSSTSCFDAFDIW | | SSYLAW | QYGNSP.WTFG | | Robbiani et al., 2020 |
| COV107_2 | IGWIV | CAAPYCSGGSCIDAFDIW | | SSYLAW | QYGSSP.WTFG | | |
| COV72 | IGWIV | CAAVDCNSTSCYDAFDIW | | SSYLAW | QYDISP.WTTG | | |
| COV21_1 | IGWIV | CAAPHCSGGSCYDAFDIW | | SSYLAW | QYDISP.WTTG | | |
| COV21_2 | IGWIV | CAANHCSGGSCYDGFDIW | | SSYLAW | QYGSSP.WTTG | | |
| COV57_1 | IGWIV | CAAPYCSGGSCNDAFDIW | | SSYLAW | QYGSSP.WTTG | | |
| COV57_2 | IGWIV | CAAPYCSGGSCNDAFDIW | | SSYLAW | QYGSSP.WTTG | | |

FIG. 10A

VSV-SARS-CoV-2 escape variant selection

| Selection condition | Replicates with escape/total | Mutations identified |
|---|---|---|
| COV2-2196 | 0/88 (0%) | N/A |
| COV2-2130 | 8/20 (40%) | K444R (6), K444E (2) |
| Cocktail (2196+2130) | 0/104 (0%) | N/A |

FIG. 11E

SARS-CoV-2 resistant variant selection

| Passaging condition | Test condition | Resistance detected | Mutations identified |
|---|---|---|---|
| AZD8895 (COV2-2196) | AZD8895 | No | N/A |
|  | AZD7442 | No |  |
| AZD1061 (COV2-2130) | AZD1061 | Yes | N74K, R346I |
|  | AZD7442 | No | N/A |
| AZD7442 (Cocktail) | AZD7442 | No | N/A |

| Heavy chain | |
|---|---|
| COV2-2196 HC | S2E12 HC |
| COV2-2381 HC | COV2-2072 HC |

| Light chain | |
|---|---|
| COV2-2196 LC | S2E12 LC |
| COV2-2381 LC | COV2-2072 LC |

| RBD | |
|---|---|
| RDB/COV2-2196 | RDB/S2E12 |
| RDB/COV2-2381 | RBD/COV2-2072 |

| Subject | Light chain amino acid multiple sequence alignment | Number of occurrences |
|---|---|---|
| HIP1 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-PWTFGQGTKVEIK | 2,323 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-PWTFGQGTKVEIK | 1,087 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPPWTFGQGTKVEIK | 1,086 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-LWTFGQGTKVEIK | 601 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-SWTFGQGTKVEIK | 539 |
| HIP2 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-PWTFGQGTKVEIK | 3,909 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYIGSS-PWTFGQGTKVEIK | 2,205 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-LWTFGQGTKVEIK | 1,747 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-SWTFGQGTKVEIK | 1,246 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPPWTFGQGTKVEIK | 1,230 |
| HIP3 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-PWTFGQGTKVEIK | 3,908 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-LWTFGQGTKVEIK | 1,889 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPPWTFGQGTKVEIK | 1,809 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSS-SWTFGQGTKVEIK | 1,293 |
| | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPPWTFGQGTKVEIK | 953 |

FIG. 15B

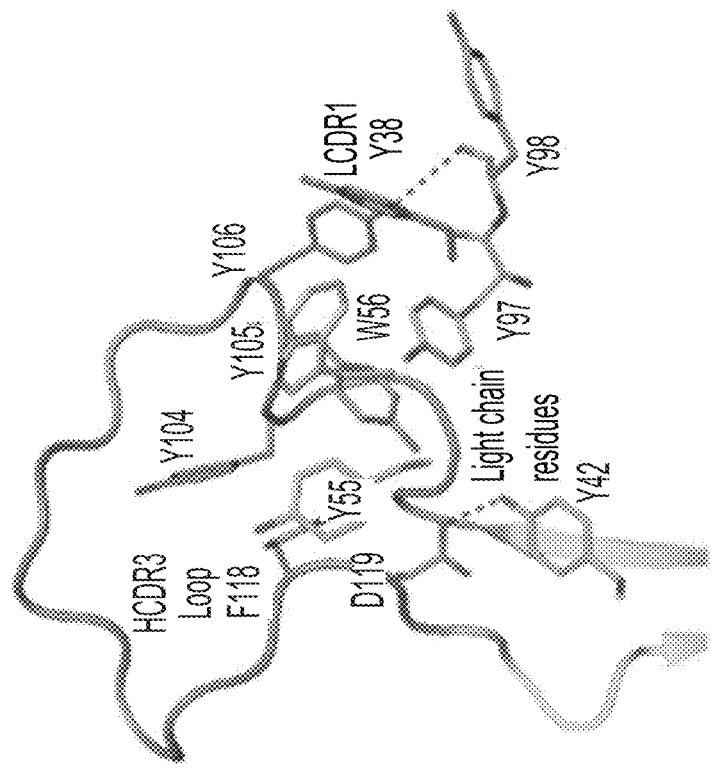
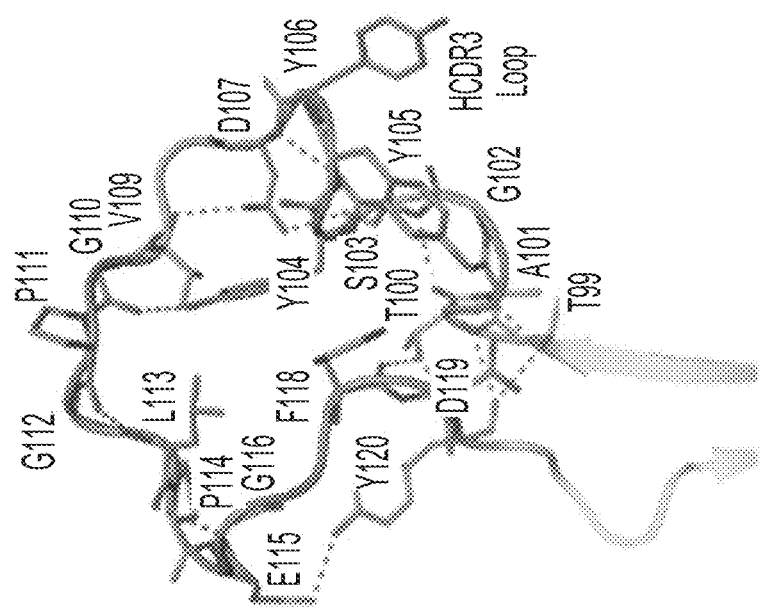
FIG. 16B
FIG. 16A

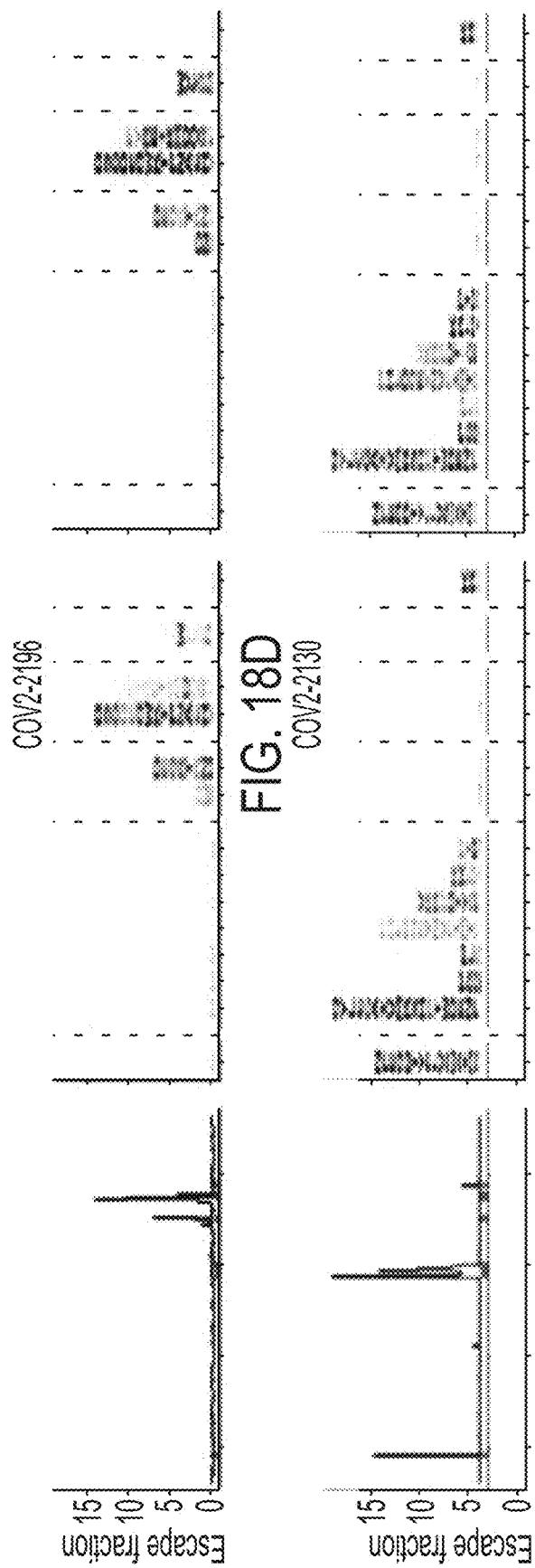
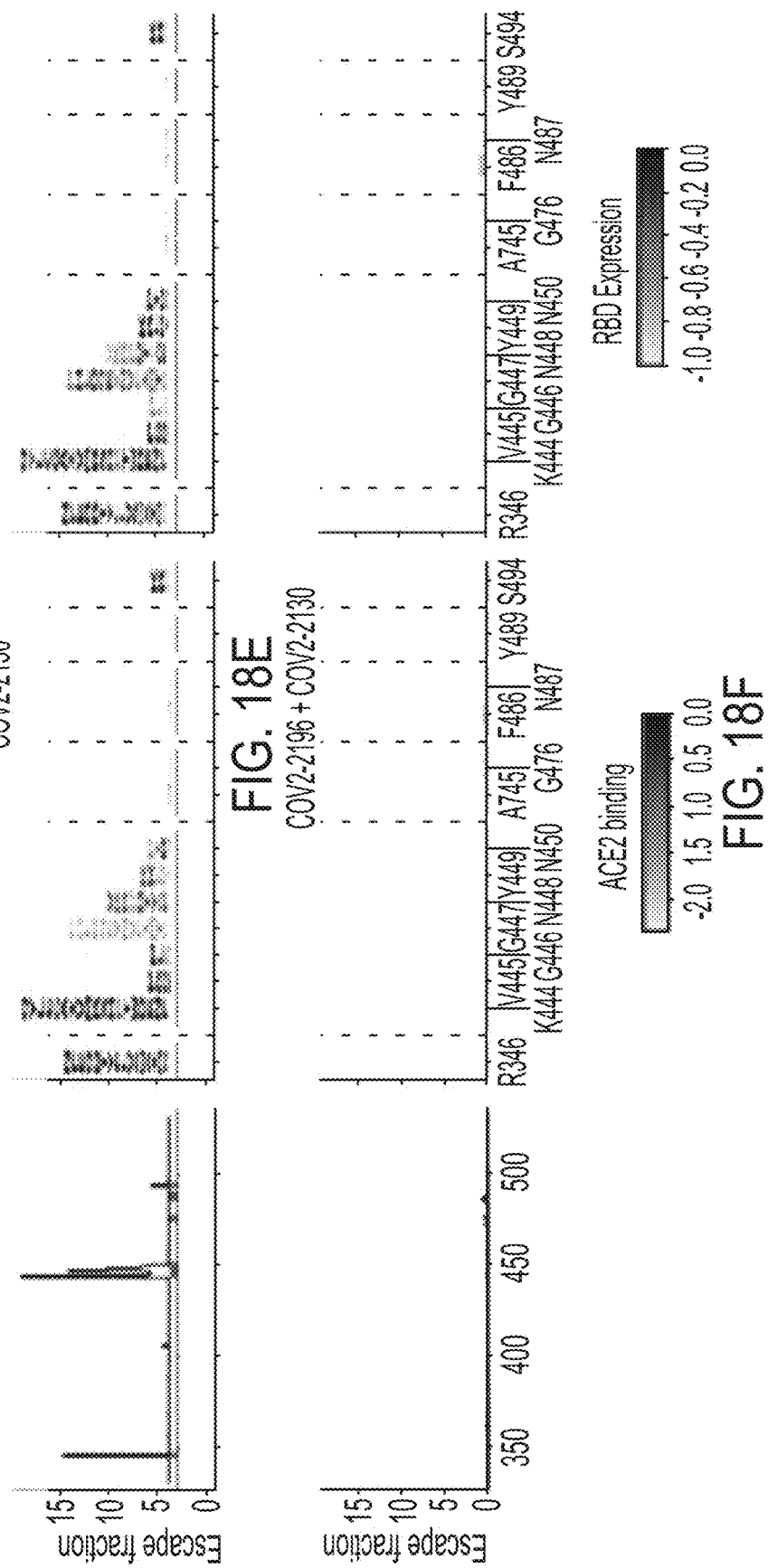
FIG. 18D COV2-2196
FIG. 18E COV2-2130
FIG. 18F COV2-2196 + COV2-2130

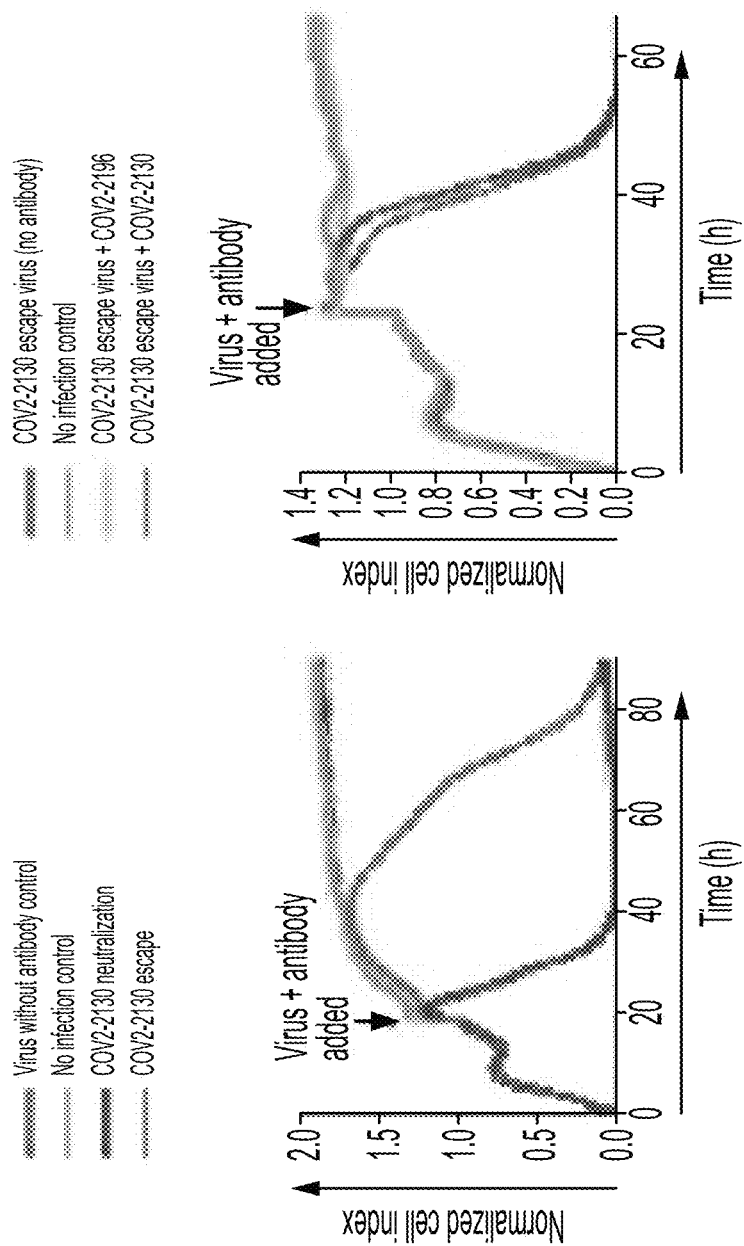

FIG. 19

SEQUENCE LISTING

```
<160> NUMBER OF SEQ ID NOS: 187

<210> SEQ ID NO 1
<211> LENGTH: 351
<212> TYPE: DNA
<213> ORGANISM: Artificial Sequence
<220> FEATURE:
<223> OTHER INFORMATION: COV2-2165 Heavy

<400> SEQUENCE: 1
gaggtgcagc tggtggagtc tgggggaggc ttggtccagc ctgggggtc tctgagactc      60 tcctgtgcag cctctggact caccgtccgt agcaactaca tgacctgggt ccgccagact     120
ccagggaagg ggctggaatg ggtgtcagtt atttatagcg gtggtagcac attctacgca     180
gactccgtga agggcagatt caccatctcc agagacaatt ccaagaacac ggtgtatctt     240
caaatgaaca gcctgagagc cgaggacacg gctgtgtatt actgtgcgag agatctcgtg     300
acttacggtt tggacgtctg gggccaaggg accacggtca ccgtctcctc a              351

<210> SEQ ID NO 2
<211> LENGTH: 321
<212> TYPE: DNA
<213> ORGANISM: Artificial Sequence
<220> FEATURE:
<223> OTHER INFORMATION: COV2-2165 Light

<400> SEQUENCE: 2
gacatccagt tgacccagtc tccatccttc ctgtctgcat ctgtaggaga cagagtcacc      60
atcacttgcc gggccagtca gggcattagc aattatttag cctggtatca gcaaaaacca    120
gggacagccc ctaacctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacta cttaatagtc accccctcac cttcggccaa    300
gggacacgac tggagattaa a                                              321

<210> SEQ ID NO 3
<211> LENGTH: 370
<212> TYPE: DNA
<213> ORGANISM: Artificial Sequence
<220> FEATURE:
<223> OTHER INFORMATION: COV2-2838 Heavy

<400> SEQUENCE: 3
caaatgcagc tggtgcagtc tgggcctgag gtgaagaagc ctgggacctc agtgaaggtc      60
tcctgcaagg cttctggatt caccttatg agctctgctg tgcagtgggt gcgacaggct    120
cgtggacaac gccttgagtg gataggatgg atcgtcattg gcagtggtaa cacaaactac    180
gcacagaagt tccaggaaag agtcaccatt accagggaca tgtccacaag cacagcctac    240
atggagctga gcagcctgag atccgaggac acggccgtgt attactgtgc ggccccatat    300
```
tgtagtagta tcagctgcaa tgatggtttt gatatctggg gccaagggac aatggtcacc     360
gtctcttcag                                                            370

<210> SEQ ID NO 4
<211> LENGTH: 328
<212> TYPE: DNA
<213> ORGANISM: Artificial Sequence
<220> FEATURE:
<223> OTHER INFORMATION: COV2-2838 Light

<400> SEQUENCE: 4
gaaattgtgt tgacgcagtc tccaggcacc ctgtctttgt ctccagggga gagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cactatggta gctcacgggg ttggacgttc    300
ggccaaggga ccaaggtgga atcaaac                                         328

<210> SEQ ID NO 5
<211> LENGTH: 351
<212> TYPE: DNA
<213> ORGANISM: Artificial Sequence
<220> FEATURE:
<223> OTHER INFORMATION: COV2-2952 heavy

<400> SEQUENCE: 5
gaggtgcagc tggtggagtc tgggggaggc ttggtccagc ctgggggtc tctgagactc      60 tcctgtgcag cctctggact caccgtccgt agcaactaca tgacctgggt ccgccagact    120
ccagggaagg gctggaatg ggtgtcagtt atttatagcg gtggtagcac attctacgca    180
gactccgtga agggcagatt caccatctcc agagacaatt ccaagaacac ggtgtatctt    240
caaatgaaca gcctgagagc cgaggacacg gctgtgtatt actgtgcgag agatctcgtg    300
acttacggtt tggacgtctg gggccaaggg accacggtca ccgtctcctc a             351

<210> SEQ ID NO 6
<211> LENGTH: 322
<212> TYPE: DNA
<213> ORGANISM: Artificial Sequence
<220> FEATURE:
<223> OTHER INFORMATION: COV2-2952 light

<400> SEQUENCE: 6
gacatccagt tgacccagtc tccatccttc ctgtctgcat ctgtaggaga cagagtcacc     60
atcacttgcc gggccagtca gggcattagc aattatttag cctggtatca gcaaaaacca    120
gggacagccc ctaacctcct gatctatgct gcatccactt tgcaaagtgg ggtcccatca    180
aggttcagcg gcagtggatc tgggacagaa ttcactctca caatcagcag cctgcagcct    240
gaagattttg caactattat ctgtcaacta cttaatagtc accccctcac cttcggccaa    300
gggacacgac tggagattaa ac                                              322

<210> SEQ ID NO 7
<211> LENGTH: 388
<212> TYPE: DNA
<213> ORGANISM: Artificial Sequence
<220> FEATURE:
<223> OTHER INFORMATION: COV2-2514 heavy

<400> SEQUENCE: 7

```
gaggtgcagc tggtggagtc tgggggaggt gtggtacggc ctgggggggtc cctgagactc    60 tcctgtgcag cctctggatt catctttgat gattatgaca tgacctgggt ccgccaagct   120
ccagggaagg ggctggagtg ggtctctggt attaattgga atggtggtag cacaggttat   180
gcagactctg tgaagggccg attcaccatc tccagagaca cgccaagaa ctccctgtat    240 ctgcaaatga acagtctgag agccgaggac acggccttgt atcactgtgc agtgattatg   300
tctccaatcc cccgttatag tggctacgat tgggcgggtg atgcttttga tatctggggc   360
caagggacaa tggtcaccgt ctcttcag                                      388

<210> SEQ ID NO 8
<211> LENGTH: 325
<212> TYPE: DNA
<213> ORGANISM: Artificial Sequence
<220> FEATURE:
<223> OTHER INFORMATION: COV2-2514 light

<400> SEQUENCE: 8
tcttctgagc tgactcagga ccctgctgtg tctgtggcct tgggacagac agtcaggatc    60
acatgccaag agacagcct cagaagctat tatgcaagtt ggtaccagca gaagccagga   120
caggtcccta cttgtcat ctatgataaa acaaccggc cctcagggat cccagaccga     180
ttctctggct ccagctcagg aaacacagct tccttgacca tcactggggc tcaggcggaa   240
gatgaggctg actattactg taactcccgg gacagcagtg gtaacgccgt ggtattcggc   300
ggagggacca agctgaccgt cctag                                         325

<210> SEQ ID NO 9
<211> LENGTH: 370
<212> TYPE: DNA
<213> ORGANISM: Artificial Sequence
<220> FEATURE:
<223> OTHER INFORMATION: COV2-2391 heavy

<400> SEQUENCE: 9
caggtgcagc tggtgcagtc tggggctgag gtgaagaagc tggggcctc agtgaaggtc     60 tcctgcaagg cttctggata caccttcggc agctttgata tcaactgggt gcgacaggcc   120
actggacaag ggcttgagtg gatgggacgg atgaactcta acagtgggaa cacagcctat   180
gcacagaagt tccagggcag agtcactatg accagggaca cctccacaaa tacagcctac   240
atggagttga gcagcctgag atctgaggac acggccatgt attactgtgc gagaatgcgc   300
agtggctggc ccacacatgg ccgcccggat gacttctggg gccggggaac cctggtcacc   360
gtctcctcag                                                          370

<210> SEQ ID NO 10
<211> LENGTH: 331
<212> TYPE: DNA
<213> ORGANISM: Artificial Sequence
<220> FEATURE:
<223> OTHER INFORMATION: COV2-2391 light

<400> SEQUENCE: 10
cagtctgtgc tgactcaggc accctcagcg tctgggaccc ccgggcagag ggtcaccatc    60
tcttgttctg gaagcaactc caatatcgga agttatacta aaactggta ccagcagctc   120 ccaggaacgg cccccaaact cctcatttat ggtaatgatc agcggacctc agggtccct   180 gaccgattct ctggctccaa gtttggcacc tcggcctccc tggccatcag tgggctccag   240
```

```
tctgaggatg aaaataatta ttactgtgca gtatgggatg acagcctgaa tggcctggta      300
ttcggcggag ggaccaaact gaccgtccta g                                    331
```

<210> SEQ ID NO 11
<211> LENGTH: 369
<212> TYPE: DNA
<213> ORGANISM: Artificial Sequence
<220> FEATURE:
<223> OTHER INFORMATION: COV2-3025 heavy

<400> SEQUENCE: 11

```
gaggtgcagc tggtgcagtc tgggcctgag gtgaagaagc ctgggacctc agtgaaggtc      60
tcctgcaagg cttctggatt caccttatg agctctgctg tgcagtgggt gcgacaggct     120
cgtggacaac gccttgagtg gataggatgg atcgtcattg cagtggtaa cacaaactac     180 gcacagaagt tccaggaaag agtcaccatt accaggaca tgtccacaag cacagcctac     240
atggagctga gcagcctgag atccgaggac acggccgtgt attactgtgc ggccccatat     300
tgtagtagta tcagctgcaa tgatgggtttt gatatctggg gccaagggac aatggtcacc     360
gtctcttca                                                              369
```

<210> SEQ ID NO 12
<211> LENGTH: 327
<212> TYPE: DNA
<213> ORGANISM: Artificial Sequence
<220> FEATURE:
<223> OTHER INFORMATION: COV2-3025 light

<400> SEQUENCE: 12

```
gaaattgtgt tgacgcagtc tccaggcacc ctgtctttgt ctccagggga gagagtcacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cactatggta gctcacgggg ttggacgttc     300
ggccaaggga ccaaggtgga aatcaaa                                          327
```

<210> SEQ ID NO 13
<211> LENGTH: 369
<212> TYPE: DNA
<213> ORGANISM: Artificial Sequence
<220> FEATURE:
<223> OTHER INFORMATION: COV2-2196 heavy

<400> SEQUENCE: 13

```
caaatgcagc tggtgcagtc tgggcctgag gtgaagaagc ctgggacctc agtgaaggtc      60
tcctgcaagg cttctggatt caccttatg agctctgctg tgcagtgggt gcgacaggct     120
cgtggacaac gccttgagtg gataggatgg atcgtcattg cagtggtaa cacaaactac     180 gcacagaagt tccaggaaag agtcaccatt accaggaca tgtccacaag cacagcctac     240
atggagctga gcagcctgag atccgaggac acggccgtgt attactgtgc ggccccatat     300
tgtagtagta tcagctgcaa tgatgggtttt gatatctggg gccaagggac aatggtcacc     360
gtctcttca                                                              369
```

<210> SEQ ID NO 14
<211> LENGTH: 327
<212> TYPE: DNA
<213> ORGANISM: Artificial Sequence
<220> FEATURE:
<223> OTHER INFORMATION: COV2-2196 light

<400> SEQUENCE: 14

```
gaaattgtgt tgacgcagtc tccaggcacc ctgtctttgt ctccagggga gagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cactatggta gctcacgggg ttggacgttc     300
ggccaaggga ccaaggtgga aatcaaa                                         327
```

<210> SEQ ID NO 15
<211> LENGTH: 387
<212> TYPE: DNA
<213> ORGANISM: Artificial Sequence
<220> FEATURE:
<223> OTHER INFORMATION: COV2-2094 heavy

<400> SEQUENCE: 15

```
gaggtgcagc tggtggagtc tgggggaggt gtggtacggc ctgggggtc cctgagactc       60
tcctgtgcag cctctggatt catctttgat gattatgaca tgacctgggt ccgccaagct    120
ccagggaagg ggctggagtg gtctctggt attaattgga atggtggtag cacaggttat     180
gcagactctg tgaagggccg attcaccatc tccagagaca cgccaagaa ctccctgtat     240
ctgcaaatga acagtctgag agccgaggac acggccttgt atcactgtgc agtgattatg    300
tctccaatcc ccgttatag tggctacgat tgggcgggtg atgcttttga tatctggggc     360
caagggacaa tggtcaccgt ctcttca                                        387
```

<210> SEQ ID NO 16
<211> LENGTH: 324
<212> TYPE: DNA
<213> ORGANISM: Artificial Sequence
<220> FEATURE:
<223> OTHER INFORMATION: COV2-2094 light

<400> SEQUENCE: 16

```
tcttctgagc tgactcagga ccctgctgtg tctgtggcct tgggacagac agtcaggatc      60
acatgccaag agacagcct cagaagctat tatgcaagtt ggtaccagca gaagccagga     120
caggtcccta tacttgtcat ctatgataaa acaaccggc cctcagggat cccagaccga     180
ttctctggct ccagctcagg aaacacagct tccttgacca tcactgggc tcaggcggaa     240
gatgaggctg actattactg taactcccgg acagcagtg gtaacgccgt ggtattcggc     300
ggagggacca gctgaccgt ccta                                            324
```

<210> SEQ ID NO 17
<211> LENGTH: 369
<212> TYPE: DNA
<213> ORGANISM: Artificial Sequence
<220> FEATURE:
<223> OTHER INFORMATION: COV2-2096 heavy

<400> SEQUENCE: 17

```
caggtgcagc tggtgcagtc tggggctgag gtgaagaagc ctggggcctc agtgaaggtc      60
tcctgcaagg cttctggata caccttcggc agctttgata tcaactgggt gcgacaggcc    120
actggacaag gccttgagtg gatgggacgg atgaactcta cagtgggaa cacagcctat    180
```

```
gcacagaagt tccagggcag agtcactatg accagggaca cctccacaaa tacagcctac    240
atggagttga gcagcctgag atctgaggac acggccatgt attactgtgc gagaatgcgc    300
agtggctggc ccacacatgg ccgcccggat gacttctggg gccggggaac cctggtcacc    360
gtctcctca                                                            369

<210> SEQ ID NO 18
<211> LENGTH: 330
<212> TYPE: DNA
<213> ORGANISM: Artificial Sequence
<220> FEATURE:
<223> OTHER INFORMATION: COV2-2096 light

<400> SEQUENCE: 18
cagtctgtgc tgactcaggc accctcagcg tctgggaccc ccgggcagag ggtcaccatc     60
tcttgttctg gaagcaactc caatatcgga agttatacta taaactggta ccagcagctc    120
ccaggaacgg cccccaaact cctcatttat ggtaatgatc agcggacctc agggtccct     180 gaccgattct ctggctccaa gtttggcacc tcggcctccc tggccatcag tgggctccag    240
tctgaggatg aaaataatta ttactgtgca gtatgggatg acagcctgaa tggcctggta    300
ttcggcggag ggaccaaact gaccgtccta                                     330

<210> SEQ ID NO 19
<211> LENGTH: 393
<212> TYPE: DNA
<213> ORGANISM: Artificial Sequence
<220> FEATURE:
<223> OTHER INFORMATION: COV2-2130 heavy

<400> SEQUENCE: 19
gaggtgcagc tggtggagtc tgggggaggc ttggtaaagc ctggggggtc ccttagactc     60
tcctgtgcag cctctggatt cactttcaga gacgtctgga tgagctgggt ccgccaggct    120
ccagggaagg ggctggagtg ggttggccgt attaaaagca aaattgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gcgggaagct attactatga tactgttggt ccaggcctcc cagagggaaa atttgactac    360
tggggccagg gaaccctggt caccgtctcc tca                                 393

<210> SEQ ID NO 20
<211> LENGTH: 336
<212> TYPE: DNA
<213> ORGANISM: Artificial Sequence
<220> FEATURE:
<223> OTHER INFORMATION: COV2-2130 light

<400> SEQUENCE: 20
gacatcgtga tgacccagtc tccagactcc ctggctgtgt ctctgggcga gagggccacc     60
atcaactgca gtccagcca gagtgtttta tacagctcca caataagaa ctacttagct     120 tggtaccagc agaaaccagg acagcctcct aagctgctca tgtactgggc atctacccgg    180
gaatccgggg tccctgaccg attcagtggc agcgggtctg ggcagagtt cactctcacc    240 atcagcagcc tgcaggctga agatgtggca atttattact gtcagcaata ttatagtacc    300
ctcactttcg gcggagggac caaggtggag atcaaa                              336

<210> SEQ ID NO 21
<211> LENGTH: 117
```

<212> TYPE: PRT
<213> ORGANISM: Artificial Sequence
<220> FEATURE:
<223> OTHER INFORMATION: COV2-2165 heavy

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Val Arg Ser Asn
            20                  25                  30

Tyr Met Thr Trp Val Arg Gln Thr Pro Gly Lys Gly Leu Glu Trp Val
        35                  40                  45

Ser Val Ile Tyr Ser Gly Gly Ser Thr Phe Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Leu Val Thr Tyr Gly Leu Asp Val Trp Gly Gln Gly Thr Thr
            100                 105                 110

Val Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: COV2-2165 light

<400> SEQUENCE: 22

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Thr Ala Pro Asn Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Leu Leu Asn Ser His Pro Leu
                85                  90                  95

Thr Phe Gly Gln Gly Thr Arg Leu Glu Ile Lys
            100                 105

<210> SEQ ID NO 23
<211> LENGTH: 123
<212> TYPE: PRT
<213> ORGANISM: Artificial Sequence
<220> FEATURE:
<223> OTHER INFORMATION: COV2-2838 heavy

<400> SEQUENCE: 23

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Met Ser Ser
            20                  25                  30

Ala Val Gln Trp Val Arg Gln Ala Arg Gly Gln Arg Leu Glu Trp Ile

```
                35                  40                  45
Gly Trp Ile Val Ile Gly Ser Gly Asn Thr Asn Tyr Ala Gln Lys Phe
         50                  55                  60

Gln Glu Arg Val Thr Ile Thr Arg Asp Met Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Pro Tyr Cys Ser Ser Ile Ser Cys Asn Asp Gly Phe Asp Ile
            100                 105                 110

Trp Gly Gln Gly Thr Met Val Thr Val Ser Ser
            115                 120

<210> SEQ ID NO 24
<211> LENGTH: 109
<212> TYPE: PRT
<213> ORGANISM: Artificial Sequence
<220> FEATURE:
<223> OTHER INFORMATION: COV2-2838 light

<400> SEQUENCE: 24

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Ser Ser Arg
                 85                  90                  95

Gly Trp Thr Phe Gly Gln Gly Thr Lys Val Glu Ile Lys
            100                 105

<210> SEQ ID NO 25
<211> LENGTH: 117
<212> TYPE: PRT
<213> ORGANISM: Artificial Sequence
<220> FEATURE:
<223> OTHER INFORMATION: COV2-2952 heavy

<400> SEQUENCE: 25

Glu Val Gln Leu Val Glu Ser Gly Gly Gly Leu Val Gln Pro Gly Gly
 1               5                  10                  15

Ser Leu Arg Leu Ser Cys Ala Ala Ser Gly Leu Thr Val Arg Ser Asn
                20                  25                  30

Tyr Met Thr Trp Val Arg Gln Thr Pro Gly Lys Gly Leu Glu Trp Val
            35                  40                  45

Ser Val Ile Tyr Ser Gly Gly Ser Thr Phe Tyr Ala Asp Ser Val Lys
         50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Leu Val Thr Tyr Gly Leu Asp Val Trp Gly Gln Gly Thr Thr
            100                 105                 110
```

<210> SEQ ID NO 26
<211> LENGTH: 107
<212> TYPE: PRT
<213> ORGANISM: Artificial Sequence
<220> FEATURE:
<223> OTHER INFORMATION: COV2-2952 light

<400> SEQUENCE: 26

```
Asp Ile Gln Leu Thr Gln Ser Pro Ser Phe Leu Ser Ala Ser Val Gly
1               5                   10                  15
Asp Arg Val Thr Ile Thr Cys Arg Ala Ser Gln Gly Ile Ser Asn Tyr
            20                  25                  30
Leu Ala Trp Tyr Gln Gln Lys Pro Gly Thr Ala Pro Asn Leu Leu Ile
        35                  40                  45
Tyr Ala Ala Ser Thr Leu Gln Ser Gly Val Pro Ser Arg Phe Ser Gly
50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Leu Leu Asn Ser His Pro Leu
                85                  90                  95
Thr Phe Gly Gln Gly Thr Arg Leu Glu Ile Lys
            100                 105
```

<210> SEQ ID NO 27
<211> LENGTH: 129
<212> TYPE: PRT
<213> ORGANISM: Artificial Sequence
<220> FEATURE:
<223> OTHER INFORMATION: COV2-2514 heavy

<400> SEQUENCE: 27

```
Glu Val Gln Leu Val Glu Ser Gly Gly Gly Val Val Arg Pro Gly Gly
1               5                   10                  15
Ser Leu Arg Leu Ser Cys Ala Ala Ser Gly Phe Ile Phe Asp Asp Tyr
            20                  25                  30
Asp Met Thr Trp Val Arg Gln Ala Pro Gly Lys Gly Leu Glu Trp Val
        35                  40                  45
Ser Gly Ile Asn Trp Asn Gly Gly Ser Thr Gly Tyr Ala Asp Ser Val
50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr His Cys
                85                  90                  95
Ala Val Ile Met Ser Pro Ile Pro Arg Tyr Ser Gly Tyr Asp Trp Ala
            100                 105                 110
Gly Asp Ala Phe Asp Ile Trp Gly Gln Gly Thr Met Val Thr Val Ser
        115                 120                 125
Ser
```

<210> SEQ ID NO 28
<211> LENGTH: 108
<212> TYPE: PRT
<213> ORGANISM: Artificial Sequence
<220> FEATURE:
<223> OTHER INFORMATION: COV2-2514 light

<400> SEQUENCE: 28

```
Val Thr Val Ser Ser
            115
```

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Val Pro Ile Leu Val Ile Tyr
            35                  40                  45

Asp Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Ala
                85                  90                  95

Val Val Phe Gly Gly Gly Thr Lys Leu Thr Val Leu
            100                 105
```

<210> SEQ ID NO 29
<211> LENGTH: 123
<212> TYPE: PRT
<213> ORGANISM: Artificial Sequence
<220> FEATURE:
<223> OTHER INFORMATION: COV2-2391 heavy

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Ser Phe
            20                  25                  30

Asp Ile Asn Trp Val Arg Gln Ala Thr Gly Gln Gly Leu Glu Trp Met
            35                  40                  45

Gly Arg Met Asn Ser Asn Ser Gly Asn Thr Ala Tyr Ala Gln Lys Phe
        50                  55                  60

Gln Gly Arg Val Thr Met Thr Arg Asp Thr Ser Thr Asn Thr Ala Tyr
65                  70                  75                  80

Met Glu Leu Ser Ser Leu Arg Ser Glu Asp Thr Ala Met Tyr Tyr Cys
                85                  90                  95

Ala Arg Met Arg Ser Gly Trp Pro Thr His Gly Arg Pro Asp Asp Phe
                100                 105                 110

Trp Gly Arg Gly Thr Leu Val Thr Val Ser Ser
            115                 120
```

<210> SEQ ID NO 30
<211> LENGTH: 110
<212> TYPE: PRT
<213> ORGANISM: Artificial Sequence
<220> FEATURE:
<223> OTHER INFORMATION: COV2-2391 light

<400> SEQUENCE: 30

```
Gln Ser Val Leu Thr Gln Ala Pro Ser Ala Ser Gly Thr Pro Gly Gln
1               5                   10                  15

Arg Val Thr Ile Ser Cys Ser Gly Ser Asn Ser Asn Ile Gly Ser Tyr
            20                  25                  30

Thr Ile Asn Trp Tyr Gln Gln Leu Pro Gly Thr Ala Pro Lys Leu Leu
            35                  40                  45

Ile Tyr Gly Asn Asp Gln Arg Thr Ser Gly Val Pro Asp Arg Phe Ser
        50                  55                  60

Gly Ser Lys Phe Gly Thr Ser Ala Ser Leu Ala Ile Ser Gly Leu Gln
```

```
                65                  70                  75                  80
Ser Glu Asp Glu Asn Asn Tyr Tyr Cys Ala Val Trp Asp Asp Ser Leu
                    85                  90                  95

Asn Gly Leu Val Phe Gly Gly Thr Lys Leu Thr Val Leu
                100                 105                 110

<210> SEQ ID NO 31
<211> LENGTH: 123
<212> TYPE: PRT
<213> ORGANISM: Artificial Sequence
<220> FEATURE:
<223> OTHER INFORMATION: COV2-3025 heavy

<400> SEQUENCE: 31

Glu Val Gln Leu Val Gln Ser Gly Pro Glu Val Lys Lys Pro Gly Thr
1               5                   10                  15

Ser Val Lys Val Ser Cys Lys Ala Ser Gly Phe Thr Phe Met Ser Ser
                20                  25                  30

Ala Val Gln Trp Val Arg Gln Ala Arg Gly Gln Arg Leu Glu Trp Ile
            35                  40                  45

Gly Trp Ile Val Ile Gly Ser Gly Asn Thr Asn Tyr Ala Gln Lys Phe
        50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Pro Tyr Cys Ser Ser Ile Ser Cys Asn Asp Gly Phe Asp Ile
                100                 105                 110

Trp Gly Gln Gly Thr Met Val Thr Val Ser Ser
            115                 120

<210> SEQ ID NO 32
<211> LENGTH: 109
<212> TYPE: PRT
<213> ORGANISM: Artificial Sequence
<220> FEATURE:
<223> OTHER INFORMATION: COV2-3025 light

<400> SEQUENCE: 32

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Arg
                85                  90                  95

Gly Trp Thr Phe Gly Gln Gly Thr Lys Val Glu Ile Lys
                100                 105

<210> SEQ ID NO 33
<211> LENGTH: 123
<212> TYPE: PRT
<213> ORGANISM: Artificial Sequence
<220> FEATURE:
```

-continued

<223> OTHER INFORMATION: COV2-2196 heavy

<400> SEQUENCE: 33

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Met Ser Ser
            20                  25                  30

Ala Val Gln Trp Val Arg Gln Ala Arg Gly Gln Arg Leu Glu Trp Ile
        35                  40                  45

Gly Trp Ile Val Ile Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Pro Tyr Cys Ser Ser Ile Ser Cys Asn Asp Gly Phe Asp Ile
            100                 105                 110

Trp Gly Gln Gly Thr Met Val Thr Val Ser Ser
        115                 120

<210> SEQ ID NO 34
<211> LENGTH: 109
<212> TYPE: PRT
<213> ORGANISM: Artificial Sequence
<220> FEATURE:
<223> OTHER INFORMATION: COV2-2196 light

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Arg
                85                  90                  95

Gly Trp Thr Phe Gly Gln Gly Thr Lys Val Glu Ile Lys
            100                 105

<210> SEQ ID NO 35
<211> LENGTH: 129
<212> TYPE: PRT
<213> ORGANISM: Artificial Sequence
<220> FEATURE:
<223> OTHER INFORMATION: COV2-2094 heavy

<400> SEQUENCE: 35

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ile Phe Asp Asp Tyr
            20                  25                  30

Asp Met Thr Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val

```
                  50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Val Ile Met Ser Pro Ile Pro Arg Tyr Ser Gly Tyr Asp Trp Ala
            100                 105                 110

Gly Asp Ala Phe Asp Ile Trp Gly Gln Gly Thr Met Val Thr Val Ser
        115                 120                 125

Ser

<210> SEQ ID NO 36
<211> LENGTH: 108
<212> TYPE: PRT
<213> ORGANISM: Artificial Sequence
<220> FEATURE:
<223> OTHER INFORMATION: COV2-2094 light

<400> SEQUENCE: 36

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Val Pro Ile Leu Val Ile Tyr
         35                  40                  45

Asp Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Ala
                 85                  90                  95

Val Val Phe Gly Gly Gly Thr Lys Leu Thr Val Leu
            100                 105

<210> SEQ ID NO 37
<211> LENGTH: 123
<212> TYPE: PRT
<213> ORGANISM: Artificial Sequence
<220> FEATURE:
<223> OTHER INFORMATION: COV2-2096 heavy

<400> SEQUENCE: 37

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Gly Ser Phe
             20                  25                  30

Asp Ile Asn Trp Val Arg Gln Ala Thr Gly Gln Gly Leu Glu Trp Met
         35                  40                  45

Gly Arg Met Asn Ser Asn Ser Gly Asn Thr Ala Tyr Ala Gln Lys Phe
     50                  55                  60

Gln Gly Arg Val Thr Met Thr Arg Asp Thr Ser Thr Asn Thr Ala Tyr
 65                  70                  75                  80

Met Glu Leu Ser Ser Leu Arg Ser Glu Asp Thr Ala Met Tyr Tyr Cys
                 85                  90                  95

Ala Arg Met Arg Ser Gly Trp Pro Thr His Gly Arg Pro Asp Asp Phe
            100                 105                 110

Trp Gly Arg Gly Thr Leu Val Thr Val Ser Ser
```

<210> SEQ ID NO 38
<211> LENGTH: 110
<212> TYPE: PRT
<213> ORGANISM: Artificial Sequence
<220> FEATURE:
<223> OTHER INFORMATION: COV2-2096 light

<400> SEQUENCE: 38

```
Gln Ser Val Leu Thr Gln Ala Pro Ser Ala Ser Gly Thr Pro Gly Gln
1               5                   10                  15
Arg Val Thr Ile Ser Cys Ser Gly Ser Asn Ser Asn Ile Gly Ser Tyr
            20                  25                  30
Thr Ile Asn Trp Tyr Gln Gln Leu Pro Gly Thr Ala Pro Lys Leu Leu
        35                  40                  45
Ile Tyr Gly Asn Asp Gln Arg Thr Ser Gly Val Pro Asp Arg Phe Ser
    50                  55                  60
Gly Ser Lys Phe Gly Thr Ser Ala Ser Leu Ala Ile Ser Gly Leu Gln
65                  70                  75                  80
Ser Glu Asp Glu Asn Asn Tyr Tyr Cys Ala Val Trp Asp Asp Ser Leu
                85                  90                  95
Asn Gly Leu Val Phe Gly Gly Gly Thr Lys Leu Thr Val Leu
            100                 105                 110
```

<210> SEQ ID NO 39
<211> LENGTH: 131
<212> TYPE: PRT
<213> ORGANISM: Artificial Sequence
<220> FEATURE:
<223> OTHER INFORMATION: COV2-2130 heavy

<400> SEQUENCE: 39

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Arg Asp Val
            20                  25                  30
Trp Met Ser Trp Val Arg Gln Ala Pro Gly Lys Gly Leu Glu Trp Val
        35                  40                  45
Gly Arg Ile Lys Ser Lys Ile Asp Gly Gly Thr Thr Asp Tyr Ala Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Thr Ala Gly Ser Tyr Tyr Tyr Asp Thr Val Gly Pro Gly
            100                 105                 110
Leu Pro Glu Gly Lys Phe Asp Tyr Trp Gly Gln Gly Thr Leu Val Thr
        115                 120                 125
Val Ser Ser
    130
```

<210> SEQ ID NO 40
<211> LENGTH: 112
<212> TYPE: PRT
<213> ORGANISM: Artificial Sequence
<220> FEATURE:
<223> OTHER INFORMATION: COV2-2130 light

<400> SEQUENCE: 40

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Met Tyr Trp Ala Ser Thr Arg Glu Ser Gly Val
50                  55                  60

Pro Asp Arg Phe Ser Gly Ser Gly Ser Gly Ala Glu Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Ser Thr Leu Thr Phe Gly Gly Gly Thr Lys Val Glu Ile Lys
            100                 105                 110

<210> SEQ ID NO 41
<211> LENGTH: 8
<212> TYPE: PRT
<213> ORGANISM: Artificial Sequence
<220> FEATURE:
<223> OTHER INFORMATION: COV2-2165 CDRH1

<400> SEQUENCE: 41

Gly Leu Thr Val Arg Ser Asn Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: COV2-2165 CDRH2

<400> SEQUENCE: 42

Ile Tyr Ser Gly Gly Ser Thr
1               5

<210> SEQ ID NO 43
<211> LENGTH: 11
<212> TYPE: PRT
<213> ORGANISM: Artificial Sequence
<220> FEATURE:
<223> OTHER INFORMATION: COV2-2165 CDRH3

<400> SEQUENCE: 43

Ala Arg Asp Leu Val Thr Tyr Gly Leu Asp Val
1               5                   10

<210> SEQ ID NO 44
<211> LENGTH: 8
<212> TYPE: PRT
<213> ORGANISM: Artificial Sequence
<220> FEATURE:
<223> OTHER INFORMATION: COV2-2838 CDRH1

<400> SEQUENCE: 44

Gly Phe Thr Phe Met Ser Ser Ala
1               5

<210> SEQ ID NO 45
<211> LENGTH: 8
<212> TYPE: PRT
<213> ORGANISM: Artificial Sequence
```

```
<220> FEATURE:
<223> OTHER INFORMATION: COV2-2838 CDRH2

<400> SEQUENCE: 45

Ile Val Ile Gly Ser Gly Asn Thr
1               5

<210> SEQ ID NO 46
<211> LENGTH: 16
<212> TYPE: PRT
<213> ORGANISM: Artificial Sequence
<220> FEATURE:
<223> OTHER INFORMATION: COV2-2838 CDRH3

<400> SEQUENCE: 46

Ala Ala Pro Tyr Cys Ser Ser Ile Ser Cys Asn Asp Gly Phe Asp Ile
1               5                   10                  15

<210> SEQ ID NO 47
<211> LENGTH: 8
<212> TYPE: PRT
<213> ORGANISM: Artificial Sequence
<220> FEATURE:
<223> OTHER INFORMATION: COV2-2952 CDRH1

<400> SEQUENCE: 47

Gly Leu Thr Val Arg Ser Asn Tyr
1               5

<210> SEQ ID NO 48
<211> LENGTH: 7
<212> TYPE: PRT
<213> ORGANISM: Artificial Sequence
<220> FEATURE:
<223> OTHER INFORMATION: COV2-2952 CDRH2

<400> SEQUENCE: 48

Ile Tyr Ser Gly Gly Ser Thr
1               5

<210> SEQ ID NO 49
<211> LENGTH: 11
<212> TYPE: PRT
<213> ORGANISM: Artificial Sequence
<220> FEATURE:
<223> OTHER INFORMATION: COV2-2952 CDRH3

<400> SEQUENCE: 49

Ala Arg Asp Leu Val Thr Tyr Gly Leu Asp Val
1               5                   10

<210> SEQ ID NO 50
<211> LENGTH: 8
<212> TYPE: PRT
<213> ORGANISM: Artificial Sequence
<220> FEATURE:
<223> OTHER INFORMATION: COV2-2514 CDRH1

<400> SEQUENCE: 50

Gly Phe Ile Phe Asp Asp Tyr Asp
1               5

<210> SEQ ID NO 51
<211> LENGTH: 8
<212> TYPE: PRT
<213> ORGANISM: Artificial Sequence
<220> FEATURE:
```

```
<223> OTHER INFORMATION: COV2-2514 CDRH2

<400> SEQUENCE: 51

Ile Asn Trp Asn Gly Gly Ser Thr
1               5

<210> SEQ ID NO 52
<211> LENGTH: 22
<212> TYPE: PRT
<213> ORGANISM: Artificial Sequence
<220> FEATURE:
<223> OTHER INFORMATION: COV2-2514 CDRH3

<400> SEQUENCE: 52

Ala Val Ile Met Ser Pro Ile Pro Arg Tyr Ser Gly Tyr Asp Trp Ala
1               5                   10                  15

Gly Asp Ala Phe Asp Ile
            20

<210> SEQ ID NO 53
<211> LENGTH: 8
<212> TYPE: PRT
<213> ORGANISM: Artificial Sequence
<220> FEATURE:
<223> OTHER INFORMATION: COV2-2391 CDRH1

<400> SEQUENCE: 53

Gly Tyr Thr Phe Gly Ser Phe Asp
1               5

<210> SEQ ID NO 54
<211> LENGTH: 8
<212> TYPE: PRT
<213> ORGANISM: Artificial Sequence
<220> FEATURE:
<223> OTHER INFORMATION: COV2-2391 CDRH2

<400> SEQUENCE: 54

Met Asn Ser Asn Ser Gly Asn Thr
1               5

<210> SEQ ID NO 55
<211> LENGTH: 16
<212> TYPE: PRT
<213> ORGANISM: Artificial Sequence
<220> FEATURE:
<223> OTHER INFORMATION: COV2-2391 CDRH3

<400> SEQUENCE: 55

Ala Arg Met Arg Ser Gly Trp Pro Thr His Gly Arg Pro Asp Asp Phe
1               5                   10                  15

<210> SEQ ID NO 56
<211> LENGTH: 8
<212> TYPE: PRT
<213> ORGANISM: Artificial Sequence
<220> FEATURE:
<223> OTHER INFORMATION: COV2-3025 CDRH1

<400> SEQUENCE: 56

Gly Phe Thr Phe Met Ser Ser Ala
1               5

<210> SEQ ID NO 57
<211> LENGTH: 8
<212> TYPE: PRT
```

```
<213> ORGANISM: Artificial Sequence
<220> FEATURE:
<223> OTHER INFORMATION: COV2-3025 CDRH2

<400> SEQUENCE: 57

Ile Val Ile Gly Ser Gly Asn Thr
1               5

<210> SEQ ID NO 58
<211> LENGTH: 16
<212> TYPE: PRT
<213> ORGANISM: Artificial Sequence
<220> FEATURE:
<223> OTHER INFORMATION: COV2-3025 CDRH3

<400> SEQUENCE: 58

Ala Ala Pro Tyr Cys Ser Ser Ile Ser Cys Asn Asp Gly Phe Asp Ile
1               5                   10                  15

<210> SEQ ID NO 59
<211> LENGTH: 8
<212> TYPE: PRT
<213> ORGANISM: Artificial Sequence
<220> FEATURE:
<223> OTHER INFORMATION: COV2-2196 CDRH1

<400> SEQUENCE: 59

Gly Phe Thr Phe Met Ser Ser Ala
1               5

<210> SEQ ID NO 60
<211> LENGTH: 8
<212> TYPE: PRT
<213> ORGANISM: Artificial Sequence
<220> FEATURE:
<223> OTHER INFORMATION: COV2-2196 CDRH2

<400> SEQUENCE: 60

Ile Val Ile Gly Ser Gly Asn Thr
1               5

<210> SEQ ID NO 61
<211> LENGTH: 16
<212> TYPE: PRT
<213> ORGANISM: Artificial Sequence
<220> FEATURE:
<223> OTHER INFORMATION: COV2-2196 CDRH3

<400> SEQUENCE: 61

Ala Ala Pro Tyr Cys Ser Ser Ile Ser Cys Asn Asp Gly Phe Asp Ile
1               5                   10                  15

<210> SEQ ID NO 62
<211> LENGTH: 8
<212> TYPE: PRT
<213> ORGANISM: Artificial Sequence
<220> FEATURE:
<223> OTHER INFORMATION: COV2-2094 CDRH1

<400> SEQUENCE: 62

Gly Phe Ile Phe Asp Asp Tyr Asp
1               5

<210> SEQ ID NO 63
<211> LENGTH: 8
<212> TYPE: PRT
<213> ORGANISM: Artificial Sequence
```

```
<220> FEATURE:
<223> OTHER INFORMATION: COV2-2094 CDRH2

<400> SEQUENCE: 63

Ile Asn Trp Asn Gly Gly Ser Thr
1               5

<210> SEQ ID NO 64
<211> LENGTH: 22
<212> TYPE: PRT
<213> ORGANISM: Artificial Sequence
<220> FEATURE:
<223> OTHER INFORMATION: COV2-2094 CDRH3

<400> SEQUENCE: 64

Ala Val Ile Met Ser Pro Ile Pro Arg Tyr Ser Gly Tyr Asp Trp Ala
1               5                   10                  15

Gly Asp Ala Phe Asp Ile
            20

<210> SEQ ID NO 65
<211> LENGTH: 8
<212> TYPE: PRT
<213> ORGANISM: Artificial Sequence
<220> FEATURE:
<223> OTHER INFORMATION: COV2-2096 CDRH1

<400> SEQUENCE: 65

Gly Tyr Thr Phe Gly Ser Phe Asp
1               5

<210> SEQ ID NO 66
<211> LENGTH: 8
<212> TYPE: PRT
<213> ORGANISM: Artificial Sequence
<220> FEATURE:
<223> OTHER INFORMATION: COV2-2096 CDRH2

<400> SEQUENCE: 66

Met Asn Ser Asn Ser Gly Asn Thr
1               5

<210> SEQ ID NO 67
<211> LENGTH: 16
<212> TYPE: PRT
<213> ORGANISM: Artificial Sequence
<220> FEATURE:
<223> OTHER INFORMATION: COV2-2096 CDRH3

<400> SEQUENCE: 67

Ala Arg Met Arg Ser Gly Trp Pro Thr His Gly Arg Pro Asp Asp Phe
1               5                   10                  15

<210> SEQ ID NO 68
<211> LENGTH: 8
<212> TYPE: PRT
<213> ORGANISM: Artificial Sequence
<220> FEATURE:
<223> OTHER INFORMATION: COV2-2130 CDRH1

<400> SEQUENCE: 68

Gly Phe Thr Phe Arg Asp Val Trp
1               5

<210> SEQ ID NO 69
<211> LENGTH: 10
```

```
<212> TYPE: PRT
<213> ORGANISM: Artificial Sequence
<220> FEATURE:
<223> OTHER INFORMATION: COV2-2130 CDRH2

<400> SEQUENCE: 69

Ile Lys Ser Lys Ile Asp Gly Gly Thr Thr
1               5                   10

<210> SEQ ID NO 70
<211> LENGTH: 22
<212> TYPE: PRT
<213> ORGANISM: Artificial Sequence
<220> FEATURE:
<223> OTHER INFORMATION: COV2-2130 CDRH3

<400> SEQUENCE: 70

Thr Thr Ala Gly Ser Tyr Tyr Tyr Asp Thr Val Gly Pro Gly Leu Pro
1               5                   10                  15

Glu Gly Lys Phe Asp Tyr
            20

<210> SEQ ID NO 71
<211> LENGTH: 6
<212> TYPE: PRT
<213> ORGANISM: Artificial Sequence
<220> FEATURE:
<223> OTHER INFORMATION: COV2-2165 CDRL1

<400> SEQUENCE: 71

Gln Gly Ile Ser Asn Tyr
1               5

<210> SEQ ID NO 72
<211> LENGTH: 3
<212> TYPE: PRT
<213> ORGANISM: Artificial Sequence
<220> FEATURE:
<223> OTHER INFORMATION: COV2-2165 CDRL2

<400> SEQUENCE: 72

Ala Ala Ser
1

<210> SEQ ID NO 73
<211> LENGTH: 9
<212> TYPE: PRT
<213> ORGANISM: Artificial Sequence
<220> FEATURE:
<223> OTHER INFORMATION: COV2-2165 CDRL3

<400> SEQUENCE: 73

Gln Leu Leu Asn Ser His Pro Leu Thr
1               5

<210> SEQ ID NO 74
<211> LENGTH: 7
<212> TYPE: PRT
<213> ORGANISM: Artificial Sequence
<220> FEATURE:
<223> OTHER INFORMATION: COV2-2838 CDRL1

<400> SEQUENCE: 74

Gln Ser Val Ser Ser Ser Tyr
1               5
```

-continued

```
<210> SEQ ID NO 75
<211> LENGTH: 3
<212> TYPE: PRT
<213> ORGANISM: Artificial Sequence
<220> FEATURE:
<223> OTHER INFORMATION: COV2-2838 CDRL2

<400> SEQUENCE: 75

Gly Ala Ser
1

<210> SEQ ID NO 76
<211> LENGTH: 10
<212> TYPE: PRT
<213> ORGANISM: Artificial Sequence
<220> FEATURE:
<223> OTHER INFORMATION: COV2-2838 CDRL3

<400> SEQUENCE: 76

Gln His Tyr Gly Ser Ser Arg Gly Trp Thr
1               5                   10

<210> SEQ ID NO 77
<211> LENGTH: 6
<212> TYPE: PRT
<213> ORGANISM: Artificial Sequence
<220> FEATURE:
<223> OTHER INFORMATION: COV2-2952 CDRL1

<400> SEQUENCE: 77

Gln Gly Ile Ser Asn Tyr
1               5

<210> SEQ ID NO 78
<211> LENGTH: 3
<212> TYPE: PRT
<213> ORGANISM: Artificial Sequence
<220> FEATURE:
<223> OTHER INFORMATION: COV2-2952 CDRL2

<400> SEQUENCE: 78

Ala Ala Ser
1

<210> SEQ ID NO 79
<211> LENGTH: 9
<212> TYPE: PRT
<213> ORGANISM: Artificial Sequence
<220> FEATURE:
<223> OTHER INFORMATION: COV2-2952 CDRL3

<400> SEQUENCE: 79

Gln Leu Leu Asn Ser His Pro Leu Thr
1               5

<210> SEQ ID NO 80
<211> LENGTH: 6
<212> TYPE: PRT
<213> ORGANISM: Artificial Sequence
<220> FEATURE:
<223> OTHER INFORMATION: COV2-2514 CDRL1

<400> SEQUENCE: 80

Ser Leu Arg Ser Tyr Tyr
1               5

<210> SEQ ID NO 81
```

```
<211> LENGTH: 3
<212> TYPE: PRT
<213> ORGANISM: Artificial Sequence
<220> FEATURE:
<223> OTHER INFORMATION: COV2-2514 CDRL2

<400> SEQUENCE: 81

Asp Lys Asn
1

<210> SEQ ID NO 82
<211> LENGTH: 11
<212> TYPE: PRT
<213> ORGANISM: Artificial Sequence
<220> FEATURE:
<223> OTHER INFORMATION: COV2-2514 CDRL3

<400> SEQUENCE: 82

Asn Ser Arg Asp Ser Ser Gly Asn Ala Val Val
1               5                   10

<210> SEQ ID NO 83
<211> LENGTH: 8
<212> TYPE: PRT
<213> ORGANISM: Artificial Sequence
<220> FEATURE:
<223> OTHER INFORMATION: COV2-2391 CDRL1

<400> SEQUENCE: 83

Asn Ser Asn Ile Gly Ser Tyr Thr
1               5

<210> SEQ ID NO 84
<211> LENGTH: 3
<212> TYPE: PRT
<213> ORGANISM: Artificial Sequence
<220> FEATURE:
<223> OTHER INFORMATION: COV2-2391 CDRL2

<400> SEQUENCE: 84

Gly Asn Asp
1

<210> SEQ ID NO 85
<211> LENGTH: 11
<212> TYPE: PRT
<213> ORGANISM: Artificial Sequence
<220> FEATURE:
<223> OTHER INFORMATION: COV2-2391 CDRL3

<400> SEQUENCE: 85

Ala Val Trp Asp Asp Ser Leu Asn Gly Leu Val
1               5                   10

<210> SEQ ID NO 86
<211> LENGTH: 7
<212> TYPE: PRT
<213> ORGANISM: Artificial Sequence
<220> FEATURE:
<223> OTHER INFORMATION: COV2-3025 CDRL1

<400> SEQUENCE: 86

Gln Ser Val Ser Ser Ser Tyr
1               5

<210> SEQ ID NO 87
<211> LENGTH: 3
```

```
<212> TYPE: PRT
<213> ORGANISM: Artificial Sequence
<220> FEATURE:
<223> OTHER INFORMATION: COV2-3025 CDRL2

<400> SEQUENCE: 87

Gly Ala Ser
1

<210> SEQ ID NO 88
<211> LENGTH: 10
<212> TYPE: PRT
<213> ORGANISM: Artificial Sequence
<220> FEATURE:
<223> OTHER INFORMATION: COV2-3025 CDRL3

<400> SEQUENCE: 88

Gln His Tyr Gly Ser Ser Arg Gly Trp Thr
1               5                   10

<210> SEQ ID NO 89
<211> LENGTH: 7
<212> TYPE: PRT
<213> ORGANISM: Artificial Sequence
<220> FEATURE:
<223> OTHER INFORMATION: COV2-2196 CDRL1

<400> SEQUENCE: 89

Gln Ser Val Ser Ser Ser Tyr
1               5

<210> SEQ ID NO 90
<211> LENGTH: 3
<212> TYPE: PRT
<213> ORGANISM: Artificial Sequence
<220> FEATURE:
<223> OTHER INFORMATION: COV2-2196 CDRL2

<400> SEQUENCE: 90

Gly Ala Ser
1

<210> SEQ ID NO 91
<211> LENGTH: 10
<212> TYPE: PRT
<213> ORGANISM: Artificial Sequence
<220> FEATURE:
<223> OTHER INFORMATION: COV2-2196 CDRL3

<400> SEQUENCE: 91

Gln His Tyr Gly Ser Ser Arg Gly Trp Thr
1               5                   10

<210> SEQ ID NO 92
<211> LENGTH: 6
<212> TYPE: PRT
<213> ORGANISM: Artificial Sequence
<220> FEATURE:
<223> OTHER INFORMATION: COV2-2094 CDRL1

<400> SEQUENCE: 92

Ser Leu Arg Ser Tyr Tyr
1               5

<210> SEQ ID NO 93
<211> LENGTH: 3
<212> TYPE: PRT
```

```
<213> ORGANISM: Artificial Sequence
<220> FEATURE:
<223> OTHER INFORMATION: COV2-2094 CDRL2

<400> SEQUENCE: 93

Asp Lys Asn
1

<210> SEQ ID NO 94
<211> LENGTH: 11
<212> TYPE: PRT
<213> ORGANISM: Artificial Sequence
<220> FEATURE:
<223> OTHER INFORMATION: COV2-2094 CDRL3

<400> SEQUENCE: 94

Asn Ser Arg Asp Ser Ser Gly Asn Ala Val Val
1               5                   10

<210> SEQ ID NO 95
<211> LENGTH: 8
<212> TYPE: PRT
<213> ORGANISM: Artificial Sequence
<220> FEATURE:
<223> OTHER INFORMATION: COV2-2096 CDRL1

<400> SEQUENCE: 95

Asn Ser Asn Ile Gly Ser Tyr Thr
1               5

<210> SEQ ID NO 96
<211> LENGTH: 3
<212> TYPE: PRT
<213> ORGANISM: Artificial Sequence
<220> FEATURE:
<223> OTHER INFORMATION: COV2-2096 CDRL2

<400> SEQUENCE: 96

Gly Asn Asp
1

<210> SEQ ID NO 97
<211> LENGTH: 11
<212> TYPE: PRT
<213> ORGANISM: Artificial Sequence
<220> FEATURE:
<223> OTHER INFORMATION: COV2-2096 CDRL3

<400> SEQUENCE: 97

Ala Val Trp Asp Asp Ser Leu Asn Gly Leu Val
1               5                   10

<210> SEQ ID NO 98
<211> LENGTH: 12
<212> TYPE: PRT
<213> ORGANISM: Artificial Sequence
<220> FEATURE:
<223> OTHER INFORMATION: COV2-2130 CDRL1

<400> SEQUENCE: 98

Gln Ser Val Leu Tyr Ser Ser Asn Asn Lys Asn Tyr
1               5                   10

<210> SEQ ID NO 99
<211> LENGTH: 3
<212> TYPE: PRT
<213> ORGANISM: Artificial Sequence
```

```
<220> FEATURE:
<223> OTHER INFORMATION: COV2-2130 CDRL2

<400> SEQUENCE: 99

Trp Ala Ser
1

<210> SEQ ID NO 100
<211> LENGTH: 8
<212> TYPE: PRT
<213> ORGANISM: Artificial Sequence
<220> FEATURE:
<223> OTHER INFORMATION: COV2-2130 CDRL3

<400> SEQUENCE: 100

Gln Gln Tyr Tyr Ser Thr Leu Thr
1               5

<210> SEQ ID NO 101
<211> LENGTH: 5
<212> TYPE: PRT
<213> ORGANISM: Artificial Sequence
<220> FEATURE:
<223> OTHER INFORMATION: IGHV1-58 FR2-HCDR2

<400> SEQUENCE: 101

Ile Gly Trp Ile Val
1               5

<210> SEQ ID NO 102
<211> LENGTH: 3
<212> TYPE: PRT
<213> ORGANISM: Artificial Sequence
<220> FEATURE:
<223> OTHER INFORMATION: IGHV1-58 HCDR3-FR4

<400> SEQUENCE: 102

Cys Ala Ala
1

<210> SEQ ID NO 103
<211> LENGTH: 10
<212> TYPE: PRT
<213> ORGANISM: Artificial Sequence
<220> FEATURE:
<223> OTHER INFORMATION: IGHD2-2 HCDR3-FR4

<400> SEQUENCE: 103

Gly Tyr Cys Ser Ser Thr Ser Cys Tyr Ala
1               5                   10

<210> SEQ ID NO 104
<211> LENGTH: 10
<212> TYPE: PRT
<213> ORGANISM: Artificial Sequence
<220> FEATURE:
<223> OTHER INFORMATION: IGHD2-8 HCDR3-FR4

<400> SEQUENCE: 104

Gly Tyr Cys Thr Asn Gly Val Cys Tyr Ala
1               5                   10

<210> SEQ ID NO 105
<211> LENGTH: 10
<212> TYPE: PRT
<213> ORGANISM: Artificial Sequence
<220> FEATURE:
```

<223> OTHER INFORMATION: IGHD2-15 HCDR3-FR4

<400> SEQUENCE: 105

Gly Tyr Cys Ser Gly Gly Ser Cys Tyr Ser
1               5                   10

<210> SEQ ID NO 106
<211> LENGTH: 6
<212> TYPE: PRT
<213> ORGANISM: Artificial Sequence
<220> FEATURE:
<223> OTHER INFORMATION: IGHJ3*02 HCDR3-FR4

<400> SEQUENCE: 106

Asp Ala Phe Asp Ile Trp
1               5

<210> SEQ ID NO 107
<211> LENGTH: 6
<212> TYPE: PRT
<213> ORGANISM: Artificial Sequence
<220> FEATURE:
<223> OTHER INFORMATION: IGKV3-20 LCDR1-FR2

<400> SEQUENCE: 107

Ser Ser Tyr Leu Ala Trp
1               5

<210> SEQ ID NO 108
<211> LENGTH: 6
<212> TYPE: PRT
<213> ORGANISM: Artificial Sequence
<220> FEATURE:
<223> OTHER INFORMATION: IGKV3-20 LCDR3-FR4

<400> SEQUENCE: 108

Gln Tyr Gly Ser Ser Pro
1               5

<210> SEQ ID NO 109
<211> LENGTH: 4
<212> TYPE: PRT
<213> ORGANISM: Artificial Sequence
<220> FEATURE:
<223> OTHER INFORMATION: IGKJ1*01 LCDR3-FR4

<400> SEQUENCE: 109

Trp Thr Phe Gly
1

<210> SEQ ID NO 110
<211> LENGTH: 5
<212> TYPE: PRT
<213> ORGANISM: Artificial Sequence
<220> FEATURE:
<223> OTHER INFORMATION: COV2-2196 FR2-HCDR2

<400> SEQUENCE: 110

Ile Gly Trp Ile Val
1               5

<210> SEQ ID NO 111
<211> LENGTH: 18
<212> TYPE: PRT
<213> ORGANISM: Artificial Sequence
<220> FEATURE:
<223> OTHER INFORMATION: COV2-2196 HCDR3-FR4

<400> SEQUENCE: 111

Cys Ala Ala Pro Tyr Cys Ser Ser Ile Ser Cys Asn Asp Gly Phe Asp
1               5                   10                  15
Ile Trp

<210> SEQ ID NO 112
<211> LENGTH: 6
<212> TYPE: PRT
<213> ORGANISM: Artificial Sequence
<220> FEATURE:
<223> OTHER INFORMATION: COV2-2196 LCDR1-FR2

<400> SEQUENCE: 112

Ser Ser Tyr Leu Ala Trp
1               5

<210> SEQ ID NO 113
<211> LENGTH: 11
<212> TYPE: PRT
<213> ORGANISM: Artificial Sequence
<220> FEATURE:
<223> OTHER INFORMATION: COV2-2196 LCDR3-FR4

<400> SEQUENCE: 113

His Tyr Gly Ser Ser Arg Gly Trp Thr Phe Gly
1               5                   10

<210> SEQ ID NO 114
<211> LENGTH: 5
<212> TYPE: PRT
<213> ORGANISM: Artificial Sequence
<220> FEATURE:
<223> OTHER INFORMATION: COV2-2381 FR2-HCDR2

<400> SEQUENCE: 114

Ile Gly Trp Ile Ala
1               5

<210> SEQ ID NO 115
<211> LENGTH: 18
<212> TYPE: PRT
<213> ORGANISM: Artificial Sequence
<220> FEATURE:
<223> OTHER INFORMATION: COV2-2381 HCDR3-FR4

<400> SEQUENCE: 115

Cys Ala Ala Pro Tyr Cys Ser Arg Thr Ser Cys His Asp Ala Phe Asp
1               5                   10                  15
Ile Trp

<210> SEQ ID NO 116
<211> LENGTH: 6
<212> TYPE: PRT
<213> ORGANISM: Artificial Sequence
<220> FEATURE:
<223> OTHER INFORMATION: COV2-2381 LCDR1-FR2

<400> SEQUENCE: 116

Ser Ser Tyr Leu Ala Trp
1               5

<210> SEQ ID NO 117
<211> LENGTH: 11
<212> TYPE: PRT

<213> ORGANISM: Artificial Sequence
<220> FEATURE:
<223> OTHER INFORMATION: COV2-2381 LCDR3-FR4

<400> SEQUENCE: 117

His Phe Gly Ser Ser Ser Gln Trp Thr Phe Gly
1               5                   10

<210> SEQ ID NO 118
<211> LENGTH: 5
<212> TYPE: PRT
<213> ORGANISM: Artificial Sequence
<220> FEATURE:
<223> OTHER INFORMATION: COV2-2072 FR2-HCDR2

<400> SEQUENCE: 118

Ile Gly Trp Ile Val
1               5

<210> SEQ ID NO 119
<211> LENGTH: 18
<212> TYPE: PRT
<213> ORGANISM: Artificial Sequence
<220> FEATURE:
<223> OTHER INFORMATION: COV2-2072 HCDR3-FR4

<400> SEQUENCE: 119

Cys Ala Ala Pro His Cys Asn Arg Thr Ser Cys Tyr Asp Ala Phe Asp
1               5                   10                  15

Leu Trp

<210> SEQ ID NO 120
<211> LENGTH: 6
<212> TYPE: PRT
<213> ORGANISM: Artificial Sequence
<220> FEATURE:
<223> OTHER INFORMATION: COV2-2072 LCDR1-FR2

<400> SEQUENCE: 120

Ser Ser Tyr Leu Gly Trp
1               5

<210> SEQ ID NO 121
<211> LENGTH: 10
<212> TYPE: PRT
<213> ORGANISM: Artificial Sequence
<220> FEATURE:
<223> OTHER INFORMATION: COV2-2072 LCDR3-FR4

<400> SEQUENCE: 121

Gln Tyr Gly Ser Ser Pro Trp Thr Phe Gly
1               5                   10

<210> SEQ ID NO 122
<211> LENGTH: 5
<212> TYPE: PRT
<213> ORGANISM: Artificial Sequence
<220> FEATURE:
<223> OTHER INFORMATION: MnC5t2p1_G1 FR2-HCDR2

<400> SEQUENCE: 122

Ile Gly Trp Ile Val
1               5

<210> SEQ ID NO 123
<211> LENGTH: 18

<212> TYPE: PRT
<213> ORGANISM: Artificial Sequence
<220> FEATURE:
<223> OTHER INFORMATION: MnC5t2p1_G1 HCDR3-FR4

<400> SEQUENCE: 123

Cys Ala Ala Pro Arg Cys Ser Gly Gly Ser Cys Tyr Asp Gly Phe Asp
1               5                   10                  15

Ile Trp

<210> SEQ ID NO 124
<211> LENGTH: 6
<212> TYPE: PRT
<213> ORGANISM: Artificial Sequence
<220> FEATURE:
<223> OTHER INFORMATION: MnC5t2p1_G1 LCDR1-FR2

<400> SEQUENCE: 124

Ser Ser Tyr Leu Ala Trp
1               5

<210> SEQ ID NO 125
<211> LENGTH: 10
<212> TYPE: PRT
<213> ORGANISM: Artificial Sequence
<220> FEATURE:
<223> OTHER INFORMATION: MnC5t2p1_G1 LCDR3-FR4

<400> SEQUENCE: 125

Gln Tyr Gly Ser Ser Pro Trp Thr Phe Gly
1               5                   10

<210> SEQ ID NO 126
<211> LENGTH: 5
<212> TYPE: PRT
<213> ORGANISM: Artificial Sequence
<220> FEATURE:
<223> OTHER INFORMATION: HbnC3t1p2_C6 FR2-HCDR2

<400> SEQUENCE: 126

Ile Gly Trp Ile Val
1               5

<210> SEQ ID NO 127
<211> LENGTH: 18
<212> TYPE: PRT
<213> ORGANISM: Artificial Sequence
<220> FEATURE:
<223> OTHER INFORMATION: HbnC3t1p2_C6 HCDR3-FR4

<400> SEQUENCE: 127

Cys Ala Ala Pro Tyr Cys Ser Ser Thr Arg Cys Tyr Asp Ala Phe Asp
1               5                   10                  15

Ile Trp

<210> SEQ ID NO 128
<211> LENGTH: 6
<212> TYPE: PRT
<213> ORGANISM: Artificial Sequence
<220> FEATURE:
<223> OTHER INFORMATION: HbnC3t1p2_C6 LCDR1-FR2

<400> SEQUENCE: 128

Ser Ser Tyr Leu Ala Trp
1               5

<210> SEQ ID NO 129
<211> LENGTH: 10
<212> TYPE: PRT
<213> ORGANISM: Artificial Sequence
<220> FEATURE:
<223> OTHER INFORMATION: HbnC3t1p2_C6 LCDR3-FR4

<400> SEQUENCE: 129

Gln Tyr Gly Arg Ser Pro Trp Thr Phe Gly
1               5                   10

<210> SEQ ID NO 130
<211> LENGTH: 5
<212> TYPE: PRT
<213> ORGANISM: Artificial Sequence
<220> FEATURE:
<223> OTHER INFORMATION: HbnC3t1p1_C6 FR2-HCDR2

<400> SEQUENCE: 130

Ile Gly Trp Ile Val
1               5

<210> SEQ ID NO 131
<211> LENGTH: 18
<212> TYPE: PRT
<213> ORGANISM: Artificial Sequence
<220> FEATURE:
<223> OTHER INFORMATION: HbnC3t1p1_C6 HCDR3-FR4

<400> SEQUENCE: 131

Cys Ala Ala Pro His Cys Ser Ser Thr Ile Cys Tyr Asp Gly Phe Asp
1               5                   10                  15

Ile Trp

<210> SEQ ID NO 132
<211> LENGTH: 6
<212> TYPE: PRT
<213> ORGANISM: Artificial Sequence
<220> FEATURE:
<223> OTHER INFORMATION: HbnC3t1p1_C6 LCDR1-FR2

<400> SEQUENCE: 132

Ser Ser Tyr Leu Ala Trp
1               5

<210> SEQ ID NO 133
<211> LENGTH: 10
<212> TYPE: PRT
<213> ORGANISM: Artificial Sequence
<220> FEATURE:
<223> OTHER INFORMATION: HbnC3t1p1_C6 LCDR3-FR4

<400> SEQUENCE: 133

Gln Tyr Gly Ser Ser Pro Trp Thr Phe Gly
1               5                   10

<210> SEQ ID NO 134
<211> LENGTH: 5
<212> TYPE: PRT
<213> ORGANISM: Artificial Sequence
<220> FEATURE:
<223> OTHER INFORMATION: S2E12 FR2-HCDR2

<400> SEQUENCE: 134

Val Gly Trp Ile Val
1               5

<210> SEQ ID NO 135
<211> LENGTH: 18
<212> TYPE: PRT
<213> ORGANISM: Artificial Sequence
<220> FEATURE:
<223> OTHER INFORMATION: S2E12 HCDR3-FR4

<400> SEQUENCE: 135

Cys Ala Ser Pro Tyr Cys Ser Gly Gly Ser Cys Ser Asp Gly Phe Asp
1               5                   10                  15

Ile Trp

<210> SEQ ID NO 136
<211> LENGTH: 6
<212> TYPE: PRT
<213> ORGANISM: Artificial Sequence
<220> FEATURE:
<223> OTHER INFORMATION: S2E12 LCDR1-FR2

<400> SEQUENCE: 136

Ser Ser Tyr Leu Ala Trp
1               5

<210> SEQ ID NO 137
<211> LENGTH: 11
<212> TYPE: PRT
<213> ORGANISM: Artificial Sequence
<220> FEATURE:
<223> OTHER INFORMATION: S2E12 LCDR3-FR4

<400> SEQUENCE: 137

Gln Tyr Val Gly Leu Thr Gly Trp Thr Phe Gly
1               5                   10

<210> SEQ ID NO 138
<211> LENGTH: 5
<212> TYPE: PRT
<213> ORGANISM: Artificial Sequence
<220> FEATURE:
<223> OTHER INFORMATION: COV107_1 FR2-HCDR2

<400> SEQUENCE: 138

Ile Gly Trp Ile Val
1               5

<210> SEQ ID NO 139
<211> LENGTH: 18
<212> TYPE: PRT
<213> ORGANISM: Artificial Sequence
<220> FEATURE:
<223> OTHER INFORMATION: COV107_1 HCDR3-FR4

<400> SEQUENCE: 139

Cys Ala Ala Pro His Cys Ser Ser Thr Ser Cys Phe Asp Ala Phe Asp
1               5                   10                  15

Ile Trp

<210> SEQ ID NO 140
<211> LENGTH: 6
<212> TYPE: PRT
<213> ORGANISM: Artificial Sequence
<220> FEATURE:
<223> OTHER INFORMATION: COV107_1 LCDR1-FR2

<400> SEQUENCE: 140

```
Ser Ser Tyr Leu Ala Trp
1               5

<210> SEQ ID NO 141
<211> LENGTH: 10
<212> TYPE: PRT
<213> ORGANISM: Artificial Sequence
<220> FEATURE:
<223> OTHER INFORMATION: COV107_1 LCDR3-FR4

<400> SEQUENCE: 141

Gln Tyr Gly Asn Ser Pro Trp Thr Phe Gly
1               5                   10

<210> SEQ ID NO 142
<211> LENGTH: 5
<212> TYPE: PRT
<213> ORGANISM: Artificial Sequence
<220> FEATURE:
<223> OTHER INFORMATION: COV107_2 FR2-HCDR2

<400> SEQUENCE: 142

Ile Gly Trp Ile Val
1               5

<210> SEQ ID NO 143
<211> LENGTH: 18
<212> TYPE: PRT
<213> ORGANISM: Artificial Sequence
<220> FEATURE:
<223> OTHER INFORMATION: COV107_2 HCDR3-FR4

<400> SEQUENCE: 143

Cys Ala Ala Pro Tyr Cys Ser Gly Gly Ser Cys Ser Asp Ala Phe Asp
1               5                   10                  15

Ile Trp

<210> SEQ ID NO 144
<211> LENGTH: 6
<212> TYPE: PRT
<213> ORGANISM: Artificial Sequence
<220> FEATURE:
<223> OTHER INFORMATION: COV107_2 LCDR1-FR2

<400> SEQUENCE: 144

Ser Ser Tyr Leu Ala Trp
1               5

<210> SEQ ID NO 145
<211> LENGTH: 10
<212> TYPE: PRT
<213> ORGANISM: Artificial Sequence
<220> FEATURE:
<223> OTHER INFORMATION: COV107_2 LCDR3-FR4

<400> SEQUENCE: 145

Gln Tyr Gly Ser Ser Pro Trp Thr Phe Gly
1               5                   10

<210> SEQ ID NO 146
<211> LENGTH: 5
<212> TYPE: PRT
<213> ORGANISM: Artificial Sequence
<220> FEATURE:
<223> OTHER INFORMATION: COV72 FR2-HCDR2
```

```
<400> SEQUENCE: 146

Ile Gly Trp Ile Val
1               5

<210> SEQ ID NO 147
<211> LENGTH: 18
<212> TYPE: PRT
<213> ORGANISM: Artificial Sequence
<220> FEATURE:
<223> OTHER INFORMATION: COV72 HCDR3-FR4

<400> SEQUENCE: 147

Cys Ala Ala Val Asp Cys Asn Ser Thr Ser Cys Tyr Asp Ala Phe Asp
1               5                  10                  15

Ile Trp

<210> SEQ ID NO 148
<211> LENGTH: 6
<212> TYPE: PRT
<213> ORGANISM: Artificial Sequence
<220> FEATURE:
<223> OTHER INFORMATION: COV72 LCDR1-FR2

<400> SEQUENCE: 148

Ser Ser Tyr Leu Ala Trp
1               5

<210> SEQ ID NO 149
<211> LENGTH: 10
<212> TYPE: PRT
<213> ORGANISM: Artificial Sequence
<220> FEATURE:
<223> OTHER INFORMATION: COV72 LCDR3-FR4

<400> SEQUENCE: 149

Gln Tyr Asp Ile Ser Pro Trp Thr Phe Gly
1               5                  10

<210> SEQ ID NO 150
<211> LENGTH: 5
<212> TYPE: PRT
<213> ORGANISM: Artificial Sequence
<220> FEATURE:
<223> OTHER INFORMATION: COV21_1 FR2-HCDR2

<400> SEQUENCE: 150

Ile Gly Trp Ile Val
1               5

<210> SEQ ID NO 151
<211> LENGTH: 18
<212> TYPE: PRT
<213> ORGANISM: Artificial Sequence
<220> FEATURE:
<223> OTHER INFORMATION: COV21_1 HCDR3-FR4

<400> SEQUENCE: 151

Cys Ala Ala Pro His Cys Ser Gly Gly Ser Cys Leu Asp Ala Phe Asp
1               5                  10                  15

Ile Trp

<210> SEQ ID NO 152
<211> LENGTH: 6
<212> TYPE: PRT
<213> ORGANISM: Artificial Sequence
```

```
<220> FEATURE:
<223> OTHER INFORMATION: COV21_1 LCDR1-FR2

<400> SEQUENCE: 152

Ser Ser Tyr Leu Ala Trp
1               5

<210> SEQ ID NO 153
<211> LENGTH: 10
<212> TYPE: PRT
<213> ORGANISM: Artificial Sequence
<220> FEATURE:
<223> OTHER INFORMATION: COV21_1 LCDR3-FR4

<400> SEQUENCE: 153

Gln Tyr Gly Ser Ser Pro Trp Thr Phe Gly
1               5                   10

<210> SEQ ID NO 154
<211> LENGTH: 5
<212> TYPE: PRT
<213> ORGANISM: Artificial Sequence
<220> FEATURE:
<223> OTHER INFORMATION: COV21_2 FR2-HCDR2

<400> SEQUENCE: 154

Ile Gly Trp Ile Val
1               5

<210> SEQ ID NO 155
<211> LENGTH: 18
<212> TYPE: PRT
<213> ORGANISM: Artificial Sequence
<220> FEATURE:
<223> OTHER INFORMATION: COV21_2 HCDR3-FR4

<400> SEQUENCE: 155

Cys Ala Ala Pro His Cys Ser Gly Gly Ser Cys Tyr Asp Ala Phe Asp
1               5                   10                  15

Ile Trp

<210> SEQ ID NO 156
<211> LENGTH: 6
<212> TYPE: PRT
<213> ORGANISM: Artificial Sequence
<220> FEATURE:
<223> OTHER INFORMATION: COV21_2 LCDR1-FR2

<400> SEQUENCE: 156

Ser Ser Tyr Leu Ala Trp
1               5

<210> SEQ ID NO 157
<211> LENGTH: 10
<212> TYPE: PRT
<213> ORGANISM: Artificial Sequence
<220> FEATURE:
<223> OTHER INFORMATION: COV21_2 LCDR3-FR4

<400> SEQUENCE: 157

Gln Tyr Gly Ser Ser Pro Trp Thr Phe Gly
1               5                   10

<210> SEQ ID NO 158
<211> LENGTH: 5
<212> TYPE: PRT
```

<213> ORGANISM: Artificial Sequence
<220> FEATURE:
<223> OTHER INFORMATION: COV57_1 FR2-HCDR2

<400> SEQUENCE: 158

Ile Gly Trp Ile Val
1               5

<210> SEQ ID NO 159
<211> LENGTH: 18
<212> TYPE: PRT
<213> ORGANISM: Artificial Sequence
<220> FEATURE:
<223> OTHER INFORMATION: COV57_1 HCDR3-FR4

<400> SEQUENCE: 159

Cys Ala Ala Asn His Cys Ser Gly Gly Ser Cys Tyr Asp Gly Phe Asp
1               5                   10                  15

Ile Trp

<210> SEQ ID NO 160
<211> LENGTH: 6
<212> TYPE: PRT
<213> ORGANISM: Artificial Sequence
<220> FEATURE:
<223> OTHER INFORMATION: COV57_1 LCDR1-FR2

<400> SEQUENCE: 160

Ser Ser Tyr Leu Ala Trp
1               5

<210> SEQ ID NO 161
<211> LENGTH: 10
<212> TYPE: PRT
<213> ORGANISM: Artificial Sequence
<220> FEATURE:
<223> OTHER INFORMATION: COV57_1 LCDR3-FR4

<400> SEQUENCE: 161

Gln Tyr Gly Ser Ser Pro Trp Met Phe Gly
1               5                   10

<210> SEQ ID NO 162
<211> LENGTH: 5
<212> TYPE: PRT
<213> ORGANISM: Artificial Sequence
<220> FEATURE:
<223> OTHER INFORMATION: COV57_2 FR2-HCDR2

<400> SEQUENCE: 162

Ile Gly Trp Ile Val
1               5

<210> SEQ ID NO 163
<211> LENGTH: 18
<212> TYPE: PRT
<213> ORGANISM: Artificial Sequence
<220> FEATURE:
<223> OTHER INFORMATION: COV57_2 HCDR3-FR4

<400> SEQUENCE: 163

Cys Ala Ala Pro Tyr Cys Ser Gly Gly Ser Cys Asn Asp Ala Phe Asp
1               5                   10                  15

Ile Trp

```
<210> SEQ ID NO 164
<211> LENGTH: 6
<212> TYPE: PRT
<213> ORGANISM: Artificial Sequence
<220> FEATURE:
<223> OTHER INFORMATION: COV57_2 LCDR1-FR2

<400> SEQUENCE: 164

Ser Ser Tyr Leu Ala Trp
1               5

<210> SEQ ID NO 165
<211> LENGTH: 10
<212> TYPE: PRT
<213> ORGANISM: Artificial Sequence
<220> FEATURE:
<223> OTHER INFORMATION: COV57_2 LCDR3-FR4

<400> SEQUENCE: 165

Gln Tyr Gly Ser Ser Pro Trp Thr Phe Gly
1               5                   10

<210> SEQ ID NO 166
<211> LENGTH: 129
<212> TYPE: PRT
<213> ORGANISM: Artificial Sequence
<220> FEATURE:
<223> OTHER INFORMATION: HIP1 HEAVY CHAIN
<220> FEATURE:
<221> NAME/KEY: MISC_FEATURE
<222> LOCATION: (81)..(81)
<223> OTHER INFORMATION: Xaa can be Met, Val
<220> FEATURE:
<221> NAME/KEY: MISC_FEATURE
<222> LOCATION: (100)..(100)
<223> OTHER INFORMATION: Xaa can be Trp, Ser, Arg
<220> FEATURE:
<221> NAME/KEY: MISC_FEATURE
<222> LOCATION: (101)..(101)
<223> OTHER INFORMATION: Xaa can be Asp, Arg, Val
<220> FEATURE:
<221> NAME/KEY: MISC_FEATURE
<222> LOCATION: (102)..(102)
<223> OTHER INFORMATION: Xaa can be Leu, Arg, Ala
<220> FEATURE:
<221> NAME/KEY: MISC_FEATURE
<222> LOCATION: (103)..(103)
<223> OTHER INFORMATION: Xaa can be Ala, Gly
<220> FEATURE:
<221> NAME/KEY: MISC_FEATURE
<222> LOCATION: (104)..(104)
<223> OTHER INFORMATION: Xaa can be Tyr, Ile
<220> FEATURE:
<221> NAME/KEY: MISC_FEATURE
<222> LOCATION: (107)..(107)
<223> OTHER INFORMATION: Xaa can be Val, Cys
<220> FEATURE:
<221> NAME/KEY: MISC_FEATURE
<222> LOCATION: (108)..(108)
<223> OTHER INFORMATION: Xaa can be Val, Tyr, Thr
<220> FEATURE:
<221> NAME/KEY: MISC_FEATURE
<222> LOCATION: (109)..(109)
<223> OTHER INFORMATION: Xaa can be Gly, Val
<220> FEATURE:
<221> NAME/KEY: MISC_FEATURE
<222> LOCATION: (110)..(110)
<223> OTHER INFORMATION: Xaa can be Asp, Val
<220> FEATURE:
<221> NAME/KEY: MISC_FEATURE
<222> LOCATION: (111)..(111)
<223> OTHER INFORMATION: Xaa can be Cys, Ala
<220> FEATURE:
<221> NAME/KEY: MISC_FEATURE
<222> LOCATION: (112)..(112)
```

<223> OTHER INFORMATION: Xaa can be Ser, Thr
<220> FEATURE:
<221> NAME/KEY: MISC_FEATURE
<222> LOCATION: (113)..(113)
<223> OTHER INFORMATION: Xaa can be Arg, His, Ala

<400> SEQUENCE: 166

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Xaa Glu Leu Ser Ser Leu Arg Ser Glu Asp Thr Ala Val Tyr Tyr Cys
                85                  90                  95

Ala Ala Pro Xaa Xaa Xaa Xaa Xaa Cys Gly Xaa Xaa Xaa Xaa Xaa Xaa
            100                 105                 110

Xaa Asp Ala Phe Asp Ile Trp Gly Gln Gly Thr Met Val Thr Val Ser
        115                 120                 125

Ser

<210> SEQ ID NO 167
<211> LENGTH: 128
<212> TYPE: PRT
<213> ORGANISM: Artificial Sequence
<220> FEATURE:
<223> OTHER INFORMATION: HIP2 HEAVY CHAIN
<220> FEATURE:
<221> NAME/KEY: misc_feature
<222> LOCATION: (3)..(3)
<223> OTHER INFORMATION: Xaa can be Gln, Pro
<220> FEATURE:
<221> NAME/KEY: misc_feature
<222> LOCATION: (4)..(4)
<223> OTHER INFORMATION: Xaa can be Leu, Arg
<220> FEATURE:
<221> NAME/KEY: misc_feature
<222> LOCATION: (34)..(34)
<223> OTHER INFORMATION: Xaa can be Met, Val
<220> FEATURE:
<221> NAME/KEY: misc_feature
<222> LOCATION: (100)..(100)
<223> OTHER INFORMATION: Xaa can be Gly, Asn, Asp, Gln, Thr, Ser, Leu,
      Arg
<220> FEATURE:
<221> NAME/KEY: misc_feature
<222> LOCATION: (101)..(101)
<223> OTHER INFORMATION: Xaa can be Pro, Gly, Leu, Ser, Val, Lys, Ala
<220> FEATURE:
<221> NAME/KEY: misc_feature
<222> LOCATION: (102)..(102)
<223> OTHER INFORMATION: Xaa can be Ser, Gly, Ile, Val, Arg, Pro, Ala,
      Met
<220> FEATURE:
<221> NAME/KEY: misc_feature
<222> LOCATION: (103)..(103)
<223> OTHER INFORMATION: Xaa can be Tyr, Leu, Ile, Arg, Asn, Ala
<220> FEATURE:
<221> NAME/KEY: misc_feature
<222> LOCATION: (104)..(104)
<223> OTHER INFORMATION: Xaa can be Cys, Ser, Val, Tyr
<220> FEATURE:
<221> NAME/KEY: misc_feature
<222> LOCATION: (105)..(105)
<223> OTHER INFORMATION: Xaa can be Ser, Arg, Val, Tyr, Met

```
<220> FEATURE:
<221> NAME/KEY: misc_feature
<222> LOCATION: (106)..(106)
<223> OTHER INFORMATION: Xaa can be Ser, Gly, Val, Cys
<220> FEATURE:
<221> NAME/KEY: misc_feature
<222> LOCATION: (107)..(107)
<223> OTHER INFORMATION: Xaa can be Gly, Thr
<220> FEATURE:
<221> NAME/KEY: misc_feature
<222> LOCATION: (108)..(108)
<223> OTHER INFORMATION: Xaa can be Ser, Gly, Val, Thr
<220> FEATURE:
<221> NAME/KEY: misc_feature
<222> LOCATION: (109)..(109)
<223> OTHER INFORMATION: Xaa can be Cys, Ala, Thr, Asp
<220> FEATURE:
<221> NAME/KEY: misc_feature
<222> LOCATION: (110)..(110)
<223> OTHER INFORMATION: Xaa can be Tyr, Arg, Phe, Pro, Thr
<220> FEATURE:
<221> NAME/KEY: misc_feature
<222> LOCATION: (111)..(111)
<223> OTHER INFORMATION: Xaa can be Ala, Pro, Gly, Val, Cys, Arg
<220> FEATURE:
<221> NAME/KEY: misc_feature
<222> LOCATION: (112)..(112)
<223> OTHER INFORMATION: Xaa can be Asp, Thr, Ser, Asn, Leu, Ile, Tyr,
      Pro

<400> SEQUENCE: 167

Gln Met Xaa Xaa Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Xaa Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Pro Xaa Xaa Xaa Xaa Xaa Xaa Xaa Xaa Xaa Xaa Xaa Xaa Xaa
            100                 105                 110

Asp Ala Phe Asp Ile Trp Gly Gln Gly Thr Met Val Thr Val Ser Ser
            115                 120                 125

<210> SEQ ID NO 168
<211> LENGTH: 129
<212> TYPE: PRT
<213> ORGANISM: Artificial Sequence
<220> FEATURE:
<223> OTHER INFORMATION: HIP3 HEAVY CHAIN
<220> FEATURE:
<221> NAME/KEY: misc_feature
<222> LOCATION: (3)..(3)
<223> OTHER INFORMATION: Xaa can be Gln, Pro
<220> FEATURE:
<221> NAME/KEY: misc_feature
<222> LOCATION: (34)..(34)
<223> OTHER INFORMATION: Xaa can be Met or Val
<220> FEATURE:
<221> NAME/KEY: misc_feature
<222> LOCATION: (35)..(35)
<223> OTHER INFORMATION: Xaa can be Gln, Arg
<220> FEATURE:
<221> NAME/KEY: misc_feature
<222> LOCATION: (43)..(43)
<223> OTHER INFORMATION: Xaa can be Gln, Arg
```

```
<220> FEATURE:
<221> NAME/KEY: misc_feature
<222> LOCATION: (100)..(100)
<223> OTHER INFORMATION: Xaa can be Tyr, Pro, Ala, Arg, Gly
<220> FEATURE:
<221> NAME/KEY: misc_feature
<222> LOCATION: (101)..(101)
<223> OTHER INFORMATION: Xaa can be Glu, Leu, Pro, Tyr, Ser
<220> FEATURE:
<221> NAME/KEY: misc_feature
<222> LOCATION: (102)..(102)
<223> OTHER INFORMATION: Xaa can be Gly, Val, Ser, Cys, Tyr
<220> FEATURE:
<221> NAME/KEY: misc_feature
<222> LOCATION: (103)..(103)
<223> OTHER INFORMATION: Xaa can be Cys, Asp, Val, Gln, Thr
<220> FEATURE:
<221> NAME/KEY: misc_feature
<222> LOCATION: (104)..(104)
<223> OTHER INFORMATION: Xaa can be Gly, Asn
<220> FEATURE:
<221> NAME/KEY: misc_feature
<222> LOCATION: (106)..(106)
<223> OTHER INFORMATION: Xaa can be Asp, Val
<220> FEATURE:
<221> NAME/KEY: misc_feature
<222> LOCATION: (108)..(108)
<223> OTHER INFORMATION: Xaa can be Tyr, Ala, His
<220> FEATURE:
<221> NAME/KEY: misc_feature
<222> LOCATION: (109)..(109)
<223> OTHER INFORMATION: Xaa can be Thr, Gln, Ser
<220> FEATURE:
<221> NAME/KEY: misc_feature
<222> LOCATION: (110)..(110)
<223> OTHER INFORMATION: Xaa can be Val, His
<220> FEATURE:
<221> NAME/KEY: misc_feature
<222> LOCATION: (111)..(111)
<223> OTHER INFORMATION: Xaa can be Thr, Arg
<220> FEATURE:
<221> NAME/KEY: misc_feature
<222> LOCATION: (112)..(112)
<223> OTHER INFORMATION: Xaa can be Ala, Pro
<220> FEATURE:
<221> NAME/KEY: misc_feature
<222> LOCATION: (113)..(113)
<223> OTHER INFORMATION: Xaa can be Leu, Phe, Ala, Gly, Asn

<400> SEQUENCE: 168

Gln Met Xaa Leu Val Gln Ser Gly Pro Glu Val Lys Pro Gly Thr
1               5                   10                  15

Ser Val Lys Val Ser Cys Lys Ala Ser Gly Phe Thr Phe Thr Ser Ser
                20                  25                  30

Ala Xaa Xaa Trp Val Arg Gln Ala Arg Gly Xaa Arg Leu Glu Trp Ile
            35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Pro Xaa Xaa Xaa Xaa Xaa Gly Xaa Cys Xaa Xaa Xaa Xaa Xaa
                100                 105                 110

Xaa Asp Ala Phe Asp Ile Trp Gly Gln Gly Thr Met Val Thr Val Ser
            115                 120                 125

Ser

<210> SEQ ID NO 169
```

```
<211> LENGTH: 106
<212> TYPE: PRT
<213> ORGANISM: Artificial Sequence
<220> FEATURE:
<223> OTHER INFORMATION: CORD HEAVY CHAIN
<220> FEATURE:
<221> NAME/KEY: misc_feature
<222> LOCATION: (19)..(19)
<223> OTHER INFORMATION: Xaa can be Arg, Leu
<220> FEATURE:
<221> NAME/KEY: misc_feature
<222> LOCATION: (78)..(78)
<223> OTHER INFORMATION: Xaa can be Val, Glu, Gly
<220> FEATURE:
<221> NAME/KEY: misc_feature
<222> LOCATION: (79)..(79)
<223> OTHER INFORMATION: Xaa can be Pro, Gly, or His
<220> FEATURE:
<221> NAME/KEY: misc_feature
<222> LOCATION: (80)..(80)
<223> OTHER INFORMATION: Xaa can be Cys, Ile, Tyr
<220> FEATURE:
<221> NAME/KEY: misc_feature
<222> LOCATION: (81)..(81)
<223> OTHER INFORMATION: Xaa can be Ser, Cys, Val
<220> FEATURE:
<221> NAME/KEY: misc_feature
<222> LOCATION: (85)..(85)
<223> OTHER INFORMATION: Xaa can be Cys, Ser, Val
<220> FEATURE:
<221> NAME/KEY: misc_feature
<222> LOCATION: (86)..(86)
<223> OTHER INFORMATION: Xaa can be Tyr, Ser, Val
<220> FEATURE:
<221> NAME/KEY: misc_feature
<222> LOCATION: (87)..(87)
<223> OTHER INFORMATION: Xaa can be Ser, Thr, Val
<220> FEATURE:
<221> NAME/KEY: misc_feature
<222> LOCATION: (88)..(88)
<223> OTHER INFORMATION: Xaa can be Tyr, Ala, Ser
<220> FEATURE:
<221> NAME/KEY: misc_feature
<222> LOCATION: (89)..(89)
<223> OTHER INFORMATION: Xaa can be Ser, Ala, Cys
<220> FEATURE:
<221> NAME/KEY: misc_feature
<222> LOCATION: (90)..(90)
<223> OTHER INFORMATION: Xaa can be Asp, Tyr

<400> SEQUENCE: 169

Lys Ala Ser Gly Phe Thr Phe Thr Ser Ser Ala Val Gln Trp Val Arg
1               5                   10                  15

Gln Ala Xaa Gly Gln Arg Leu Glu Trp Ile Gly Trp Ile Val Val Gly
            20                  25                  30

Ser Gly Asn Thr Asn Tyr Ala Gln Lys Phe Gln Glu Arg Val Thr Ile
        35                  40                  45

Thr Arg Asp Met Ser Thr Ser Thr Ala Tyr Met Glu Leu Ser Ser Leu
    50                  55                  60

Arg Ser Glu Asp Thr Ala Val Tyr Tyr Cys Ala Ala Pro Xaa Xaa Xaa
65                  70                  75                  80

Xaa Gly Gly Ser Xaa Xaa Xaa Xaa Xaa Asp Ala Phe Asp Ile Trp
                85                  90                  95

Gly Gln Gly Thr Met Val Thr Val Ser Ser
            100                 105

<210> SEQ ID NO 170
<211> LENGTH: 109
<212> TYPE: PRT
<213> ORGANISM: Artificial Sequence
<220> FEATURE:
```

<223> OTHER INFORMATION: HIP1 LIGHT CHAIN
<220> FEATURE:
<221> NAME/KEY: misc_feature
<222> LOCATION: (97)..(97)
<223> OTHER INFORMATION: Xaa can be Pro, Leu, Ser, Thr

<400> SEQUENCE: 170

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Xaa Trp Thr Phe Gly Gln Gly Thr Lys Val Glu Ile Lys
            100                 105
```

<210> SEQ ID NO 171
<211> LENGTH: 109
<212> TYPE: PRT
<213> ORGANISM: Artificial Sequence
<220> FEATURE:
<223> OTHER INFORMATION: HIP2 LIGHT CHAIN
<220> FEATURE:
<221> NAME/KEY: misc_feature
<222> LOCATION: (97)..(97)
<223> OTHER INFORMATION: Xaa can be Pro, Leu, Ser, Thr

<400> SEQUENCE: 171

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Xaa Trp Thr Phe Gly Gln Gly Thr Lys Val Glu Ile Lys
            100                 105
```

<210> SEQ ID NO 172
<211> LENGTH: 109
<212> TYPE: PRT
<213> ORGANISM: Artificial Sequence
<220> FEATURE:
<223> OTHER INFORMATION: HIP3 LIGHT CHAIN
<220> FEATURE:
<221> NAME/KEY: misc_feature
<222> LOCATION: (97)..(97)
<223> OTHER INFORMATION: Xaa can be Pro, Leu, Ser, Thr

<400> SEQUENCE: 172

```
Glu Ile Val Leu Thr Gln Ser Pro Gly Thr Leu Ser Leu Ser Pro Gly
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Xaa Trp Thr Phe Gly Gln Gly Thr Lys Val Glu Ile Lys
            100                 105

<210> SEQ ID NO 173
<211> LENGTH: 108
<212> TYPE: PRT
<213> ORGANISM: Artificial Sequence
<220> FEATURE:
<223> OTHER INFORMATION: HIP1 Light Chain

<400> SEQUENCE: 173

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 174
<211> LENGTH: 109
<212> TYPE: PRT
<213> ORGANISM: Artificial Sequence
<220> FEATURE:
<223> OTHER INFORMATION: HIP1 Light Chain

<400> SEQUENCE: 174

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

```
Pro Trp Thr Phe Gly Gln Gly Thr Lys Val Glu Ile Lys
            100                 105
```

<210> SEQ ID NO 175
<211> LENGTH: 108
<212> TYPE: PRT
<213> ORGANISM: Artificial Sequence
<220> FEATURE:
<223> OTHER INFORMATION: HIP1 Light Chain

<400> SEQUENCE: 175

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Trp Thr Phe Gly Gln Gly Thr Lys Val Glu Ile Lys
            100                 105
```

<210> SEQ ID NO 176
<211> LENGTH: 108
<212> TYPE: PRT
<213> ORGANISM: Artificial Sequence
<220> FEATURE:
<223> OTHER INFORMATION: HIP1 Light Chain

<400> SEQUENCE: 176

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Trp Thr Phe Gly Gln Gly Thr Lys Val Glu Ile Lys
            100                 105
```

<210> SEQ ID NO 177
<211> LENGTH: 109
<212> TYPE: PRT
<213> ORGANISM: Artificial Sequence
<220> FEATURE:
<223> OTHER INFORMATION: HIP1 Light Chain

<400> SEQUENCE: 177

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Trp Thr Phe Gly Gln Gly Thr Lys Val Glu Ile Lys
                100                 105

<210> SEQ ID NO 178
<211> LENGTH: 108
<212> TYPE: PRT
<213> ORGANISM: Artificial Sequence
<220> FEATURE:
<223> OTHER INFORMATION: HIP2 Light Chain

<400> SEQUENCE: 178

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 179
<211> LENGTH: 108
<212> TYPE: PRT
<213> ORGANISM: Artificial Sequence
<220> FEATURE:
<223> OTHER INFORMATION: HIP2 Light Chain

<400> SEQUENCE: 179

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Trp Thr Phe Gly Gln Gly Thr Lys Val Glu Ile Lys
            100                 105
```

```
<210> SEQ ID NO 180
<211> LENGTH: 109
<212> TYPE: PRT
<213> ORGANISM: Artificial Sequence
<220> FEATURE:
<223> OTHER INFORMATION: HIP2 Light Chain

<400> SEQUENCE: 180

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 181
<211> LENGTH: 108
<212> TYPE: PRT
<213> ORGANISM: Artificial Sequence
<220> FEATURE:
<223> OTHER INFORMATION: HIP2 Light Chain

<400> SEQUENCE: 181

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Trp Thr Phe Gly Gln Gly Thr Lys Val Glu Ile Lys
            100                 105

<210> SEQ ID NO 182
<211> LENGTH: 109
<212> TYPE: PRT
<213> ORGANISM: Artificial Sequence
<220> FEATURE:
<223> OTHER INFORMATION: HIP2 Light Chain

<400> SEQUENCE: 182

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
                35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Thr Trp Thr Phe Gly Gln Gly Thr Lys Val Glu Ile Lys
                100                 105
```

<210> SEQ ID NO 183
<211> LENGTH: 108
<212> TYPE: PRT
<213> ORGANISM: Artificial Sequence
<220> FEATURE:
<223> OTHER INFORMATION: HIP3 Light Chain

<400> SEQUENCE: 183

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105
```

<210> SEQ ID NO 184
<211> LENGTH: 108
<212> TYPE: PRT
<213> ORGANISM: Artificial Sequence
<220> FEATURE:
<223> OTHER INFORMATION: HIP3 Light Chain

<400> SEQUENCE: 184

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Leu
                 85                  90                  95

Trp Thr Phe Gly Gln Gly Thr Lys Val Glu Ile Lys
            100                 105
```

<210> SEQ ID NO 185
<211> LENGTH: 109

```
<212> TYPE: PRT
<213> ORGANISM: Artificial Sequence
<220> FEATURE:
<223> OTHER INFORMATION: HIP3 Light Chain

<400> SEQUENCE: 185

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 186
<211> LENGTH: 108
<212> TYPE: PRT
<213> ORGANISM: Artificial Sequence
<220> FEATURE:
<223> OTHER INFORMATION: HIP3 Light Chain

<400> SEQUENCE: 186

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Trp Thr Phe Gly Gln Gly Thr Lys Val Glu Ile Lys
            100                 105

<210> SEQ ID NO 187
<211> LENGTH: 109
<212> TYPE: PRT
<213> ORGANISM: Artificial Sequence
<220> FEATURE:
<223> OTHER INFORMATION: HIP3 Light Chain

<400> SEQUENCE: 187

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
                50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Thr Trp Thr Phe Gly Gln Gly Thr Lys Val Glu Ile Lys
                100                 105
```

HUMAN MONOCLONAL ANTIBODIES TO SEVERE ACUTE RESPIRATORY SYNDROME CORONAVIRUS 2 (SARS-COV-2)

REFERENCE TO RELATED APPLICATIONS

This application claims priority to U.S. Provisional Application Nos. 63/000,299, filed Mar. 26, 2020, 63/002,896, filed Mar. 31, 2020, 63/003,716, filed Apr. 1, 2020, 63/023,545, filed May 12, 2020, 63/024,204, filed May 13, 2020, 63/024,248, filed May 13, 2020, 63/027,173, filed May 19, 2020, 63/037,984, filed Jun. 11, 2020, 63/040,224, filed Jun. 17, 2020, 63/040,246, filed Jun. 17, 2020, 63/142,196, filed Jan. 27, 2021, and 63/161,890, filed Mar. 16, 2021, each of which is herein incorporated by reference in its entirety.

FEDERAL FUNDING DISCLOSURE

This invention was made with government support under HR0011-18-2-0001 awarded by the Defense Advanced Research Projects Agency (DARPA) and HHS Contract 75N93019C00074 awarded by the National Institutes of Allergy and Infection Disease/National Institutes of Health. The government has certain rights in the invention.

REFERENCE TO SEQUENCE LISTING SUBMITTED ELECTRONICALLY

The content of the electronically submitted sequence listing (Name: 4815-001000C_SL_ST25.txt; Size: 87,769 Bytes; and Date of Creation: Mar. 24, 2021) is herein incorporated by reference in its entirety.

BACKGROUND

1. Field of the Disclosure

The present disclosure relates generally to the fields of medicine, infectious disease, and immunology. More particular, the disclosure relates to human antibodies binding to a novel coronavirus designated SARS-CoV-2 and methods of use therefor.

2. Background

An epidemic of a novel coronavirus (SARS-CoV-2) affected mainland China, along with cases in 179 other countries and territories. It was identified in Wuhan, the capital of China's Hubei province, after 41 people developed pneumonia without a clear cause. The virus, which causes acute respiratory disease designated coronavirus disease 2019 (COVID-19), is capable of spreading from person to person. The incubation period (time from exposure to onset of symptoms) ranges from 0 to 24 days, with a mean of 3-5 days, but it may be contagious during this period and after recovery. Symptoms include fever, coughing and breathing difficulties. An estimate of the death rate in February 2020 was 2% of confirmed cases, higher among those who require admission to hospital.

As of 10 Feb. 2020, 40,627 cases have been confirmed (6,495 serious), including in every province-level division of China. A larger number of people may have been infected, but not detected (especially mild cases). As of 10 Feb. 2020, 910 deaths have been attributed to the virus since the first confirmed death on 9 January, with 3,323 recoveries. The first local transmission outside China occurred in Vietnam between family members, while the first international transmission not involving family occurred in Germany on 22 January. The first death outside China was in the Philippines, where a man from Wuhan died on 1 February. As of 10 Feb. 2020, the death toll from this virus had surpassed the global SARS outbreak in 2003.

As of early February 2020, there is no licensed vaccine and no specific treatment, although several vaccine approaches and antivirals are being investigated. The outbreak has been declared a Public Health Emergency of International Concern (PHEIC) by the World Health Organization (WHO), based on the possible effects the virus could have if it spreads to countries with weaker healthcare systems. Thus, there is an urgent need to explore the biology and pathology of SARS-CoV-2 and well as the human immune response to this virus.

SUMMARY

Thus, in accordance with the present disclosure, there is provided a method of detecting COVID-19 infection with SARS-CoV-2 in a subject comprising (a) contacting a sample from said subject with an antibody or antibody fragment having clone-paired heavy and light chain CDR sequences from Tables 3 and 4, respectively; and (b) detecting SARS-CoV-2 in said sample by binding of said antibody or antibody fragment to a SARS-CoV-2 antigen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or western blot. The method may further comprise performing steps (a) and (b) a second time and determining a change in SARS-CoV-2 antigen levels as compared to the first assay. The antibody or antibody fragment may be encoded by clone-paired variable sequences as set forth in Table 1. The antibody or antibody fragment may be encoded by light and heavy chain variable sequences having at least 70%, 80%, 90% or 95% identity to clone-paired variable sequences as set forth in Table 1, or by light and heavy chain variable sequences having 100% identity to clone-paired sequences as set forth in Table 1. The antibody or antibody fragment may comprise light and heavy chain variable sequences according to clone-paired sequences from Table 2, or light and heavy chain variable sequences having at least 70%, 80%, 90% or 95% identity to clone-paired sequences from Table 2. The antibody or antibody fragment may bind to a SARS-CoV-2 surface spike protein. The antibody fragment may be a recombinant scFv (single chain fragment variable) antibody, Fab fragment, F(ab')$_2$ fragment, or Fv fragment.

In another embodiment, there is provided a method of treating a subject infected with SARS-CoV-2 or reducing the likelihood of infection of a subject at risk of contracting SARS-CoV-2, comprising delivering to said subject an antibody or antibody fragment having clone-paired heavy and light chain CDR sequences from Tables 3 and 4, respectively. The antibody or antibody fragment may be encoded by light and heavy chain variable sequences having at least 70%, 80%, 90% or 95% identity to clone-paired variable sequences as set forth in Table 1, or by light and heavy chain variable sequences having 100% identity to clone-paired sequences as set forth in Table 1. The antibody or antibody fragment may comprise light and heavy chain variable sequences according to clone-paired sequences from Table 2, or light and heavy chain variable sequences having at least 70%, 80%, 90% or 95% identity to clone-paired sequences from Table 2. The antibody fragment may be a recombinant scFv (single chain fragment variable) antibody, Fab fragment, F(ab')$_2$ fragment, or Fv fragment. The antibody may be a chimeric antibody or a bispecific antibody. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may bind to a SARS-CoV-2 antigen such as a surface spike protein. The antibody or antibody fragment may be administered prior to infection or after infection. The subject may be of age 60 or older, may be immunocompromised, or may suffer from a respiratory and/or cardiovascular disorder. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by light and heavy chain variable sequences having at least 70%, 80%, 90% or 95% identity to clone-paired variable sequences as set forth in Table 1, or by light and heavy chain variable sequences having 100% identity to clone-paired sequences as set forth in Table 1. The antibody or antibody fragment may comprise light and heavy chain variable sequences according to clone-paired sequences from Table 2, or light and heavy chain variable sequences having at least 70%, 80%, 90% or 95% identity to clone-paired sequences from Table 2. The antibody fragment may be a recombinant scFv (single chain fragment variable) antibody, Fab fragment, F(ab')$_2$ fragment, or Fv fragment. The antibody may be a chimeric antibody, is bispecific antibody, or is an intrabody. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may bind to a SARS-CoV-2 surface spike protein.

A hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by light and heavy chain variable sequences having at least 70%, 80%, 90% or 95% identity to clone-paired variable sequences as set forth in Table 1, or by light and heavy chain variable sequences having 100% identity to clone-paired sequences as set forth in Table 1. The antibody or antibody fragment may comprise light and heavy chain variable sequences according to clone-paired sequences from Table 2, or light and heavy chain variable sequences having at least 70%, 80%, 90% or 95% identity to clone-paired sequences from Table 2. The antibody fragment may be a recombinant scFv (single chain fragment variable) antibody, Fab fragment, F(ab')$_2$ fragment, or Fv fragment. The antibody may be a chimeric antibody, a bispecific antibody, or an intrabody. The antibody may bean IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may bind to a SARS-CoV-2 surface spike protein.

In still yet another embodiment, there is provided a vaccine formulation comprising one or more antibodies or antibody fragments characterized by clone-paired heavy and light chain CDR sequences from Tables 3 and 4, respectively. The at least one of said antibodies or antibody fragments may be encoded by light and heavy chain variable sequences according to clone-paired sequences from Table 1, by light and heavy chain variable sequences having at least 70%, 80%, or 90% identity to clone-paired sequences from Table 1, or by light and heavy chain variable sequences having at least 95% identity to clone-paired sequences from Table 1. The at least one of said antibodies or antibody fragments may comprise light and heavy chain variable sequences according to clone-paired sequences from Table 2, or may comprise light and heavy chain variable sequences having at least 70%, 80%, 90% or 95% identity to clone-paired sequences from Table 2. The at least one of said antibody fragments is a recombinant scFv (single chain fragment variable) antibody, Fab fragment, F(ab')$_2$ fragment, or Fv fragment. The at least one of said antibodies may a chimeric antibody, a bispecific antibody or an intrabody. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may bind to a SARS-CoV-2 antigen surface spike protein.

In a further embodiment, there is provided a vaccine formulation comprising one or more expression vectors encoding a first antibody or antibody fragment as described herein. The expression vector(s) may be Sindbis virus or VEE vector(s). The vaccine may be formulated for delivery by needle injection, jet injection, or electroporation. The vaccine formulation may further comprise one or more expression vectors encoding for a second antibody or antibody fragment, such as a distinct antibody or antibody fragment.

In yet a further embodiment, there is provided a method of protecting the health of a subject of age 60 or older, an immunocompromised, subject or a subject suffering from a respiratory and/or cardiovascular disorder that is infected with or at risk of infection with SARS-CoV-2 comprising delivering to said subject an antibody or antibody fragment having clone-paired heavy and light chain CDR sequences from Tables 3 and 4, respectively. The antibody or antibody fragment may be encoded by light and heavy chain variable sequences having at least 70%, 80%, 90% or 95% identity to clone-paired variable sequences as set forth in Table 1, or by light and heavy chain variable sequences having 100% identity to clone-paired sequences as set forth in Table 1. The antibody or antibody fragment may comprise light and heavy chain variable sequences according to clone-paired sequences from Table 2, or light and heavy chain variable sequences having at least 70%, 80%, 90% or 95% identity to clone-paired sequences from Table 2. The antibody fragment may be a recombinant scFv (single chain fragment variable) antibody, Fab fragment, F(ab')$_2$ fragment, or Fv fragment. The antibody may an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The said antibody or antibody fragment may be administered prior to infection or after infection. The antibody or antibody fragment may bind to a SARS-CoV-2 antigen such as a surface spike protein. Delivering may comprise antibody or antibody fragment administration, or genetic delivery with an RNA or DNA sequence or vector encoding the antibody or antibody fragment. The antibody or antibody fragment may improve the subject's respiration as compared to an untreated control and/or may reduce viral load as compared to an untreated control.

In still yet a further embodiment, there is provided a method of determining the antigenic integrity, correct conformation and/or correct sequence of a SARS-CoV-2 surface spike protein comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen or a vaccine formulation or vaccine production batch. Detection may comprise ELISA, RIA, western blot, a biosensor using surface plasmon resonance or biolayer interferometry, or flow cytometric staining. The first antibody or antibody fragment may be encoded by clone-paired variable sequences as set forth in Table 1, by light and heavy chain variable sequences having at least 70%, 80%, or 90% identity to clone-paired variable sequences as set forth in Table 1, or by light and heavy chain variable sequences having at least 95% identity to clone-paired sequences as set forth in Table 1. The first antibody or antibody fragment may comprise light and heavy chain variable sequences according to clone-paired sequences from Table 2, may comprise light and heavy chain variable sequences having at least 70%, 80% or 90% identity to clone-paired sequences from Table 2, or may comprise light and heavy chain variable sequences having at least 95% identity to clone-paired sequences from Table 2. The first antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may be encoded by clone-paired variable sequences as set forth in Table 1, by light and heavy chain variable sequences having at least 70%, 80%, or 90% identity to clone-paired variable sequences as set forth in Table 1, or by light and heavy chain variable sequences having at least 95% identity to clone-paired sequences as set forth in Table 1. The second antibody or antibody fragment may comprise light and heavy chain variable sequences according to clone-paired sequences from Table 2, may comprise light and heavy chain variable sequences having at least 70%, 80% or 90% identity to clone-paired sequences from Table 2, or may comprise light and heavy chain variable sequences having at least 95% identity to clone-paired sequences from Table 2. The second first antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the antigen over time.

Also provided is human monoclonal antibody or antibody fragment, or hybridoma or engineered cell producing the same, wherein said antibody binds to a SARS-CoV-2 antigen surface spike protein.

In one aspect (A1) provided herein, a method of detecting COVID-19 infection with SARS-CoV-2 in a subject comprises: (a) contacting a sample from said subject with an antibody or antibody fragment having clone-paired heavy and light chain CDR sequences from Tables 3 and 4, respectively; and (b) detecting SARS-CoV-2 in said sample by binding of said antibody or antibody fragment to a SARS-CoV-2 antigen in said sample. In one aspect (A2) of A1, said sample is a body fluid. In one aspect (A3) of A1 or A2, said sample is blood, sputum, tears, saliva, mucous or serum, semen, cervical or vaginal secretions, amniotic fluid, placental tissues, urine, exudate, transudate, tissue scrapings or feces. In one aspect (A4) of any one of of A1-A3, the detection comprises ELISA, RIA, lateral flow assay or western blot. In one aspect (A5) of any one of A1-A4, the method further comprises performing steps (a) and (b) a second time and determining a change in SARS-CoV-2 antigen levels as compared to the first assay. In one aspect (A6) of any one of A1-A5, the antibody or antibody fragment is encoded by clone-paired variable sequences as set forth in Table 1. In one aspect (A7) of any one of A1-A5, said antibody or antibody fragment is encoded by light and heavy chain variable sequences having at least 70%, 80%, 90% or 95% identity to clone-paired variable sequences as set forth in Table 1. In one aspect (A8) of any one of A1-A5, said antibody or antibody fragment is encoded by light and heavy chain variable sequences having 100% identity to clone-paired sequences as set forth in Table 1. In one aspect (A9) of any one of A1-A5, said antibody or antibody fragment comprises light and heavy chain variable sequences according to clone-paired sequences from Table 2. In one aspect (A10) of any one of A1-A5, said antibody or antibody fragment comprises light and heavy chain variable sequences having at least 70%, 80%, 90% or 95% identity to clone-paired sequences from Table 2. In one aspect (A11) of any one of A1-A10, said antibody or antibody fragment binds to a SARS-CoV-2 surface spike protein. In one aspect (A12) of any one of A1-A11, the antibody fragment is a recombinant scFv (single chain fragment variable) antibody, Fab fragment, F(ab')$_2$ fragment, or Fv fragment.

In one aspect (A13) provided herein, a method of treating a subject infected with SARS-CoV-2 or reducing the likelihood of infection of a subject at risk of contracting SARS-CoV-2, comprises delivering to said subject an antibody or antibody fragment having clone-paired heavy and light chain CDR sequences from Tables 3 and 4, respectively. In one aspect (A14) of A13, the antibody or antibody fragment is encoded by clone-paired light and heavy chain variable sequences as set forth in Table 1. In one aspect (A15) of A13 or A14, said antibody or antibody fragment is encoded by light and heavy chain variable sequences having at least 70%, 80%, 90% or 95% identity to clone-paired sequences from Table 1. In one aspect (A16) of A13, said antibody or antibody fragment comprises light and heavy chain variable sequences according to clone-paired sequences from Table 2. In one aspect (A17) of A13, said antibody or antibody fragment comprises light and heavy chain variable sequences having at least 70%, 80% or 90% identity to clone-paired sequences from Table 2. In one aspect (A18) of A13, said antibody or antibody fragment comprises light and heavy chain variable sequences having at least 95% identity to clone-paired sequences from Table 2. In one aspect (A19) of any one of A13-A18, the antibody fragment is a recombinant scFv (single chain fragment variable) antibody, Fab fragment, F(ab')$_2$ fragment, or Fv fragment. In one aspect (A20) of any one of A13-A19, said antibody is an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. In one aspect (A21) of any one of A13-A18, said antibody is a chimeric antibody or a bispecific antibody. In one aspect (A22) of any one of A13-A21 said antibody or antibody fragment binds to a SARS-CoV-2 surface spike protein. In one aspect (A23) of any one of A13-A22, said antibody or antibody fragment is administered prior to infection or after infection. In one aspect (A24) of any one of A13-A23, said subject is of age 60 or older, is immunocompromised, or suffers from a respiratory and/or cardiovascular disorder. In one aspect (A25) of any one of A13-A24, delivering comprises antibody or antibody fragment administration, or genetic delivery with an RNA or DNA sequence or vector encoding the antibody or antibody fragment.

In one aspect (A26) provided herein is a monoclonal antibody, wherein the antibody or antibody fragment is characterized by clone-paired heavy and light chain CDR sequences from Tables 3 and 4, respectively. In one aspect (A27) of A26, said antibody or antibody fragment is encoded by light and heavy chain variable sequences according to clone-paired sequences from Table 1. In one aspect (A28) of A26, said antibody or antibody fragment is encoded by light and heavy chain variable sequences having at least 70%, 80%, 90%, or 95% identity to clone-paired sequences from Table 1. In one aspect (A29) of A26, said antibody or antibody fragment comprises light and heavy chain variable sequences according to clone-paired sequences from Table 2. In one aspect (A30) of A26, said antibody or antibody fragment comprises light and heavy chain variable sequences having at least 70%, 80%, 90%, or 95% identity to clone-paired sequences from Table 2. In one aspect (A31) of any one of A26-A30, the antibody fragment is a recombinant scFv (single chain fragment variable) antibody, Fab fragment, F(ab')$_2$ fragment, or Fv fragment. In one aspect (A32) of any one of A26-A30, said antibody is a chimeric antibody, or is a bispecific antibody. In one aspect (A33) of any one of A26-A32, said antibody is an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. In one aspect (A34) of any one of A26-A33, said antibody or antibody fragment binds to a SARS-CoV-2 antigen such as a surface spike protein. In one aspect (A35) of any one of A26-A34, said antibody is an intrabody.

In one aspect (A36) provided herein, a hybridoma or engineered cell encodes an antibody or antibody fragment wherein the antibody or antibody fragment is characterized by clone-paired heavy and light chain CDR sequences from Tables 3 and 4, respectively. In one aspect (A37) of A36, said antibody or antibody fragment is encoded by light and heavy chain variable sequences according to clone-paired sequences from Table 1. In one aspect (A38) of A36, said antibody or antibody fragment is encoded by light and heavy chain variable sequences having at least 70%, 80%, or 90% identity to clone-paired variable sequences from Table 1. In one aspect (A39) of A36, said antibody or antibody fragment is encoded by light and heavy chain variable sequences having at least 95% identity to clone-paired variable sequences from Table 1. In one aspect (A40) of A36, said antibody or antibody fragment comprises light and heavy chain variable sequences according to clone-paired sequences from Table 2. In one aspect (A41) of A36, said antibody or antibody fragment is encoded by light and heavy chain variable sequences having at least 70%, 80%, or 90% identity to clone-paired variable sequences from Table 2. In one aspect (A42) of A36, said antibody or antibody fragment comprises light and heavy chain variable sequences having at least 95% identity to clone-paired sequences from Table 2. In one aspect (A43) of any one of A36-A42, the antibody fragment is a recombinant scFv (single chain fragment variable) antibody, Fab fragment, F(ab')$_2$ fragment, or Fv fragment. In one aspect (A44) of any one of A36-A43, said antibody is a chimeric antibody, a bispecific antibody, or an intrabody. In one aspect (A45) of any one of A36-A43, said antibody is an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. In one aspect (A46) of any one of A36-A45, said antibody or antibody fragment binds to a SARS-CoV-2 surface spike protein.

In one aspect (A47) provided herein, a vaccine formulation comprises one or more antibodies or antibody fragments characterized by clone-paired heavy and light chain CDR sequences from Tables 3 and 4, respectively. In one aspect (A48) of A47, at least one of said antibodies or antibody fragments is encoded by light and heavy chain variable sequences according to clone-paired sequences from Table 1. In one aspect (A49) of A47, at least one of said antibodies or antibody fragments is encoded by light and heavy chain variable sequences having at least 70%, 80%, or 90% identity to clone-paired sequences from Table 1. In one aspect (A50) of A47, at least one of said antibodies or antibody fragments is encoded by light and heavy chain variable sequences having at least 95% identity to clone-paired sequences from Table 1. In one aspect (A51) of A47, at least one of said antibodies or antibody fragments comprises light and heavy chain variable sequences according to clone-paired sequences from Table 2. In one aspect (A52) of A47, at least one of said antibodies or antibody fragments comprises light and heavy chain variable sequences having at least 70%, 80%, 90% or 95% identity to clone-paired sequences from Table 2. In one aspect (A53) of any one of A47-A52, at least one of said antibody fragments is a recombinant scFv (single chain fragment variable) antibody, Fab fragment, F(ab')$_2$ fragment, or Fv fragment. In one aspect (A54) of any one of A47-A52, at least one of said antibodies is a chimeric antibody, is bispecific antibody or an intrabody. In one aspect (A55) of any one of A47-A54, said antibody is an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS YTE or LS mutation or glycan modified to alter (eliminate or enhance) FcR interactions such as enzymatic or chemical addition or removal of glycans or expression in a cell line engineered with a defined glycosylating pattern. In one aspect (A56) of any one of A47-A55, said antibody or antibody fragment binds to a SARS-CoV-2 surface spike protein.

In one aspect (A57) provided herein, a vaccine formulation comprises one or more expression vectors encoding a first antibody or antibody fragment according to any one of A26-A34. In one aspect (A58) of A57, said expression vector(s) is/are Sindbis virus or VEE vector(s). In one aspect (A59) of A57 or A58, the vaccine formulation is formulated for delivery by needle injection, jet injection, or electroporation. In one aspect (A60) of A57, the vaccine formulation further comprises one or more expression vectors encoding for a second antibody or antibody fragment, such as a distinct antibody or antibody fragment of any one of A26-A34.

In one aspect (A61) provided herein, a method of protecting the health of a subject of age 60 or older, an immunocompromised subject, or a subject suffering from a respiratory and/or cardiovascular disorder that is infected with or at risk of infection with SARS-CoV-2 comprises delivering to said subject an antibody or antibody fragment having clone-paired heavy and light chain CDR sequences from Tables 3 and 4, respectively. In one aspect (A62) of A61, the antibody or antibody fragment is encoded by clone-paired light and heavy chain variable sequences as set forth in Table 1. In one aspect (A63) of A61 or A62, the antibody or antibody fragment is encoded by clone-paired light and heavy chain variable sequences having at least 95% identity to as set forth in Table 1. In one aspect (A64) of A61 or A62, said antibody or antibody fragment is encoded by light and heavy chain variable sequences having at least 70%, 80%, or 90% identity to clone-paired sequences from Table 1. In one aspect (A65) of A61, said antibody or antibody fragment comprises light and heavy chain variable sequences according to clone-paired sequences from Table 2. In one aspect (A66) of A61, said antibody or antibody fragment comprises light and heavy chain variable sequences having at least 70%, 80% or 90% identity to clone-paired sequences from Table 2. In one aspet (A67) of A61, said antibody or antibody fragment comprises light and heavy chain variable sequences having at least 95% identity to clone-paired sequences from Table 2. In one aspect (A68) of any one of A61-A67, the antibody fragment is a recombinant scFv (single chain fragment variable) antibody, Fab fragment, F(ab')$_2$ fragment, or Fv fragment. In one aspect (A69), of any one of A61-A68, said antibody is an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. In one aspect (A70) of any one of A61-A67, said antibody is a chimeric antibody or a bispecific antibody. In one aspect (A71) of any one of A61-A70, said antibody or antibody fragment is administered prior to infection or after infection. In one aspect (A72) of any one of A61-A71, said antibody or antibody fragment binds to a SARS-CoV-2 surface spike protein. In one aspect (A73) of any one of A61-A72, delivering comprises antibody or antibody fragment administration, or genetic delivery with an RNA or DNA sequence or vector encoding the antibody or antibody fragment. In one aspect (A74) of A61, the antibody or antibody fragment improves the subject's respiration as compared to an untreated control. In one aspect (A75) of A61, the antibody or antibody fragment reduces viral load as compared to an untreated control.

In one aspect (A76) provided herein, a method of determining the antigenic integrity, correct conformation and/or correct sequence of a SARS-CoV-2 surface spike protein comprises: (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. In one aspect (A77) of A76, said sample comprises recombinantly produced antigen. In one aspect (A78) of A76, said sample comprises a vaccine formulation or vaccine production batch. In one aspect (A79) of A76-A78, detection comprises ELISA, RIA, western blot, a biosensor using surface plasmon resonance or biolayer interferometry, or flow cytometric staining. In one aspect (A80) of A76-A79, the first antibody or antibody fragment is encoded by clone-paired variable sequences as set forth in Table 1. In one aspect (A81) of A76-A79, said first antibody or antibody fragment is encoded by light and heavy chain variable sequences having at least 70%, 80%, or 90% identity to clone-paired variable sequences as set forth in Table 1. In one aspect (A82) of any one of A76-A79, said first antibody or antibody fragment is encoded by light and heavy chain variable sequences having at least 95% identity to clone-paired sequences as set forth in Table 1. In one aspect (A83) of any one of A76-A79, said first antibody or antibody fragment comprises light and heavy chain variable sequences according to clone-paired sequences from Table 2. In one aspect (A84) of any one of A76-A79, said first antibody or antibody fragment comprises light and heavy chain variable sequences having at least 70%, 80% or 90% identity to clone-paired sequences from Table 2. In one aspect (A85) of any one of A76-A79, said first antibody or antibody fragment comprises light and heavy chain variable sequences having at least 95% identity to clone-paired sequences from Table 2. In one aspect (A86) of any one of A76-A85, the first antibody fragment is a recombinant scFv (single chain fragment variable) antibody, Fab fragment, F(ab')$_2$ fragment, or Fv fragment. In one aspect (A87) of any one of A76-A86, the method further comprises performing steps (a) and (b) a second time to determine the antigenic stability of the antigen over time. In one aspect (A88) of any one of A76-A87, the method further comprises (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. In one aspect (A89) of A88, the second antibody or antibody fragment is encoded by clone-paired variable sequences as set forth in Table 1. In one aspect (A90) of A89, said second antibody or antibody fragment is encoded by light and heavy chain variable sequences having at least 70%, 80%, or 90% identity to clone-paired variable sequences as set forth in Table 1. In one aspect (A91) of A89, said second antibody or antibody fragment is encoded by light and heavy chain variable sequences having at least 95% identity to clone-paired sequences as set forth in Table 1. In one aspect (A92) of A89, said second antibody or antibody fragment comprises light and heavy chain variable sequences according to clone-paired sequences from Table 2. In one aspect (A93) of A89, said second antibody or antibody fragment comprises light and heavy chain variable sequences having at least 70%, 80% or 90% identity to clone-paired sequences from Table 2. In one aspect (A94) of A89, said second antibody or antibody fragment comprises light and heavy chain variable sequences having at least 95% identity to clone-paired sequences from Table 2. In one aspect (A95) of A89, the second antibody fragment is a recombinant scFv (single chain fragment variable) antibody, Fab fragment, $F(ab')_2$ fragment, or Fv fragment. In one aspect (A96) of A89, the method further comprises performing steps (c) and (d) a second time to determine the antigenic stability of the antigen over time.

In one aspect (A97) provided herein is a human monoclonal antibody or antibody fragment, or hybridoma or engineered cell producing the same, wherein said antibody binds to a SARS-CoV-2 surface spike protein.

In one aspect (A101) provided herein is an isolated antibody or antibody fragment that binds to a SARS-CoV-2 surface spike protein, wherein the antibody or fragment comprises a CDRH1 comprising the amino acid sequence of SEQ ID NO:59, a CDRH2 comprising the amino acid sequence of SEQ ID NO:60, a CDRH3 comprising the amino acid sequence of SEQ ID NO:61, a CDRL1 comprising the amino acid sequence of SEQ ID NO:89, a CDRH2 comprising the amino acid sequence of SEQ ID NO:90, a CDRH3 comprising the amino acid sequence of SEQ ID NO:91; a CDRH1 comprising the amino acid sequence of SEQ ID NO:68, a CDRH2 comprising the amino acid sequence of SEQ ID NO:69, a CDRH3 comprising the amino acid sequence of SEQ ID NO:70, a CDRL1 comprising the amino acid sequence of SEQ ID NO:98, a CDRH2 comprising the amino acid sequence of SEQ ID NO:99, a CDRH3 comprising the amino acid sequence of SEQ ID NO:100; a CDRH1 comprising the amino acid sequence of SEQ ID NO:41, a CDRH2 comprising the amino acid sequence of SEQ ID NO:42, a CDRH3 comprising the amino acid sequence of SEQ ID NO:43, a CDRL1 comprising the amino acid sequence of SEQ ID NO:71, a CDRH2 comprising the amino acid sequence of SEQ ID NO:72, a CDRH3 comprising the amino acid sequence of SEQ ID NO:73; a CDRH1 comprising the amino acid sequence of SEQ ID NO:44, a CDRH2 comprising the amino acid sequence of SEQ ID NO:45, a CDRH3 comprising the amino acid sequence of SEQ ID NO:46, a CDRL1 comprising the amino acid sequence of SEQ ID NO:74, a CDRH2 comprising the amino acid sequence of SEQ ID NO:75, a CDRH3 comprising the amino acid sequence of SEQ ID NO:76; a CDRH1 comprising the amino acid sequence of SEQ ID NO:47, a CDRH2 comprising the amino acid sequence of SEQ ID NO:48, a CDRH3 comprising the amino acid sequence of SEQ ID NO:49, a CDRL1 comprising the amino acid sequence of SEQ ID NO:77, a CDRH2 comprising the amino acid sequence of SEQ ID NO:78, a CDRH3 comprising the amino acid sequence of SEQ ID NO:79; a CDRH1 comprising the amino acid sequence of SEQ ID NO:50, a CDRH2 comprising the amino acid sequence of SEQ ID NO:51, a CDRH3 comprising the amino acid sequence of SEQ ID NO:52, a CDRL1 comprising the amino acid sequence of SEQ ID NO:80, a CDRH2 comprising the amino acid sequence of SEQ ID NO:81, a CDRH3 comprising the amino acid sequence of SEQ ID NO:82; a CDRH1 comprising the amino acid sequence of SEQ ID NO:53, a CDRH2 comprising the amino acid sequence of SEQ ID NO:54, a CDRH3 comprising the amino acid sequence of SEQ ID NO:55, a CDRL1 comprising the amino acid sequence of SEQ ID NO:83, a CDRH2 comprising the amino acid sequence of SEQ ID NO:84, a CDRH3 comprising the amino acid sequence of SEQ ID NO:85; a CDRH1 comprising the amino acid sequence of SEQ ID NO:56, a CDRH2 comprising the amino acid sequence of SEQ ID NO:57 a CDRH3 comprising the amino acid sequence of SEQ ID NO:58, a CDRL1 comprising the amino acid sequence of SEQ ID NO:86, a CDRH2 comprising the amino acid sequence of SEQ ID NO:87, a CDRH3 comprising the amino acid sequence of SEQ ID NO:88; a CDRH1 comprising the amino acid sequence of SEQ ID NO:62, a CDRH2 comprising the amino acid sequence of SEQ ID NO:63 a CDRH3 comprising the amino acid sequence of SEQ ID NO:64, a CDRL1 comprising the amino acid sequence of SEQ ID NO:65, a CDRH2 comprising the amino acid sequence of SEQ ID NO:66, a CDRH3 comprising the amino acid sequence of SEQ ID NO:67; or a CDRH1 comprising the amino acid sequence of SEQ ID NO:65, a CDRH2 comprising the amino acid sequence of SEQ ID NO:66, a CDRH3 comprising the amino acid sequence of SEQ ID NO:67, a CDRL1 comprising the amino acid sequence of SEQ ID NO:95, a CDRH2 comprising the amino acid sequence of SEQ ID NO:96, a CDRH3 comprising the amino acid sequence of SEQ ID NO:97. In one aspect (A102) of A101, the antibody or fragment comprises heavy and light chain variable sequences having at least 70%, 80%, 90%, or 95% identity to the amino acid sequence of SEQ ID NO:33 and the amino acid sequence of SEQ ID NO:34; the amino acid sequence of SEQ ID NO:39 and the amino acid sequence of SEQ ID NO:40; the amino acid sequence of SEQ ID NO:21 and the amino acid sequence of SEQ ID NO:22; the amino acid sequence of SEQ ID NO:23 and the amino acid sequence of SEQ ID NO:24; the amino acid sequence of SEQ ID NO:25 and the amino acid sequence of SEQ ID NO:26; the amino acid sequence of SEQ ID NO:27 and the amino acid sequence of SEQ ID NO:28; the amino acid sequence of SEQ ID NO:29 and the amino acid sequence of SEQ ID NO:30; the amino acid sequence of SEQ ID NO:31 and the amino acid sequence of SEQ ID NO:32; the amino acid sequence of SEQ ID NO:35 and the amino acid sequence of SEQ ID NO:36; or the amino acid sequence of SEQ ID NO:37 and the amino acid sequence of SEQ ID NO:38. In one aspect (A103) of A101 or A102, the antibody or fragment comprises a heavy chain variable sequence comprising the amino acid sequence of SEQ ID NO:33 and/or a light chain variable sequence comprising the amino acid sequence of SEQ ID NO:34; a heavy chain variable sequence comprising the amino acid sequence of SEQ ID NO:39 and/or a light chain variable sequence comprising the amino acid sequence of SEQ ID NO:40; a heavy chain variable sequence comprising the amino acid sequence of SEQ ID NO:21 and/or a light chain variable sequence comprising the amino acid sequence of SEQ ID NO:22; a heavy chain variable sequence comprising the amino acid sequence of SEQ ID NO:23 and/or a light chain variable sequence comprising the amino acid sequence of SEQ ID NO:24; a heavy chain variable sequence comprising the amino acid sequence of SEQ ID NO:25 and/or a light chain variable sequence comprising the amino acid sequence of SEQ ID NO:26; a heavy chain variable sequence comprising the amino acid sequence of SEQ ID NO:27 and/or a light chain variable sequence comprising the amino acid sequence of SEQ ID NO:28;a heavy chain variable sequence comprising the amino acid sequence of SEQ ID NO:29 and/or a light chain variable sequence comprising the amino acid sequence of SEQ ID NO:30; a heavy chain variable sequence comprising the amino acid sequence of SEQ ID NO:31 and/or a light chain variable sequence comprising the amino acid sequence of SEQ ID NO:32; a heavy chain variable sequence comprising the amino acid sequence of SEQ ID NO:35 and/or a light chain variable sequence comprising the amino acid sequence of SEQ ID NO:36; or a heavy chain variable sequence comprising the amino acid sequence of SEQ ID NO:37 and/or a light chain variable sequence comprising the amino acid sequence of SEQ ID NO:38. In one aspect (A104) of any one of A101-A103, the antibody or fragment is monoclonal. In one aspect (A105) of any one of A101-A104, the antibody fragment is a recombinant scFv (single chain fragment variable) antibody, Fab fragment, F(ab')$_2$ fragment, or Fv fragment. In one aspect (A106) of any one of A101-A105, the antibody or fragment comprises a YTE mutation. In one aspect (A107) of any one of A101-A106, the antibody or fragment is an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. In one aspect (A108) of any one of A101-A107, the antibody or antibody fragment is capable of neutralizing live BSL3 SARS-CoV-2 virus in a focus reduction neutralization test (FRNT) assay using Vero-E2 cell culture monolayers, optionally wherein the antibody or antibody fragment is capable of neutralizing 96% of the live BSL3 SARS-CoV-2 virus at a concentration of 250 ng/mL. In one aspect (A109) of any one of A101-A108, the antibody or antibody fragment blocks receptor binding domain (RBD) binding to human receptor angiotensin converting enzyme 2 (ACE2), optionally wherein the antibody or antibody fragment blocks activity against hACE2 with an IC50<150 ng/mL. In one aspect (A110) of any one of A101-A109, the antibody or antibody fragment is capable of neutralizing SARS-CoV-2 virus comprising a spike protein comprising a D614G substitution, optionally wherein the spike protein does not comprise a E484K substitution. In one aspect (A111) of any one of A101-A110, the antibody or antibody fragment is able to bind RBD in the "up" conformation. In one aspect (A112) of any one of A101-A110, the antibody or antibody fragment is able to bind RBD in the "up" and "down" conformations. In one aspect (A113) of any one of A101-A111, the antibody or antibody fragment is not able to bind RBD in the "down" conformation. In one aspect (A114) of any one of A101-A113, the antibody or fragment is able to bind a trimeric spike protein ectodomain and is able to bind to a monomeric spike protein RBD, optionally wherein the binding to the trimeric spike protein ectodomain and/or the binding to the monomeric spike protein RBD is with an EC50<2 ng/mL. In one aspect (A115) of any one of A101-A114, the antibody or antibody fragment further comprises a detectable label.

In one aspect (A116) provided herein, a method of treating a subject infected with SARS-CoV-2 or reducing the likelihood of infection of a subject at risk of contracting SARS-CoV-2, comprises delivering to the subject a first antibody or antibody fragment of any one of A101-A115.

In one aspect (A117) provided herein, a method of protecting the health of a subject of age 60 or older, an immunocompromised, subject or a subject suffering from a respiratory and/or cardiovascular disorder that is infected with or at risk of infection with SARS-CoV-2 comprises delivering to the subject a first antibody or antibody fragment of any one of A101-A115.

In one aspect (A118) of A116 or A117, the method further comprises delivering to the subject a second antibody or antibody fragment, optionally wherein the second antibody or antibody fragment is an antibody or antibody fragment of any one of claims 1-15.

In one aspect (A119) provided herein, a method of treating a subject infected with SARS-CoV-2 or reducing the likelihood of infection of a subject at risk of contracting SARS-CoV-2, comprises delivering to the subject a first antibody or antibody fragment and a second antibody or antibody fragment, wherein the first and second antibodies or antibody fragments are synergistic in neutralizing SARS-CoV-2.

In one aspect (A120) of A118 or A119, the first antibody or antibody fragment and the second antibody or antibody fragment have a synergy score of 17.4. In one aspect (A121) of any one of A118-A120, the dose of the first antibody or antibody fragment and the second antibody or antibody fragment can be reduced by more than 3 times the dose of the first antibody or antibody fragment or the second antibody or antibody fragment alone to achieve the same potency in virus neutralization. In one aspect (A122) of any one of A118-A121, the first antibody or antibody fragment is able to bind to RBD in the "up" confirmation and is not able to bind to RBD in the "down" confirmation. In one aspect (A123) of any one of A118-A122, the second antibody or antibody fragment is able to bind RBD in both "up" and "down" conformations. In one aspect (A124) of any one of A118-A123, the first antibody or antibody fragment and the second antibody or antibody fragment do not compete for binding to RBD. In one aspect (A125) of any one of A118-A124, the first antibody or antibody fragment comprises a CDRH1 comprising the amino acid sequence of SEQ ID NO:59, a CDRH2 comprising the amino acid sequence of SEQ ID NO:60, a CDRH3 comprising the amino acid sequence of SEQ ID NO:61, a CDRL1 comprising the amino acid sequence of SEQ ID NO:89, a CDRH2 comprising the amino acid sequence of SEQ ID NO:90, a CDRH3 comprising the amino acid sequence of SEQ ID NO:91. In one aspect (A126) of any one of A118-A125, the second antibody or antibody fragment comprises a CDRH1 comprising the amino acid sequence of SEQ ID NO:68, a CDRH2 comprising the amino acid sequence of SEQ ID NO:69, a CDRH3 comprising the amino acid sequence of SEQ ID NO:70, a CDRL1 comprising the amino acid sequence of SEQ ID NO:98, a CDRH2 comprising the amino acid sequence of SEQ ID NO:99, a CDRH3 comprising the amino acid sequence of SEQ ID NO:100. In one aspect (A127) of any one of A118-A126, the first antibody or antibody fragment comprises a heavy chain variable sequence comprising the amino acid sequence of SEQ ID NO:33 and/or a light chain variable sequence comprising the amino acid sequence of SEQ ID NO:34. In one aspect (A128) of any one of A118-A127, the second antibody or antibody fragment comprises a heavy chain variable sequence comprising the amino acid sequence of SEQ ID NO:39 and/or a light chain variable sequence comprising the amino acid sequence of SEQ ID NO:40.

In one aspect (A129) of any one of A116-A128, the delivering reduces the expression of INF-γ, IL-6, CXCL10 and CCL2 in the subject. In one aspect (A130) of any one of A116-A129, the delivering is intravenous. In one aspect (A131) of any one of A116-A130, the subject is of age 60 or older, is immunocompromised, or suffers from a respiratory and/or cardiovascular disorder. In one aspect (A132) of any one of A116-A131, the delivering improves the subject's respiration as compared to an untreated control. In one aspect (A133) of any one of A116-A132, the delivering reduces viral load as compared to an untreated control.

In one aspect (A134) of any one of A116-A133, the delivering is prior to infection. In one aspect (A135) of any one of A116-A133, the delivering is after infection.

In one aspect (A136) provided herein, a vaccine formulation comprises one or more antibodies or antibody fragment of any one of A101-A115. In one aspect (A137) of A136, the vaccine further comprises a second antibody or antibody fragment, optionally wherein the second antibody or antibody fragment is an antibody or antibody fragment of any one of A101-A115.

In one aspect (A138) provided herein, a vaccine formulation comprises one or more expression vectors encoding a first antibody or antibody fragment according to any one of A101-A115. In one aspect (A139) of A138, the expression vector(s) is/are Sindbis virus or VEE vector(s). In one aspect (A140) of A138 or A139, the vaccine formulation is formulated for delivery by needle injection, jet injection, or electroporation. In one aspect (A141) of A140, the vaccine formulation further comprises one or more expression vectors encoding for a second antibody or antibody fragment, optionally wherein the second antibody or antibody fragment is an antibody or antibody fragment of any one of claims 1-15.

In one aspect (A142) provided herein, a method of detecting COVID-19 infection with SARS-CoV-2 in a subject comprises contacting a sample from the subject with the antibody or fragment of any one of A101-A115; and detecting SARS-CoV-2 in the sample by binding of the antibody or antibody fragment to a SARS-CoV-2 antigen in the sample. In one aspect (A143) of A142, the sample is a body fluid. In one aspect (A144) of A142 or A143, the sample is blood, sputum, tears, saliva, mucous or serum, semen, cervical or vaginal secretions, amniotic fluid, placental tissues, urine, exudate, transudate, tissue scrapings or feces. In one aspect (A145) of any one of A142-A144, the detection comprises ELISA, RIA, lateral flow assay or western blot.

In one aspect (A146) provided herein, a method of determining the antigenic integrity, correct conformation and/or correct sequence of a SARS-CoV-2 surface spike protein comprises: (a) contacting a sample comprising the antigen with the antibody or fragment of any one of A101-A115; and (b) determining antigenic integrity, correct conformation and/or correct sequence of the antigen by detectable binding of the antibody or antibody fragment to the antigen. In one aspect (A147) of A146, the sample comprises recombinantly produced antigen. In one aspect (A148) of A146, the sample comprises a vaccine formulation or vaccine production batch. In one aspect (A149) of any one of A146-A148, the detection comprises ELISA, RIA, western blot, a biosensor using surface plasmon resonance or biolayer interferometry, or flow cytometric staining. In one aspect (A150) of any one of A146-A149, the method further comprises performing steps (a) and (b) a second time to determine the antigenic stability of the antigen over time.

In one aspect (A151) provided herein is a hybridoma or engineered cell comprising a polynucleotide encoding the antibody or antibody fragment of any one of A101-A115.

In one aspect (A152) provided herein is an isolated human monoclonal antibody or antibody fragment, or hybridoma or engineered cell producing the same, wherein the antibody binds to a SARS-CoV-2 surface spike protein.

In one aspect (A153) provided herein, an isolated polynucleotide comprises a nucleic acid sequence encoding the heavy chain variable region of the antibody or antibody fragment of any one of A101-A115 and/or a nucleic acid sequence encoding the light chain variable region of the antibody or antibody fragment. In one aspect (A154) of A153, the polynucleotide comprises the sequence of any one of SEQ ID NOs:1-20.

In one aspect (A155) provided herein, a vector comprises the polynucleotide of A154.

In one aspect (A156) provided herein, a host cell comprises the polynucleotide of A153 or A154, the vector of A155, or a first vector comprising a nucleic acid molecule encoding the heavy chain variable region and a second vector comprising a nucleic acid molecule encoding the light chain variable region of the antibody or antibody fragment thereof of any one of A101-A115.

In one aspect (A157) provided herein, a method of making an antibody or antibody fragment comprises (a) culturing the cell of A156; and (b) isolating the antibody or antibody fragment thereof from the cultured cell.

In one aspect (A158) provided herein, a composition comprises a first antibody or antibody fragment that binds to a SARS-CoV-2 surface spike protein and a second antibody or antibody fragment that binds to a SAR-CoV-2 surface spike protein, optionally wherein the composition is a pharmaceutically acceptable composition.

In one aspect (A159) provided herein, a kit comprises a first antibody or antibody fragment that binds to a SARS-CoV-2 surface spike protein and a second antibody or antibody fragment that binds to a SAR-CoV-2 surface spike protein, optionally wherein the kit further comprises instructions for using the first antibody or antibody fragment and the second antibody or antibody fragment for treating a subject infected with SARS-CoV-2 or for reducing the likelihood of infection of a subject at risk of contracting SARS-CoV-2.

In one aspect (A160) of A158 or A159, the first antibody or antibody fragment and the second antibody or antibody fragment have a synergy score of 17.4. In one aspect (A161) of any one of A158-A160, the dose of the first antibody or antibody fragment and the second antibody or antibody fragment can be reduced by more than 3 times the dose of the first antibody or antibody fragment or the second antibody or antibody fragment alone to achieve the same potency in virus neutralization. In one aspect (A162) of any one of A158-A161, the first antibody or antibody fragment is able to bind to RBD in the "up" confirmation and is not able to bind to RBD in the "down" confirmation. In one aspect (A163) of any one of A158-A162, the second antibody or antibody fragment is able to bind RBD in both "up" and "down" conformations. In one aspect (A164) of any one of A158-A163, the first antibody or antibody fragment and the second antibody or antibody fragment do not compete for binding to RBD. In one aspect (A165) of any one of A158-A164, the first antibody or antibody fragment comprises a CDRH1 comprising the amino acid sequence of SEQ ID NO:59, a CDRH2 comprising the amino acid sequence of SEQ ID NO:60, a CDRH3 comprising the amino acid sequence of SEQ ID NO:61, a CDRL1 comprising the amino acid sequence of SEQ ID NO:89, a CDRH2 comprising the amino acid sequence of SEQ ID NO:90, a CDRH3 comprising the amino acid sequence of SEQ ID NO:91. In one aspect (A166) of any one of A158-A165, the second antibody or antibody fragment comprises a CDRH1 comprising the amino acid sequence of SEQ ID NO:68, a CDRH2 comprising the amino acid sequence of SEQ ID NO:69, a CDRH3 comprising the amino acid sequence of SEQ ID NO:70, a CDRL1 comprising the amino acid sequence of SEQ ID NO:98, a CDRH2 comprising the amino acid sequence of SEQ ID NO:99, a CDRH3 comprising the amino acid sequence of SEQ ID NO:100. In one aspect (A167) of any one of A158-A166, the first antibody or antibody fragment comprises a heavy chain variable sequence comprising the amino acid sequence of SEQ ID NO:33 and/or a light chain variable sequence comprising the amino acid sequence of SEQ ID NO:34. In one aspect (A168) of any one of a158-A167, the second antibody or antibody fragment comprises a heavy chain variable sequence comprising the amino acid sequence of SEQ ID NO:39 and/or a light chain variable sequence comprising the amino acid sequence of SEQ ID NO:40.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIGS. 2A-B. Dose-response matrix to assess synergistic neutralizing activity by the cocktail of mAb COV2-2196+ mAb COV2-2130 using BSL3 SARS-CoV-2 live virus. Average of triplicate values for technical replicates is shown. Data were visualized and synergy was assessed using SynergyFinder software.

(FIG. 4A) Mice were inoculated by the intranasal route with $10^5$ PFU of MA-SARS-CoV-2 and 12 hrs later given the indicated antibody treatments by intraperitoneal injection. Viral burden in the lungs was measured at 2 days after viral challenge using plaque assay. Measurements from individual mice and median titer is shown, and each group was compared to the isotype control using Kruskal-Wallis ANOVA with Dunn's post-test (* p<0.05). Data represent one experiment. (FIG. 4B) Ten to eleven-week-old BALB/c mice (one experiment of 3 to 9 mice per group) were treated with anti-Ifnar1 mAb and transduced with AdV-hACE2 via the intranasal route one day later. After four days, mice were inoculated via the intranasal route with $10^5$ FFU of authentic SARS-CoV-2 and 12 hrs later given the indicated mAb treatments by intraperitoneal injection. Viral burden in the lungs was measured at 2 dpi after viral challenge using plaque assay. Two controls for plaque neutralization assay performance included lung homogenates from individual isotype treated mice that were mixed 1:1 (volume:volume) with lung homogenates from individual uninfected or mAb COV2-2196+ COV2-2130 cocktail treated mice. Measurements from individual mice and median titer is shown, and each group was compared to the isotype control using Kruskal-Wallis ANOVA with Dunn's post-test (** p<0.01). Data represent one experiment. (FIG. 4C) Cytokine and chemokine gene expression was measured by qPCR analysis from the lungs harvested as in FIG. 4B. Measurements from individual mice and median values are shown. Groups were compared using the Mann-Whitney U test (* p<0.05; ** p<0.01).

(FIG. 8A) Cartoon representation of COV2-2196 in complex with RBD. COV2-2196 heavy chain is shown in cyan, light chain in magenta, and RBD in green. (FIG. 8B) Structure of COV2-2196-RBD complex is superimposed onto the structure of RBD-human ACE2 complex (PDB ID: 6M0J), using the RBD structure as the reference. The color scheme of COV2-2196-RBD complex is the same as that in FIG. 8A. The RBD in the RBD-ACE2 complex is colored in light blue, the human ACE2 peptidase domain in grey. (FIG. 8C) Structure of COV2-2196-RBD complex is superimposed onto the structure of spike with single RBD in the "up" conformation (PDB ID: 6XM4), using the RBD in "up" conformation as the reference. The color scheme of COV2-2196-RBD complex is the same as that in FIG. 8A. The three subunits of spike are colored in grey, yellow, or light blue respectively (the subunit with its RBD in "up" conformation is yellow). (FIG. 8D) Surface representation of RBD epitope recognized by COV2-2196. The epitope residues are colored in different shades of green and labeled in black. (FIG. 8E) Antibody-antigen interactions between COV2-2196 and RBD. RBD is shown in the same surface representation and orientation as that in FIG. 8D. COV2-2196 paratope residues are shown in stick representation. The heavy chain is colored in cyan, and light chain is colored in magenta.

FIGS. 9A-F. Crystal structure of S protein RBD in complex with both Fabs COV2-2196 and COV2-2130. (FIG. 9A) Cartoon representation of crystal structure of S protein RBD in complex with COV2-2196 and COV2-2130 Fabs. RBD is shown in green, COV2-2196 heavy chain in cyan, COV2-2196 light chain in magenta, COV2-2130 heavy chain in yellow, and COV2-2130 light chain in orange. CDRs of COV2-2130 are labeled. (FIG. 9B) Structure of COV2-2130-RBD complex is superimposed onto the structure of the RBD-ACE2 complex (PDB ID: 6M0J), using the RBD structure as the reference. The color scheme of the COV2-2130-RBD complex is the same to that of FIG. 9A. The RBD in the RBD-ACE2 complex is colored in light blue, the human ACE2 peptidase domain in grey. (FIG. 9C) Structure of COV2-2130-RBD complex is superimposed onto the structure of spike with all RBD in "down" conformation (PDB ID: 6ZOY), using the RBD in one protomer as the reference. The color scheme of COV2-2130-RBD complex is the same as that in FIG. 9A. The three protomers of spike are colored in grey, light blue, or purple respectively. (FIG. 9D) Structure of COV2-2196-2130-RBD complex is superimposed onto the structure of spike with one RBD in "up" conformation (PDB ID: 7CAK), using the RBD in "up" conformation as the reference. The color scheme of COV2-2130-RBD complex is the same as that in FIG. 9A. The three protomers of spike are colored in grey, light blue, or purple respectively. (FIG. 9E) Surface representation of RBD epitope recognized by COV2-2130. The epitope residues are indicated in different colors and labeled in black. (FIG. 9F) Interactions of COV2-2130 paratope residues with the epitope. RBD is shown in the same surface representation and orientation as those in FIG. 9E. The paratope residues are shown in stick representation. The heavy chain is colored in yellow, and the light chain in orange.

FIGS. 10A-B. (FIG. 10A) IMGT/DomainGapAlign results of COV2-2196 heavy and light chains. Key interacting residues and their corresponding residues in germline genes are shown in boxes. The SEQ ID NOs for the sequences in FIG. 10A are as follows:

|  | FR2-HCDR2 | HCDR3-FR4 | LCDR1-FR2 | LCDR3-FR4 |
| --- | --- | --- | --- | --- |
| IGHV1-58 | SEQ ID NO. 101 | SEQ ID NO. 102 |  |  |
| IGHD2-2 |  | SEQ ID NO. 103 |  |  |
| IGHD2-8 |  | SEQ ID NO. 104 |  |  |
| IGHD2-15 |  | SEQ ID NO. 105 |  |  |
| IGHJ3*02 |  | SEQ ID NO. 106 |  |  |
| IGKV3-20 |  |  | SEQ ID NO. 107 | SEQ ID NO. 108 |
| IGKJ1*01 |  |  |  | SEQ ID NO. 109 |
| COV2-2196 | SEQ ID NO. 110 | SEQ ID NO. 111 | SEQ ID NO. 112 | SEQ ID NO. 113 |
| COV2-2381 | SEQ ID NO. 114 | SEQ ID NO. 115 | SEQ ID NO. 116 | SEQ ID NO. 117 |
| COV2-2072 | SEQ ID NO. 118 | SEQ ID NO. 119 | SEQ ID NO. 120 | SEQ ID NO. 121 |
| McC5t2p1_G1 | SEQ ID NO. 122 | SEQ ID NO. 123 | SEQ ID NO. 124 | SEQ ID NO. 125 |
| HbnC3t1p2_C6 | SEQ ID NO. 126 | SEQ ID NO. 127 | SEQ ID NO. 128 | SEQ ID NO. 129 |
| HbnC3t1p1_C6 | SEQ ID NO. 130 | SEQ ID NO. 131 | SEQ ID NO. 132 | SEQ ID NO. 133 |
| S2E12 | SEQ ID NO. 134 | SEQ ID NO. 135 | SEQ ID NO. 136 | SEQ ID NO. 137 |
| COV107_1 | SEQ ID NO. 138 | SEQ ID NO. 139 | SEQ ID NO. 140 | SEQ ID NO. 141 |
| COV107_2 | SEQ ID NO. 142 | SEQ ID NO. 143 | SEQ ID NO. 144 | SEQ ID NO. 145 |
| COV72 | SEQ ID NO. 146 | SEQ ID NO. 147 | SEQ ID NO. 148 | SEQ ID NO. 149 |
| COV21_1 | SEQ ID NO. 150 | SEQ ID NO. 151 | SEQ ID NO. 152 | SEQ ID NO. 153 |
| COV21_2 | SEQ ID NO. 154 | SEQ ID NO. 155 | SEQ ID NO. 156 | SEQ ID NO. 157 |
| COV57_1 | SEQ ID NO. 158 | SEQ ID NO. 159 | SEQ ID NO. 160 | SEQ ID NO. 161 |
| COV57_2 | SEQ ID NO. 162 | SEQ ID NO. 163 | SEQ ID NO. 164 | SEQ ID NO. 165 |

(FIG. 10B) Binding curves of point mutants of COV2-2196. cDNAs encoding point mutants for the heavy chain, boxed above, were designed, synthesized as DNA to make recombinant IgG proteins, and tested for binding activity to spike protein. Mutants of D108 residue are in the top left graph, revertant mutation of inferred somatic mutations to germline sequence are in the top right graph, P99 mutants are in the bottom left graph, and a mutant removing the disulfide bond in HCDR3 is in the bottom right graph.

Figure 11A:
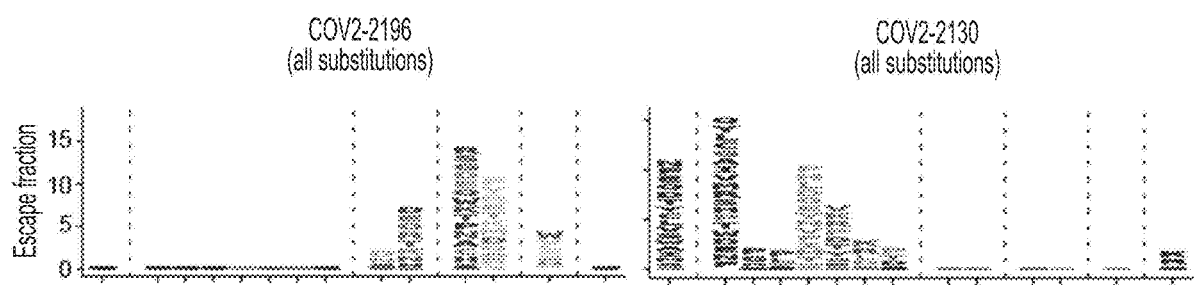

FIGS. 11A-H. Identification of critical residues for COV2-2196 and COV2-2130 through deep mutational scanning coupled with resistant variant selection. (FIG. 11A) Logo plots of mutation escape fractions of all at RBD sites with strong escape for COV2-2196 (left) or COV2-2130 (right). Taller letters indicate greater antibody binding escape. Mutations are colored based on the degree to which they reduce RBD binding to human ACE2. Data shown are the average of two independent escape selection experiments using two independent yeast libraries; correlations are shown in FIGS. 18B-C. Interactive, zoomable versions of these logo plots are at jbloomlab.github.io/SARS-CoV-2-RBD_MAP_AZ_Abs/. The inventors determined escape fractions, as described in methods, which represent the estimated fraction of cells expressing that specific variant that fall in the antibody escape bin, such that a value of 0 means the variant is always bound by antibody and a value of 1 means that it always escapes antibody binding. (FIG. 11B) Logo plots of mutation escape fractions for COV2-2196 and COV2-2130 that are accessible by single nucleotide substitutions from the Wuhan-Hu-1 reference strain used in escape selections (FIGS. 11E-F). The effect of each substitution on ACE2 binding is represented as in FIG. 11A. (FIG. 11C) Left panel: mapping deep mutational scanning escape mutations for COV2-2196 onto the RBD surface in the RBD-COV2-2196 structure. Mutations that abrogate COV2-2196 binding are displayed on the RBD structure using a heatmap, where blue represents the RBD site with the greatest cumulative antibody escape and white represents no detected escape. Grey denotes residues where deleterious effects on RBD expression prevented assessment of the effect of the mutation on antibody binding. Right panel: the blow-up of the left panel showing interacting residues around the strongest escape sites of RBD. COV2-2196 heavy chain is colored cyan and the light chain magenta. Two replicates were performed with independent libraries, as described in FIG. 11A. (FIG. 11D) Right panel: mapping deep mutational scanning escape mutations for COV2-2130 onto the RBD surface in the RBD-COV2-2130 structure. Mutations that abrogate COV2-2130 binding are displayed on the RBD structure using a heatmap as in FIG. 11C. Left panel: the blow-up of the left panel showing interacting residues around the strongest escape sites of RBD. COV2-2130 heavy chain is colored yellow and the light chain salmon. (FIG. 11E) Table showing the results of VSV-SARS-CoV-2 escape selection experiments with COV2-2196, COV2-2130, and their combination. The number of escape mutants selected and the total number of escape selection replicates performed is noted, as well as the residues identified by sequencing escape mutant viruses. (FIG. 11F) Table showing the results of passage of SARS-CoV-2 in the presence of sub-neutralizing concentrations of AZD8895 (based on COV2-2196), AZD1061 (based on COV2-2130), and AZD7442 (AZD8895+AZD1061). Resistance-associated viral mutations identified by sequencing neutralization-resistant plaques are denoted. (FIG. 11G) Scatter plot showing DMS data from FIG. 11A, with mutation escape fraction on the x-axis and effect on ACE2 binding on the y-axis. Crosses denote mutations accessible only by multi-nucleotide substitutions, while circles indicate mutations accessible by single-nucleotide substitution. Amino acid substitutions selected by COV2-2130 in VSV-SARS-CoV-2 (K444R, K444E) or authentic SARS-CoV-2 (R346I) are denoted. (FIG. 11H) Antibody neutralization as measured by FRNT against reference strains and SARS-CoV-2 variants of concern. Neutralization assays were performed in duplicate and repeated twice, with results shown from one experimental replicate. Error bars denote the range for each point. Mutations compared to the WA-1 reference strain are denoted. B.1.1.7-OXF contains 69-70 and 144-145 deletion and the following substitutions: N501Y, A570D, D614G, P681H, and T716I.

Figure 12:
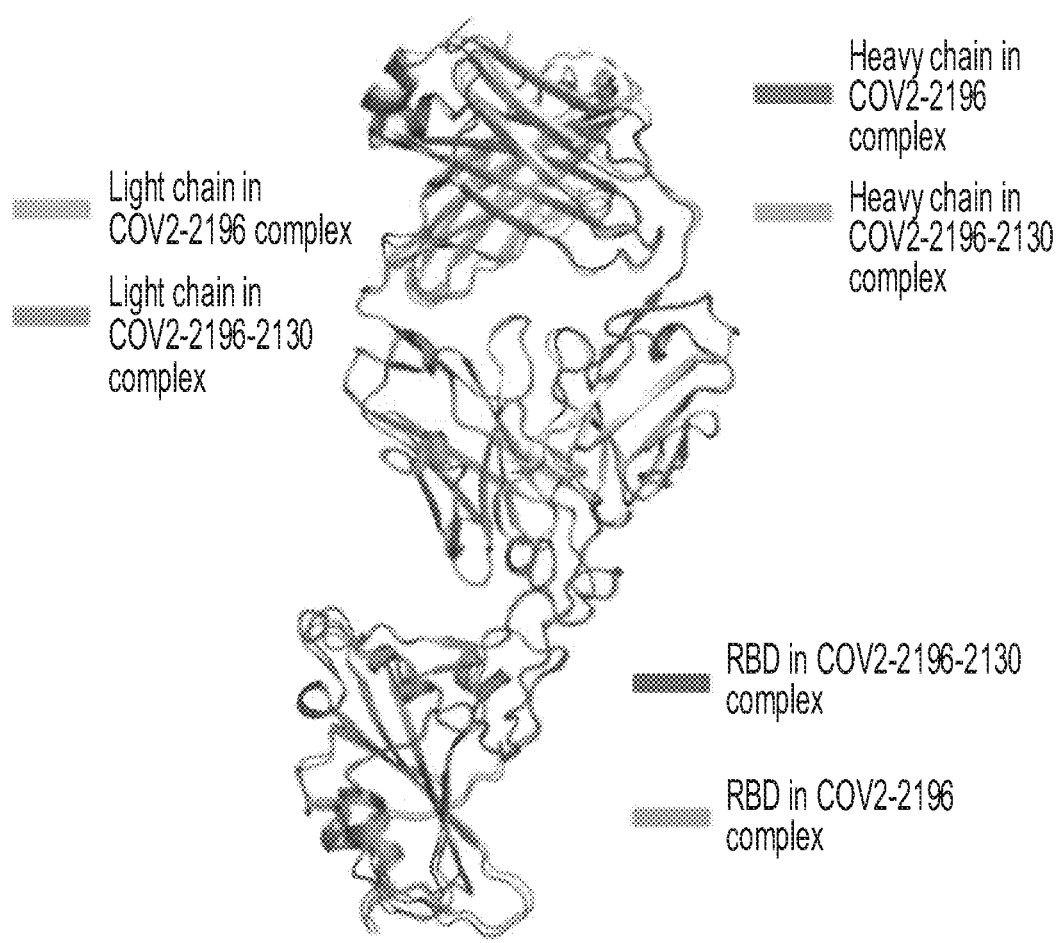

FIG. 12. Overlay of substructure of RBD-COV2-2196 in RBD-COV2-2196-2130 complex and RBD-COV2-2196 crystal structure.

FIGS. 13A-F. Similar aromatic stacking and hydrophobic interaction patterns at the RBD site F486 shared between RBD-COV2-2196 and spike-S2E12 complexes. (FIGS. 13A and B) Same hydrogen bonding pattern surrounding residue F486 in the structures of the two complexes. (FIG. 13C) Detailed interactions between COV2-2196 and RBD. COV2-2196 heavy chain is colored in cyan, the light chain is colored in magenta, and RBD is colored in green. Important interacting residues are shown in stick representation. Water molecules involved in Ab-Ag interaction are represented as pink spheres. Direct hydrogen bonds are shown as orange dashed lines, and water-mediated hydrogen bonds as yellow dashed lines. (FIG. 13D) Superimposition of S2E12/RBD cryo-EM structure onto the COV2-2196/RBD crystal structure, with the variable domains of antibodies as references. COV2-2196 heavy chain is in cyan, and its light chain in magenta; S2E12 heavy chain is in pale cyan, and its light chain in light pink. The two corresponding RBD structures are colored in green or yellow, respectively. (FIG. 13E) Detailed interactions between COV2-2130 heavy chain and RBD. Paratope residues are shown in stick representation and colored in yellow, epitope residues in green sticks. Hydrogen-bonds or strong polar interactions are represented as dashed magenta lines. (FIG. 13F) Detailed interactions between COV2-2130 light chain and RBD. Paratope residues are shown in stick representation and colored in orange, epitope residues in green sticks. Hydrogen-bonds are represented as dashed magenta lines.

Figure 14A:
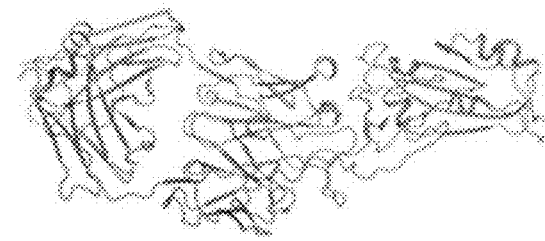
Figure 14B:
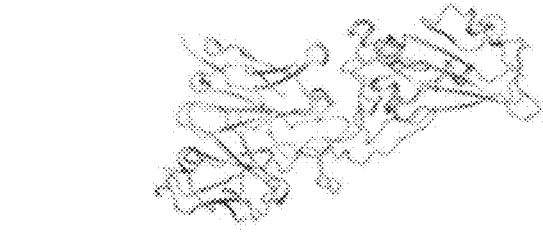
Figure 14C:
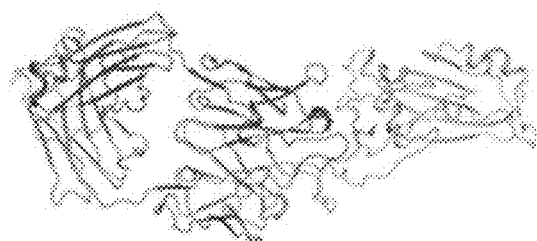
Figure 14D:

FIGS. 14A-E. A common clonotype of anti-RBD antibodies with the same binding mechanism. (FIG. 14A) COV2-2196/RBD crystal structure. (FIG. 14B) S2E12/RBD cryo-EM structure. (FIG. 14C) COV2-2381/RBD homology model. COV2-2072 encodes an N-linked glycosylation sequon in the HCDR3, indicated by the gray spheres. (FIG. 14D) COV2-2072/RBD homology model. (FIG. 14E) Overlay of the COV2-2196/RBD crystal structure (FIG. 14A) and S2E12/RBD cryo-EM structure (FIG. 14B).

Figure 15A:
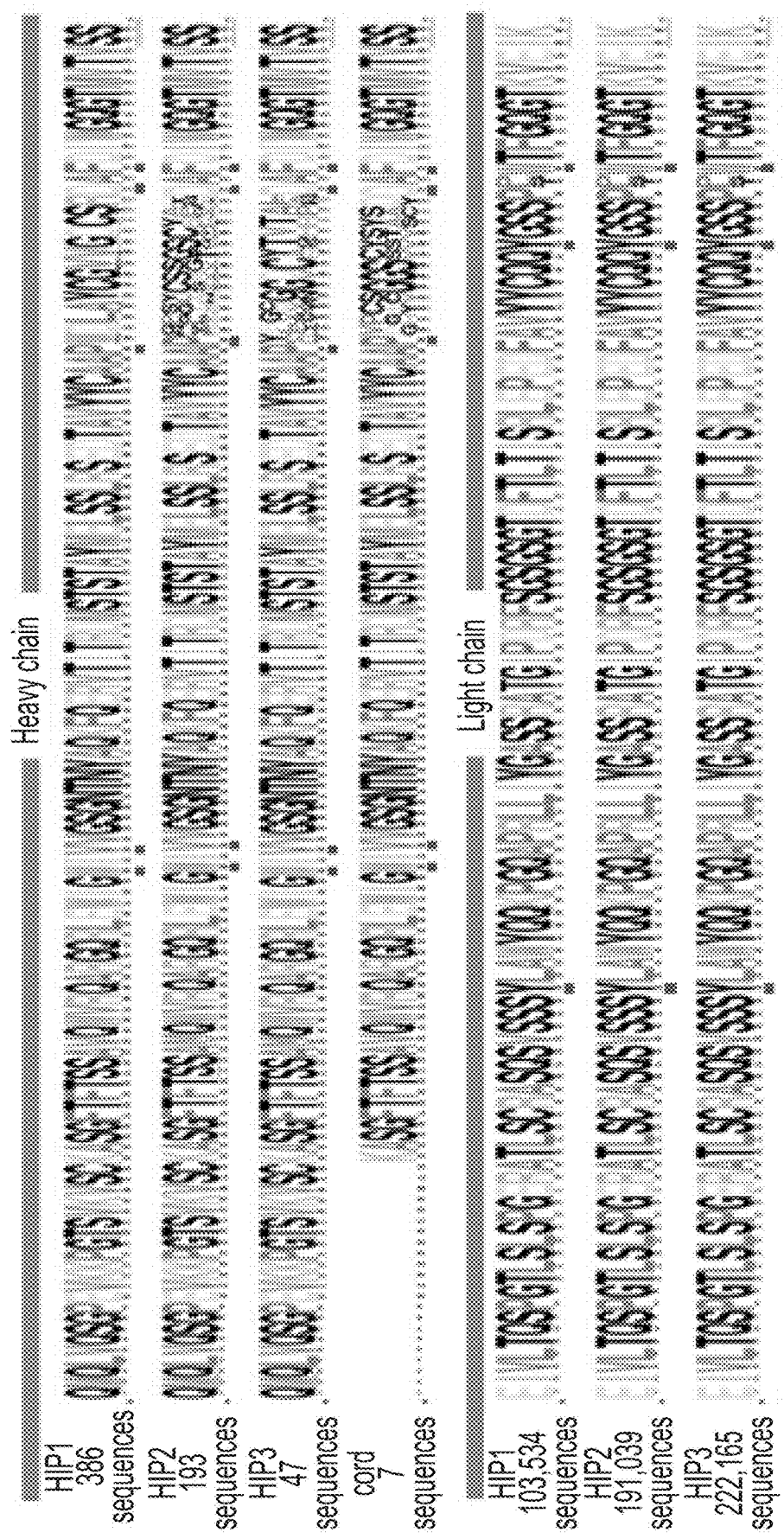

FIGS. 15A-B. Identification of putative public clonotype members genetically similar to COV2-2196 in the antibody variable gene repertoires of virus-nave individuals. Antibody variable gene sequences from healthy individuals with the same sequence features as COV2-2196 heavy chain (FIG. 15A) and light chain (FIGS. 15A and 15B) are aligned. Sequences from three different donors as well as cord blood included sequences with the features of the public clonotype. The sequence features and contact residues used in COV2-2196 are highlighted with boxes below each multiple sequence alignment. The SEQ ID NOs for the heavy chain sequences in FIG. 15A are as follows: HIP1: SEQ ID NO. 166, HIP2: SEQ ID NO. 167, HIP3: SEQ ID NO. 168, and CORD: SEQ ID NO. 169. The SEQ ID NOs for the light chain sequences in FIG. 15A are follows: HIP1: SEQ ID NO. 170, HIP2: SEQ ID NO. 171, and HIP3: SEQ ID NO. 172. The SEQ ID NOs for the HIP1 light chain sequences in FIG. 15B are as follows: SEQ ID NO. 173, SEQ ID NO. 174, SEQ ID NO. 175, SEQ ID NO. 176, and SEQ ID NO. 177 (from top to bottom). The SEQ ID NOs for the HIP2 light chain sequences in FIG. 15B are as follows: SEQ ID NO. 178, SEQ ID NO. 179, SEQ ID NO. 180, SEQ ID NO. 181, and SEQ ID NO. 182 (form top to bottom). The SEQ ID NOs for the HIP3 light chain sequences in FIG. 15B are as follows: SEQ ID NO. 183, SEQ ID NO. 184, SEQ ID NO. 185, SEQ ID NO. 186, and SEQ ID NO. 187 (from top to bottom).

FIGS. 16A-D. (FIG. 16A) Detailed COV2-2130 HCDR3 loop structure. Short-range hydrogen bonds, stabilizing the loop conformation, are shown as dashed lines (dashed lines are colored magenta). (FIG. 16B) Residues of COV2-2130 light chain form aromatic stacking interactions and hydrogen bonds with HCDR3 to further stabilize the HCDR3 loop. (FIG. 16C) Long LCDR1, HCDR2, and HCDR3 form complementary binding surface to the RBD epitope. RBD is shown as surface representation in grey. COV2-2130 heavy chain is colored in yellow with HCDR3 in orange, and the light chain in salmon with LCDR1 in magenta. (FIG. 16D) 180° rotation view of FIG. 16C.

Figure 17:
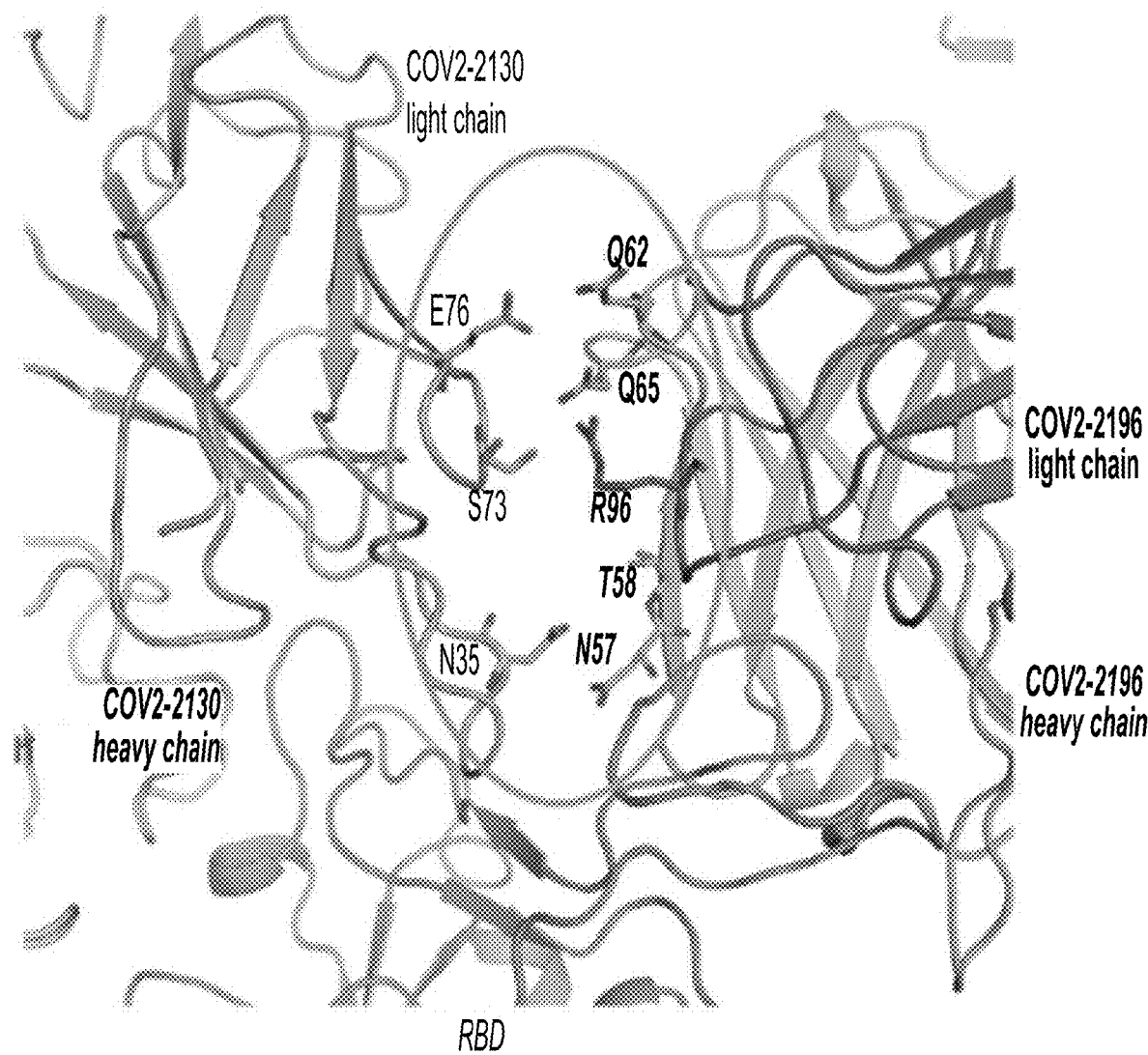

FIG. 17. Interface between COV2-2196 and COV2-2130 in the crystal structure of RBD in complex with COV2-2196 and COV2-2130. COV2-2196 heavy or light chain are shown as cartoon representation in cyan or magenta, respectively, and COV2-2130 heavy or light chain in yellow or salmon, respectively. The RBD is colored in green. Interface residues are shown in stick representation.

Figure 18A:
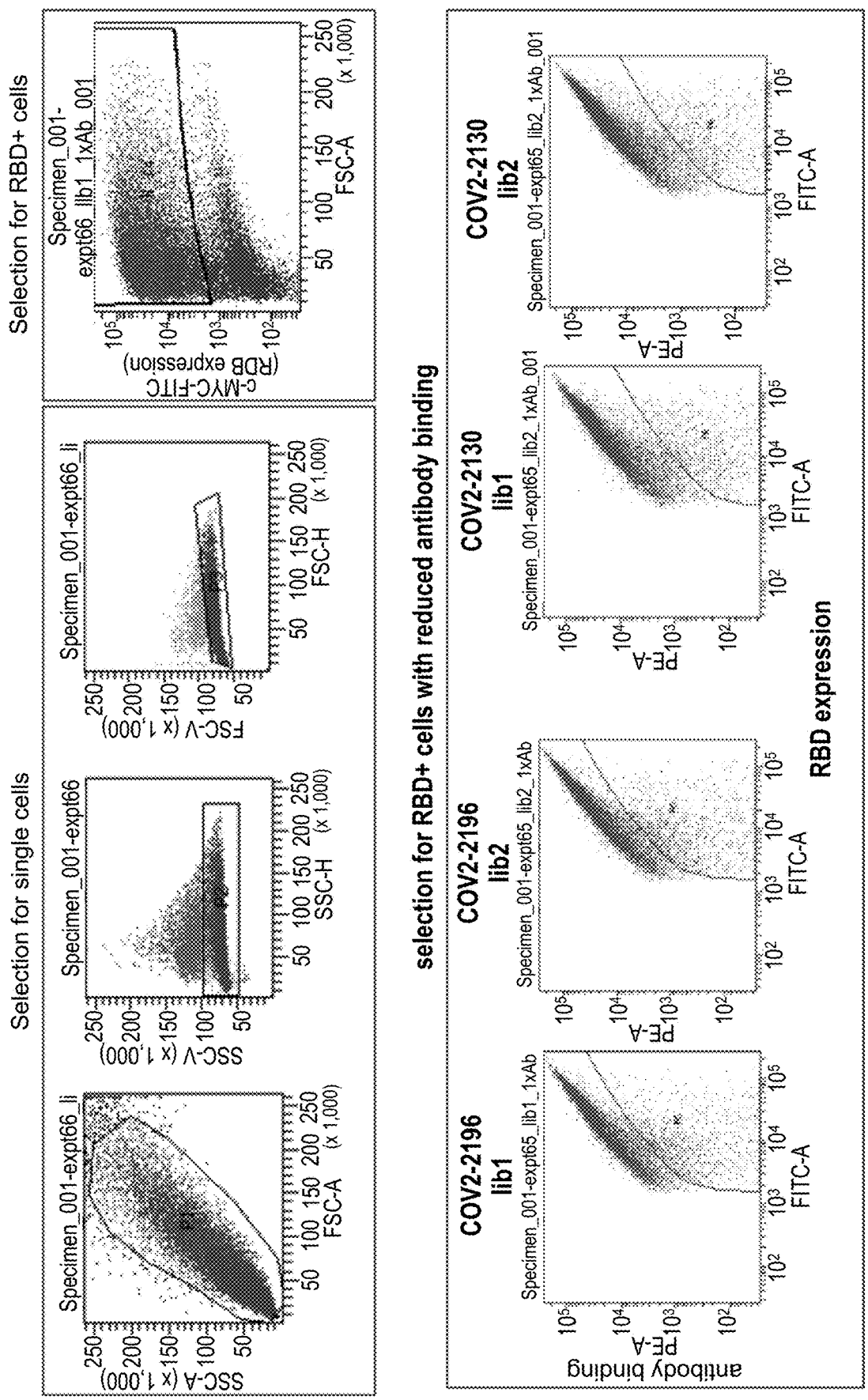
Figure 18B:
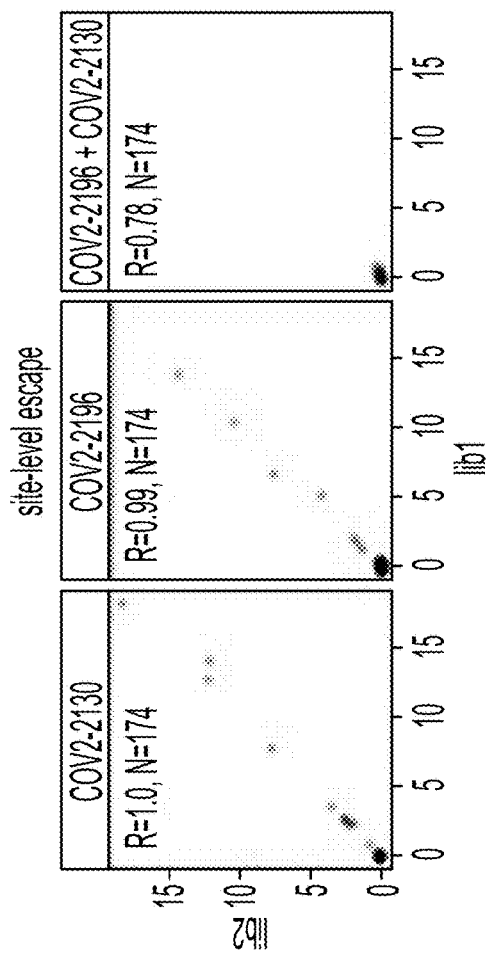
Figure 18C:
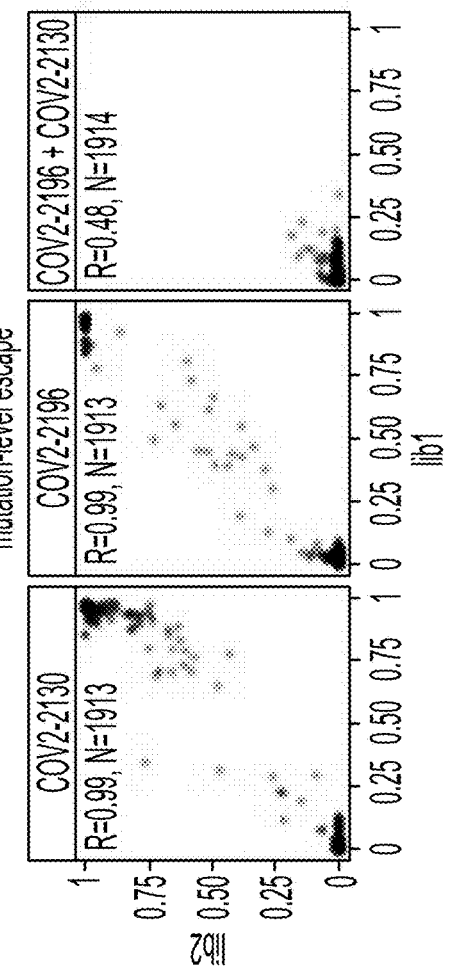
Figure 18I:
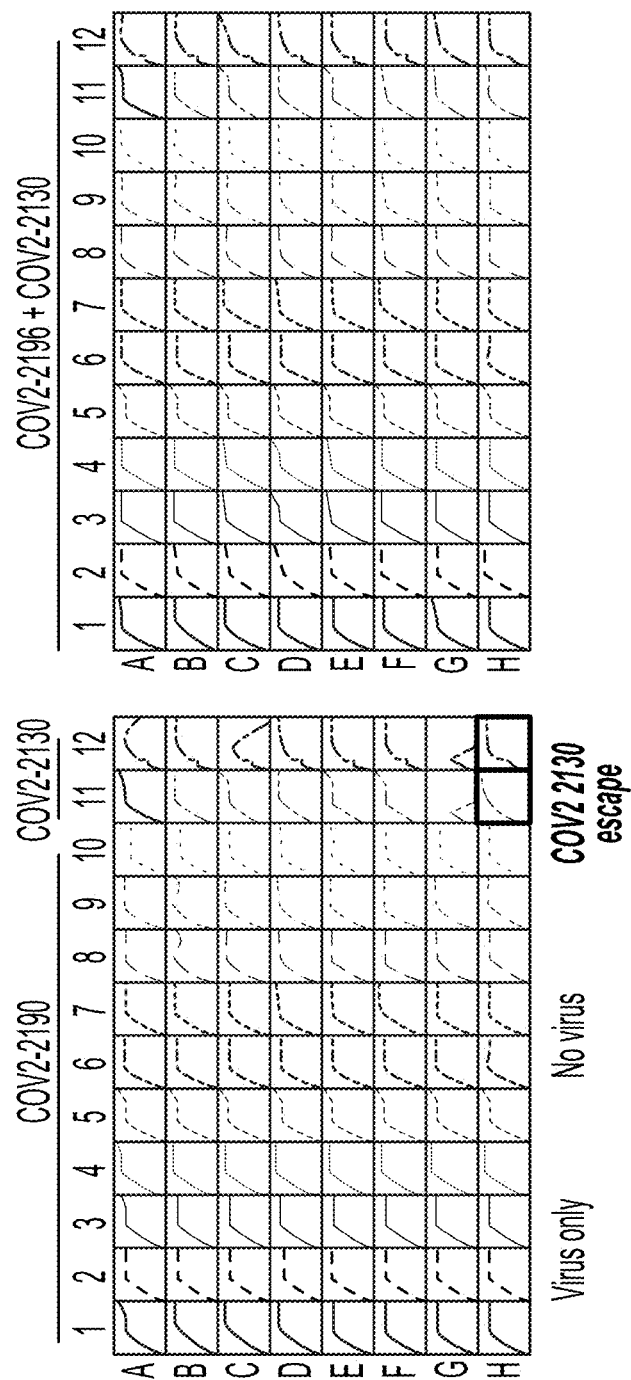

FIGS. 18A-I. Identification by deep mutational scanning of mutations affecting antibody binding and method of selection of antibody resistant mutants with VSV-SARS-CoV-2 virus. (FIG. 18A) Top: Flow cytometry plots showing representative gating strategy for selection of single yeast cells using forward- and side-scatter (first three panels) and selection of yeast cells expressing RBD (right panel). Each plot is derived from the preceding gate. Bottom: Flow cytometry plots showing gating for RBD$^+$, antibody$^-$yeast cells (i.e., cells that express RBD but where a mutation prevents antibody binding). Selection experiments are shown for COV2-2196 or COV2-2130, with two independent libraries shown for each. (FIG. 18B) Correlation of observed sites of escape from antibody binding between yeast library selection experiments using COV2-2196, COV2-2130, or a 1:1 mixture of COV2-2196 and COV2-2130. The x-axes show cumulative escape fraction for each site for library 1, and the y-axes show cumulative escape fraction for each site for library 2. Correlation coefficient and n are denoted for each graph. (FIG. 18C) Correlation of observed mutations that escape antibody binding between yeast library selection experiments using COV2-2196, COV2-2130, or a 1:1 mixture of COV2-2196 and COV2-2130. The x-axes show each amino acid mutation's escape fraction for library 1, and the y-axes show each amino acid mutation's escape fraction for library 2. Correlation coefficient and n are denoted for each graph. (FIGS. 18D-F) DMS results for COV2-2196 (FIG. 18D), COV2-2130 (FIG. 18E), or a 1:1 mixture of COV2-2196 and COV2 2130 (FIG. 18F). Left panels: sites of escape across the entire RBD are indicated by peaks that correspond to the logo plots in the middle and right panel. Middle panel: as in FIG. 11A, logo plot of cumulative escape mutation fractions of all RBD sites with strong escape mutations for COV2-2196, or COV2-2130, or COV2-2196+COV2-2130. Mutations are colored based on the degree to which they abrogate RBD binding to human ACE2. Right panel: again, logo plots show cumulative escape fractions, but colored based on the degree to which mutations effect RBD expression in the yeast display system. Interactive, zoomable versions of these logo plots are at jbloomlab.github.io/SARS-CoV-2-RBD_MAP_AZ_Abs/. (FIG. 18G) Representative RTCA sensograms showing virus that escaped antibody neutralization. Cytopathic effect (CPE) was monitored kinetically in Vero E6 cells inoculated with virus in the presence of a saturating concentration (5 µg/mL) of antibody COV2-2130. Representative instances of escape (magenta) or lack of detectable escape (blue) are shown. Uninfected cells (green) or cells inoculated with virus without antibody (red) serve as controls. Magenta and blue curves represent a single representative well; the red and green controls are the mean of technical duplicates. (FIG. 18H) Representative RTCA sensograms validating that a variant virus selected by COV2-2130 in FIG. 18G indeed escaped COV2-2130 (magenta) but was neutralized by COV2-2196 (light blue). (FIG. 18I) Example sensograms from individual wells of 96-well E-plate analysis for escape selection experiments with COV2-2196, COV2-2130, or a 1:1 mix of COV2-2196 and COV2-2130. Instances of escape from COV2-2130 are noted, while escape was not detected in the presence of COV2-2196 or COV2-2196+COV2-2130. Positive and negative controls are denoted on the first plate.

Figure 19:
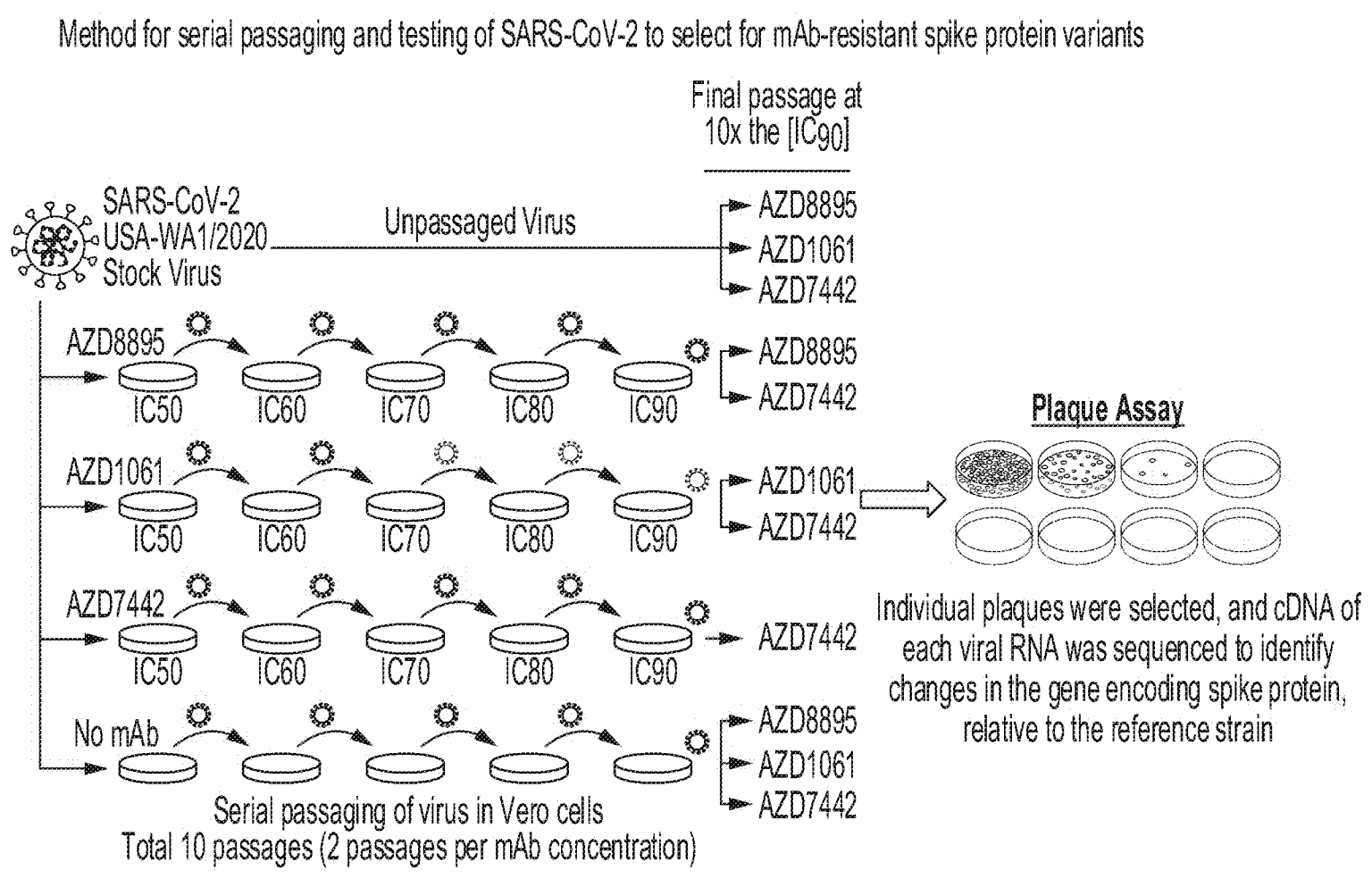

FIG. 19. Method of selection of antibody resistant mutants with authentic SARS-CoV-2 virus.

Figure 20:
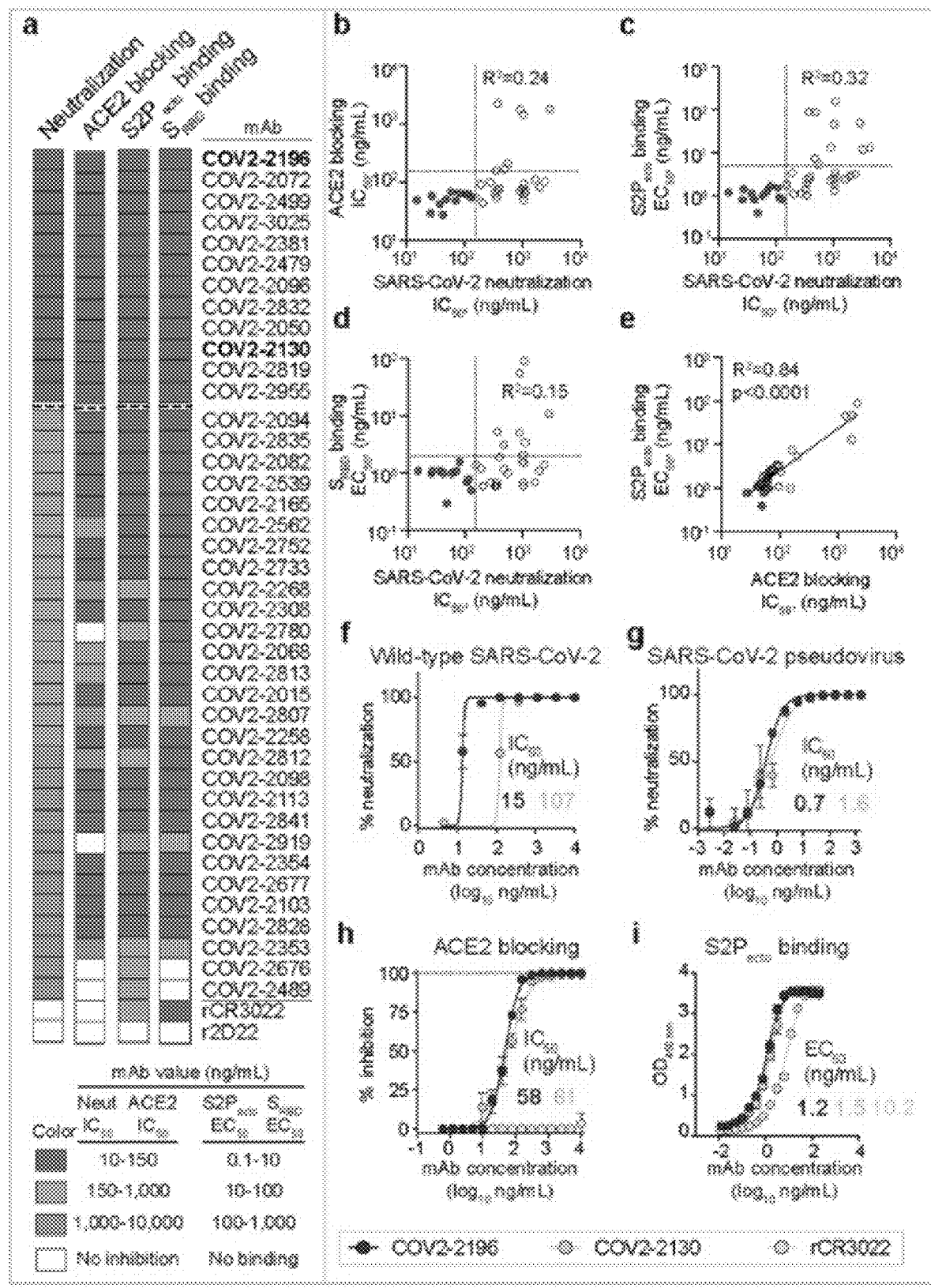

FIG. 20(A-I). Functional characteristics of neutralizing SARS-CoV-2 mAbs. (FIG. 20A) Heatmap of mAb neutralization activity, hACE2 blocking activity, and binding to either trimeric S2Pecto protein or monomeric SRBD. MAbs are ordered by neutralization potency (highest at the top, lowest at the bottom). Dashed lines indicate the 13 antibodies with a neutralization IC50 value lower than 150 ng/mL for wt virus. IC50 values are visualized for viral neutralization and hACE2 blocking, while EC50 values are visualized for binding. A recombinant form of the cross-reactive SARS-CoV SRBD mAb CR3022 is shown as a positive control, while the anti-dengue mAb 2D22 is shown as a negative control. Data are representative of at least 2 independent experiments, each performed in technical duplicate. No inhibition indicates an IC50 value of >10,000 ng/mL, while no binding indicates an EC50 value of >10,000 ng/mL. (FIGS. 20B-E) Correlation of hACE2 blocking, S2Pecto trimer binding, or SRBD binding of mAbs with their neutralization activity. R2 values are shown for linear regression analysis of log-transformed values. Dark circles (shown in purple) indicate mAbs with a neutralization IC50 value lower than 150 ng/mL. (FIG. 20E) Correlation of hACE2 blocking and S2Pecto trimer binding. R2 values are shown for linear regression analysis of log-transformed values. (FIG. 20F) Neutralization curves for COV2-2196 and COV2-2130 in a neutralization assay against authentic SARS-CoV-2 virus. Calculated IC50 values are denoted on the graph. Error bars denote the standard deviation of each point. Data are representative of at least 2 independent experiments, each performed in technical duplicate. (FIG. 20G) Neutralization curves for COV2-2196 and COV2-2130 in a pseudovirus neutralization assay. Error bars denote the standard deviation of each point. Values shown are technical duplicates from a single experiment. Calculated IC50 values from a minimum of 6 experiments are denoted on the graph. (FIG. 20H) hACE2 blocking curves for COV2-2196, COV2-2130, and the non-blocking SARS-CoV mAb rCR3022 in the hACE2 blocking ELISA. Calculated IC50 values are denoted on the graph. Error bars denote the standard deviation of each point. Values shown are technical triplicates from a representative experiment repeated twice. (FIG. 20I) ELISA binding of COV2-2196, COV2-2130, and rCR3022 to trimeric S2Pecto. Calculated EC50 values are denoted on the graph. Error bars denote the standard deviation of each point. Values shown are technical triplicates from a representative experiment repeated twice.

Figure 21:
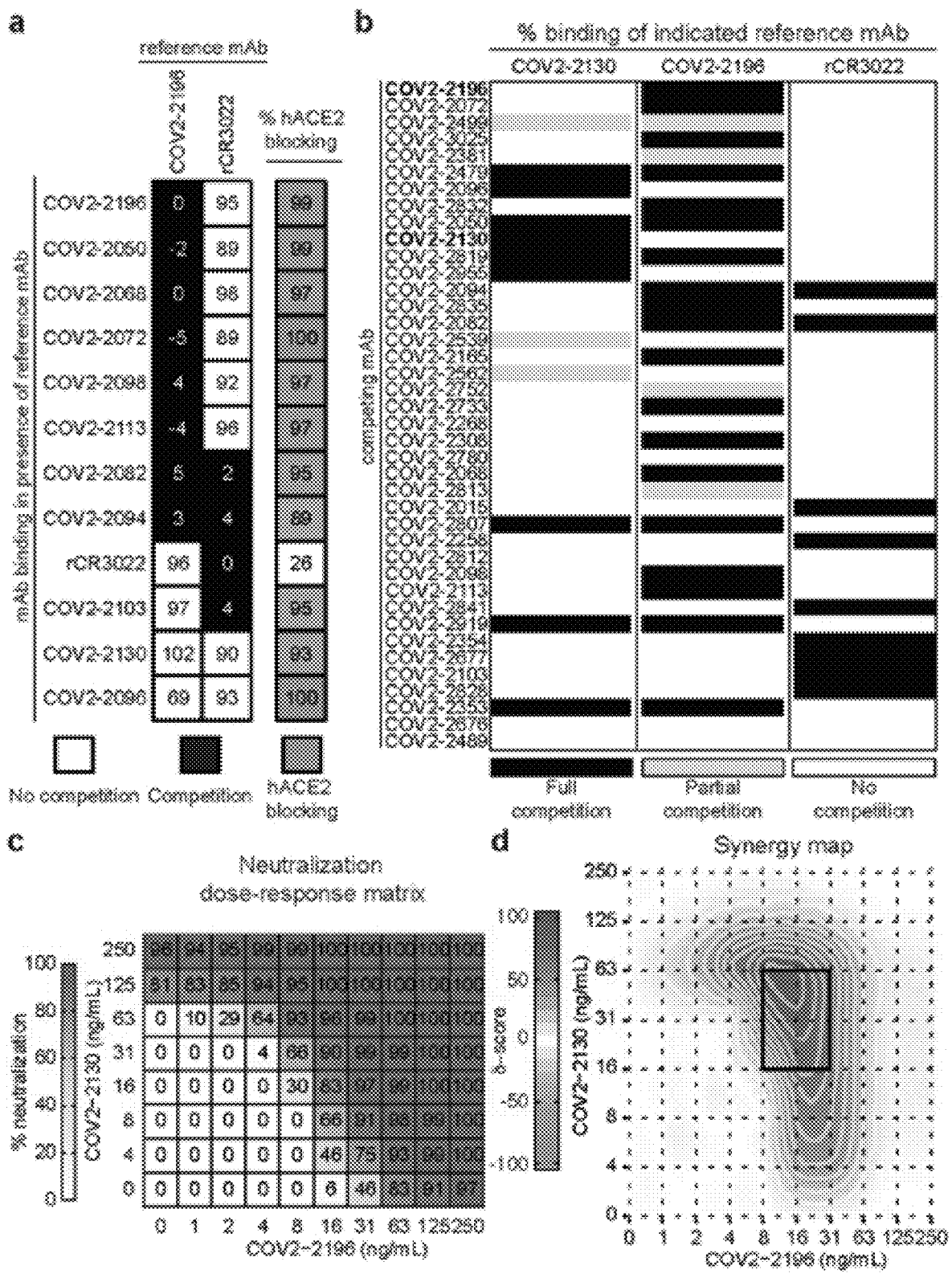

FIG. 21 (A-D). Epitope mapping of mAbs by competition-binding analysis and synergistic neutralization by a pair of mAbs. (FIG. 21A) Left: biolayer interferometry-based competition binding assay measuring the ability of mAbs to prevent binding of reference mAbs COV2-2196 and rCR3022 to RBD fused to mouse Fc (RBD-mFc) loaded onto anti-mouse Fc biosensors. Values in squares are % of binding of the reference mAb in the presence of the competing mAb relative to a mock-competition control. Black squares denote full competition (<33% of binding relative to no-competition control), while white squares denote no competition (>67% of binding relative to no-competition control). Right: biolayer interferometry-based competition binding assay measuring the ability of mAbs to prevent binding of hACE2. Values denote % binding of hACE2, normalized to hACE2 binding in the absence of competition. Shading denotes competition of mAb with hACE2. (FIG. 21B) Competition of neutralizing mAb panel with reference mAbs COV2-2130, COV2-2196, or rCR3022. Reference mAbs were biotinylated and binding of reference mAbs to trimeric S2Pecto was measured in the presence of saturating amounts of each mAb in a competition ELISA. ELISA signal for each reference mAb was normalized to the signal in the presence of the non-binding anti-dengue mAb 2D22. Black denotes full competition (<25% binding of reference mAb), grey denotes partial competition (25-60% binding of reference mAb), and white denotes no competition (>60% binding of reference mAb). (FIG. 21C) Synergistic neutralization of wild-type SARS-CoV-2 by COV2-2196 and COV2-2130. Top: neutralization matrix with serial dilutions of each mAb. Experiment was performed in technical triplicate. Shown is a representative experiment of how many that was performed in technical triplicate. % neutralization for each combination of mAbs is shown in each square. A white-to-black heatmap denotes 0% neutralization to 100% neutralization, respectively. (Heatmap shown in white-to-red) (FIG. 21D) Synergy matrix calculated based on the SARS-CoV-2 neutralization in the FIG. 21C. Darker color (shown in red) denotes areas where synergistic neutralization was observed, and a black box denotes the area of maximal synergy between the two mAbs.

Figure 22:
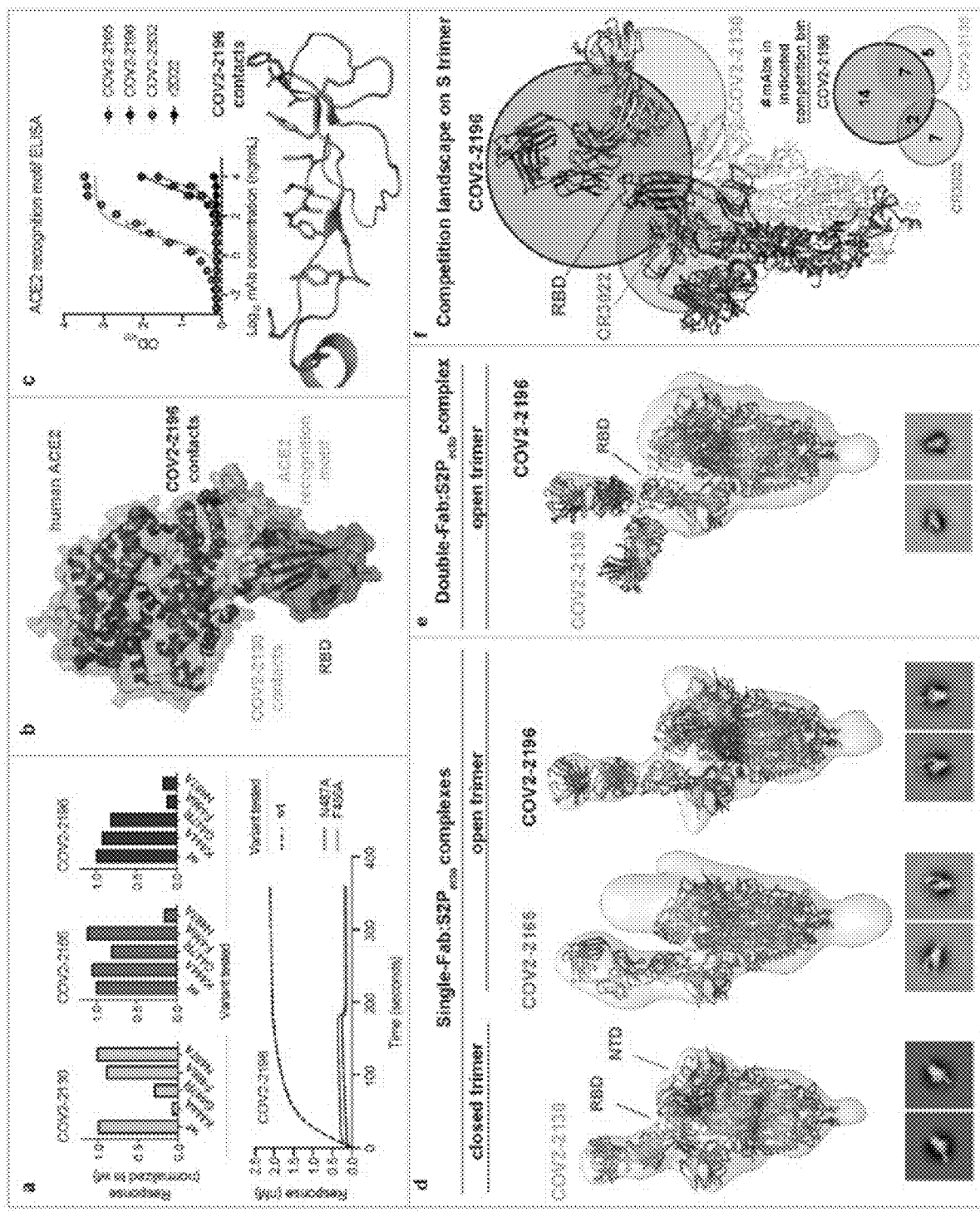

FIG. 22 (A-F). Epitope identification and structural characterization of mAbs. (FIG. 22A) Identification of critical contact residues by alanine and arginine mutagenesis. Top: binding of COV2-2130 (gold), COV2-2165 (maroon) or COV2-2196 (dark purple) to wild-type (wt) or mutant SRBD constructs measured by biolayer interferometry. Shown on y-axis is the response normalized to the signal observed for binding to wt SRBD. Bottom: representative binding curves for COV2-2196 to wt or SRBD constructs with critical contact residues mutated. (FIG. 22B) Crystal structure of SARS-CoV-2 (blue) and hACE2 (green) (PDB (6M0J). The hACE2 recognition motif is colored orange. Critical contact residues for COV2-2130 are shown as gold spheres, while critical contact residues for COV2-2196 are shown as purple spheres. (FIG. 22C) ELISA binding of mAbs to the 60-amino-acid hACE2 recognition motif r2D22, an anti-dengue mAb, is shown as a negative control. Bottom: structure of hACE2 recognition motif in orange with COV2-2196 critical contact residues shown in purple. (FIG. 22D) Single-Fab:S2Pecto trimer complexes visualized by negative-stain electron microscopy for COV2-2130 (gold), COV2-2165 (maroon), or COV2-2196 (dark purple). The RBD is shown in blue and the S N-terminal domain (NTD) is shown in red. Electron density is shown in grey. Trimer state (open or closed) is denoted for each complex. Representative 2D class averages for each complex are shown at the bottom (box size 128 pixel). (FIG. 22E) COV2-2130 and COV2-2196 Fabs in complex with S2Pecto trimer. Simultaneous binding of COV2-2130 (gold) and COV2-2196 (purple) Fabs to S2Pecto trimer. Electron density is shown in grey. Trimer state (open or closed) is denoted. Representative 2D class averages for the complexes are shown at the bottom (box size 128 pixels). All images were made with Chimera. (FIG. 22F) Competition-binding analysis visualized on S2Pecto trimer. The CR3022 crystal structure was docked into the double-Fab:S2Pecto trimer structure. CR3022 is shown in cyan. Bottom: a quantitative Venn diagram notes the number of mAbs in each competition group and the overlap between groups.

Figure 23:
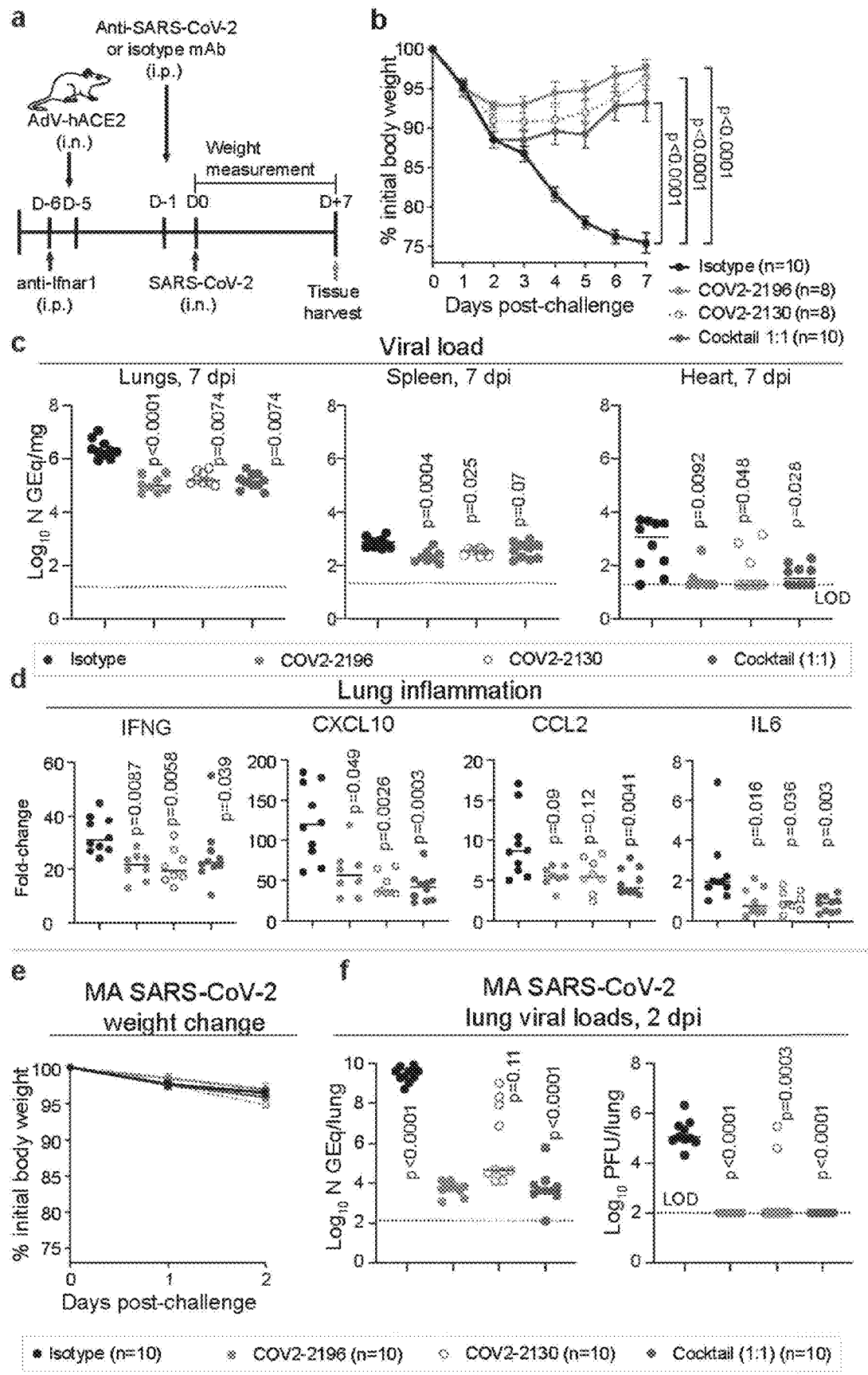

FIG. 23(A-F). Protective efficacy of neutralizing human mAbs against SARS-CoV-2 infection. (FIG. 23A) SARS-CoV-2 challenge model. Ten to eleven-week-old BALB/c mice (two experiments of 4-5 mice per group) were treated with anti-Ifnar1 mAb and transduced with AdV-hACE2 via the i.n. route one day later. After four days, mice were treated via the i.p. route with 200 µg of mAbs CoV2-2196, -2130, or combination (1:1 ratio) or isotype control mAb. One day later, SARS-CoV-2 was inoculated via the i.n. route. Tissues were harvested at 7 dpi for analysis (FIGS. 23C and 23D). (FIG. 23B) Body weight change of mice in panel a. (two-way ordinary ANOVA with Tukey's post-test: **** P<0.0001). (FIG. 2C) Viral burden in the lung, spleen and heart was measured by RT-qPCR: Kruskal-Wallis ANOVA with Dunn's post-test (*, P<0.05,  P<0.01, * P<0.001, **** P<0.0001). The dashed line indicates the assay limit of detection. (FIG. 23D) Cytokine and chemokine gene expression was measured by qPCR analysis. Kruskal-Wallis ANOVA with Dunn's post-test (*, P<0.05,  P<0.01, * P<0.001). (FIG. 23E) MA-SARS-CoV-2 challenge model. Twelve-week-old BALB/c mice (n=10) were inoculated with 105 PFU of MA-SARS-CoV-2 via the i.n. route. Body weight change of mice is shown. (FIG. 23F) Viral burden in the lung was measured at 2 dpi by RT-qPCR (left) or plaque assay (right) from (FIG. 23E): Kruskal-Wallis ANOVA with Dunn's post-test (* P<0.001, ** P<0.0001).

Figure 24:
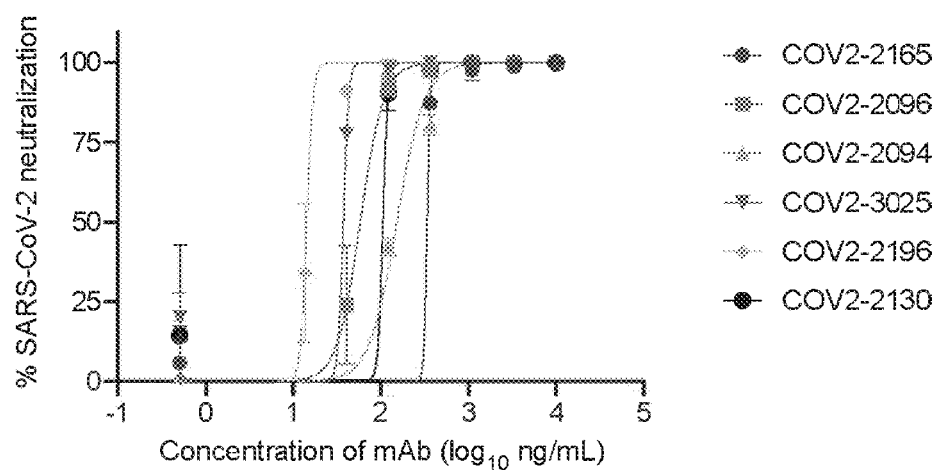

FIG. 24. SARS-CoV-2 neutralization curves for mAb panel. Neutralization of authentic SARS-CoV-2 by human mAbs. Mean±SD of technical duplicates is shown. Data represent one of two or more independent experiments.

Figure 25A:
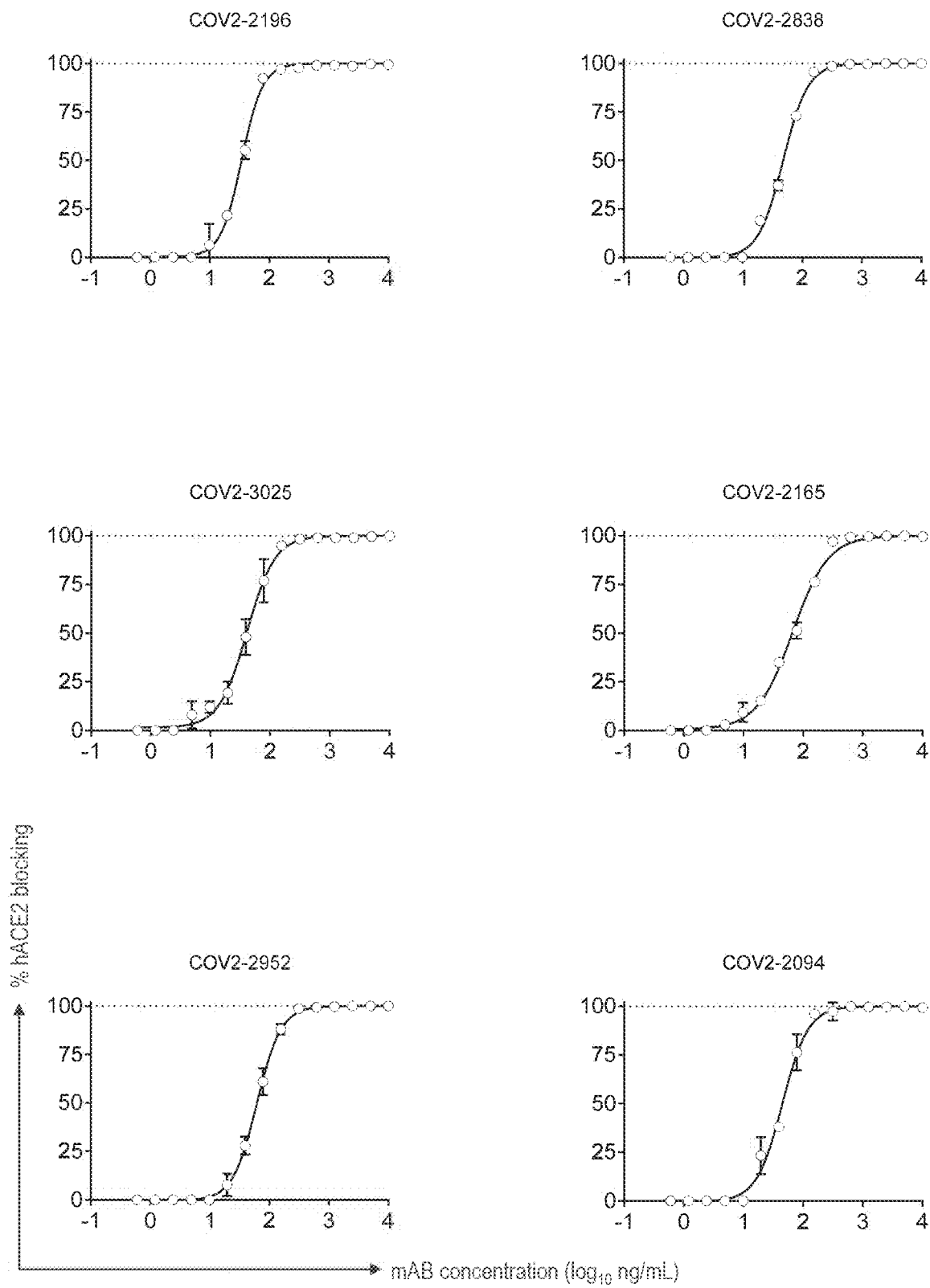
Figure 25B:
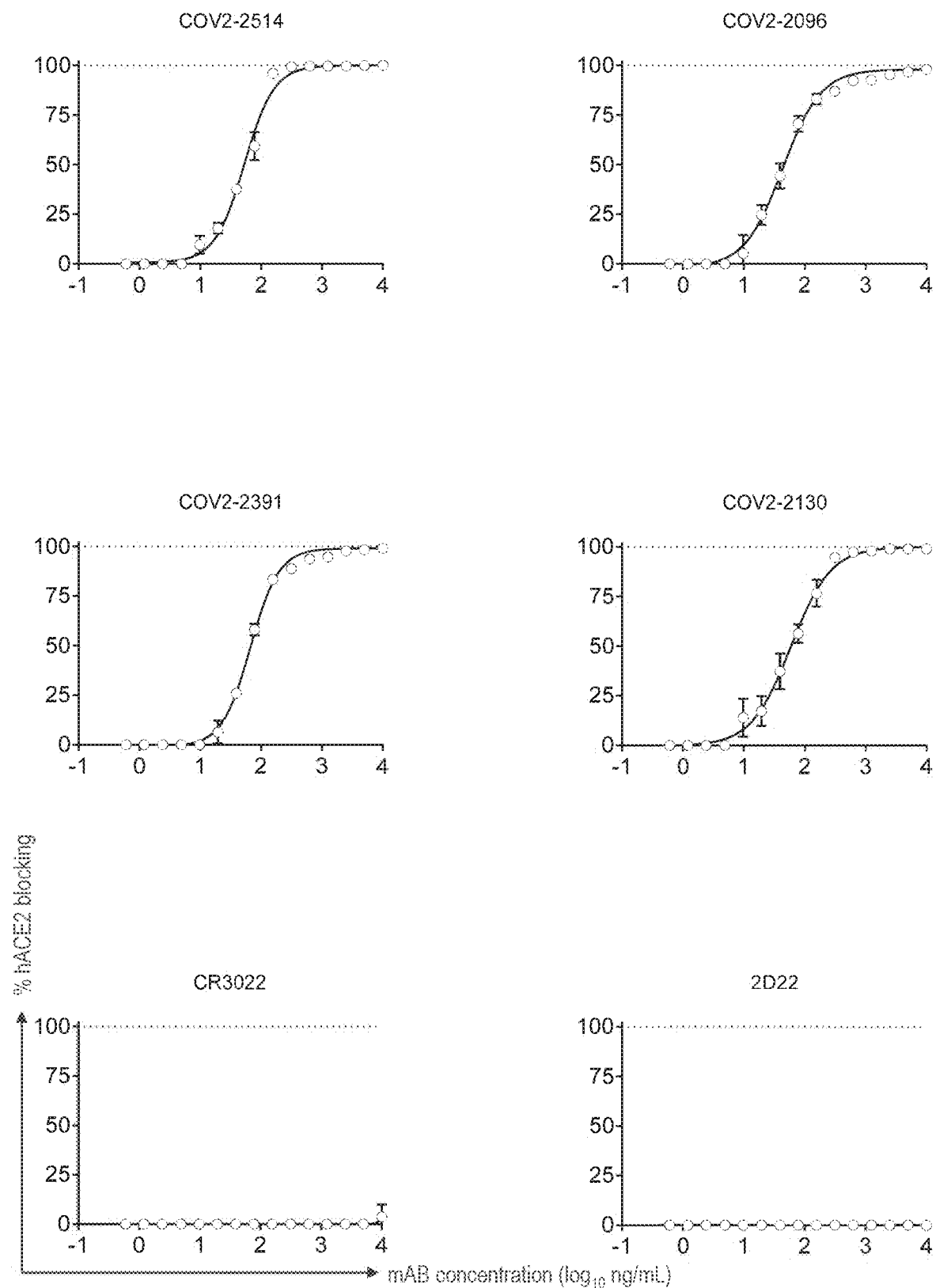

FIGS. 25A-B. Inhibition curves for mAb inhibition of S2Pecto binding to hACE2. Blocking of hACE2 binding to S2Pecto by anti-SARS-CoV-2 neutralizing human mAbs. Mean±SD of triplicates of one experiment is shown. Antibodies CR3022 and 2D22 served as controls.

Figure 26A:
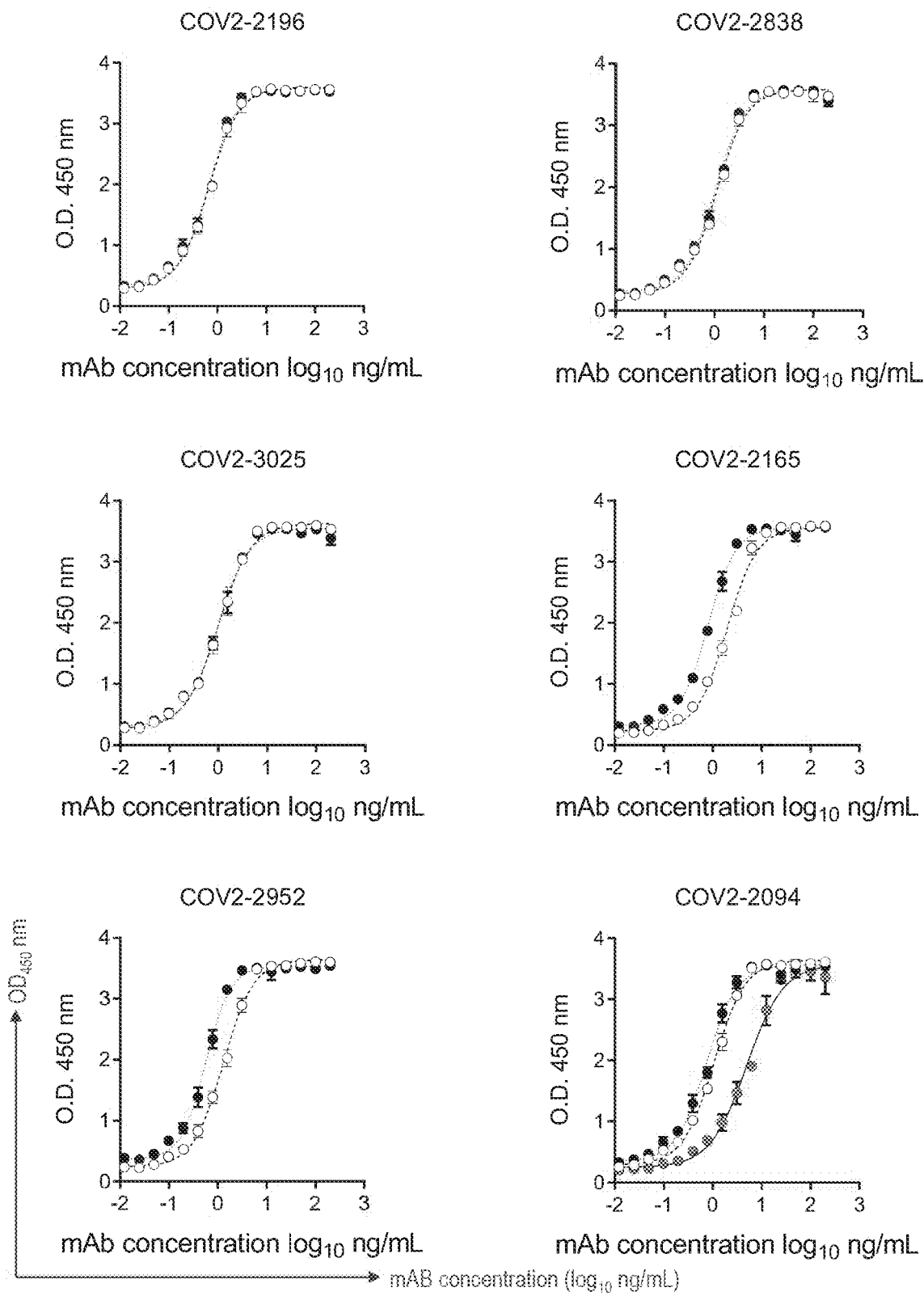
Figure 26B:
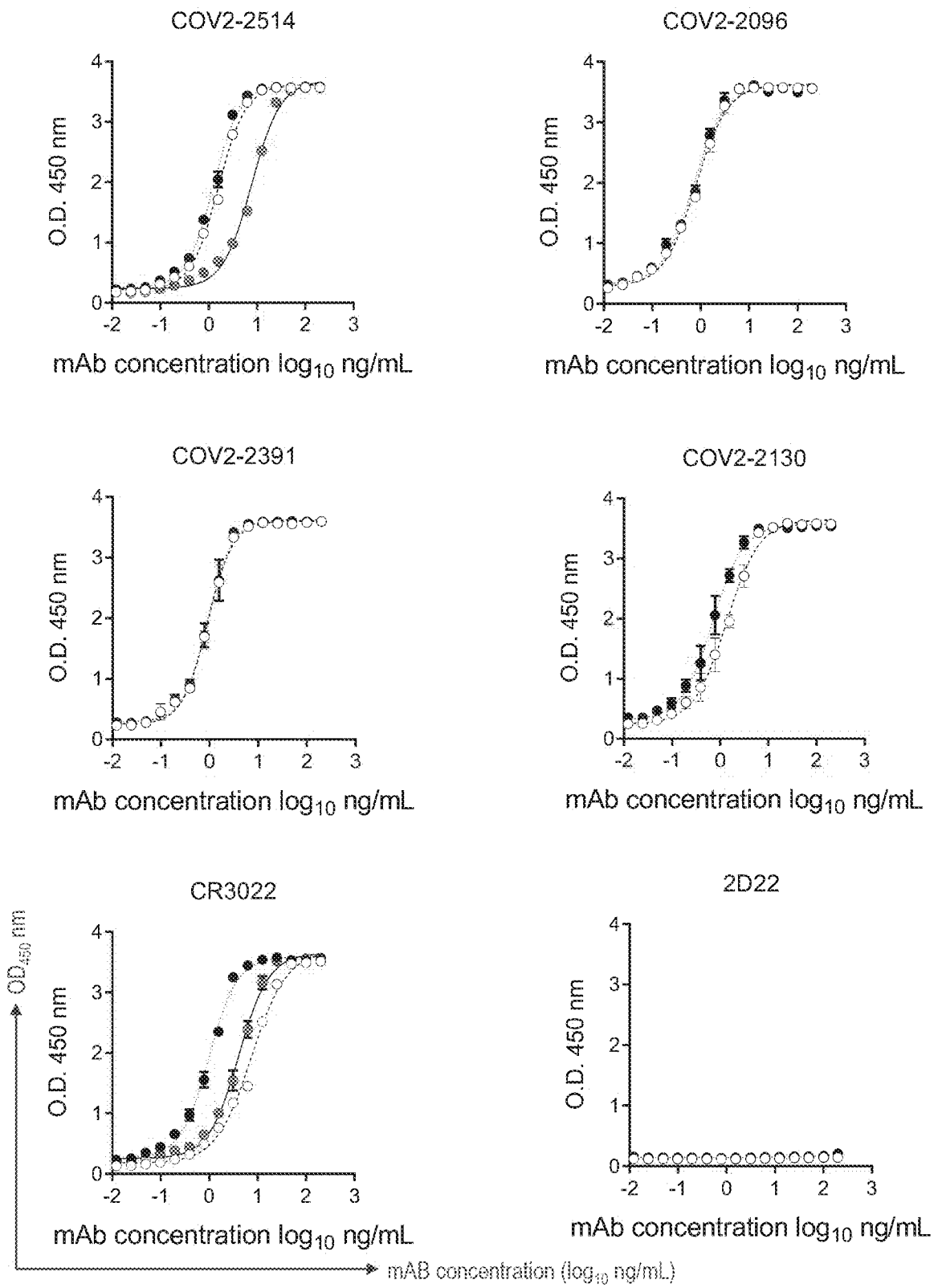

FIGS. 26A-B. ELISA binding of anti-SARS-CoV-2 neutralizing human mAbs to trimeric SRBD, S2Pecto, or SARS-CoV S2Pecto antigen. Mean±SD of triplicates and representative of two experiments are shown. Antibodies CR3022 and 2D22 served as controls.

Figure 27A:
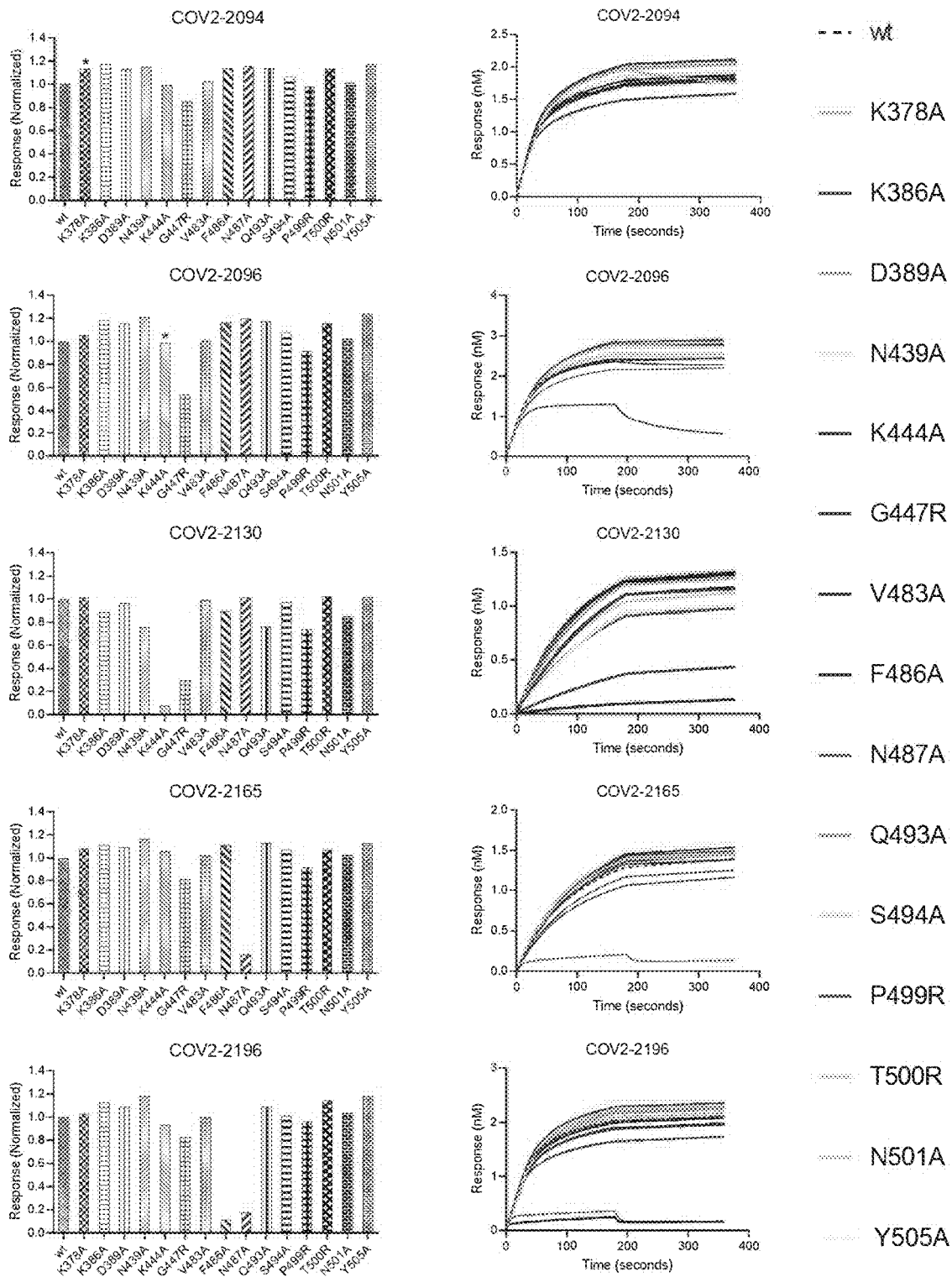
Figure 27B:
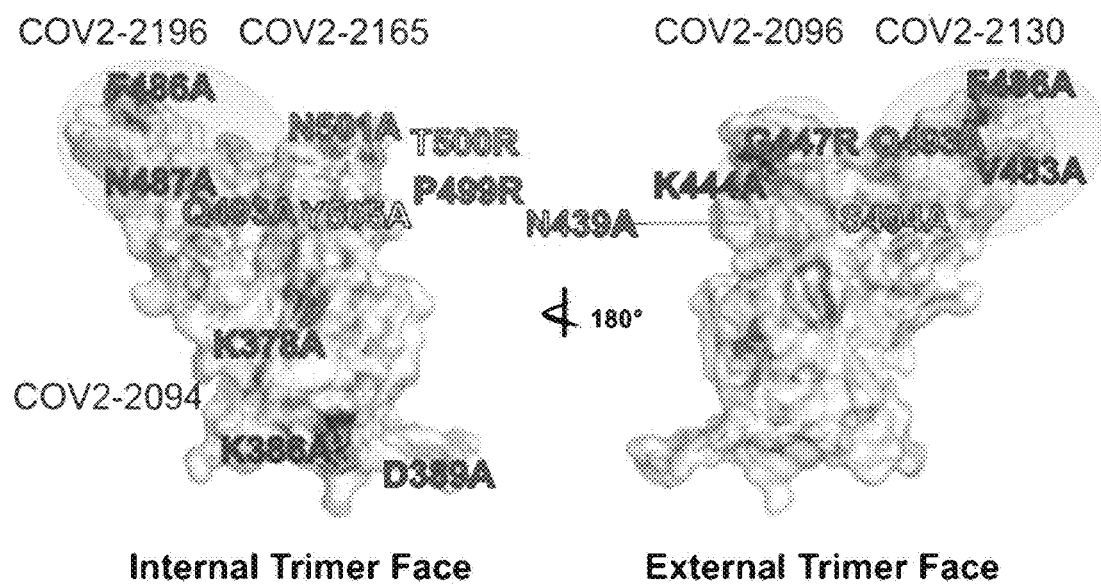

FIG. 27A-B. Mapping of mAb critical contact residues by alanine and arginine mutagenesis and biolayer interferometry. (FIG. 27A) Left: Response values for mAb binding to wt or mutant SRBD constructs normalized to wt. Asterisks denote residues where increased dissociation of mAb was observed, likely indicating the residue is proximal to mAb epitope. Right: full response curves for mAb association and dissociation with wt or mutant SRBD constructs. (FIG. 27B) Structure of the RBD highlighting the critical contact residues for several mAbs and their location on the structure.

DESCRIPTION OF ILLUSTRATIVE EMBODIMENTS

As discussed above, SARS-CoV-2 is a major health concern with active cases increasing daily. Therefore, understanding the biology of this virus and the nature and extent of the human immune response to the virus is of paramount importance. The inventors have identified the sequences of human antibodies to SARS-CoV-2. Those sequences and uses for such antibodies are disclosed herein.

Moreover, by studying the interaction of one antibody (COV2-2196) with RBD in detail, the inventors identify the molecular basis for selection of a public clonotype for SARS-CoV-2 that is driven by a complex structural configuration involving both heavy and light chains. The shared structural features of this clonotype contribute to the formation of a paratope comprising residues in both the heavy and light chains, but remarkably are independent of the HCDR3 that usually dominates antigen-antibody interactions. The inventors show this public clonotype is one of the more frequently shared types of potent neutralizing antibodies made by humans to the SARS-CoV-2 S protein RBD. Detailed structural studies revealed that the commonly formed antibody paratope contributes an "aromatic cage" formed by five aromatic residues in the paratope surrounding the interface of the heavy and light chains. This cage structure coordinates an aromatic residue on the SARS-CoV-2 S protein, accounting for the high specificity and affinity of these antibodies. Remarkably, although both the heavy and light chains are required to form this public clonotype (thus defining canonical IGHV, IGHJ, IGLV and IGLJ genes in the clonotype), the HCDR3 minimally affects the interaction. Since these IGHV1-58-IGHJ3 heavy chain and IGKV3-20-IGKJ1 light chain recombinations are common in the pre-immune B cell repertoire, many individuals likely make such clones during the response to SARS-CoV-2 infection or vaccination. The antigenic site recognized by the complex pre-configured structure of this public clonotype likely is an important component of a protective vaccine for COVID-19 because of the frequency of the B cell clone in the human population and the neutralizing and protective potency of the antibodies encoded by the variable gene segments.

These and other aspects of the disclosure are described in detail below.

I. CORONAVIRUS 2019 (SARS-COV-2)

SARS-CoV-2 is a contagious virus that causes the acute respiratory disease designated coronavirus disease 2019 (COVID-19), a respiratory infection. It is the cause of the ongoing 2019-20 coronavirus outbreak, a global health emergency. Genomic sequencing has shown that it is a positive-sense, single-stranded RNA coronavirus.

During the ongoing outbreak, the virus has often been referred to in common parlance as "the coronavirus", "the new coronavirus" and "the Wuhan coronavirus", while the WHO recommends the designation "SARS-CoV-2". The International Committee on Taxonomy of Viruses (ICTV) announced that the official name for the virus is SARS-CoV-2.

Many early cases were linked to a large seafood and animal market in the Chinese city of Wuhan, and the virus is thought to have a zoonotic origin. Comparisons of the genetic sequences of this virus and other virus samples have shown similarities to SARS-CoV (79.5%) and bat coronaviruses (96%). This finding makes an ultimate origin in bats likely, although an intermediate host, such as a pangolin, cannot be ruled out. The virus could be a recombinant virus formed from two or more coronaviruses.

Human-to-human transmission of the virus has been confirmed. Coronaviruses are primarily spread through close contact, in particular through respiratory droplets from coughs and sneezes within a range of about 6 feet (1.8 m). Viral RNA has also been found in stool samples from infected patients. It is possible that the virus can be infectious even during the incubation period.

Animals sold for food were originally suspected to be the reservoir or intermediary hosts of SARS-CoV-2 because many of the first individuals found to be infected by the virus were workers at the Huanan Seafood Market. A market selling live animals for food was also blamed in the SARS outbreak in 2003; such markets are considered to be incubators for novel pathogens. The outbreak has prompted a temporary ban on the trade and consumption of wild animals in China. However, some researchers have suggested that the Huanan Seafood Market may not be the original source of viral transmission to humans.

With a sufficient number of sequenced genomes, it is possible to reconstruct a phylogenetic tree of the mutation history of a family of viruses. Research into the origin of the 2003 SARS outbreak has resulted in the discovery of many SARS-like bat coronaviruses, most originating in the *Rhinolophus* genus of horseshoe bats. SARS-CoV-2 falls into this category of SARS-related coronaviruses. Two genome sequences from *Rhinolophus sinicus* published in 2015 and 2017 show a resemblance of 80% to SARS-CoV-2. A third virus genome from *Rhinolophus affinis*, "RaTG13" collected in Yunnan province, has a 96% resemblance to SARS-CoV-2.[28][29] For comparison, this amount of variation among viruses is similar to the amount of mutation observed over ten years in the H3N2 human influenza virus strain.

SARS-CoV-2 belongs to the broad family of viruses known as coronaviruses; "nCoV" is the standard term used to refer to novel coronaviruses until the choice of a more specific designation. It is a positive-sense single-stranded RNA (+ssRNA) virus. Other coronaviruses are capable of causing illnesses ranging from the common cold to more severe diseases such as Middle East respiratory syndrome (MERS) and Severe acute respiratory syndrome (SARS). It is the seventh known coronavirus to infect people, after 229E, NL63, OC43, HKU1, MERS-CoV, and SARS-CoV.

Like SARS-CoV, SARS-CoV-2 is a member of the subgenus Sarbecovirus (Beta-CoV lineage B). Its RNA sequence is approximately 30,000 bases in length. By 12 January, five genomes of SARS-CoV-2 had been isolated from Wuhan and reported by the Chinese Center for Disease Control and Prevention (CCDC) and other institutions; the number of genomes increased to 28 by 26 January. Except for the earliest GenBank genome, the genomes are under an embargo at GISAID. A phylogenic analysis for the samples is available through Nextstrain.

Publication of the SARS-CoV-2 genome led to several protein modeling experiments on the receptor binding protein (RBD) of the spike (S) protein of the virus. Results suggest that the S protein retains sufficient affinity to the Angiotensin converting enzyme 2 (ACE2) receptor to use it as a mechanism of cell entry. On 22 January, a group in China working with the full virus and a group in the U.S. working with reverse genetics independently and experimentally demonstrated human ACE2 as the receptor for SARS-CoV-2.

To look for potential protease inhibitors, the viral 3C-like protease M(pro) from the ORF1a polyprotein has also been modeled for drug docking experiments. Innophore has produced two computational models based on SARS protease, and the Chinese Academy of Sciences has produced an unpublished experimental structure of a recombinant SARS-CoV-2 protease. In addition, researchers at the University of Michigan have modeled the structures of all mature peptides in the SARS-CoV-2 genome using I-TASSER.

The first known human infection occurred in early December 2019. An outbreak of SARS-CoV-2 was first detected in Wuhan, China, in mid-December 2019, likely originating from a single infected animal. The virus subsequently spread to all provinces of China and to more than two dozen other countries in Asia, Europe, North America, and Oceania. Human-to-human spread of the virus has been confirmed in all of these regions. On 30 Jan. 2020, SARS-CoV-2 was designated a global health emergency by the WHO.

As of 10 Feb. 2020 (17:15 UTC), there were 40,645 confirmed cases of infection, of which 40,196 were within mainland China. Initially, nearly all cases outside China occurred in people who either traveled from Wuhan, or were in direct contact with someone who traveled from the area. Later, spread from travelers to other countries resulted in trasmission in many countries in the world. While the proportion of infections that result in confirmed infection or progress to diagnosable SARS-CoV-2 acute respiratory disease remains unclear, the total number of deaths attributed to the virus was over 19,000 as of 25 Mar. 2020.

The basic reproduction number (R-zero) of the virus has been estimated to be between 1.4 and 3.9. This means that, when unchecked, the virus typically results in 1.4 to 3.9 new cases per established infection. It has been established that the virus is able to transmit along a chain of at least four people.

In January 2020, multiple organizations and institutions began work on creating vaccines for SARS-CoV-2 based on the published genome. In China, the Chinese Center for Disease Control and Prevention is developing a vaccine against the novel coronavirus. The University of Hong Kong has also announced that a vaccine is under development there. Shanghai East Hospital is also developing a vaccine in partnership with the biotechnology company Stemirna Therapeutics.

Elsewhere, three vaccine projects are being supported by the Coalition for Epidemic Preparedness Innovations (CEPI), including projects by the biotechnology companies Moderna and Inovio Pharmaceuticals and another by the University of Queensland. The United States National Institutes of Health (NIH) is cooperating with Moderna to create an RNA vaccine matching a spike of the coronavirus surface; Phase I clinical trials began in March 2020. Inovio Pharmaceuticals is developing a DNA-based vaccination and collaborating with a Chinese firm in order to speed its acceptance by regulatory authorities in China, hoping to perform human trials of the vaccine in the summer of 2020. In Australia, the University of Queensland is investigating the potential of a molecular clamp vaccine that would genetically modify viral proteins to make them mimic the coronavirus and stimulate an immune reaction.

In an independent project, the Public Health Agency of Canada has granted permission to the International Vaccine Centre (VIDO-InterVac) at the University of Saskatchewan to begin work on a vaccine. VIDO-InterVac aims to start production and animal testing in March 2020, and human testing in 2021. The Imperial College Faculty of Medicine in London is now at the stage of testing a vaccine on animals.

COVID-19 acute respiratory disease is a viral respiratory disease caused by SARS-CoV-2. It was first detected during the 2019-20 Wuhan coronavirus outbreak. Symptoms may include fever, dry cough, and shortness of breath. There is no specific licensed treatment available as of March 2020, with efforts focused on lessening symptoms and supporting functioning.

Those infected may either be asymptomatic or have mild to severe symptoms, like fever, cough, shortness of breath. Diarrhoea or upper respiratory symptoms (e.g., sneezing, runny nose, sore throat) are less frequent. Cases of severe infection can progress to severe pneumonia, multi-organ failure, and death. The time from exposure to onset of symptoms is estimated at 2 to 10 days by the World Health Organization, and 2 to 14 days by the US Centers for Disease Control and Prevention (CDC).

Global health organizations have published preventive measures individuals can take to reduce the chances of SARS-CoV-2 infection. Recommendations are similar to those previously published for other coronaviruses and include: frequent washing of hands with soap and water; not touching the eyes, nose, or mouth with unwashed hands; and practicing good respiratory hygiene.

The WHO has published several testing protocols for SARS-CoV-2. Testing uses real time reverse transcription-polymerase chain reaction (rRT-PCR). The test can be done on respiratory or blood samples. Results are generally available within a few hours to days.

Research into potential treatments for the disease were initiated in January 2020. The Chinese Center for Disease Control and Prevention started testing existing pneumonia treatments in coronavirus-related pneumonia in late January. There has also been examination of the RNA polymerase inhibitor remdesivir, and interferon beta. In late January 2020, Chinese medical researchers expressed an intent to start clinical testing on remdesivir, chloroquine, and lopinavir/ritonavir, all of which seemed to have "fairly good inhibitory effects" on SARS-CoV-2 at the cellular level in exploratory research. On 5 Feb. 2020, China started patenting use of remdesivir for the disease.

Overall mortality and morbidity rates due to infection with SARS-CoV-2 are unknown, both because the case fatality rate may be changing over time in the current outbreak, and because the proportion of infections that progress to diagnosable disease remains unclear. However, preliminary research into SARS-CoV-2 acute respiratory disease has yielded case fatality rate numbers between 2% and 3%, and in January 2020 the WHO suggested that the case fatality rate was approximately 3%. An unreviewed Imperial College preprint study among 55 fatal cases noted that early estimates of mortality may be too high as asymptomatic infections are missed. They estimated a mean infection fatality ratio (the mortality among infected) ranging from 0.8% when including asymptomatic carriers to 18% when including only symptomatic cases from Hubei province.

Early data indicates that among the first 41 confirmed cases admitted to hospitals in Wuhan, 13 (32%) individuals required intensive care, and 6 (15%) individuals died. Of those who died, many were in unsound health to begin with, exhibiting conditions like hypertension, diabetes, or cardiovascular disease that impaired their immune systems. In early cases of SARS-CoV-2 acute respiratory disease that resulted in death, the median time of disease was found to be 14 days, with a total range from six to 41 days.

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to SARS-CoV-2 will have several applications. These include the production of diagnostic kits for use in detecting and diagnosing SARS-CoV-2 infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed Mycobacterium tuberculosis), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce SARS-CoV-2-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells identified as responding to infection or vaccination because of plasmablast aor activated B cell markers, or memory B cells labelled with the antigen of interest, can be sorted physically using paramagnetic bead selection or flow cytometric sorting, then RNA can be isolated from the single cells and antibody genes amplified by RT-PCR. Various single-cell RNA-seq methods are available to obtain antibody variable genes from single cells. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes from single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Two main categories of SARS-CoV-2 antigens are the surface spike (S) protein and the internal proteins, especially the nucleocapsid (N) protein. Antibodies to the S protein will be useful for prophylaxis, or therapy, or diagnostics, or for characterizing vaccines. S protein antibodies will have additional binding specificity with that protein, with particular antibodies binding to the full-length ectodomain of the SARS-CoV-2 S protein (presented as a monomer or oligomer such as a timer; with our without conformation stabilizing mutations such as introduction of prolines at critical sites ("2P mutation")) and (a) anti-S protein antibodies that binds to the receptor binding domain (RBD), (b) anti-S protein antibodies that bind to domains other than the RBD. Some of the subset that bind to domains other than the RBD bind to the N terminal domain (NTD), while others bind to an epitope other than the NTD or RBD), and (c) S protein antibodies may further be found to neutralize SARS-CoV-2 by blocking binding of the SARS-CoV-2 S protein to its receptor, human angiotensin-converting enzyme 2 (hACE2), with others that neutralize but do not block receptor binding. Finally, antibodies can cross-react with both SARS-CoV-2 S protein and the S protein of other coronaviruses such as SARS-CoV, MERS-CoV, HCoV-229E, HCoV-OC43, HCoV-NL63 and/or HCoV-HKU1, as well as cross-neutralize both SARS-CoV-2 and these other coronaviruses.

Another specificity will be antibodies that bind to N antibodies (or other internal targets) that will have primarily diagnostics uses. For example, antibodies to N or other internal proteins of SARS-CoV-2 that specifically recognize SARS-CoV-2 or that cross-reactively recognize SARS-CoV-2 and other coronaviruses such as SARS-CoV, MERS-CoV, HCoV-229E, HCoV-OC43, HCoV-NL63 and/or HCoV-HKU1.

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke, Methods Mol. Biol. 248: 443-63, 2004), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer Prot. Sci. 9: 487-496, 2000). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring, Analytical Biochemistry 267: 252-259 (1999), Engen and Smith, Anal. Chem. 73: 256A-265A (2001). When the antibody neutralizes SARS-CoV-2, antibody escape mutant variant organisms can be isolated by propagating SARS-CoV-2 in vitro or in animal models in the presence of high concentrations of the antibody. Sequence analysis of the SARS-CoV-2 gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see U.S. Patent Publication 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-SARS-CoV-2 antibody, the above-described binding methodology is performed in two orientations: to a first orientation, the reference antibody is allowed to bind to the SARS-CoV-2 antigen under saturating conditions followed by assessment of binding of the test antibody to the SARS-CoV-2 molecule. In a second orientation, the test antibody is allowed to bind to the SARS-CoV-2 antigen molecule under saturating conditions followed by assessment of binding of the reference antibody to the SARS- CoV-2 molecule. If, in both orientations, only the first (saturating) antibody is capable of binding to SARS-CoV-2, then it is concluded that the test antibody and the reference antibody compete for binding to SARS-CoV-2. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et at., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other. In some aspects an antibody or antibody fragment that binds to the same or overlapping epitope as COV2-2196 is used in combination with an antibody or antibody fragment that binds to the same or overlapping eptiope as COV2-2130.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences and the amino acid sequences.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example, with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example, antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha (1-6) Dextran Increases Its Affinity For Antigen*," J. Exp. Med. 168(3): 1099-1109; Tao, M. H. et al. (1989) "*Studies Of Aglycosylated Chimeric Mouse-Human IgG. Role of Carbohydrate in The Structure And Effector Functions Mediated By The Human IgG Constant Region*," J. Immunol. 143(8): 2595-2601; Routledge, E. G. et al. (1995) "*The Effect of Aglycosylation on The Immunogenicity of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack of Fucose on Human IgG N-Linked Oligosaccharide Improves Binding to Human Fcgamma RIII And Antibody-Dependent Cellular Toxicity*," J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include:

arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:
1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., Nature Biotech., 22 (10), 1302-1306, 2004; Chennamsetty et al., PNAS, 106 (29), 11937-11942, 2009; Voynov et al., Biocon. Chem., 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, Biochem. Biophys. Res. Commun. 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol*, 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293 S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')$_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from E. coli, which can be chemically coupled to form bispecific antibodies. Shalaby et al., J. Exp. Med., 175: 217-225 (1992) describe the production of a humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., Nat. Biotechnol. 16, 677-681 (1998). doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264; Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., *Science*, 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1)$_n$-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a C$_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
 (a) a first Fab molecule which specifically binds to a first antigen
 (b) a second Fab molecule which specifically binds to a second antigen, and wherein the variable domains VL and VH of the Fab light chain and the Fab heavy chain are replaced by each other,
 wherein the first antigen is an activating T cell antigen and the second antigen is a target cell antigen, or the first antigen is a target cell antigen and the second antigen is an activating T cell antigen; and
 wherein
  i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
  ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/antiviral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker. The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF SARS-COV-2 INFECTION

A. Formulation and Administration

The present disclosure provides pharmaceutical compositions comprising anti-SARS-CoV-2 virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of SARS-CoV-2 infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example, by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting SARS-CoV-2 and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of SARS-CoV-2 in a subject. A wide variety of assay formats are contemplated, but specifically those that would be used to detect SARS-CoV-2 in a fluid obtained from a subject, such as saliva, blood, plasma, sputum, semen or urine. In particular, semen has been demonstrated as a viable sample for detecting SARS-CoV-2 (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of SARS-CoV-2 antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing SARS-CoV-2, and contacting the sample with a first antibody in accordance with the present disclosure, as the case may be, under conditions effective to allow the formation of immunocomplexes.

These methods include methods for purifying SARS-CoV-2 or related antigens from a sample. The antibody will preferably be linked to a solid support, such as in the form of a column matrix, and the sample suspected of containing the SARS-CoV-2 or antigenic component will be applied to the immobilized antibody. The unwanted components will be washed from the column, leaving the SARS-CoV-2 antigen immunocomplexed to the immobilized antibody, which is then collected by removing the organism or antigen from the column.

The immunobinding methods also include methods for detecting and quantifying the amount of SARS-CoV-2 or related components in a sample and the detection and quantification of any immune complexes formed during the binding process. Here, one would obtain a sample suspected of containing SARS-CoV-2 or its antigens and contact the sample with an antibody that binds SARS-CoV-2 or components thereof, followed by detecting and quantifying the amount of immune complexes formed under the specific conditions. In terms of antigen detection, the biological sample analyzed may be any sample that is suspected of containing SARS-CoV-2 or SARS-CoV-2 antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to SARS-CoV-2 or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, for example, with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/ antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAS

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the SARS-CoV-2 or SARS-CoV-2 antigen is added to the wells. After binding and washing to remove non-specifically bound immune complexes, the bound antigen may be detected. Detection may be achieved by the addition of another anti-SARS-CoV-2 antibody that is linked to a detectable label. This type of ELISA is a simple "sandwich ELISA." Detection may also be achieved by the addition of a second anti-SARS-CoV-2 antibody, followed by the addition of a third antibody that has binding affinity for the second antibody, with the third antibody being linked to a detectable label.

In another exemplary ELISA, the samples suspected of containing the SARS-CoV-2 or SARS-CoV-2 antigen are immobilized onto the well surface and then contacted with the anti-SARS-CoV-2 antibodies of the disclosure. After binding and washing to remove non-specifically bound immune complexes, the bound anti-SARS-CoV-2 antibodies are detected. Where the initial anti-SARS-CoV-2 antibodies are linked to a detectable label, the immune complexes may be detected directly. Again, the immune complexes may be detected using a second antibody that has binding affinity for the first anti-SARS-CoV-2 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of SARS-CoV-2 antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled SARS-CoV-2 monoclonal antibodies to determine the amount of SARS-CoV-2 antibodies in a sample. The basic format would include contacting a known amount of SARS-CoV-2 monoclonal antibody (linked to a detectable label) with SARS-CoV-2 antigen or particle. The SARS-CoV-2 antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. WESTERN BLOT

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. LATERAL FLOW ASSAYS

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. IMMUNOHISTOCHEMISTRY

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. IMMUNODETECTION KITS

In still further embodiments, the present disclosure concerns immunodetection kits for use with the immunodetection methods described above. As the antibodies may be used to detect SARS-CoV-2 or SARS-CoV-2 antigens, the antibodies may be included in the kit. The immunodetection kits will thus comprise, in suitable container means, a first antibody that binds to SARS-CoV-2 or SARS-CoV-2 antigen, and optionally an immunodetection reagent.

In certain embodiments, the SARS-CoV-2 antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the SARS-CoV-2 or SARS-CoV-2 antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. VACCINE AND ANTIGEN QUALITY CONTROL ASSAYS

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective SARS-CoV-2 antibodies. Antibodies, antibody fragment, or variants and derivatives thereof, as described in the present disclosure may also be used in a kit for monitoring vaccine manufacture with the desired immunogenicity.

G. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Antibody Synergy

Figure 1:
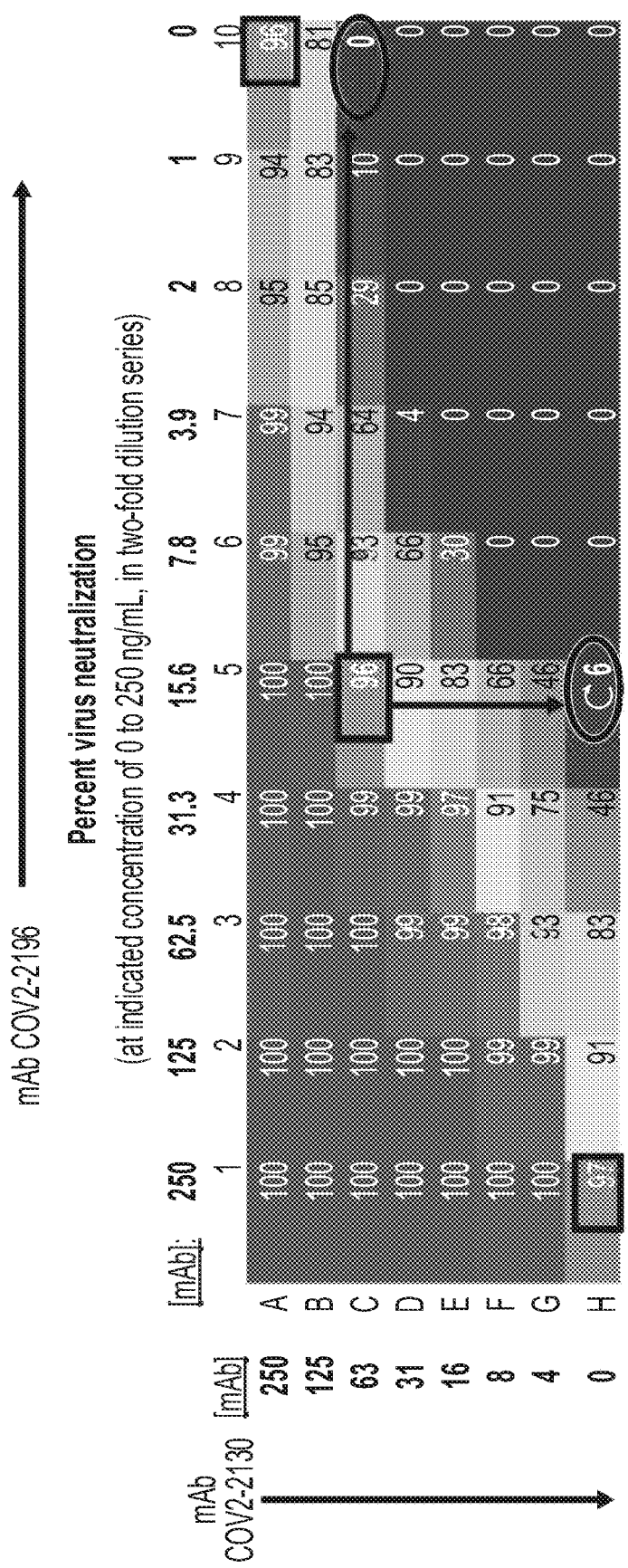
FIG. 1. Dose-response matrix to assess synergistic neutralizing activity by the cocktail of COV2-2196+COV2-2130 using live BSL3 SARS-CoV-2 virus. Qualitatively there was a small fraction of non-neutralized virus at the highest tested concentrations (250 ng/mL) of individual mAbs (boxes at 0 ng/mL COV2-2196+250 ng/mL COV2-2130 and 250 ng/mL COV2-2196+0 ng/mL COV2-2130) but full neutralization (100%) at the range of lower Ab concentrations by the combo. Box at 15.6 ng/mL COV2-2196+63 ng/mL COV2-2130 indicates the area with maximal synergy with 15.6 ng/mL of mAb COV2-2196 and 63 ng/mL of mAb COV2-2130 in a combination that neutralized 96% of virus, while the individual Abs showed only 6 or 0% neutralization, respectively (ovals at 0 ng/mL COV2-2196+63 ng/mL COV2-2130 and 15.6 ng/mL COV2-2196+0 ng/mL COV2-2130). The average values for triplicate technical replicates is shown.
Figure 2A:
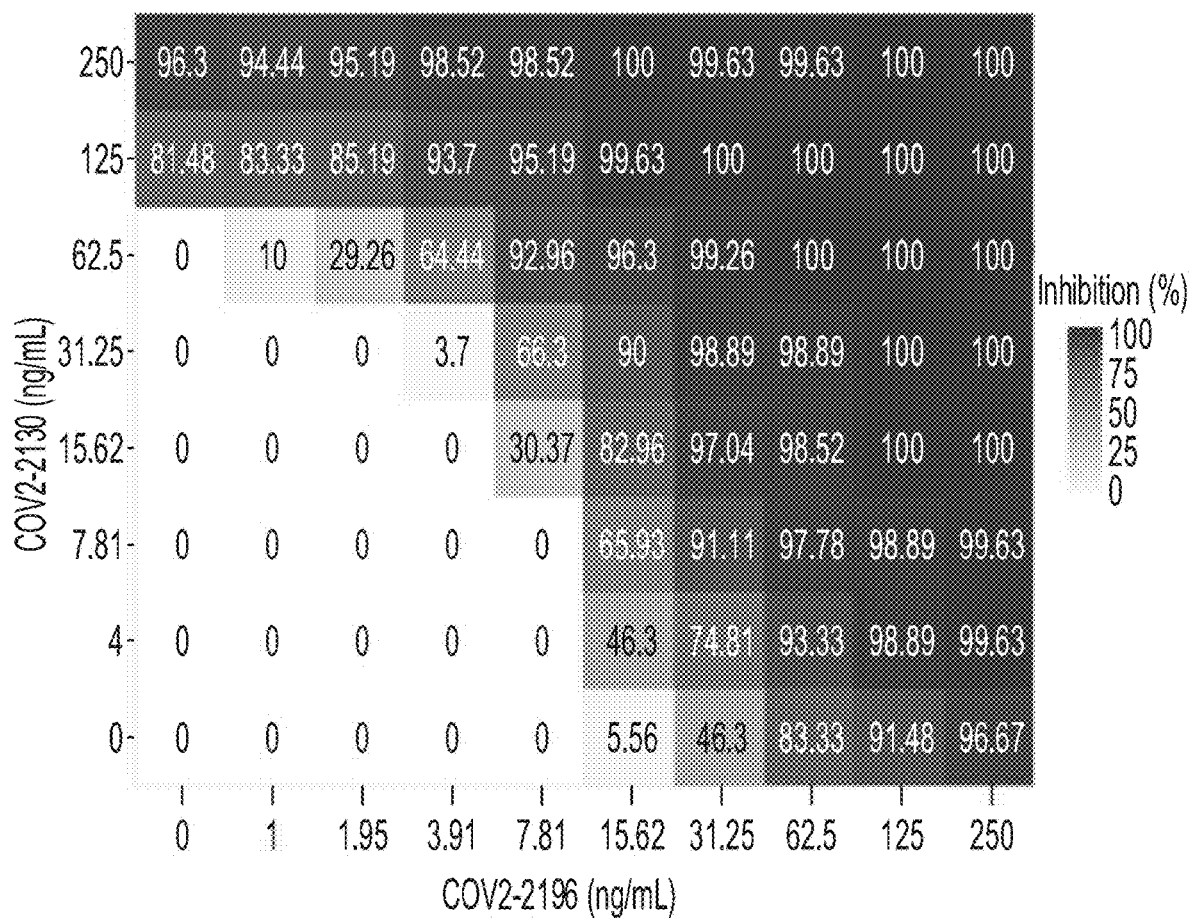
Figure 3:
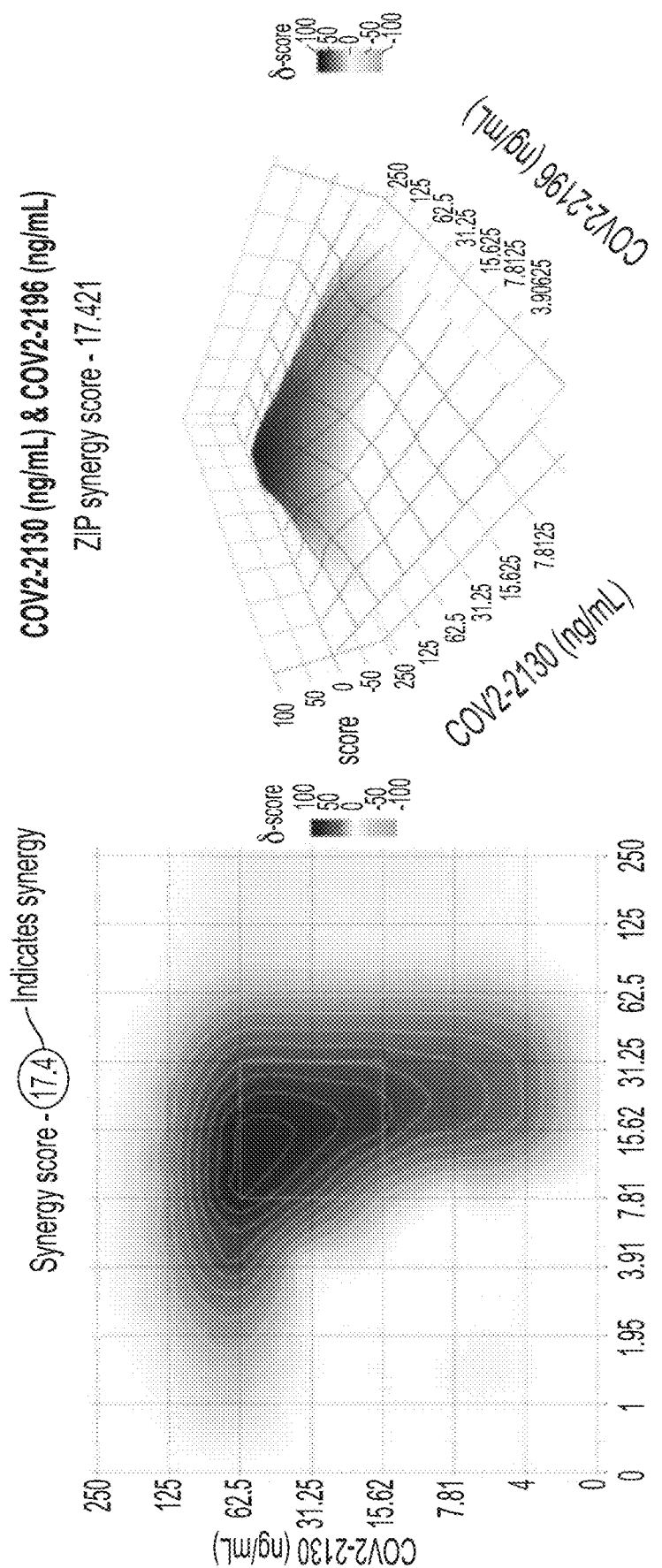
FIG. 3. Dose-response matrix to assess synergistic neutralizing activity by the cocktail of mAb COV2-2196+mAb COV2-2130 using BSL3 SARS-CoV-2 live virus. Synergy score interpretation: <−10: the interaction is likely to be antagonistic; From −10 to 10: the interaction is likely to be additive; >10: the interaction is likely to be synergistic.

Synergy is defined herein as higher neutralizing activity mediated by a cocktail of two mAbs when compared to that mediated by individual mAbs at the same total concentration (in vitro) or dose (in vivo) of antibodies. To assess if two mAbs synergize in a cocktail to neutralize SARS-CoV-2, the inventor used a previously reported approach to quantitate synergy (Ianevski A, He L, Aittokallio T, Tang J. *Bioinformatics*. 33, 2413-2415, 2017). To evaluate the significance of the beneficial effect from combining mAbs, the observed combination responses (dose-response matrix) were compared with the expected responses calculated by means of synergy scoring models (Ianevski A, He L, Aittokallio T, Tang J. *Bioinformatics*. 33, 2413-2415, 2017). Virus neutralization was measured in a conventional focus reduction neutralization test (FRNT) assay using wild-type SARS-CoV-2 and Vero-E2 cell culture monolayers. Individual mAbs COV2-2196 and COV2-2130 were mixed at different concentrations to assess neutralizing activity of different mAb ratios in the cocktail. Specifically, each of seven-fold dilutions of mAb COV2-2130 (starting from 500 ng/mL) were mixed with each of nine dilutions of mAb COV2-2196 (starting from 500 ng/mL) in total volume 50 µL of per each condition and then incubated with 50 µL of live SARS-CoV-2 in cell culture medium (RPMI-1640 medium supplemented with 2% FBS) before applying to confluent Vero-E2 cells grown in 96-well plates. The control values included those for dose-response of the neutralizing activity measured separately for individual mAbs COV2-2196 and COV2-2130 that were assessed at the same doses as in the cocktail (see FIGS. 1-3). Each measurement was performed in duplicate. The inventor next calculated percent virus neutralization for each condition and then calculated the synergy score value, which defined interaction between these two mAbs in the cocktail as synergistic (synergy score=17.4). Note, a synergy score of less than −10 indicates antagonism, a score from −10 to 10 indicates an additive effect, and a score greater than 10 indicates a synergistic effect. The example in FIGS. 1-3 shows the dose-response matrix and demonstrates that a combined mAb dose of 79 ng/mL in the cocktail (16 ng/mL of COV2-2196 and 63 ng/mL of COV2-2130) had the same activity as 250 ng/mL of each individual mAb. This finding shows that in the cocktail the dose can be reduced by more than 3 times to achieve the same potency in virus neutralization.

Figures 4A, 4B:
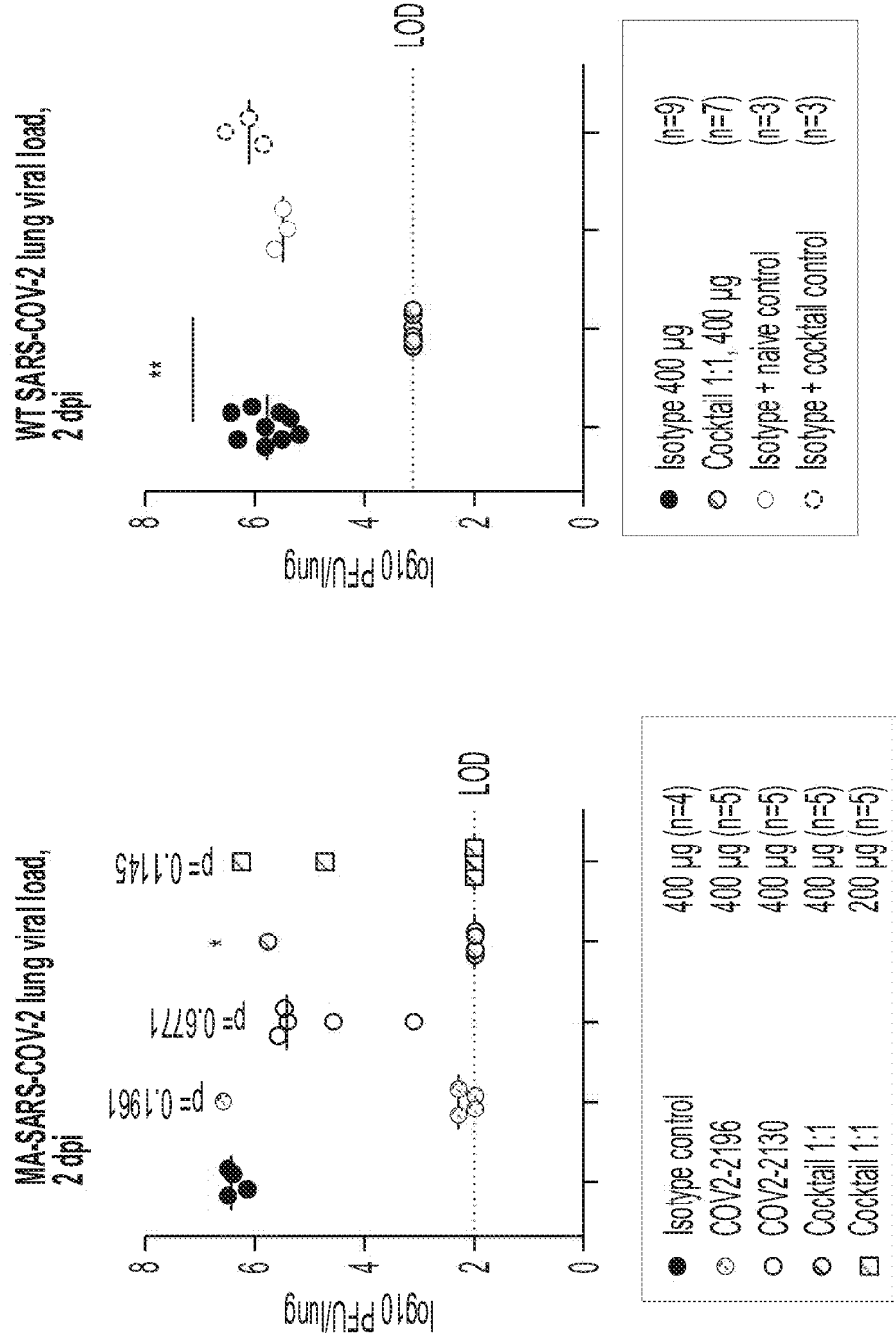
FIGS. 4A-C. Therapeutic efficacy of neutralizing human mAbs against established SARS-CoV-2 infection.
Figure 4C:
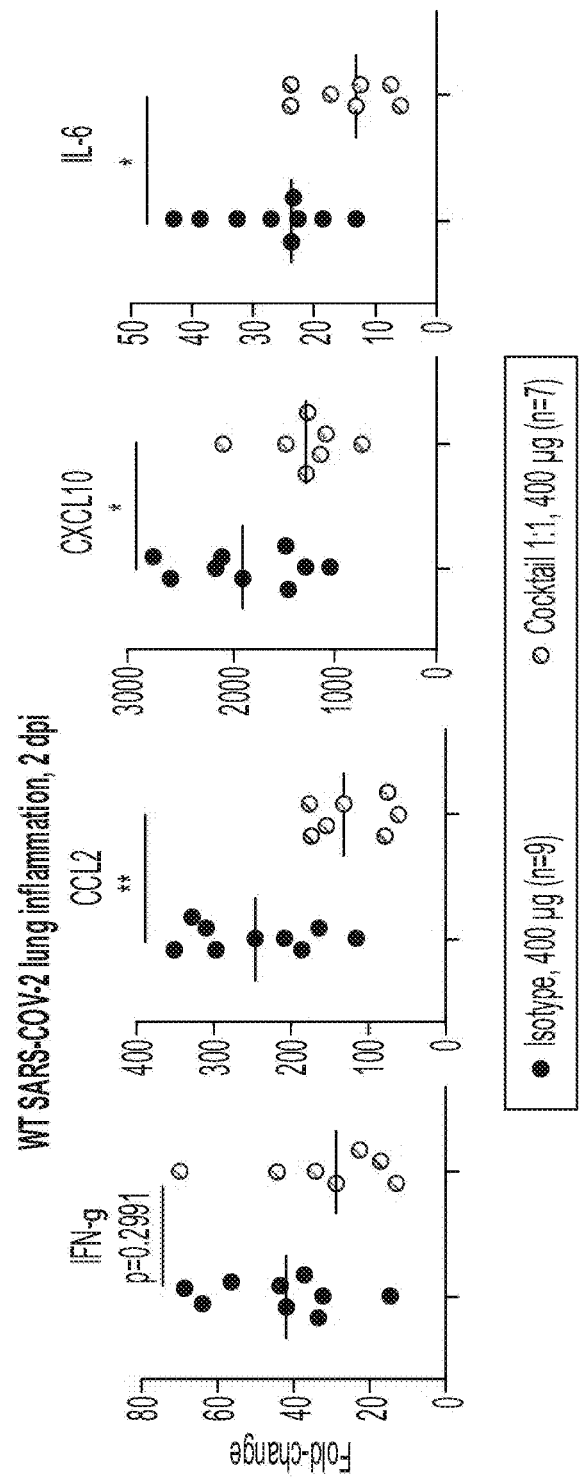
Figure 5:
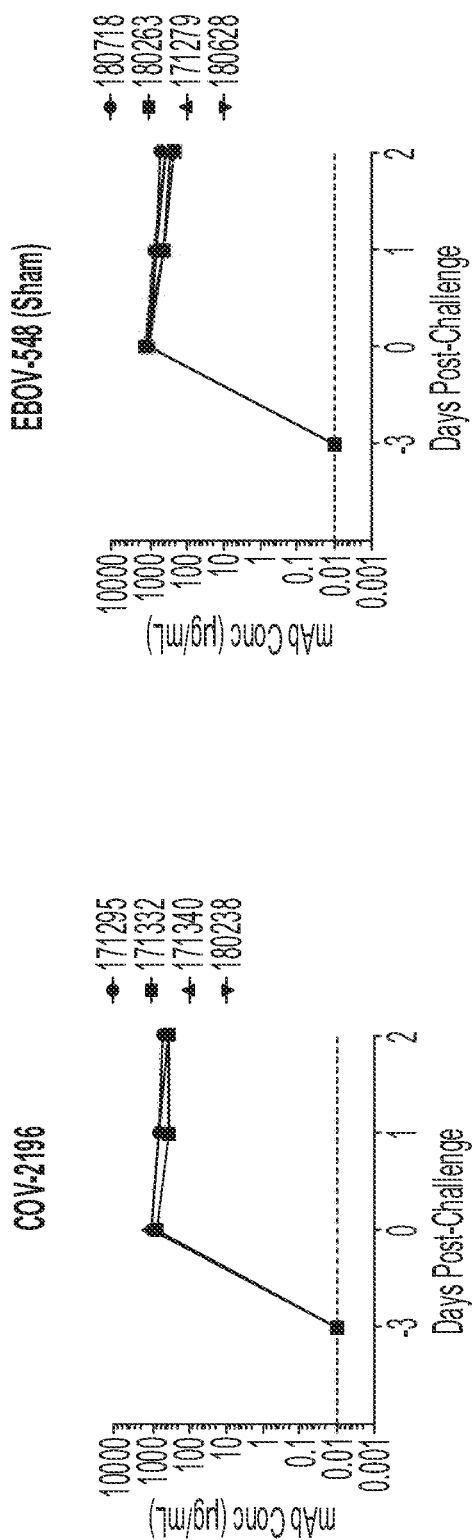
FIG. 5. Antibody pharmacokinetics following infusion of human mAb into macaques.
Figure 6:
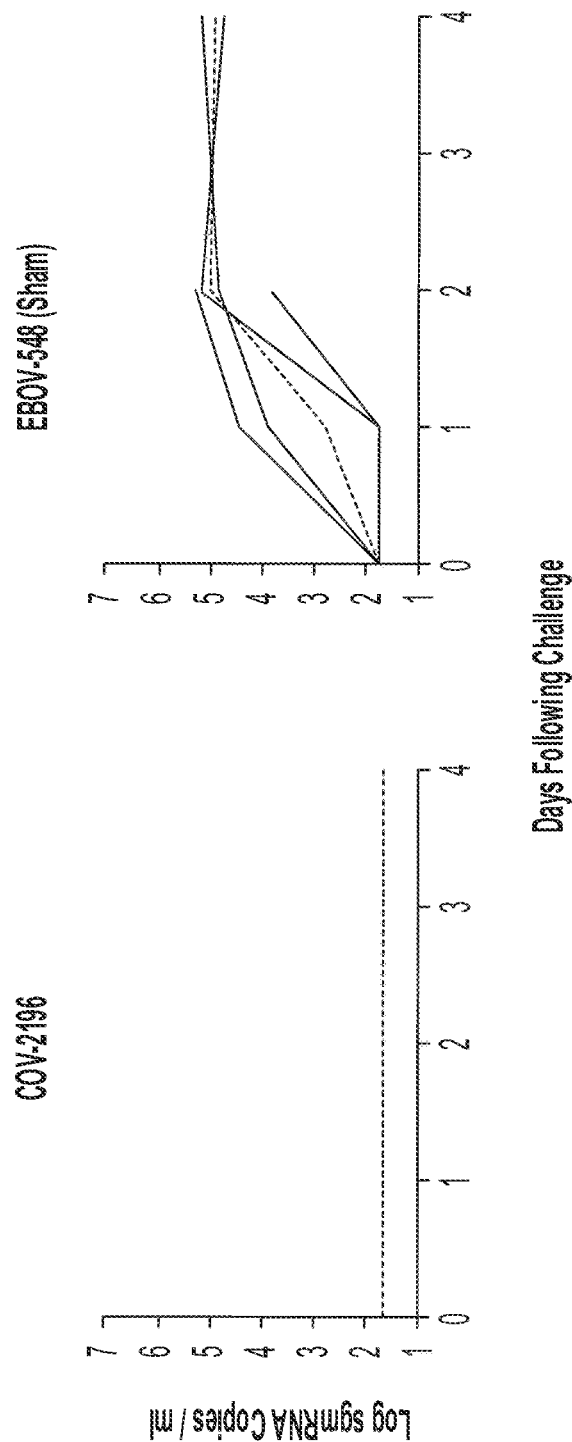
FIG. 6. SARS-CoV-2 viral loads (measured as subgenomic newly made RNA) in macaque bronchoalveolar lavage following intranasal and intratracheal challenge with wild-type SARS-CoV-2 virus.
Figure 7:
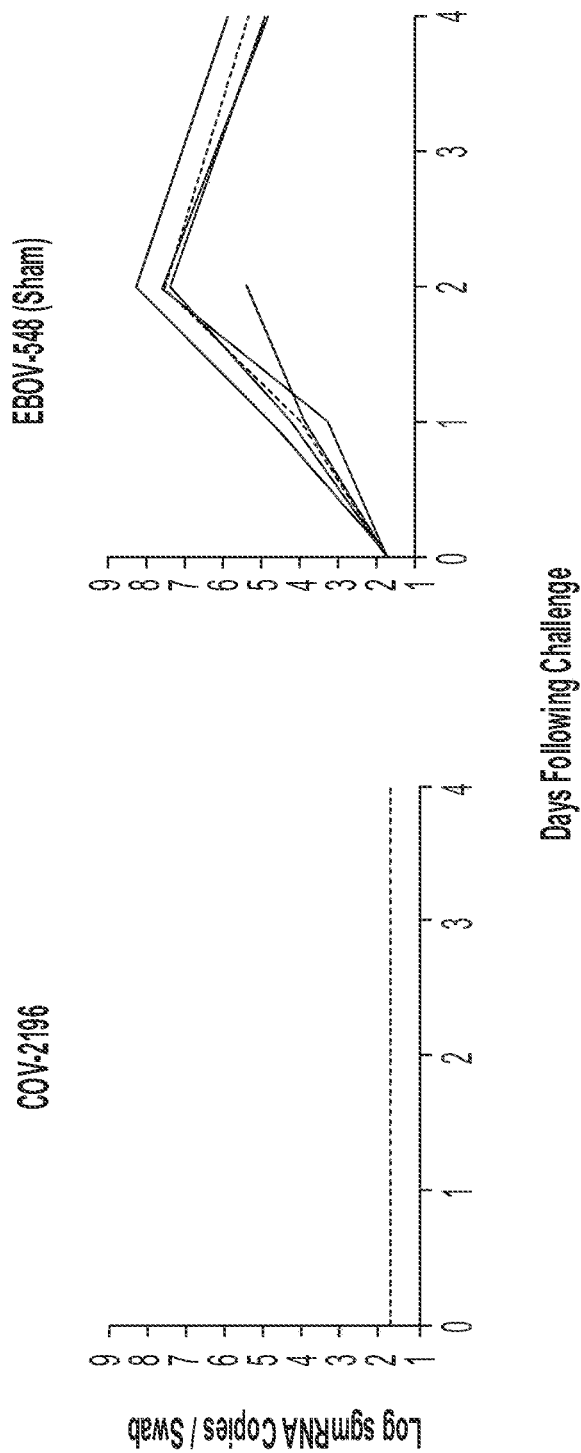
FIG. 7. SARS-CoV-2 viral loads (measured as subgenomic newly made RNA) in macaque nasal swab specimens following intranasal and intratracheal challenge with wild-type SARS-CoV-2 virus.

To assess therapeutic efficacy of treatment, the inventors first tested mAb COV2-2196 or COV2-2130 or their 1:1 combination using MA-SARS-CoV-2 challenge model. All treatments reduced infectious virus in the lung as measured by plaque titer of lung tissue at 2 days after virus inoculation. The cocktail treatment delivered at a dose of 400 µg/mouse (~20 mg/kg) was the most efficient, as it significantly reduced lung burden up to $3 \times 10^4$-fold; 4 of 5 animals from this treatment group no longer had infectious virus in the lung (FIG. 4A). Similarly, treatment of mice with lungs transduced with a recombinant adenovirus to the express the SARS-CoV-2 receptor human ACE2 (AdV-hACE2) with 400 µg/mouse of the mAb cocktail 12 hrs after authentic SARS-CoV-2 virus challenge revealed full neutralization of infectious virus in the lungs in vivo (FIG. 4B). The expression of INF-γ, IL-6, CXCL10 and CCL2 cytokine and chemokine genes, which are indicators of inflammation, also were reduced in the lungs of mAb cocktail-treated mice when compared to the lungs of isotype control-treated mice (FIG. 4C). Together these results suggested a post-exposure treatment efficacy mediated by the cocktail of COV2-2196+ COV2-2130 in mouse SARS-CoV-2 challenge models.

Example 2

Nonhuman Primate Challenge Studies

MAb production and purification. Sequences of mAbs that had been synthesized (Twist Bioscience) and cloned into an IgG1 monocistronic expression vector (designated as pTwist-mCis_G1) were used for mammalian cell culture mAb secretion. This vector contains an enhanced 2A sequence and GSG linker that allows simultaneous expression of mAb heavy and light chain genes from a single construct upon transfection[1]. The inventors previously described microscale expression of mAbs in 1 mL ExpiCHO cultures in 96-well plates[2]. For larger scale mAb expression, the inventors performed transfection (1 to 300 mL per antibody) of CHO cell cultures using the Gibco™ ExpiCHO™ Expression System and protocol for 50 mL mini bioreactor tubes (Corning) as described by the vendor. Culture supernatants were purified using HiTrap Mab Select SuRe (Cytiva, formerly GE Healthcare Life Sciences) on a 24-column parallel protein chromatography system (Protein BioSolutions). Purified mAbs were buffer-exchanged into PBS, concentrated using Amicon® Ultra-4 50 KDa Centrifugal Filter Units (Millipore Sigma) and stored at 4° C. until use. Purified mAbs were tested routinely for endotoxin levels that found to be <1 EU/mg IgG for NHP studies. Endotoxin testing was performed using the PTS201F cartridge (Charles River), with sensitivity range from 10 to 0.1 EU/mL, and an Endosafe Nexgen-MCS instrument (Charles River).

The inventors tested the protective efficacy of mAbs using a recently described SARS-CoV-2 non-human primate (NHP) challenge model[3,4]. For this model, the inventors tested as monotherapy COV2-2196 a neutralizing mAb encoded by the same variable gene segments as COV2-2196 but using a number of notable amino acid differences in the HCDR3 and LCDR3. Animals received one 50 mg/kg dose of mAb COV2-2196 or isotype control mAb intravenously on day −3 and then were challenged intranasally and intratracheally on day 0 with a dose of $1.1 \times 10^4$ PFU SARS-CoV-2. Following challenge, the inventors assessed viral RNA by RT-qPCR in bronchoalveolar lavage (BAL) and nasal swabs. High levels of subgenomic viral RNA were observed in the isotype control mAb-treated NHPs, with a median peak of 7.53 (range 5.37 to 8.23) $\log_{10}$ RNA copies/swab in nasal swab and a median peak of 4.97 (range 3.81 to 5.24) $\log_{10}$ RNA copies/mL in BAL. Subgenomic viral RNA was not detected in samples from the mAb treatment group (LOD=50 [1.7 $\log_{10}$] RNA copies/swab or per mL) showing protection. A pharmacokinetics analysis revealed stable concentrations of circulating human mAbs in NHPs.

NHP challenge study. The NHP research studies adhered to principles stated in the eighth edition of the Guide for the Care and Use of Laboratory Animals. The facility where this research was conducted (Bioqual Inc., Rockville, Md.) is fully accredited by the Association for Assessment and Accreditation of Laboratory Animal Care International (AAALAC) and has an approved Office of Laboratory Animal Welfare. NHP studies were conducted in compliance with all relevant local, state, and federal regulations and were approved by the relevant Institutional Animal Care and Use Committee (IACUC).

Eight healthy adult rhesus macaques (*Macaca mulatta*) of Indian origin (5 to 15 kg body weight) were studied. Animals were allocated randomly to the anti-SARS-CoV-2 mAb treatment group (n=4 per group) and one control (isotype-treated) group (n=4 per group). Animals received one 50 mg/kg dose of mAb COV2-2196 or isotype control mAb intravenously on day −3 and then were challenged in three days with $1.1 \times 10^4$ PFU SARS-CoV-2, administered as 1 mL by the i.n route and 1 mL by the intratracheal route. Following challenge, viral RNA was assessed by RT-qPCR in bronchoalveolar lavage and nasal swabs at multiple time points as described[5,6]. All animals were given physical examinations. In addition, all animals were monitored daily with an internal scoring protocol approved by the Institutional Animal Care and Use Committee. These studies were not blinded.

Detection of circulating human mAbs in NHP serum. ELISA plates were coated overnight at 4° C. with 1 µg/mL of goat anti-human IgG (H+L) secondary antibody (monkey pre-adsorbed) (Novus Biological) and then blocked for 2 hrs. The serum samples were assayed at 3-fold dilutions starting at a 1:3 dilution in Blocker Casein in PBS (ThermoFisher) diluent. Samples were incubated for 1 hr at ambient temperature and then removed, and plates were washed. Wells then were incubated for 1 hr with HRP-conjugated goat anti-Human IgG (monkey pre-adsorbed) (Southern Biotech) at a 1:4,000 dilution. Wells were washed and then incubated with SureBlue Reserve TMB Microwell Peroxidase Substrate (Seracare) (100 µL/well) for 3 min followed by TMB Stop Solution (Seracare) to stop the reaction (100 µL/well). Microplates were read at 450 nm. The concentrations of the human mAbs were interpolated from the linear range of purified human IgG (Sigma) standard curves using Prism software, version 8.0 (GraphPad).

Example 3

Materials and Methods for Example 4

Expression and purification of recombinant receptor binding domain (RBD) of SARS-CoV-2 spike protein. The DNA segments correspondent to the S protein RBD (residues 319-528) was sequence optimized for expression, synthesized, and cloned into the pTwist-CMV expression DNA plasmid downstream of the IL-2 signal peptide (MYRMQLLSCIALSLALVTNS) (Twist Bioscience). A three amino acid linker (GSG) and a His-tag were incorporated at the C-terminus of the expression constructs to facilitate protein purification. Expi293F cells were transfected transiently with the plasmid encoding RBD, and culture supernatants were harvested after 5 days. RBD was purified from the supernatants by nickel affinity chromatography with HisTrap Excel columns (GE Healthcare Life Sciences). For protein production used in crystallization trials, 5 µM kifunensine was included in the culture medium to produce RBD with high mannose glycans. The high mannose glycoproteins subsequently were treated with endoglycosidase F1 (Millipore) to obtain homogeneously deglycosylated RBD.

Expression and purification of recombinant COV2-2196 and COV2-2130 Fabs. The DNA fragments corresponding to the COV2-2196 and COV2-2130 heavy chain variable domains with human IgG1 CH1 domain and light chain variable domains with human kappa chain constant domain were synthesized and cloned into the pTwist vector (Twist Bioscience). This vector includes the heavy chain of each Fab, followed by a GGGGS linker, a furin cleavage site, a T2A ribosomal cleavage site, and the light chain of each Fab. Expression of the heavy and light chain are driven by the same CMV promoter. COV2-2196 and COV2-2130 Fabs were expressed in ExpiCHO cells by transient transfection with the expression plasmid. The recombinant Fab was purified from culture supernatant using an anti-CH1 CaptureSelect column (Thermo Fisher Scientific). For the RBD/COV2-2196 complex, the wt sequence of COV2-2196 was used for expression. For the RBD/COV2-2196/COV2-2130 complex, a modified version of COV2-2196 Fab was used in which the first two amino acids of the variable region were mutated from QM to EV.

Crystallization and structural determination of antibody-antigen complexes. Purified COV2-2196 Fab was mixed with deglycosylated RBD in a molar ratio of 1:1.5, and the mixture was purified further by size-exclusion chromatography with a Superdex-200 Increase column (GE Healthcare Life Sciences) to obtain the antibody-antigen complex. To obtain RBD/COV2-2196/COV2-2130 triple complex, purified and deglycosylated RBD was mixed with both COV2-2196 and COV2-2130 Fabs in a molar ratio of 1:1.5:1.5, and the triple complex was purified with a Superdex-200 Increase column. The complexes were concentrated to about 10 mg/mL and subjected to crystallization trials. The RBD/COV2-2196 complex was crystallized in 16%-18% PEG 3350, 0.2 Tris-HCl pH 8.0-8.5, and the RBD/COV2-2196/COV2-2130 complex was crystallized in 5% (w/v) PEG 1000, 100 mM sodium phosphate dibasic/citric acid pH 4.2, 40% (v/v) reagent alcohol. Cryo-protection solution was made by mixing crystallization solution with 100% glycerol in a volume ratio of 20:7 for crystals of both complexes. Protein crystals were flash-frozen in liquid nitrogen after a quick soaking in the cryo-protection solution. Diffraction data were collected at the beamline 21-ID-F for RBD/COV2-2196 complex and 21-ID-G for RBD/COV2-2196/COV2-2130 complex at the Advanced Photon Source. The diffraction data were processed with XDS[58] and CCP4 suite[59]. The crystal structures were solved by molecular replacement using the structure of RBD in complex with Fab CC12.1 (PDB ID 6XC2) and Fab structure of MR78 (PDB ID SJRP) with the program Phaser[60]. The structures were refined and rebuilt manually with Phenix[61] or Coot[62], respectively. The models have been deposited into the Protein Data Bank. PyMOL software' was used to make all of the structural figures.

Hydrogen deuterium mass spectrometry (HDX-MS) experiments. HDX-MS experiments were conducted using an automated sample handling robot (LEAP technologies, Fort Lauderdale, Fla., USA) coupled to an M-Class Acquity LC system and HDX manager (Waters Ltd., Wilmslow, UK). 7.6 µL of 4.3 µM SARS-CoV-2 S2P spike trimer either alone, or with a 1:1.12 molar ratio of AZD1061 or AZD8895 was added to 52.4 µL label buffer (50 mM potassium phosphate pD 6.2) and incubated for 1 min at 20° C. After incubation, 50 µL of this sample was added to 50 µL quench solution (50 mM potassium phosphate, 200 mM TCEP, 2 M Gdn-HCl, pH 2.3) at 1° C. 50 µL of quenched sample was passed through an immobilised BEH pepsin column (Waters Ltd., Wilmslow, UK) at 20° C. at 100 µL min$^{-1}$ (~4,000 psi) for 4 min before the resulting peptides were trapped using a Vanguard pre-column Acquity UPLC BEH C18 trap column (1.7 µm, 2.1 mm×5 mm, Waters Ltd., Wilmslow, UK). After valve switching, peptides were separated at 1° C. by gradient elution of 0 to 35% MeCN (0.2% v/v formic acid) in H$_2$O (0.2% v/v formic acid) over 6 minutes at 40 µL min$^{-1}$ using an Acquity UPLC BEH C18 analytical column (1.7 µm, 1 mm×100 mm). Peptides were analysed using an Orbitrap Fusion mass spectrometer (Thermo Fisher, Bremen, Germany) operating in either orbitrap detection mode at a resolution of 120K (deuterated samples) or orbitrap-iontrap DDA mode (t=0 samples). Peptide MS/MS data used to identify peptides was analysed using BioPharma Finder v3.0 (Thermo Fisher, Bremen, Germany) and deuterium uptake was quantified using HDExaminer v2.0 (Sierra Analytics). Peptide pool results and uptake summary table csv exports from HDExaminer were reformatted using an in-house R: script in order to generate uptake plot figures and structural heat maps using PAVED (University of Leeds)[64].

ELISA binding of COV2-2196 mutants. Wells of 384-well microtiter plates were coated with purified recombinant SARS-CoV-2 S 6P protein at 4° C. overnight. Plates were blocked with 2% non-fat dry milk and 2% normal goat serum in DPBS containing 0.05% Tween-20 (DPBS-T) for 1 h. Antibodies were diluted to 10 µg/mL and titrated two-fold 23 times in DPBS-T and added to the wells, followed by an incubation for 1 h at room temperature. The bound antibodies were detected using goat anti-human IgG conjugated with horseradish peroxidase (Southern Biotech) and TMB substrate (Thermo Fischer Scientific). Reactions were quenched with 1 N hydrochloric acid and absorbance was measured at 450 nm using a spectrophotometer (Biotek).

Mapping of all mutations that escape antibody binding. All mutations that escape antibody binding were mapped via a DMS approach[41]. The inventors used previously described yeast-display RBD mutant libraries41,42. Briefly, duplicate mutant libraries were constructed in the spike receptor binding domain (RBD) from SARS-CoV-2 (isolate Wuhan-Hu-1, Genbank accession number MN908947, residues N331-T531) and contain 3,804 of the 3,819 possible amino-acid mutations, with >95% present as single mutants. Each RBD variant was linked to a unique 16-nucleotide barcode sequence to facilitate downstream sequencing. As previously described, libraries were sorted for RBD expression and ACE2 binding to eliminate RBD variants that are completely misfolded or non-functional (i.e., lacking modest ACE2 binding affinity[41]).

Antibody escape mapping experiments were performed in biological duplicate using two independent mutant RBD libraries, as previously described[41], with minor modifications. Briefly, mutant yeast libraries induced to express RBD were washed and incubated with antibody at 400 ng/mL for 1 h at room temperature with gentle agitation. After the antibody incubations, the libraries were secondarily labeled with 1:100 FITC-conjugated anti-MYC antibody (Immunology Consultants Lab, CYMC-45F) to label for RBD expression and 1:200 PE-conjugated goat anti-human-IgG (Jackson ImmunoResearch 109-115-098) to label for bound antibody. Flow cytometric sorting was used to enrich for cells expressing RBD variants with reduced antibody binding via a selection gate drawn to capture unmutated SARS-CoV-2 cells labeled at 1% the antibody concentration of the library samples. For each sample, approximately 10 million RBD+ cells were processed on the cytometer. Antibody-escaped cells were grown overnight in SD-CAA (6.7 g/L Yeast Nitrogen Base, 5.0 g/L Casamino acids, 1.065 g/L IVIES acid, and 2% w/v dextrose) to expand cells prior to plasmid extraction.

Plasmid samples were prepared from pre-selection and overnight cultures of antibody-escaped cells (Zymoprep Yeast Plasmid Miniprep II) as previously described[41]. The 16-nucleotide barcode sequences identifying each RBD variant were amplified by PCR and sequenced on an Illumina HiSeq 2500 with 50 bp single-end reads as described[41,42].

Escape fractions were computed as described[41], with minor modifications as noted below. The inventors used the dms_variants package (jbloomlab.github.io/dms_variants/, version 0.8.2) to process Illumina sequences into counts of each barcoded RBD variant in each pre-sort and antibody-escape population using the barcode/RBD look-up table previously described[65].

For each antibody selection, the inventors computed the "escape fraction" for each barcoded variant using the deep sequencing counts for each variant in the original and antibody-escape populations and the total fraction of the library that escaped antibody binding via a previously described formula[41]. These escape fractions represent the estimated fraction of cells expressing that specific variant that fall in the antibody escape bin, such that a value of 0 means the variant is always bound by serum and a value of 1 means that it always escapes antibody binding. The inventors then applied a computational filter to remove variants with low sequencing counts or highly deleterious mutations that might cause antibody escape simply by leading to poor expression of properly folded RBD on the yeast cell surface[41,42]. Specifically, they removed variants that had (or contained mutations with) ACE2 binding scores<−2.35 or expression scores<−1, using the variant- and mutation-level deep mutational scanning scores as previously described[42]. Note that these filtering criteria are slightly more stringent than those previously used to map a panel of human antibodies[41] but are identical to those used in recent studies defining RBD residues that impact the binding of mAbs[65] and polyclonal serum[54].

The inventors next deconvolved variant-level escape scores into escape fraction estimates for single mutations using global epistasis models[66] implemented in the dms_variants package, as detailed at (jbloomlab.github.io/dms_variants/dms_variants.globalepistasis.html) and described[41]. The reported escape fractions throughout the paper are the average across the libraries (correlations shown in FIGS. 18A-B); these scores are also in Table B. Sites of strong escape from each antibody for highlighting in logo plots were determined heuristically as sites whose summed mutational escape scores were at least 10 times the median sitewise sum of selection, and within 10-fold of the sitewise sum of the most strongly selected site. Full documentation of the computational analysis is at github.com/jbloomlab/SARS-CoV-2-RBD_MAP_AZ_Abs. These results are also available in an interactive form at https://jbloomlab.github.io/SARS-CoV-2-RBD_MAP_AZ_Abs/.

Antibody escape selection experiments with VSV-SARS-CoV-2. For escape selection experiments with COV2-2196 and COV2-2130, The inventors used a replication competent recombinant VSV virus encoding the spike protein from SARS-CoV-2 with a 21 amino-acid C-terminal deletion[43]. The spike-expressing VSV virus was propagated in MA104 cells (African green monkey, ATCC CRL-2378.1) as described previously[43], and viral stocks were titrated on Vero E6 cell monolayer cultures. Plaques were visualized using neutral red staining. To screen for escape mutations selected in the presence of COV2-2196, COV2-2130, or a cocktail composed of a 1:1 mixture of COV2-2196 and COV2-2130, the inventors used a real-time cell analysis assay (RTCA) and xCELLigence RTCA MP Analyzer (ACEA Biosciences Inc.) and a previously described escape selection scheme[41]. Briefly, 50 µL of cell culture medium (DMEM supplemented with 2% FBS) was added to each well of a 96-well E-plate to obtain a background reading. Eighteen thousand (18,000) Vero E6 cells in 50 µL of cell culture medium were seeded per well, and plates were placed on the analyzer. Measurements were taken automatically every 15 min and the sensograms were visualized using RTCA software version 2.1.0 (ACEA Biosciences Inc). VSV-SARS-CoV-2 virus (5e3 plaque forming units (PFU) per well, ~0.3 MOI) was mixed with a saturating neutralizing concentration of COV2-2196, COV2-2130, or a 1:1 mixture of COV2-2196 and COV2-2130 antibody (5 µg/mL total concentration of antibodies) in a total volume of 100 µL and incubated for 1 h at 37° C. At 16-20 h after seeding the cells, the virus-antibody mixtures were added to cell monolayers. Wells containing only virus in the absence of antibody and wells containing only Vero E6 cells in medium were included on each plate as controls. Plates were measured continuously (every 15 min) for 72 h. Escape mutations were identified by monitoring the cell index for a drop in cellular viability. To verify escape from antibody selection, wells where cytopathic effect was observed in the presence of COV2-2130 were assessed in a subsequent RTCA experiment in the presence of 10 µg/mL of COV2-2130 or COV2-2196. After confirmation of resistance of selected viruses to neutralization by COV2-2130, viral isolates were expanded on Vero E6 cells in the presence of 10 µg/mL of COV2-2130. Viral RNA was isolated using a QiAmp Viral RNA extraction kit (QIAGEN) according to manufacturer protocol, and the SARS-CoV-2 spike gene was reverse-transcribed and amplified with a SuperScript IV One-Step RT-PCR kit (ThermoFisher Scientific) using primers flanking the S gene. The amplified PCR product was purified using SPRI magnetic beads (Beckman Coulter) at a 1:1 ratio and sequenced by the Sanger method, using primers giving forward and reverse reads of the RBD.

Serial passaging and testing of SARS-CoV-2 to select for mAb resistant mutations. SARS-CoV-2 strain USA-WA1/2020 was passaged serially in Vero cell monolayer cultures with AZD8895, AZD1061 or AZD7442, at concentrations beginning at their respective $IC_{50}$ values and increased stepwise to their $IC_{90}$ value with each passage. As a control, virus was passaged in the absence of antibody. Following the final passage, viruses were evaluated for susceptibility against the reciprocal antibody at a final concentration of 10 times the $IC_{90}$ concentration by plaque assay. Plaques (n=6) were selected randomly for AZD1061 cultures, and their virus spike-encoding gene was sequenced.

Isolation or generation of authentic SARS-CoV-2 viruses, including viruses with variant residues. The UK B.1.1.7-OXF isolate was obtained from a nasopharyngeal swab from an infected individual in Kent, England. The clinical studies to obtain specimens after written informed consent were approved by John Radcliffe Hospital in Oxford, U.K. The sample was diluted in DMEM with 2% FBS and passed through a 0.45 µm filter before adding to monolayers of Vero-hACE2-TMPRSS2 cells (a gift of A. Creanga and B. Graham). Two days later, supernatant was harvested to establish a passage zero (p0) stock. The 2019n-CoV/USA_WA1/2019 isolate of SARS-CoV-2 was obtained from the U.S. Centers for Disease Control (CDC) and passaged on Vero E6 cells. Individual point mutations in the spike gene (D614G and E484K/D614G) were introduced into an infectious cDNA clone of the 2019n-CoV/USA_WA1/2019 strain as described previously[67]. Nucleotide substitutions were introduced into a subclone puc57-CoV-2-F6 containing the spike gene of the SARS-CoV-2 wild-type infectious clone[68]. The full-length infectious cDNA clones of the variant SARS-CoV-2 viruses were assembled by in vitro ligation of seven contiguous cDNA fragments following the previously described protocol[68]. In vitro transcription then was performed to synthesize full-length genomic RNA. To recover the mutant viruses, the RNA transcripts were electroporated into Vero E6 cells. The viruses from the supernatant of cells were collected 40 h later and served as p0 stocks. All virus stocks were confirmed by sequencing.

Focus reduction neutralization test. Serial dilutions of mAbs or serum were incubated with $10^2$ focus-forming units (FFU) of different strains or variants of SARS-CoV-2 for 1 h at 37° C. Antibody-virus complexes were added to Vero-hACE2-TMPRSS2 cell monolayer cultures in 96-well plates and incubated at 37° C. for 1 h. Subsequently, cells were overlaid with 1% (w/v) methylcellulose in MEM supplemented with 2% FBS. Plates were harvested 20 h later by removing overlays and fixed with 4% PFA in PBS for 20 min at room temperature. Plates were washed and sequentially incubated with an oligoclonal pool of anti-S mAbs and HRP-conjugated goat anti-human IgG in PBS supplemented with 0.1% saponin and 0.1% bovine serum albumin. SARS-CoV-2-infected cell foci were visualized using TrueBlue peroxidase substrate (KPL) and quantitated on an Immuno-Spot microanalyzer (Cellular Technologies).

Multiple sequence alignments. The inventors searched for antibody variable gene sequences originating with the same features as those encoding COV2-2196 and retrieved the matching sequences from the repertoires of each individual examined. They searched for similar sequences in the publicly available large-scale antibody sequence repertoires for three healthy individuals and cord blood repertoires (deposited at SRP174305). The search parameters for the heavy chain were sequences with IGHV1-58 and IGHJ3 with the P99, D108, and F110 residues. Additionally, the search parameters for the light chain were sequences with Y92 and W98 residues. Sequences from a matching clonotype that belonged to each individual were aligned with either ClustalO (heavy chains) or with MUSCLE (light chains). Then, LOGOs plots of aligned sequences were generated using WebLogo.

Data and materials availability: The crystal structures reported in this paper have been deposited to the Protein Data Bank under the accession numbers 7L7D, 7L7E. Sequence Read Archive deposition for the aligned human antibody gene repertoire data set is deposited at the NCBI: PRJNA511481. All other data are available in the main text or the supplementary materials.

Software availability. The computational pipeline for the deep mutational scanning analysis of antibody escape mutations is available on GitHub: github.com/jbloomlab/SARS-CoV-2-RBD_MAP_AZ_Abs. The FASTQ files are available on the NCBI Sequence Read Archive under BioSample SAMN17532001 as part of BioProject PRJNA639956. Permutation escape fractions are available on GitHub (github.com/jbloomlab/SARS-CoV-2-RBD_MAP_AZ_Abs/blob/main/results/supp_data/AZ_cocktail_raw_data.csv) and in Table B.

Example 4

Result and Discussion

Figures 8A, 8B, 8C:
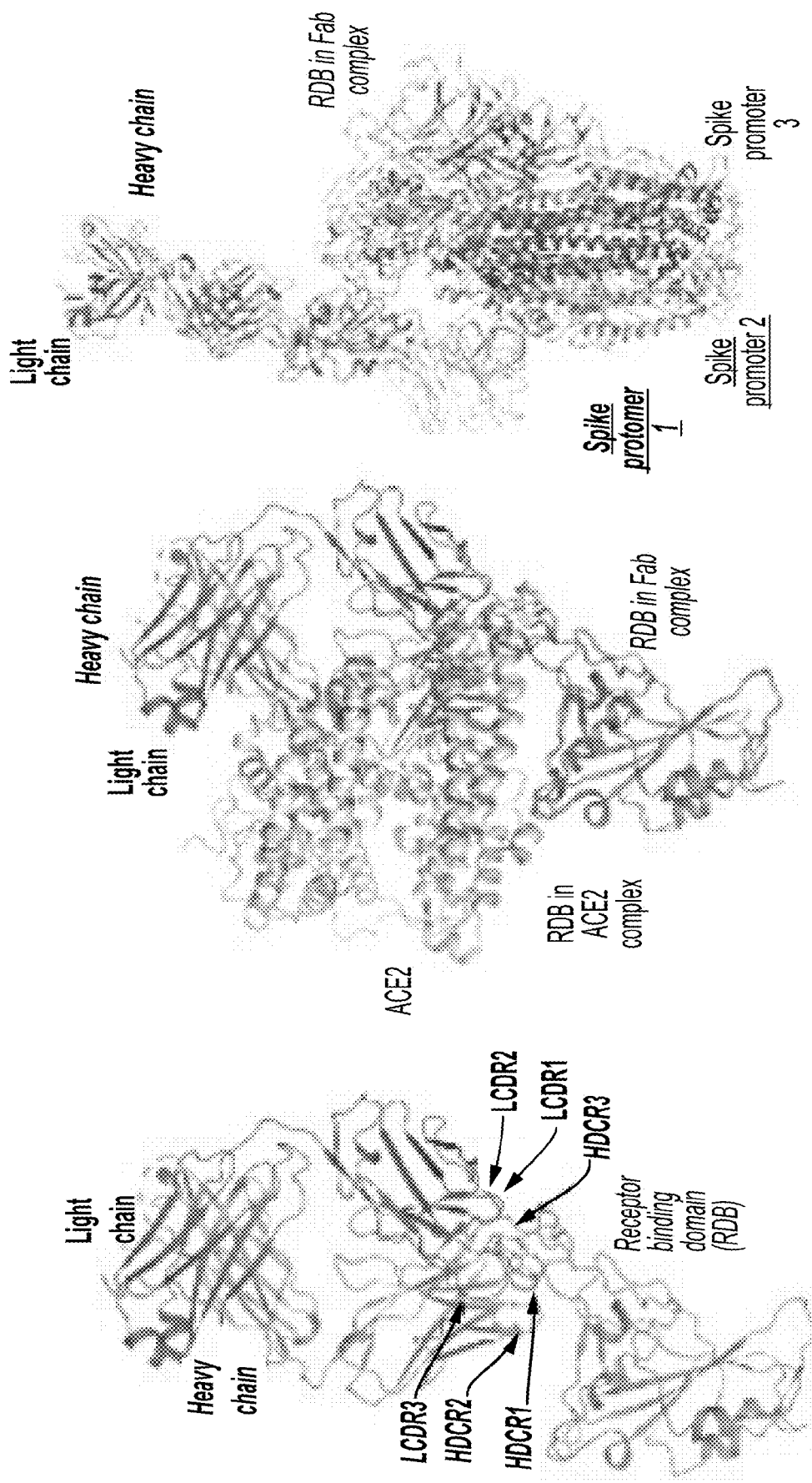
FIGS. 8A-E. Crystal structure of S protein RBD in complex with Fab COV2-2196.
Figures 8D, 8E:
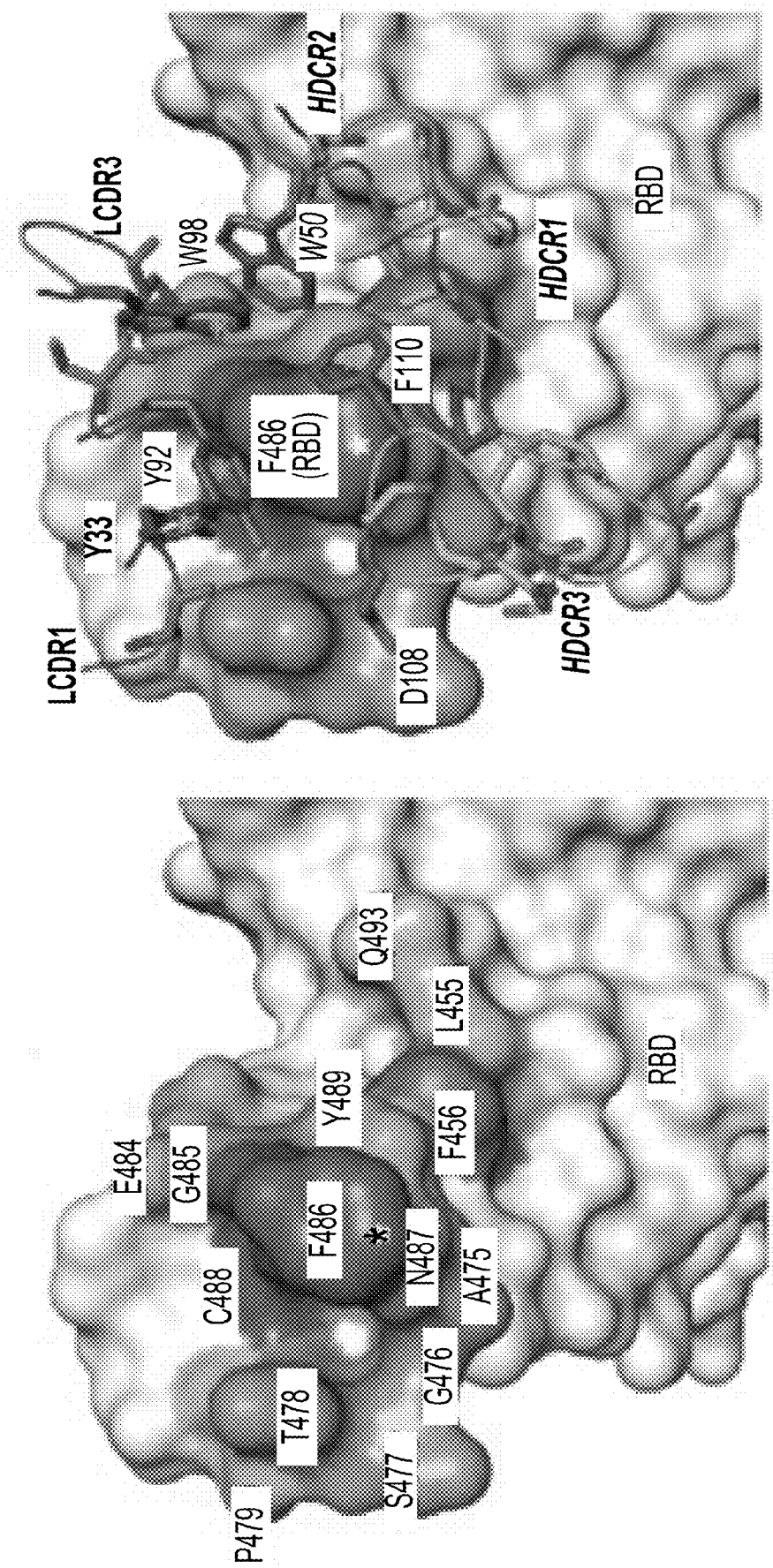
Figure 13B:
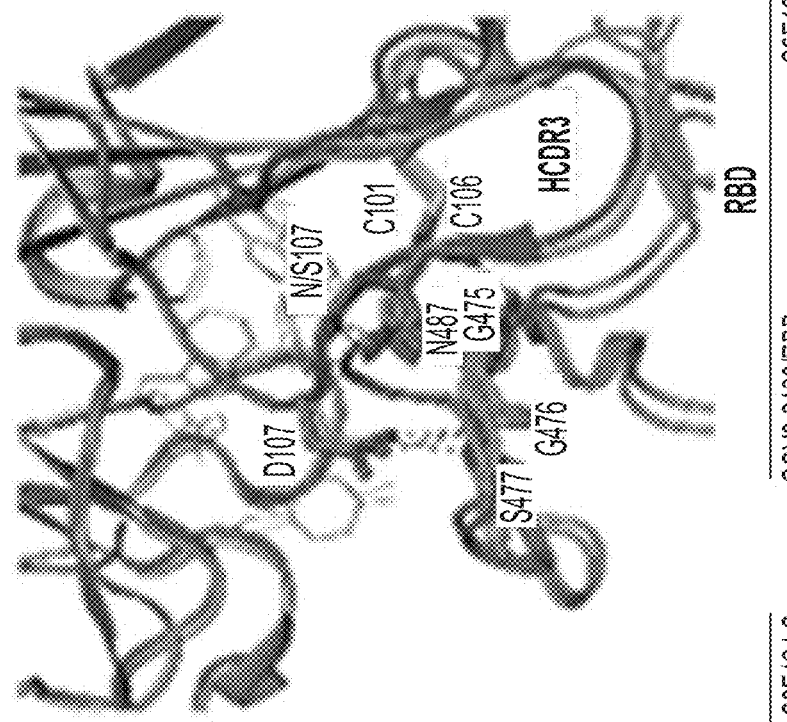
Figure 13A:
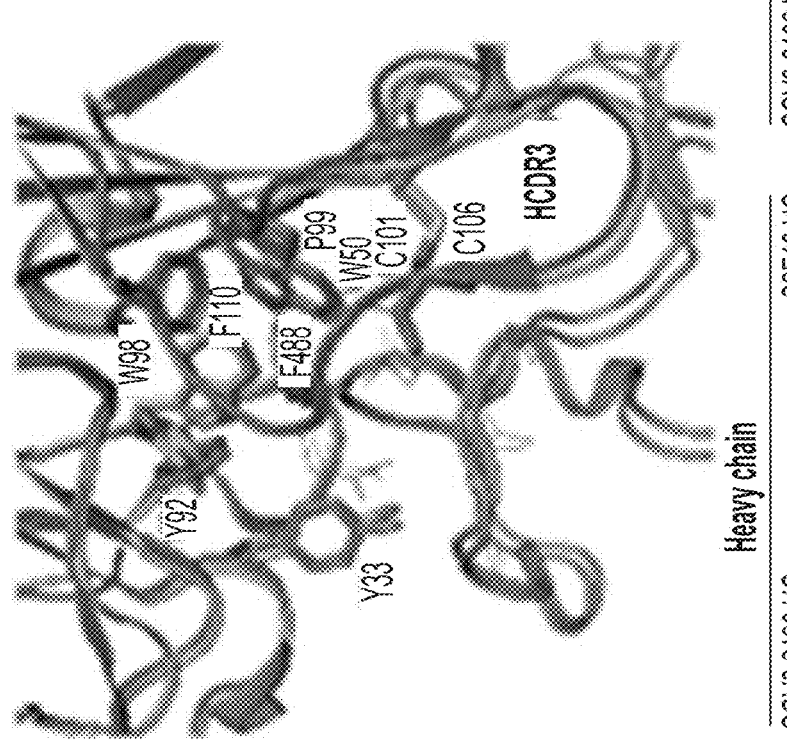
Figure 13D:
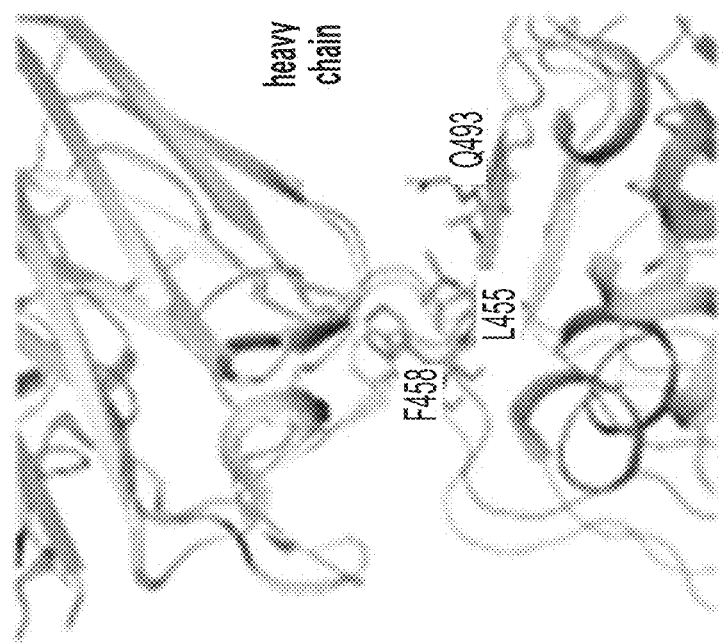
Figure 13C:
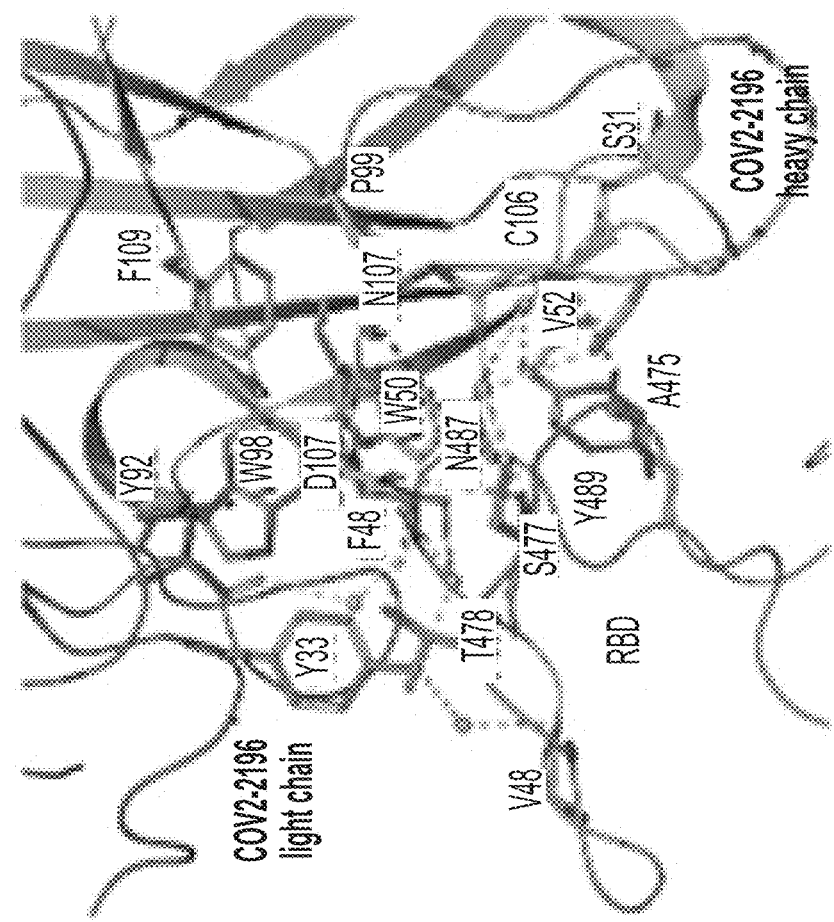

An antibody based on COV2-2196 is being investigated for prophylaxis or therapy in combination with an antibody based on the non-competing RBD-specific antibody COV2-2130. To understand the molecular details of the recognition of RBD by COV2-2196 and COV2-2130, and possible structural mechanisms underlying the synergy shown in the prophylactic protection of the two noncompeting mAbs in animal models[1], the inventors determined the crystal structures of the S protein RBD in complex with COV2-2196 at 2.50 Å (FIGS. 8A-E, Table B) and in complex with both COV2-2196 and COV2-2130 at 3.00 Å (FIGS. 9A-F, Table B). The substructure of RBD-COV2-2196 in the RBD-COV2-2196-2130 complex is superimposable with the structure of the RBD-COV2-2196 complex (FIG. 12). The buried surface area of the interface between COV2-2196 and the RBD is about 650 Å$^2$ in both crystal structures, and that of the interface between COV2-2130 and RBD is about 740 Å$^2$. COV2-2196 binds to the receptor-binding ridge of RBD, and COV2-2130 binds to one side of the RBD edge around residue K444 and the saddle region of the receptor binding motif (RBM), overlapping the ACE2 binding site (FIGS. 8A-B, FIGS. 9A-B). These features explain the competition between the antibodies and ACE2 for RBD binding from our previous study, e.g., both COV2-2196 and COV2-2130 neutralize the virus by blocking RBD access to the human receptor ACE2[1]. Aromatic residues from the COV2-2196 heavy and light chains form a hydrophobic pocket that surrounds RBD residue F486 and adjacent residues (G485, N487) (FIGS. 8A, 8D and 8E; FIGS. 13A-C). This mode of Ab-Ag interaction is unusual in that the formation of the antibody pocket is caused by wide spatial separation of the HCDR3 and LCDR3. In addition, although the antigenic site recognized by COV2-2196 is not buried at the interface between protomers of S trimer per se, COV2-2196 is not able to bind RBD in the "down" conformation due to steric clashes with RBD in an adjacent S protomer. Therefore, COV2-2196 only binds to RBD in the "up" conformation (FIG. 8C). Overlays of the substructure of RBD in complex with COV2-2130 (FIG. 9C) and the structure of RBD in complex with both COV2-2196 and COV2-2130 (FIG. 9D) indicate that COV2-2130 is able to bind RBD in both "up" and "down" conformations of the S trimer. These structural findings are consistent with our previous lower resolution results for the complex using negative stain electron microscopy[1].

Structural analysis of COV2-2196 in complex with RBD reveals how COV2-2196 recognizes the receptor-binding ridge on the RBD. One of the major contact residues, F486, situates at the center of the binding site, interacting extensively with the hydrophobic pocket (residue P99 of heavy chain and an "aromatic cage" formed by 5 aromatic side chains) between COV2-2196 heavy/light chains via a hydrophobic effect and van der Waals interactions (FIGS. 8D-E, FIGS. 13A-B). A hydrogen bond (H-bond) network, constructed with 4 direct Ab-Ag H-bonds and 16 water-mediated H-bonds, surround residue F486 and strengthen the Ab-Ag interaction (FIG. 13C). Importantly, for all residues except one (residue P99 of the heavy chain) that interact extensively with the epitope, they are encoded by germline sequences (IGHV1-58*01 and IGHJ3*02 for the heavy chain, IGKV3-20*01 and IGKJ1*01 for the light chain) (FIG. 10A) or only their backbone atoms are involved in the Ab-Ag interactions, such as heavy chain N107 and G99 and light chain S94. The inventors noted another antibody in the literature, S2E12, that is encoded by the same IGHV/IGHJ and IGKV/IGKJ recombinations, with similar but most likely different IGHD genes to those of COV2-2196 (IGHD2-15 vs IGHD2-2)[38]. A comparison of the cryo-EM structure of S2E12 in complex with S protein (PDB 7K4N) suggests that the mAb S2E12 likely uses nearly identical Ab-Ag interactions as those of COV2-2196, although variations in conformations of interface residue side-chains can be seen (FIG. 13D). For example, for light chain residue Y92, the phenyl ring in the crystal structure is perpendicular to that ring in the EM structure as fitted.

Figure 14E:
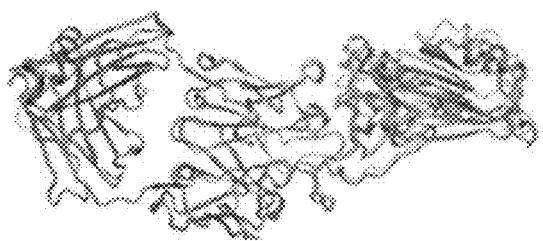

The inventors searched genetic databases to determine if these structural features are present in additional SARS-CoV-2 mAbs isolated by others and found additional members of the clonotype (FIG. 10A). Two other studies reported the same or a similar clonotype of antibodies isolated from multiple COVID-19 convalescent patients[4,38], and one study found three antibodies with the same IGHV1-58 and IGKV3-20 pairing, without providing information on D or J gene usage[39]. All of these antibodies are reported to bind SARS-CoV-2 RBD avidly and to neutralize virus with high potency[1,4,38,39]. So far, there are only two atomic resolution structures of antibodies encoded by these $V_H(D_H)J_H$ and $V_K$-$J_K$ recombinations available, the structure for COV2-2196 presented here and that for S2E12[38]. The inventors performed homology modeling for two additional antibodies of this clonotype from our own panel of anti-SARS-CoV-2 antibodies, designated COV2-2072 and COV2-2381. As expected, given that these antibodies are members of a shared genetic clonotype, the modeled structures of COV2-2072/RBD and COV2-2381/RBD complexes are virtually superimposable with those of COV2-2196/RBD and S2E12/RBD at the Ab-Ag interfaces (FIGS. 14A-E). Additionally, COV2-2072 encodes an N-linked glycosylation sequon in the HCDR3 (FIG. 14D), an unusual feature for antibodies, given that glycosylation of CDRs might adversely affect antigen recognition. However, the COV2-2196 structure shows that the disulfide-stapled HCDR3 in this clonotype is angled away from the binding site, explaining how this unusual HCDR3 glycosylation in COV2-2072 can be tolerated without compromising binding (FIG. 14E).

The inventors next determined whether they could identify potential precursors of this public clonotype in the antibody variable gene repertoires of circulating B cells from SARS-CoV-2-naïve individuals. The inventors searched for the V(D)J and VJ genes in previously described comprehensive repertoire datasets originating from 3 healthy human donors, without a history of SARS-CoV-2 infection, and in datasets from cord blood collected prior to the COVID-19 pandemic[40]. A total of 386, 193, 47, or 7 heavy chain sequences for this SARS-CoV-2 reactive public clonotype was found in each donor or cord blood repertoire, respectively (FIG. 15A). Additionally, the inventors found 516,738 human antibody sequences with the same light chain V-J recombination (IGKV3-20-IGKJ1*01). A total of 103,534, 191,039, or 222,165 light chain sequences was found for this public clonotype in each donor respectively. Due to the large number of sequences, the top five abundant sequences were aligned from each donor. Multiple sequence alignments were generated for each donor's sequences using ClustalOmega, and logo plots were generated. The top 5 sequences with the same recombination event in each donor were identical, resulting in the same logo plots (FIGS. 15A-B).

Figure 10B:
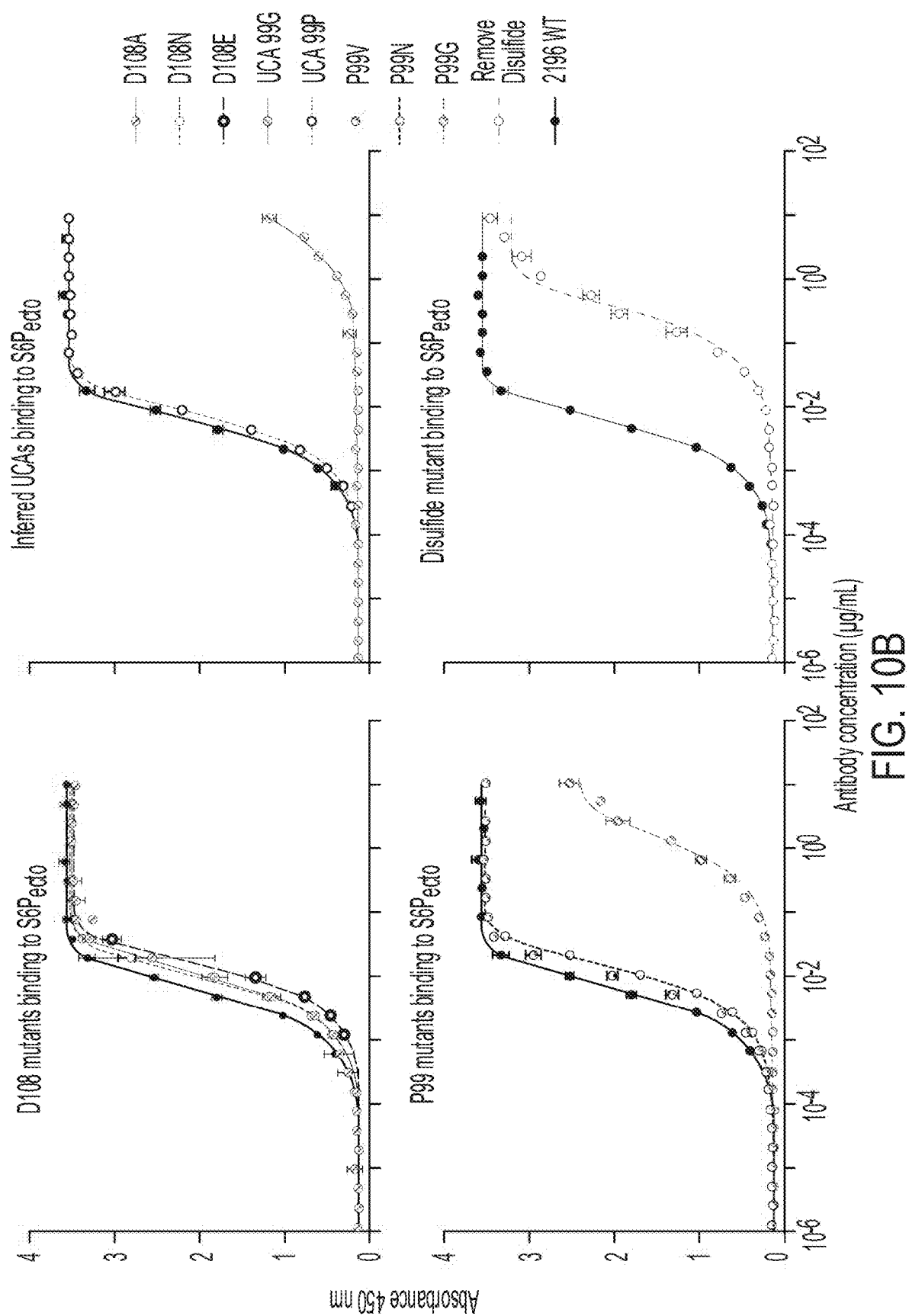

The inventors noted that 8 of the 9 common residues important for binding in the antibody were encoded by germline gene sequences, and all were present all 14 members of the public clonotype listed here from four different antibody-discovery teams (FIG. 10A). To validate the importance of these features, they expressed variant antibodies with point mutations in the paratope to determine the effect of variation at conserved residues (FIG. 10B). Altering the D108 residue to A, N, or E had little effect, but removing the disulfide bond in the HCDR3 that rigidifies that loop reduced binding. The P99 residue that orients the HCDR3 loop away from the interaction site with antigen also was important, as a P99G mutant exhibited reduced binding, and the germline revertant form of COV2-2196 with P99 bound to antigen, but P99G in the germline revertant background did not (FIG. 10B).

Figure 13E:
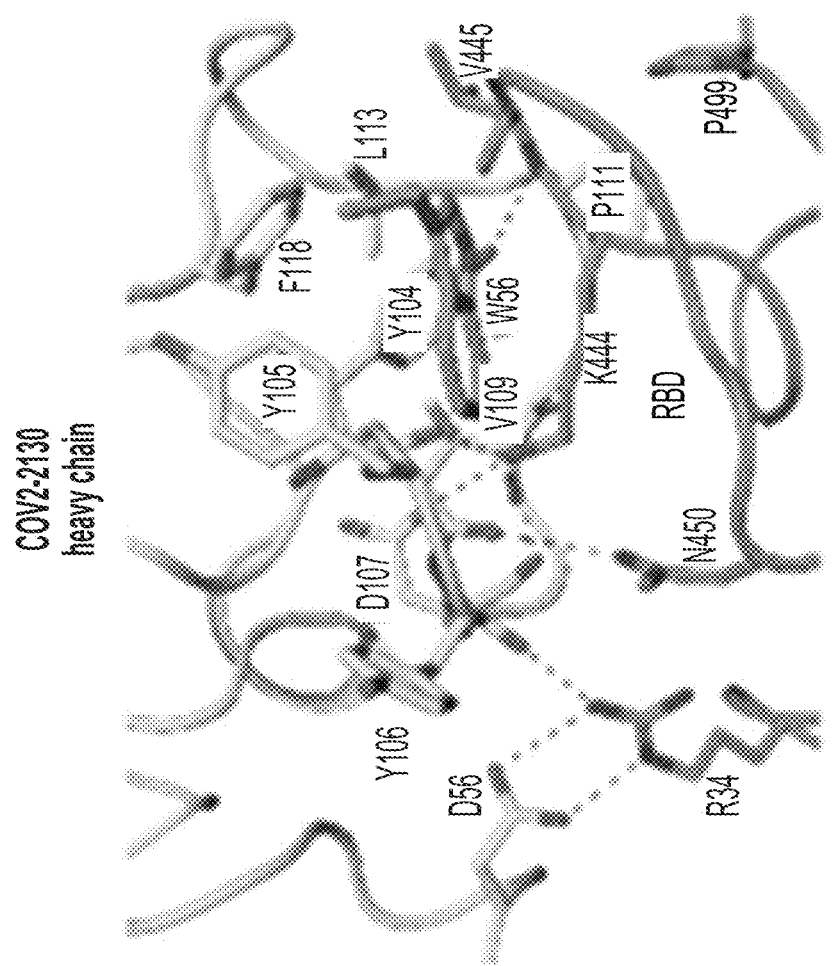
Figure 13F:
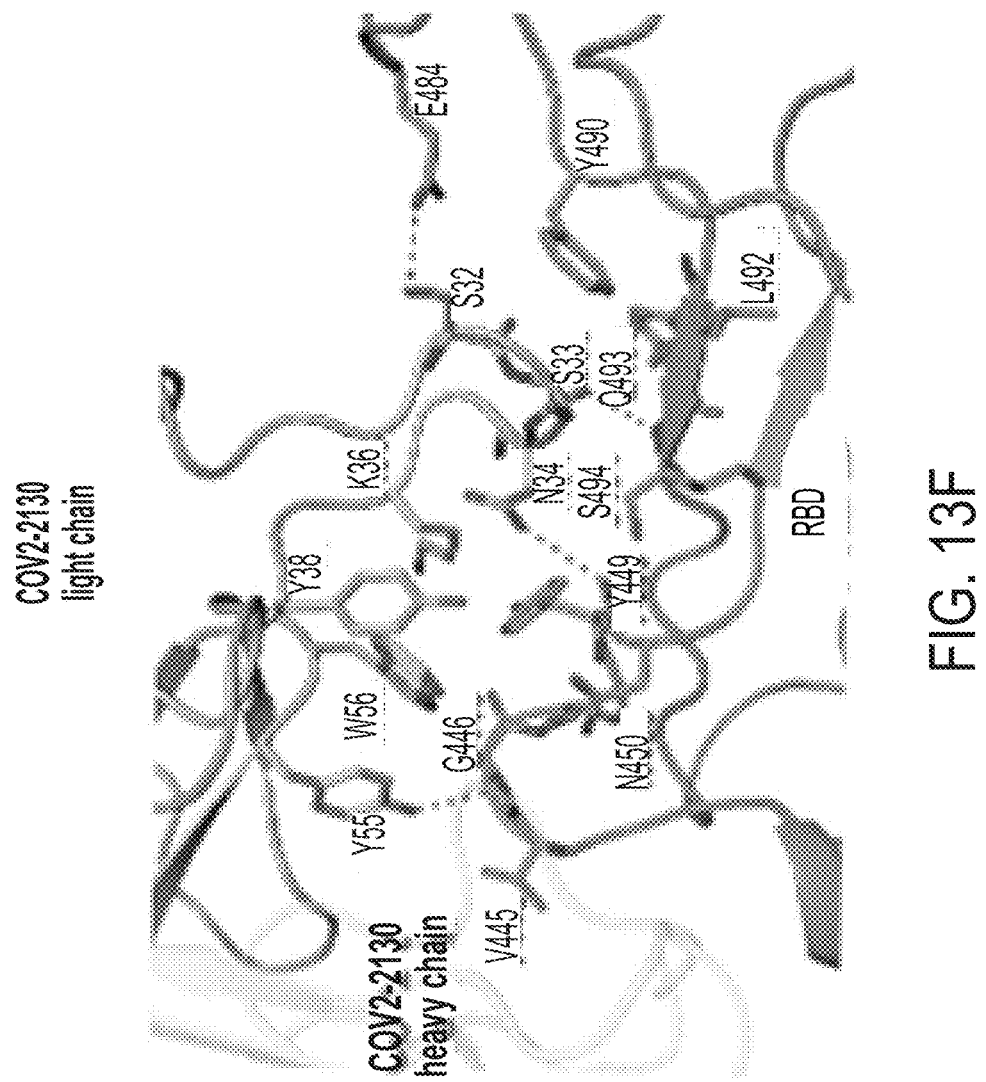
Figures 16C, 16D:
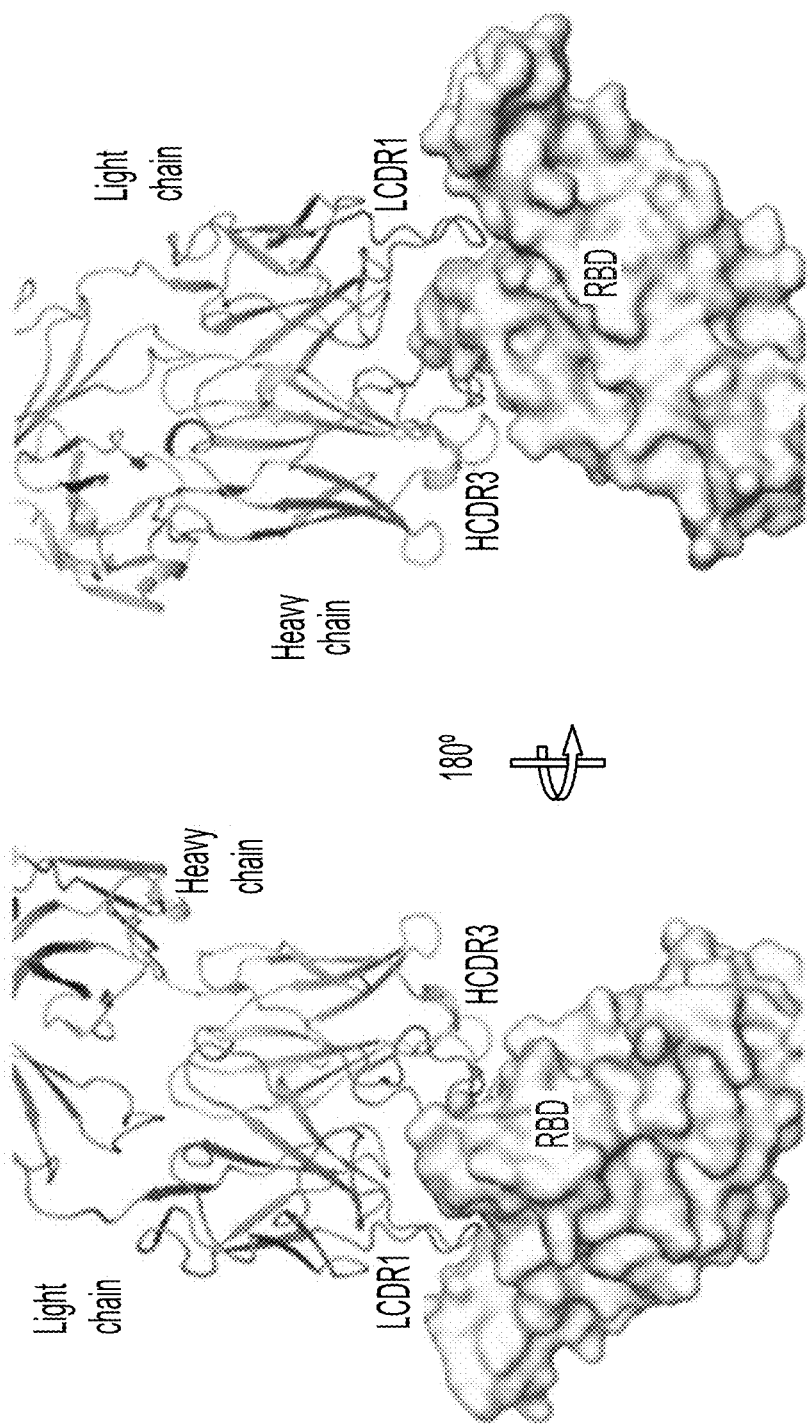

An antibody based on the COV2-2196 variable region is being tested in combination with an antibody based on the COV2-2130 variable region in clinical trials. The COV2-2130 HCDR3, with 22 amino acid residues, is relatively long for human antibodies, and highly mutated from the inferred germline IGHD3 gene. The HCDR3 forms a long, structured loop made up of small loops, is stabilized by short-ranged hydrogen bonds and hydrophobic interactions/aromatic stackings within the HCDR3, and is further strengthened by its interactions (hydrogen bonds and aromatic stackings) with residues of the light chain (FIGS. 16A-B). The COV2-2130 heavy and light chains are encoded by the germline genes IGHV3-15 and IGKV4-1, respectively, and the two genes encode the longest germline-encoded HCDR2 (10 aa) and LCDR1 (12 aa) loops, which are used in COV2-2130. The heavy chain V(D)J recombination, HCDR3 mutations, and the pairing of heavy and light chains result in a binding cleft between the heavy and light chains, matching the shape of the RBD region centered at S443-Y449 loop (FIG. 9A, FIG. 16C). Closely related to these structural features, only HCDR3, LCDR1, HCDR2, and LCDR2 are involved in the formation of the paratope (FIGS. 9E-F, FIGS. 13E-F). Inspection of the Ab-Ag interface reveals a region that likely drives much of the energy of interaction. The RBD residue K444 sidechain is surrounded by subloop Y104-V109 of the HCDR3 loop, and the positive charge on the side chain NZ atom is neutralized by the HCDR3 residue D107 side chain, three mainchain carbonyl oxygen atoms from Y105, D107, and V109, and the electron-rich face of the Y104 phenyl ring (cation-π interaction) (FIG. 13E). Since the interacting atoms are completely protected from solvent, the highly concentrated interactions within such a restricted space are energetically favorable. Furthermore, this "hotspot" of the Ab-Ag interface is surrounded by or protected from the solvent by Ab-Ag interactions with lesser free energy gains, including salt bridge between the RBD residue R346 and HCDR2 D56, electrostatic interaction between RBD R346 and the mainchain oxygen of HCDR3 Y106, a hydrogen bond between RBD N450 and HCDR3 Y105 mainchain oxygen, a hydrogen bond between RBD V445 mainchain oxygen and HCDR3 Y104 sidechain, a hydrophobic interaction between V445 sidechain and sidechains of HCDR3 L113 and F118 (FIG. 13E). Also, aromatic stacking between the HCDR3 residue Y105 and LCDR2 residue W56 participates in the shielding of the "hotspot" from solvent (FIG. 13E). In addition, COV2-2130 light chain LCDR1 and LCDR2 make extensive contacts with the RBD. Among them, the LCDR1 S32 sidechain, S33 mainchain oxygen, N34 sidechain, and LCDR2 Y55 sidechain form hydrogen bonds with RBD E484 sidechain, S494 mainchain nitrogen, Y449 mainchain oxygen, and G446 mainchain nitrogen (FIG. 13F). Residues LCDR1 K36, Y38, and LCDR2 W56 interact with the RBD Y449 via aromatic stackings and cation-π interactions, forming an "interaction cluster" (FIG. 13F), although these interactions are likely not energetically as strong as in the case of RBD K444.

In the crystal structure of the RBD in complex with both COV2-2196 and COV2-2130, the inventors noted an interaction between the closely spaced COV2-2196 and COV2-2130 Fabs (FIG. 17). It is possible that the interactions between the two Fabs in the RBD-bound state could contribute to the synergistic neutralization of SARS-CoV-2 observed previously[1]. However, it is not clear how much of the synergy effect could be attributed to this Fab-Fab interaction.

Figure 11B:
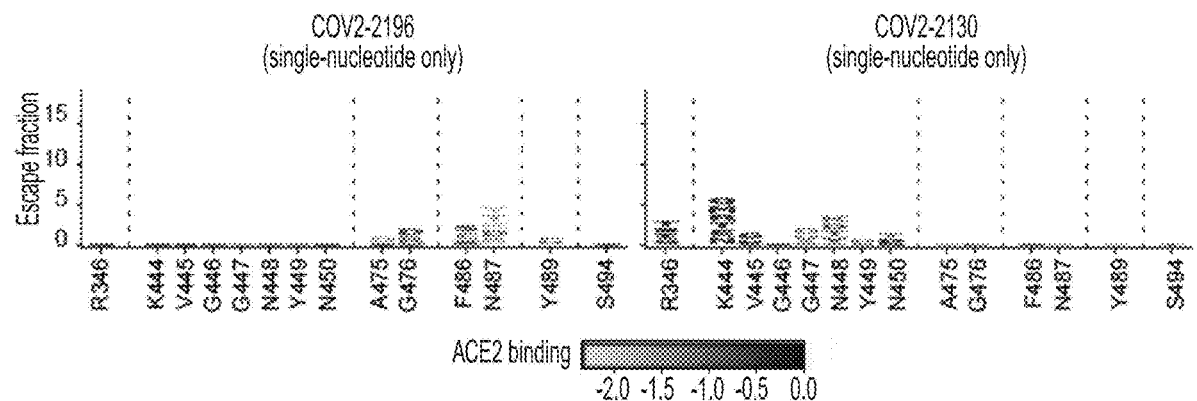
Figure 11C:
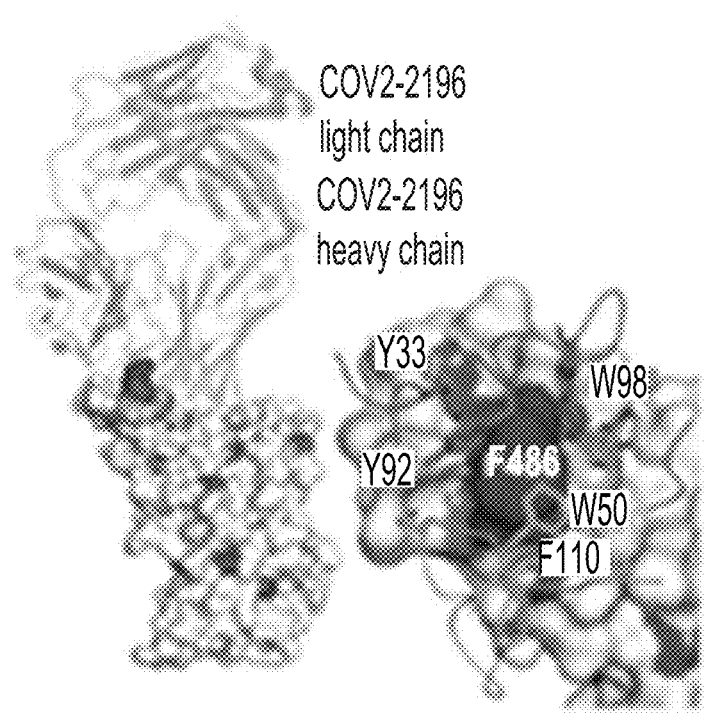
Figure 11D:
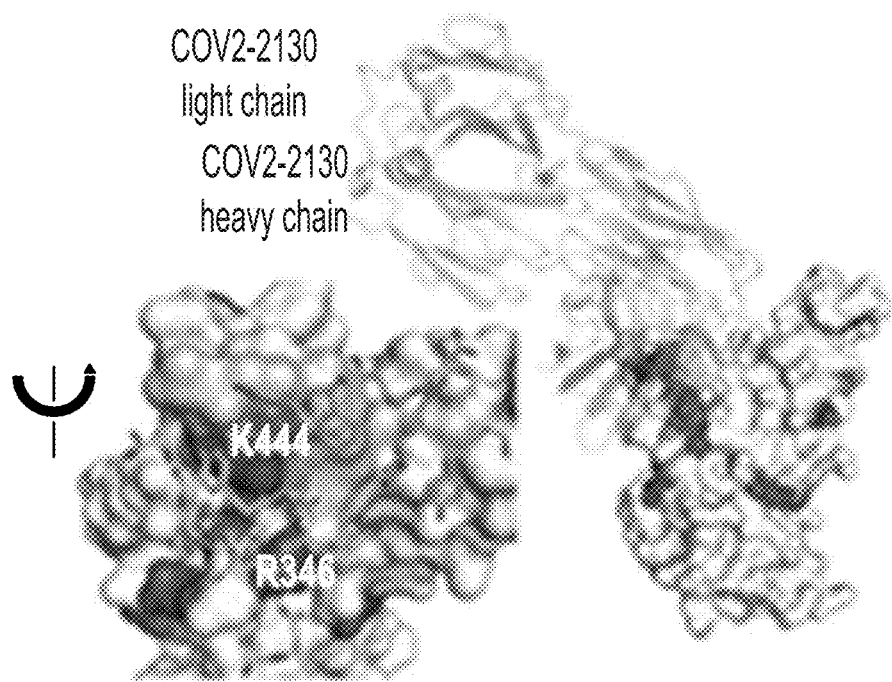

To better understand the RBD sites critical for binding of COV2-2196 and COV2-2130, the inventors used a deep mutational scanning (DMS) approach to map all mutations to the RBD that escape antibody binding[41]; (FIG. 18). For both antibodies, they identified several key sites, all in the antibody structural footprint, where RBD mutations strongly disrupted binding (FIGS. 11A-D). The inventors leveraged our previous work quantifying the effects of RBD mutations on ACE2 binding[42] to overlay the effect on ACE2 binding for mutations that abrogated antibody binding to RBD (FIGS. 11A-B). For COV2-2196, many mutations to F486 and N487 had escape fractions approaching 1 (i.e., those RBD variants completely escaped antibody binding under the conditions tested), reinforcing the importance of the contributions of these two residues to antibody binding. Similarly, for COV2-2130, mutation at site K444 to any of the other 19 amino acids abrogated antibody binding, indicating that the lysine at this position is critical to the Ab-Ag interaction.

Nevertheless, not all antibody contact residues were identified as sites where mutations greatly reduced binding. Several explanations are possible: 1) some binding site residues may be not critical for binding, 2) some residues may use their backbone atoms to interact with their side chain pointing away from the binding interface, or 3) mutations to some sites may not be tolerated[42]. For instance, residues L455, F456, and Q493 are part of the structurally-defined binding site for COV2-2196 (FIG. 8D), but mutations to these sites did not impact antibody binding detectably (FIGS. 11A and 11C), suggesting that these residues do not make critical binding contributions. Superimposition of the COV2-2196/RBD structure onto the S2E12/RBD structure clearly demonstrates a flexible hinge region between the RBD ridge and the rest of the RBD that is maintained when antibody is bound (FIG. 13D). This finding indicates that mutations at these three positions could be well tolerated for Ab-Ag binding and supports the non-essential nature of these particular residues for COV2-2196 or S2E12 binding.

Importantly, COV2-2196 and COV2-2130 do not compete for binding to the RBD[1], suggesting they could comprise an escape-resistant cocktail for prophylactic or therapeutic use. Indeed, the structural binding sites and escape variant maps for these two antibodies are non-overlapping. To test whether there were single mutations that could escape binding of both antibodies, the inventors performed escape variant mapping experiments with a 1:1 mixture of the COV2-2196 and COV2-2130 antibodies, but they did not detect any mutation that had an escape fraction of greater than 0.2, whereas the mutations with the largest effects for each of the single antibodies was approximately 1 (FIG. 18D).

Although these experiments map all mutations that escape antibody binding to the RBD, the inventors also sought to determine which mutations have the potential to arise during viral growth. To address this question, they first attempted to select escape mutations using a recombinant VSV expressing the SARS-CoV-2 S glycoprotein (VSV-SARS-CoV-2)[43]; (FIG. 11E). The inventors expected that the only amino acid mutations that would be selected during viral growth were those 1) arising by single-nucleotide RNA changes, 2) causing minimal deleterious effect on ACE2 binding and expression, and 3) substantially impacting antibody binding[41,42]. Indeed, the inventors did not detect any COV2-2196-induced mutations that were both single-nucleotide accessible and relatively well-tolerated with respect to effects on ACE2 binding (FIG. 11B), which may explain why escape mutants were not selected in any of the 88 independent replicates of recombinant VSV growth in the presence of antibody (FIG. 11E, FIG. 18G). For COV2-2130, mutations to site K444, a site that is relatively tolerant to mutation[42], demonstrated the most frequent escape of antibody binding in the high-throughput antibody escape selection with the VSV chimeric virus. In 40% of the antibody selection experiments, two of the single-nucleotide mutations with the greatest effects on antibody binding, K444R (selected in 6 out of 20 replicates) and K444E (selected in 2 out of 20 replicates) emerged during viral growth (FIG. 11E, FIG. 18G).

To explore resistance with authentic infectious virus, SARS-CoV-2 strain USA-WA1/2020 was passaged serially in Vero cell monolayer cultures with the clinical antibodies based on COV2-2196 (AZD8895), COV2-2130 (AZD1061) or their 1:1 combination (AZD7442), at concentrations beginning at their respective $IC_{50}$ values and increased step-wise to their $IC_{90}$ value with each passage (FIG. 19). As a control, virus was passaged in the absence of antibody. Following the final passage, viruses were evaluated for susceptibility against the reciprocal antibody at a final concentration of 10 times the $IC_{90}$ concentration by plaque assay. The inventors did not detect any plaques resistant to neutralization by AZD8895 (based on COV2-2196) or the AZD7442 cocktail. Virus that was passaged serially in AZD1061 formed plaques to a titer of $1.2 \times 10^7$ pfu/mL in the presence of 10 times the $IC_{90}$ value concentration of AZD1061, but plaques were not formed with AZD7442. Plaques (n=6) were selected randomly, and their virus spike-encoding gene was sequenced, revealing the same 3 amino acid changes in all 6 of the independently selected and sequenced plaques: N74K, R346I and S686G (FIG. 11F). The S686G change has been reported previously to be associated with serial passaging of SARS-CoV-2 in Vero cells[44], isolated from challenge studies in ferrets[45] or NHPs[46], and is predicted to decrease furin activity[44]. The N74K residue is located in the N-terminal domain outside of the AZD1061 binding site and results in the loss of a glycan[47]. The R346I residue is located in the binding site of AZD1061 and may be associated with AZD1061-resistance. The impact of the R346I changes on AZD1061 (COV2-2130) binding to S protein is shown in FIG. 11G. The K444R and K444E substitutions selected in the VSV-SARS-CoV-2 system and the R346I substitution selected by passage with authentic SARS-CoV-2 are accessible by single nucleotide substitution and preserve ACE2 binding activity (FIG. 11G), indicating that our DMS analysis predicted the mutations selected in the presence of COV2-2130 antibody. Taken together, these results comprehensively map the effects of all amino acid substitutions on the binding of COV2-2196 and COV2-2130 and identify sites of possible concern for viral evolution. That said, variants containing mutations at residues K444 and R346 are rare among all sequenced viruses present in the GISAID databases (all ≤0.01% when accessed on Dec. 23, 2020).

Figure 11H:
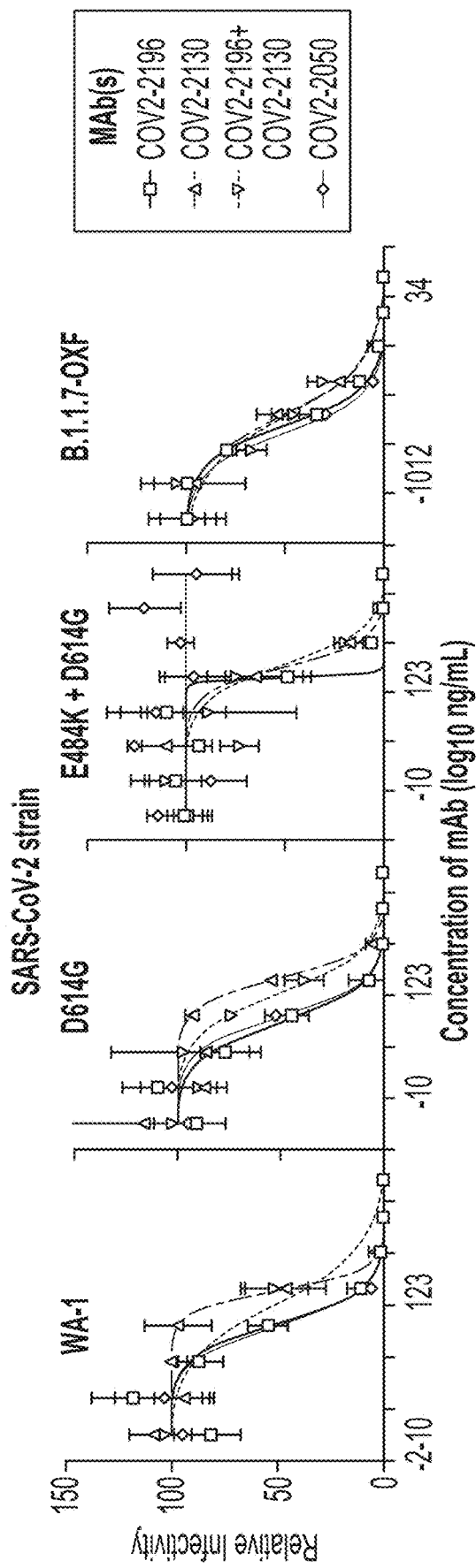

Recently, viral variants with increased transmissibility and potential antigenic mutations have been reported in clinical isolates[48-51]. The inventors tested whether some of the variant residues in these rapidly emerging strains would abrogate the activity of these potently neutralizing antibodies. They tested a viral isolate from a nasal sample obtained at Oxford in the United Kingdom (a B.1.1.7 virus designated UK B.1.1.7-OXF), which contains B.1.1.7 lineage defining spike gene changes including the 69-70 and 144-145 deletions in the NTD, and substitutions at N501Y, A570D, D614G, and P681H[49]. The inventors also tested isogenic D614G and E484K variants in the WA-1 strain background (2019n-CoV/USA_WA1/2019, [WA-1]), all prepared as authentic SARS-CoV-2 viruses and used in focus reduction neutralization tests[43]. The E484K mutation was of special interest, since this residue is located within 4.5 Å of each of the mAbs in the complex of Fabs and RBD, albeit at the very periphery of the Fab footprints, is present in emerging lineages B.1.351 (501Y.V2)[50] and P.1 (501Y.V3)[51], and has been demonstrated to alter the binding of some monoclonal antibodies[52,53] as well as human polyclonal serum antibodies[54]. Variants containing E484K also have been shown to be neutralized less efficiently by convalescent serum and plasma from SARS-CoV-2 survivors[55,56]. For COV2-2196, COV2-2130, and COV2-2050 (a third neutralizing antibody the inventors included for comparison as it interacts with the residue E484), they found virtually no impact of the D614G mutation or the suite of mutations present in the UK B.1.1.7-OXF strain; if anything, the inventors observed a trend toward slightly improved (2- to 3-fold reduction in $IC_{50}$ values) against the latter circulating virus (FIG. 11H). However, they did observe effects on neutralization with the D614G/E484K virus. COV2-2050 completely lost neutralization activity, consistent with our previous study defining E484K as a mutation abrogating COV2-2050 binding[41]. In contrast, COV2-2196, COV2-2130, and COV2-2196+COV2-2130 showed only slightly less inhibitory capacity (2- to 5-fold increases in $IC_{50}$ values).

Discussion. These structural analyses define the molecular basis for the frequent selection of a public clonotype of human antibodies sharing heavy chain V-D-J and light chain V-J recombinations that target the same region of the SARS-CoV-2 S RBD. Germline antibody gene-encoded residues in heavy and light chains play a vital role in antigen recognition, suggesting that few somatic mutations are required for antibody maturation of this clonotype. An IGHD2-gene-encoded disulfide bond provides additional restraint for the HCDR3 to adopt a conformation with shape and chemical complementarity to the antigenic site on RBD. It appears that three different IGHD2 genes (IGHD2-2, IGHD2-8, and IGHD2-15) encode portions of the HCDR3 that can function in the context of this clonotype. The inventors suggest that this occurrence of common germline gene-encoded antibodies with preconfigured structural features enabling high specificity and potent neutralizing activity is an unanticipated and beneficial feature of the primary human immune response to SARS-CoV-2. The selection of B cells from this public clonotype enabled rapid isolation of ultra-potent neutralizing antibodies that resist escape and possibly could account in part for the remarkable efficacy of S protein-based vaccines that is being observed in the clinic. One might envision an opportunity to elicit serum neutralizing antibody titers with even higher neutralization potency using domain- or motif-based vaccine designs for this antigenic site to prime human immune responses to elicit this clonotype.

The structural analysis of RBD-COV2-2196 and RBD-COV2-2130 complexes presented here suggest that the two antibodies bind to the RBD antigen by forming "rivet-like" interactions with a high energy density per unit of interface surface area, and this finding explains how such potent antibodies can have such relatively small (<750 Å$^2$) buried surface areas in the Ab-Ag interfaces. The mapping of escape mutations for the two antibodies studied here indicated the loci of escape mutations is consistent with the binding site determined by our Ab-Ag crystal structures, further confirming the precision of the DMS methodology. The inventors suggest that the escape fraction data could be used in future as restraints for computational docking of antibodies onto antigens or more generally for proteins onto proteins, since for example, the K444 or F486 residues with the highest escape fractions for COV2-2130 or COV2-2196, respectively, show the most intensive interactions with the antibodies in the structure of the antigen-antibody complex.

The recent emergence of variant virus lineages with increased transmissibility and altered sequences in many known sites of neutralization is concerning for the capacity of SARS-CoV-2 to evade current antibody countermeasures in development and testing. The inventors tested the activity of the antibodies and the cocktail of both and found sustained activity against several important variants, including a virus containing the E484K mutation and a B.1.1.7 virus with multiple S gene variations. The genetic and structural basis for this broad activity is revealed in the crystal structures and DMS studies the inventors present here. The central recognition of the relatively invariant F486 residue by an "aromatic cage" domain in COV2-2196 is beneficial, since variation of this residue is associated with reduced viral fitness. Targeting this binding site appears especially effective in the setting of synergistic neutralization in a combination with the mAb COV2-2130 that recognizes both "open" and "closed" S trimers. Thus, this combination appears to offer a broad and potent mechanism of inhibition that resists escape.

EXTENDED DATA TABLE 1

Data collection and refinement statistics for the crystals of RBD-COV2-2196 and RBD-COV2-2196-2130 complexes

| Data collection | | |
|---|---|---|
| Crystal | RBD-COV2-2196 | RBD-COV2-2196-2130 |
| PDB ID | 7L7D | 7L7E |
| Wave Length (Å) | 0.97872 | 0.97857 |
| Space group | P2$_1$ | P2$_1$ |

EXTENDED DATA TABLE 1-continued

Data collection and refinement statistics for the crystals of RBD-COV2-2196 and RBD-COV2-2196-2130 complexes

| Unit cell dimensions | | |
|---|---|---|
| a, b, c (Å) | 44.1, 81.6, 101.2 | 97.2, 152.5, 199.2 |
| α, β, γ | 90.0, 96.6, 90.0 | 90.0, 94.7, 90.0 |
| Resolution (Å) | 43.98-2.50 | 35.21-3.00 |
| Unique reflections | 24896 (134117) | 115751 (16908) |
| Redundancy | 3.7 (3.7) | 7.7 (7.7) |
| Completeness (%) | 99.9 (99.6) | 99.9 (100) |
| $R_{merge}$ (%) | 4.6 (24.5) | 23.1 (81.0) |
| I/σ(I) | 19.2 (4.8) | 6.4 (2.3) |
| Refinement statistics | | |
| $R_{factor}$ (%) | 18.5 | 21.5 |
| $R_{free}$ (%) | 23.1 | 27.3 |
| R.m.s.d. (bond) (Å) | 0.0030 | 0.0023 |
| R.m.s.d. (angle) (deg) | 0.563 | 0.598 |
| Ramachandran plot | | |
| Favored (%) | 95.82 | 95.34 |
| Allowed (%) | 4.18 | 4.37 |
| Outliers (%) | 0.00 | 0.09 |

$R_{merge} = \Sigma\Sigma|I_{hkl} - I_{hkl(j)}|/\Sigma I_{hkl}$, where $I_{hkl(j)}$ is the observed intensity and $I_{hkl}$ is the final average intensity.
$R_{work} = \Sigma||Fobs| - |Fcalc||/\Sigma|Fobs|$ and $R_{free} = \Sigma||Fobs| - |Fcalc||/\Sigma|Fobs|$, where $R_{free}$ and $R_{work}$ are calculated using a randomly selected test set of 5% of the data and all reflections excluding the 5% test set, respectively. Numbers in parentheses are for the highest resolution shell.

REFERENCES FOR EXAMPLES 1 AND 2

1. ter Meulen, J., et al. Human monoclonal antibody as prophylaxis for SARS coronavirus infection in ferrets. *Lancet* 363, 2139-2141 (2004).
2. Zhou, P., et al. A pneumonia outbreak associated with a new coronavirus of probable bat origin. *Nature* 579, 270-273 (2020).
3. Robbiani, D. F., et al. Convergent antibody responses to SARS-CoV-2 infection in convalescent individuals. *bioRxiv*, 2020.2005.2013.092619 (2020).
4. Brouwer, P. J. M., et al. Potent neutralizing antibodies from COVID-19 patients define multiple targets of vulnerability. *bioRxiv*, 2020.2005.2012.088716 (2020).
5. Niu, P., et al. Ultrapotent human neutralizing antibody repertoires against Middle East Respiratory Syndrome coronavirus from a recovered patient. *J Infect Dis* 218, 1249-1260 (2018).
6. Wang, L., et al. Importance of neutralizing monoclonal antibodies targeting multiple antigenic sites on the Middle East Respiratory Syndrome coronavirus spike glycoprotein to avoid neutralization escape. *J Virol* 92, e02002-17 (2018).

REFERENCES FOR EXAMPLES 3 AND 4

1 Zost, S. J. et al. Potently neutralizing and protective human antibodies against SARS-CoV-2. *Nature* 584, 443-449, doi:10.1038/s41586-020-2548-6 (2020).
2 Yuan, M. et al. Structural basis of a shared antibody response to SARS-CoV-2. *Science* 369, 1119-1123, doi:10.1126/science.abd2321 (2020).
3 Nielsen, S. C. A. et al. Human B Cell Clonal Expansion and Convergent Antibody Responses to SARS-CoV-2. *Cell Host Microbe* 28, 516-525 e515, doi:10.1016/j.chom.2020.09.002 (2020).
4 Robbiani, D. F. et al. Convergent antibody responses to SARS-CoV-2 in convalescent individuals. *Nature* 584, 437-442, doi:10.1038/s41586-020-2456-9 (2020).
5 Brouwer, P. J. M. et al. Potent neutralizing antibodies from COVID-19 patients define multiple targets of vulnerability. *Science* 369, 643-650, doi:10.1126/science.abc5902 (2020).
6 Zhou, P. et al. A pneumonia outbreak associated with a new coronavirus of probable bat origin. *Nature* 579, 270-273, doi:10.1038/s41586-020-2012-7 (2020).
7 Zhu, N. et al. A Novel Coronavirus from Patients with Pneumonia in China, 2019. *N Engl J Med* 382, 727-733, doi:10.1056/NEJMoa2001017 (2020).
8 Hoffmann, M. et al. SARS-CoV-2 Cell Entry Depends on ACE2 and TMPRSS2 and Is Blocked by a Clinically Proven Protease Inhibitor. *Cell* 181, 271-280 e278, doi:10.1016/j.cell.2020.02.052 (2020).
9 Letko, M., Marzi, A. & Munster, V. Functional assessment of cell entry and receptor usage for SARS-CoV-2 and other lineage B betacoronaviruses. *Nat Microbiol* 5, 562-569, doi:10.1038/s41564-020-0688-y (2020).
10 Wahba, L. et al. An Extensive Meta-Metagenomic Search Identifies SARS-CoV-2-Homologous Sequences in Pangolin Lung Viromes. *mSphere* 5, doi:10.1128/mSphere.00160-20 (2020).
11 Walls, A. C. et al. Tectonic conformational changes of a coronavirus spike glycoprotein promote membrane fusion. *Proc Natl Acad Sci USA* 114, 11157-11162, doi:10.1073/pnas.1708727114 (2017).
12 Algaissi, A. et al. SARS-CoV-2 S1 and N-based serological assays reveal rapid seroconversion and induction of specific antibody response in COVID-19 patients. *Sci Rep* 10, 16561, doi:10.1038/s41598-020-73491-5 (2020).
13 Long, Q. X. et al. Antibody responses to SARS-CoV-2 in patients with COVID-19. *Nat Med* 26, 845-848, doi:10.1038/s41591-020-0897-1 (2020).
14 Piccoli, L. et al. Mapping Neutralizing and Immunodominant Sites on the SARS-CoV-2 Spike Receptor-Binding Domain by Structure-Guided High-Resolution Serology. *Cell*, doi:10.1016/j.cell.2020.09.037 (2020).
15 Cao, Y. et al. Potent Neutralizing Antibodies against SARS-CoV-2 Identified by High-Throughput Single-Cell Sequencing of Convalescent Patients' B Cells. *Cell* 182, 73-84 e16, doi:10.1016/j.cell.2020.05.025 (2020).
16 Hansen, J. et al. Studies in humanized mice and convalescent humans yield a SARS-CoV-2 antibody cocktail. *Science* 369, 1010-1014, doi:10.1126/science.abd0827 (2020).
17 Ju, B. et al. Human neutralizing antibodies elicited by SARS-CoV-2 infection. *Nature* 584, 115-119, doi:10.1038/s41586-020-2380-z (2020).
18 Liu, L. et al. Potent neutralizing antibodies against multiple epitopes on SARS-CoV-2 spike. *Nature* 584, 450-456, doi:10.1038/s41586-020-2571-7 (2020).
19 Rogers, T. F. et al. Isolation of potent SARS-CoV-2 neutralizing antibodies and protection from disease in a small animal model. *Science* 369, 956-963, doi:10.1126/science.abc7520 (2020).
20 Shi, R. et al. A human neutralizing antibody targets the receptor-binding site of SARS-CoV-2. *Nature* 584, 120-124, doi:10.1038/s41586-020-2381-y (2020).
21 Weitkamp, J. H. et al. Infant and adult human B cell responses to rotavirus share common immunodominant variable gene repertoires. *J Immunol* 171, 4680-4688, doi:10.4049/jimmunol.171.9.4680 (2003).
22 Benton, D. J. et al. Receptor binding and priming of the spike protein of SARS-CoV-2 for membrane fusion. *Nature*, doi:10.1038/s41586-020-2772-0 (2020).

23 Wrapp, D. et al. Cryo-EM structure of the 2019-nCoV spike in the prefusion conformation. *Science* 367, 1260-1263, doi:10.1126/science.abb2507 (2020).

24 Wrobel, A. G. et al. SARS-CoV-2 and bat RaTG13 spike glycoprotein structures inform on virus evolution and furin-cleavage effects. *Nat Struct Mol Biol* 27, 763-767, doi:10.1038/s41594-020-0468-7 (2020).

25 Zost, S. J. et al. Rapid isolation and profiling of a diverse panel of human monoclonal antibodies targeting the SARS-CoV-2 spike protein. *Nat Med* 26, 1422-1427, doi:10.1038/s41591-020-0998-x (2020).

26 Tian, C. et al. Immunodominance of the VH1-46 antibody gene segment in the primary repertoire of human rotavirus-specific B cells is reduced in the memory compartment through somatic mutation of nondominant clones. *J Immunol* 180, 3279-3288, doi:10.4049/jimmunol.180.5.3279 (2008).

27 Wu, X. et al. Focused evolution of HIV-1 neutralizing antibodies revealed by structures and deep sequencing. *Science* 333, 1593-1602, doi:10.1126/science.1207532 (2011).

28 Zhou, T. et al. Structural Repertoire of HIV-1-Neutralizing Antibodies Targeting the CD4 Supersite in 14 Donors. *Cell* 161, 1280-1292, doi:10.1016/j.cell.2015.05.007 (2015).

29 Huang, C. C. et al. Structural basis of tyrosine sulfation and VH-gene usage in antibodies that recognize the HIV type 1 coreceptor-binding site on gp120. *Proc Natl Acad Sci USA* 101, 2706-2711, doi:10.1073/pnas.0308527100 (2004).

30 Williams, W. B. et al. HIV-1 VACCINES. Diversion of HIV-1 vaccine-induced immunity by gp41-microbiota cross-reactive antibodies. *Science* 349, aab1253, doi:10.1126/science.aab1253 (2015).

31 Joyce, M. G. et al. Vaccine-Induced Antibodies that Neutralize Group 1 and Group 2 Influenza A Viruses. *Cell* 166, 609-623, doi:10.1016/j.cell.2016.06.043 (2016).

32 Pappas, L. et al. Rapid development of broadly influenza neutralizing antibodies through redundant mutations. *Nature* 516, 418-422, doi:10.1038/nature13764 (2014).

33 Sui, J. et al. Structural and functional bases for broad-spectrum neutralization of avian and human influenza A viruses. *Nat Struct Mol Biol* 16, 265-273, doi:10.1038/nsmb.1566 (2009).

34 Wheatley, A. K. et al. H5N1 Vaccine-Elicited Memory B Cells Are Genetically Constrained by the IGHV Locus in the Recognition of a Neutralizing Epitope in the Hemagglutinin Stem. *J Immunol* 195, 602-610, doi:10.4049/jimmunol.1402835 (2015).

35 Bailey, J. R. et al. Broadly neutralizing antibodies with few somatic mutations and hepatitis C virus clearance. *JCI Insight* 2, doi:10.1172/jci.insight.92872 (2017).

36 Giang, E. et al. Human broadly neutralizing antibodies to the envelope glycoprotein complex of hepatitis C virus. *Proc Natl Acad Sci USA* 109, 6205-6210, doi:10.1073/pnas.1114927109 (2012).

37 Rappuoli, R., Bottomley, M. J., D'Oro, U., Finco, O. & De Gregorio, E. Reverse vaccinology 2.0: Human immunology instructs vaccine antigen design. *J Exp Med* 213, 469-481, doi:10.1084/jem.20151960 (2016).

38 Tortorici, M. A. et al. Ultrapotent human antibodies protect against SARS-CoV-2 challenge via multiple mechanisms. *Science*, doi:10.1126/science.abe3354 (2020).

39 Kreer, C. et al. Longitudinal Isolation of Potent Near-Germline SARS-CoV-2-Neutralizing Antibodies from COVID-19 Patients. *Cell* 182, 843-854 e812, doi:10.1016/j.cell.2020.06.044 (2020).

40 Soto, C. et al. High frequency of shared clonotypes in human B cell receptor repertoires. *Nature* 566, 398-402, doi:10.1038/s41586-019-0934-8 (2019).

41 Greaney, A. J. et al. Complete mapping of mutations to the SARS-CoV-2 spike receptor-binding domain that escape antibody recognition. *Cell Host Microbe*, doi:10.1016/j.chom.2020.11.007 (2020).

42 Starr, T. N. et al. Deep mutational scanning of SARS-CoV-2 receptor binding domain reveals constraints on folding and ACE2 binding. *Cell* 182, 1295-1310 e1220, doi:10.1016/j.cell.2020.08.012 (2020).

43 Case, J. B. et al. Neutralizing antibody and soluble ACE2 inhibition of a replication-competent VSV-SARS-CoV-2 and a clinical isolate of SARS-CoV-2. *Cell Host Microbe* 28, 475-485 e475, doi:10.1016/j.chom.2020.06.021 (2020).

44 Klimstra, W. B. et al. SARS-CoV-2 growth, furin-cleavage-site adaptation and neutralization using serum from acutely infected hospitalized COVID-19 patients. *J Gen Virol* 101, 1156-1169, doi:10.1099/jgv.0.001481 (2020).

45 Sawatzki, K. et al. Ferrets not infected by SARS-CoV-2 in a high-exposure domestic setting. *bioRxiv*, 2020.2008.2021.254995, doi:10.1101/2020.08.21.254995 (2020).

46 Baum, A. et al. REGN-COV2 antibodies prevent and treat SARS-CoV-2 infection in rhesus macaques and hamsters. *Science* 370, 1110-1115, doi:10.1126/science.abe2402 (2020).

47 Li, Q. et al. The impact of mutations in SARS-CoV-2 spike on viral infectivity and antigenicity. *Cell* 182, 1284-1294 e1289, doi:10.1016/j.cell.2020.07.012 (2020).

48 Galloway, S. E. et al. Emergence of SARS-CoV-2 B.1.1.7 Lineage—United States, Dec. 29, 2020-Jan. 12, 2021. *MMWR Morb Mortal Wkly Rep* 70, 95-99, doi:10.15585/mmwr.mm7003e2 (2021).

49 Leung, K., Shum, M. H., Leung, G. M., Lam, T. T. & Wu, J. T. Early transmissibility assessment of the N501Y mutant strains of SARS-CoV-2 in the United Kingdom, October to November 2020. *Euro Surveill* 26, doi:10.2807/1560-7917.ES.2020.26.1.2002106 (2021).

50 Tegally, H. et al. Emergence and rapid spread of a new severe acute respiratory syndrome-related coronavirus 2 (SARS-CoV-2) lineage with multiple spike mutations in South Africa. *medRxiv*, 2020.2012.2021.20248640, doi:10.1101/2020.12.21.20248640 (2020).

51 Voloch, C. M. et al. Genomic characterization of a novel SARS-CoV-2 lineage from Rio de Janeiro, Brazil. *medRxiv*, 2020.2012.2023.20248598, doi:10.1101/2020.12.23.20248598 (2020).

52 Liu, Z. et al. Landscape analysis of escape variants identifies SARS-CoV-2 spike mutations that attenuate monoclonal and serum antibody neutralization. *bioRxiv*, 2020.2011.2006.372037, doi:10.1101/2020.11.06.372037 (2021).

53 Weisblum, Y. et al. Escape from neutralizing antibodies by SARS-CoV-2 spike protein variants. *Elife* 9, doi:10.7554/eLife.61312 (2020).

54 Greaney, A. J. et al. Comprehensive mapping of mutations to the SARS-CoV-2 receptor-binding domain that affect recognition by polyclonal human serum antibodies. *bioRxiv*, 2020.2012.2031.425021, doi:10.1101/2020.12.31.425021 (2021).

55 Wibmer, C. K. et al. SARS-CoV-2 501Y.V2 escapes neutralization by South African COVID-19 donor plasma. bioRxiv, 2021.2001.2018.427166, doi:10.1101/2021.01.18.427166 (2021).

56 Andreano, E. et al. SARS-CoV-2 escape in vitro from a highly neutralizing COVID-19 convalescent plasma. bioRxiv, 2020.2012.2028.424451, doi:10.1101/2020.12.28.424451 (2020).

57 Huo, J. et al. Neutralization of SARS-CoV-2 by destruction of the prefusion spike. Cell Host Microbe 28, 445-454 e446, doi:10.1016/j.chom.2020.06.010 (2020).

66 Otwinowski, J., McCandlish, D. M. & Plotkin, J. B. Inferring the shape of global epistasis. Proc Natl Acad Sci USA 115, E7550-E7558, doi:10.1073/pnas.1804015115 (2018).

67 Plante, J. A. et al. Spike mutation D614G alters SARS-CoV-2 fitness. Nature, doi:10.1038/s41586-020-2895-3 (2020).

68 Xie, X. et al. An infectious cDNA clone of SARS-CoV-2. Cell Host Microbe 27, 841-848 e843, doi:10.1016/j.chom.2020.04.004 (2020).

TABLE A

Activity Data

| | BINDING ASSAY RESULTS | | | | NEUTRALIZATION ASSAY RESULTS (Yes/No qualitative test, or IC50 value (ng/mL)) | | | | | |
|---|---|---|---|---|---|---|---|---|---|---|
| | ELISA - Purified IgG (OD 450 nm) | | | | SARS-CoV-2 xCelligence neutralization test (cell impedence) | | SARS-CoV-2 focus | Nano-luciferase virus reduction test | | |
| Clone ID (COV2-xxxx) | SARS-CoV-2 Spike trimer | SARS-CoV-2 RBD | SARS-CoV-2 NTD | SARS-CoV Spike trimer? | hACE2 blocking | Qualitative | Estimated IC50 | reduction test | SARS-CoV-2 | SARS |
| 2196 | 4.2 | 4.2 | 0.05 | 0.09 | Yes | Yes | nt | 29 | <100 | nt |
| 2838 | 3.67 | 3.62 | 0.12 | 0.21 | nt | Yes | <60 | 14 | nt | nt |
| 2952 | 3.54 | 3.55 | 0.1 | 0.15 | nt | Yes | >304 | 89 | NT | nt |
| 2514 | 3.56 | 3.56 | 0.09 | 3.6 | nt | Yes | <200 | 84 | nt | nt |
| 2165 | 4.2 | 4.2 | 0.05 | 0.17 | nt | Yes | nt | 185 | <400 | nt |
| 2391 | 3.57 | 3.65 | 0.1 | 0.1 | nt | Yes | <600 | 45 | nt | nt |
| 3025 | 3.70 | 3.70 | NT | 0.21 | Yes | Yes | nt | 31 | nt | nt |
| 2094 | 4.3 | 4.3 | 0.1 | 4.1 | Yes | Yes | nt | 151 | <50 | >1,000 |
| 2096 | 4.3 | 4.3 | 0.12 | 0.11 | Yes | Yes | nt | 290 | <200 | nt |
| 2130 | 4.3 | 4.2 | 0.18 | 0.1 | Yes | Yes | nt | 121 | <100 | nt |

58 Kabsch, W. Xds. Acta Crystallogr D Biol Crystallogr 66, 125-132, doi:10.1107/S0907444909047337 (2010).

59 Winn, M. D. et al. Overview of the CCP4 suite and current developments. Acta Crystallogr D Biol Crystallogr 67, 235-242, doi:10.1107/S0907444910045749 (2011).

60 McCoy, A. J. et al. Phaser crystallographic software. J Appl Crystallogr 40, 658-674, doi:10.1107/S0021889807021206 (2007).

61 Adams, P. D. et al. PHENIX: a comprehensive Python-based system for macromolecular structure solution. Acta Crystallogr D Biol Crystallogr 66, 213-221, doi:10.1107/S0907444909052925 (2010).

62 Emsley, P. & Cowtan, K. Coot: model-building tools for molecular graphics. Acta Crystallogr D Biol Crystallogr 60, 2126-2132, doi:10.1107/S0907444904019158 (2004).

63 Schrodinger, LLC. The PyMOL Molecular Graphics System, Version 1.8 (2015).

64 Cornwell, O., Radford, S. E., Ashcroft, A. E. & Ault, J. R. Comparing hydrogen deuterium exchange and fast photochemical oxidation of proteins: a structural characterisation of wild-type and deltaN6 beta2-microglobulin. J Am Soc Mass Spectrom 29, 2413-2426, doi:10.1007/s13361-018-2067-y (2018).

65 Starr, T. N. et al. Prospective mapping of viral mutations that escape antibodies used to treat COVID-19. bioRxiv, doi:10.1101/2020.11.30.405472 (2020).

Example 5

Potently Neutralizing Human Antibodies that Block SARS-CoV-2 Receptor Binding and Protect Animals AUTHORS: Seth J. Zost[1]*, Pavlo Gilchuk[1]*, James Brett Case[3], Elad Binshtein[1], Rita E. Chen[2,3] Joseph X. Reidy[1], Andrew Trivette[1], Rachel S. Nargi[1], Rachel E. Sutton[1], Naveenchandra Suryadevara[1], Lauren E. Williamson[4], Elaine C. Chen[4], Taylor Jones[1], Samuel Day[1], Luke Myers[1], Ahmed O. Hassan[3], Natasha M. Kafai[2,3], Emma S. Winkler[2,3], Julie M. Fox[3], James J. Steinhardt[6], Kuishu Ren[7], Yueh-Ming Loo[7], Nicole L. Kallewaard[7], David R. Martinez[5], Alexandra Schäfer[5], Lisa E. Gralinski[5], Ralph S. Baric[5], Larissa B. Thackray[3], Michael S. Diamond[2,3,8,9], Robert H. Carnahan[1,10], James E. Crowe, Jr.[1,4,10]

Affiliations:

[1]Vanderbilt Vaccine Center, Vanderbilt University Medical Center, Nashville, Tenn., 37232, USA

[2]Department of Pathology & Immunology, Washington University School of Medicine, St. Louis, Mo., 63110, USA

[3]Department of Medicine, Washington University School of Medicine, St. Louis, 63110, MO, USA

[4]Department of Pathology, Microbiology, and Immunology, Vanderbilt University Medical Center, Nashville, Tenn., 37232, USA

[5]Department of Epidemiology, University of North Carolina at Chapel Hill, Chapel Hill, N.C., 27599, USA

[6]Antibody Discovery and Protein Engineering, BioPharmaceuticals R&D, AstraZeneca, Gaithersburg, Md., 20878, USA

[7]Microbial Sciences, BioPharmaceuticals R&D, AstraZeneca, Gaithersburg, Md., 20878, USA
[8]Department of Molecular Microbiology, Washington University School of Medicine, St. Louis, Mo., 63110, USA
[9]Andrew M. and Jane M. Bursky Center for Human Immunology and Immunotherapy Programs, Washington University School of Medicine, St. Louis, Mo., 63110, USA
[10]Department of Pediatrics, Vanderbilt University Medical Center, Nashville, Tenn., 37232, USA
Contact Information:
James E. Crowe, Jr., M.D. [LEAD CONTACT]
Departments of Pediatrics, Pathology, Microbiology, and Immunology, and the Vanderbilt Vaccine Center
Mail:
Vanderbilt Vaccine Center
11475 Medical Research Building IV
2213 Garland Avenue
Nashville, Tenn. 37232-0417, USA
Telephone (615) 343-8064
Email james.crowe@vumc.org
Additional Title Page Footnotes
* These authors contributed equally
** Corresponding authors
Keywords: Coronavirus; SARS-CoV-2; SARS-CoV; COVID-19; Antibodies, Monoclonal; Human; Adaptive Immunity.

The COVID49 pandemic is a major threat to global health for which there are only limited medical countermeasures, and we lack a thorough understanding of mechanisms of humoral immunity[1,2]. From a panel of monoclonal antibodies (mAbs) targeting the spike (S) glycoprotein isolated from the B cells of infected subjects, we identified several mAbs that exhibited potent neutralizing a activity with $IC_{50}$ values as low as 0.9 or 15 ng/mL in pseudovirus or wild-type (wt) SARS-CoV-2 neutralization tests, respectively. The most potent mAbs fully block the receptor-binding domain of S ($S_{RBD}$) from interacting with human ACE2. Competition-binding, structural, and functional studies allowed clustering of the mAbs into defined classes recognizing distinct epitopes within major antigenic sites on the SRBD. Electron microscopy studies revealed that these mAbs recognize distinct conformational states of trimeric S protein. Potent neutralizing mAbs recognizing unique sites, COV2-2196 and COV2-2130, bound simultaneously S and synergistically neutralized authentic SARS-CoV-2 virus. In two murine models of SARS-CoV-2 infection, passive transfer of either COV2-2916 or COV2-2130 alone or a combination of both mAbs protected mice from severe weight loss and reduced viral burden and inflammation in the lung. These results identify protective epitopes on the $S_{RBD}$ and provide a structure-based framework for rational vaccine design and the selection of robust immunotherapeutic cocktails.

The S protein of SARS-CoV-2 is the molecular determinant of viral attachment, fusion, and entry into host cells[3]. The cryo-EM structure of a prefusion-stabilized trimeric S protein ectodomain ($S2P_{ecto}$) for SARS-CoV-2 reveals similar features to that of the SARS-CoV S protein[4]. This type I integral membrane protein and class I fusion protein possesses an N-terminal subunit (S1) that mediates binding to receptor and a C-terminal subunit (S2) that mediates virus-cell membrane fusion. The S1 subunit contains an N-terminal domain ($S_{NTD}$) and a receptor-binding domain ($S_{RBD}$). SARS-CoV-2 and SARS-CoV, which share approximately 78% sequence identity in their genomes[1] both use human angiotensin-converting enzyme 2 (hACE2) as an entry receptor[5-7]. Previous studies of human immunity to other high-pathogenicity zoonotic betacoronaviruses including SARS-CoV[8-12] and Middle East respiratory syndrome (MERS)[13-22] showed that Abs to the viral surface spike (S) glycoprotein mediate protective immunity. The most potent S protein-specific mAbs appear to neutralize betacoronaviruses by blocking attachment of virus to host cells by binding to the region on $S_{RBD}$ that directly mediates engagement of the receptor. It is likely that human Abs have promise for use in modifying disease during SARS-CoV-2 infection, when used for prophylaxis, post-exposure prophylaxis, or treatment of SARS-CoV-2 infection[23]. Many studies including randomized controlled trials evaluating convalescent plasma and one trial evaluating hyperimmune immunoglobulin are ongoing, but it is not yet clear whether such treatments can reduce morbidity or mortality[24].

We isolated a large panel of SARS-CoV-2 S protein-reactive mAbs from the B cells of two individuals who were previously infected with SARS-CoV-2 in Wuhan China[25]. A subset of those antibodies bound to the receptor-binding domain of S ($S_{RBD}$) and exhibited neutralizing activity in a rapid screening assay with authentic SARS-CoV-2[25]. Here, we defined the antigenic landscape of SARS-CoV-2 and determined which sites of $S_{RBD}$ are the target of protective mAbs. We tested a panel of 40 anti-S human mAbs we previously pre-selected by a rapid neutralization screening assay in a quantitative focus reduction neutralization test (FRNT) with SARS-CoV-2 strain WA1/2020. These assays revealed the panel exhibited a range of half-maximal inhibitory concentration ($IC_{50}$) values, from 15 to over 4,000 ng/mL (visualized as a heatmap in FIG. 20a, values shown in Table B, and full curves shown in FIG. 24). We hypothesized that many of these $S_{RBD}$-reactive mAbs neutralize virus infection by blocking $S_{RBD}$ binding to hACE2. Indeed, most neutralizing mAbs we tested inhibited the interaction of hACE2 with trimeric S protein directly (FIG. 20a, FIG. 25). Consistent with these results, these mAbs also bound strongly to a trimeric S ectodomain ($S2P_{ecto}$) protein or monomeric $S_{RBD}$ (FIG. 20a, FIG. 26). We evaluated whether $S2P_{ecto}$ or $S_{RBD}$ binding or hACE2-blocking potency predicted binding neutralization potency independently, but none of these measurements correlated with neutralization potency (FIG. 20b-d). However, each of the mAbs in the highest neutralizing potency tier ($IC_{50}$<150 ng/mL) also revealed strongest blocking activity against hACE2 ($IC_{50}$<150 ng/mL) and exceptional binding activity ($EC_{50}$<2 ng/mL) to $S2P_{ecto}$ trimer and $S_{RBD}$ (FIG. 20e). Representative neutralization curves for two potently neutralizing mAbs designated COV2-2196 and COV2-2130 are shown in (FIG. 20f). Potent neutralization was confirmed using pseudovirus neutralization assays, which revealed far more sensitive neutralization phenotypes than wt virus and demonstrated a requirement for the use of live virus assays for assessment of mAb potency (FIG. 20g). Both of these mAbs bound strongly to $S2P_{ecto}$ trimer and fully blocked hACE2 binding (FIG. 20h-i).

We next defined the major antigenic sites on $S_{RBD}$ for neutralizing mAbs by competition-binding analysis. We first used a biolayer interferometry-based competition assay with a minimal $S_{RBD}$ domain to screen for mAbs that competed for binding with the potently neutralizing mAb COV2-2196 or a recombinant version of the previously described SARS-CoV mAb CR3022, which recognizes a conserved cryptic epitope[10,26]. We identified three major groups of competing mAbs (FIG. 21a). The largest group of mAbs blocked COV2-2196 but not rCR3022, while some mAbs were blocked by rCR3022 but not COV2-2196. Two mAbs, including COV2-2130, were not blocked by either reference mAb. Most mAbs competed with hACE2 for binding, suggesting that they bound near the hACE2 binding site of the $S_{RBD}$. We used COV2-2196, COV2-2130, and rCR3022 in an ELISA-based competition-binding assay with trimeric $S2P_{ecto}$ protein and also found that $S_{RBD}$ contained three major antigenic sites, with some mAbs likely making contacts in more than one site (FIG. 21b). Most of the potently neutralizing mAbs directly competed for binding with COV2-2196.

Since COV2-2196 and COV2-2130 did not compete for binding to $S_{RBD}$, we assessed if these mAbs synergize for virus neutralization, a phenomenon previously observed for SARS-CoV mAbs[10]. We tested combination responses (see dose-response neutralization matrix, FIG. 21c) in the FRNT using SARS-CoV-2 and compared these experimental values with the expected responses calculated by synergy scoring models[27]. The comparison revealed that the combination of COV2-2196+COV2-2130 was synergistic (with a synergy score of 17.4, where any score of >10 indicates synergy). The data in FIG. 21c shows the dose-response synergy matrix and demonstrates that a combined mAb dose of 79 ng/mL in the cocktail (16 ng/mL of COV2-2196 and 63 ng/mL of COV2-2130) had the same activity as 250 ng/mL of each individual mAb (see FIG. 21c). This finding shows that using a cocktail the dose of each mAb can be reduced by more than three-fold to achieve the same potency of virus neutralization in vitro.

We next defined the epitopes recognized by representative mAbs in the two major competition-binding groups that synergize for neutralization. We performed mutagenesis studies of the $S_{RBD}$ using alanine or arginine substitution to determine critical residues for binding of neutralizing mAbs (FIG. 27). Loss of binding studies revealed F486A or N487A as critical residues for COV2-2196 and N487A as a critical residue for COV2-2165, which compete with one another for binding, and likewise mutagenesis studies for COV2-2130 using K444A and G447R mutants defined these residues as critical for recognition (FIG. 22a). Previous structural studies have defined the interaction between the $S_{RBD}$ and hACE2 (FIG. 22b)[28]. Most of the interacting residues in the SRBD are contained within a 60-amino-acid linear peptide that defines the hACE2 recognition motif (FIG. 22c). We next tested binding of human mAbs to this minimal peptide and found that potent neutralizing members of the largest competition-binding group including COV2-2196, COV2-2165, and COV2-2832 recognized this peptide (FIG. 22c), suggesting these mAbs make critical contacts within the hACE2 recognition motif.

We used negative-stain electron microscopy of $S2P_{ecto}$ trimer/Fab complexes to structurally determine the epitopes for these mAbs. The potently neutralizing antibodies COV2-2196 and COV2-2165 bound to the hACE2 recognition motif of $S_{RBD}$ and recognized the 'open' conformational state of the $S2P_{ecto}$ trimer (FIG. 22d). The mode of engagement of these two antibodies differed, however, as the binding pose and the angle relative to the spike 'body' for one was different compared to the other. COV2-2130, which represents the second competition-binding group, bound to the RBD in the $S2P_{ecto}$ trimer in the 'closed' position (FIG. 22d). Since COV2-2196 and COV2-2130 did not compete for binding, we attempted to make complexes of both Fabs bound at the same time to the $S2P_{ecto}$ trimer. We found that both Fabs bound simultaneously when the $S2P_{ecto}$ trimer was in the open position, indicating that COV2-2130 can recognize the $S_{RBD}$ in both conformations (FIG. 22e). Overlaying the two-Fab complex with the structure of the RBD:CR3022 complex[26], we observed that these antibodies bind to three distinct sites on $S_{RBD}$, as predicted based on our competition-binding studies (FIG. 22f).

Next, we tested the prophylactic efficacy of COV2-2196 or COV2-2130 monotherapy or a combination of COV2-2196+COV2-2130 in a newly developed SARS-CoV-2 infection model in BALB/c mice in which hACE2 is expressed in the lung after intranasal adenovirus (AdV-hACE2) transduction. In this relatively stringent disease model, we also administered a single dose of anti-Ifnar1 antibody to augment virus infection and pathogenesis, which results in a disseminated interstitial pneumonia (A. Hassan and M. Diamond, submitted for publication). We passively transferred a single dose of mAb COV2-2196 (10 mg/kg), COV2-2130 (10 mg/kg), a combination of COV2-2196+COV2-2130 (5 mg/kg each), or an isotype control mAb (10 mg/kg) to AdV-hACE2-transduced mice one day before intranasal challenge with $4\times10^5$ PFU of SARS-CoV-2. Prophylaxis with COV2-2196 or COV2-2130 or their combination prevented severe SARS-CoV-2-induced weight loss through the first week of infection (FIG. 23a). Viral RNA levels were reduced significantly at 7 dpi in the lung and distant sites including the heart and spleen (FIG. 23b). The expression of interferon gamma (INF-g), IL-6, CXCL10 and CCL2 cytokine and chemokine genes, which are indicators of inflammation, also was reduced in the lung of treated mice at 7 dpi—the peak of the disease (FIG. 23c).

We also tested COV2-2196 or COV2-2130 or their combination for prophylactic efficacy in an immunocompetent model using a mouse-adapted (MA) SARS-CoV-2 virus[29] (FIG. 23d). In vitro tests showed that the $IC_{50}$ values for neutralization were comparable for the wt and MA SARS-CoV-2 viruses for these mAbs (data not shown). Each of the mAb treatments delivered at a dose of 200 μg/mouse (~8 mg/kg) reduced viral RNA levels up to $10^5$-fold at 2 dpi in the lung when compared to the isotype control group (FIG. 23e, left). Concordantly, all animals from COV2-2196 and COV2-2196+COV2-2130 treatment group and 8 of 10 animals from COV2-2130 treatment no longer had infectious virus at 2 dpi in the lung as measured by plaque titer of lung tissue (FIG. 23e, right). Collectively, these results in mice suggested that COV2-2196 or COV2-2130 alone or in combination are promising candidates for treatment or prevention of COVID-19.

Here, we defined the antigenic landscape for a large panel of highly potent mAbs against SARS-CoV-2. These detailed studies and the screening studies that identified this panel of mAbs from a larger panel of hundreds[25] demonstrate that although diverse human neutralizing antibodies are elicited by natural infection with SARS-CoV-2, only a small subset of those mAbs are of high potency ($IC_{50}$<50 ng/mL against live SARS-CoV-2 virus), and therefore, suitable for therapeutic development. Biochemical and structural analysis of these potent mAbs defined three principal antigenic sites of vulnerability to neutralization by human mAbs elicited by natural infection with SARS-CoV on the $S_{RBD}$. Representative mAbs from the two most potent antigenic sites were shown to synergize in vitro and protect as an in vivo cocktail. This finding reveals critical features of effective humoral immunity to SARS-CoV-2 and suggests that the role of synergistic neutralization activity in polyclonal responses should be explored further. Moreover, as SARS-CoV-2 continues to circulate, population immunity elicited by natural infection may start to select for antigenic variants that escape from the selective pressure of neutralizing antibodies, reinforcing the need to target multiple epitopes of S protein in vaccines or immunotherapeutics.

The common S gene variants across the globe reported to date are located at positions D614G, V483A, L5F, Q675H, H655Y and S939F[30], far away from the amino acid variants at residues 486 or 487 identified in our mutation studies for the lead mAbs studied here. Rationally-selected therapeutic cocktails like the one described here might offer even greater resistance to SARS-CoV-2 escape. These studies set the stage for preclinical evaluation and development of the identified mAbs as candidates for use as COVID-19 immunotherapeutics in humans.

Data availability. The EM maps have been deposited at the Electron Microscopy Data Bank with accession codes EMBD 21965 ($S2P_{ecto}$ apo), EMD-21974 ($S2P_{ecto}$+Fab COVs-2165), EMD-21975 ($S2P_{ecto}$+Fab COVs-2196), EMD-21976 ($S2P_{ecto}$+Fab COVs-2130) and EMD-21977 ($S2P_{ecto}$+Fab COV2-2196+Fab COV2-2130). Materials reported in this study will be made available but may require execution of a Materials Transfer Agreement.

Acknowledgements. We thank Angela Jones and the staff of the Vanderbilt VANTAGE core laboratory for expedited sequencing, Ross Trosseth for assistance with data management and analysis, Robin Bombardi and Cinque Soto of VUMC for technical consultation on genomics approaches, Arthur Kim, Adam Bailey, Laura VanBlargan, James Earnest, Broc McCune and Swathi Shrihari of WUSTL for experimental assistance and key reagents, and Kevin M. Tuffy, Seme Diallo, Patrick M. McTamney, and Lori Clarke of AstraZeneca for generation of protein and pseudovirus reagents and related data. This study was supported by Defense Advanced Research Projects Agency (DARPA) grants HR0011-18-2-0001 and HROO 11-18-3-0001, NIH contracts 75N93019C00074 and 75N93019C00062 and the Dolly Parton COVID-19 Research Fund at Vanderbilt. This work was supported by NIH grant 1S10RR028106-01A1 for the Next Generation Nucleic Acid Sequencer, housed in Vanderbilt Technologies for Advanced Genomics (VANTAGE) and the Vanderbilt Institute for Clinical and Translational Research with grant support from (UL1TR002243 from NCATS/NIH). S. J. Z. was supported by NIH T32 AI095202. J. B. C. is supported by a Helen Hay Whitney Foundation postdoctoral fellowship. D. R. M. was supported by NIH T32 AI007151 and a Burroughs Wellcome Fund Postdoctoral Enrichment Program Award. J. E. C. is the recipient of the 2019 Future Insight Prize from Merck KGaA, Darmstadt Germany, which supported this research with a research grant. The content is solely the responsibility of the authors and does not necessarily represent the official views of the U.S. government or the other sponsors.

Author contributions. Conceived of the project: S. J. Z., P. G., R. H. C., L. B. T., M. S. D., J. E. C.; Obtained funding: J. E. C. and M. S. D. Performed laboratory experiments: S. J. Z., P. G., J. B. C., E. B., R. E. C., J. X. R., A. T., R. S. N., R. E. S., N. S., L. E. W., A. O. H., N. M. K., E. W., J. M. F., L. B. T., J. J. S., K. R., Y.-M. L., A. S., L. E. G., D. R. M.; Performed computational work: E. C. C., T. J., S. D., L. M.; Supervised research: N. L. K, M. S. D., L. B. T., R. S. B., R. H. C., J. E. C. Wrote the first draft of the paper: S. J. Z., P. G., R. H. C., J. E. C.; All authors reviewed and approved the final manuscript.

Competing interests. R. S. B. has served as a consultant for Takeda and Sanofi Pasteur on issues related to vaccines. M. S. D. is a consultant for Inbios, Vir Biotechnology, NGM Biopharmaceuticals, Eli Lilly, and is on the Scientific Advisory Board of Moderna, a past recipient of unrelated research grant from Moderna and a current recipient of an unrelated research grant Emergent BioSolutions. J. E. C. has served as a consultant for Sanofi and is on the Scientific Advisory Boards of CompuVax and Meissa Vaccines, is a recipient of previous unrelated research grants from Moderna and Sanofi and is Founder of IDBiologics, Inc. Vanderbilt University has applied for patents concerning SARS-CoV-2 antibodies that are related to this work. AstraZeneca has filed patents for materials/findings related to this work. J. J. S., K. R., Y.-M. L., and N. L. K. are employees of AstraZeneca and currently hold AstraZeneca stock or stock options. All other authors declared no competing interests.

Additional Information

Supplementary information is available for this paper.

Correspondence and requests for materials should be addressed to J. E. C.

REFERENCES

1. Zhou, P., et al. A pneumonia outbreak associated with a new coronavirus of probable bat origin. Nature 579, 270-273 (2020).
2. Zhu, N., et al. A novel coronavirus from patients with pneumonia in China, 2019. N Engl J Med 382, 727-733 (2020).
3. Pillay, T. S. Gene of the month: the 2019-nCoV/SARS-CoV-2 novel coronavirus spike protein. J Clin Pathol (2020).
4. Wrapp, D., et al. Cryo-EM structure of the 2019-nCoV spike in the prefusion conformation. Science 367, 1260-1263 (2020).
5. Wan, Y., Shang, J., Graham, R., Baric, R. S. & Li, F. Receptor recognition by the novel Coronavirus from Wuhan: an Analysis Based on Decade-Long Structural Studies of SARS Coronavirus. J Virol 94(2020).
6. Hoffmann, M., et al. SARS-CoV-2 cell entry depends on ACE2 and TMPRSS2 and is blocked by a clinically proven protease inhibitor. Cell 181, 271-280 e278 (2020).
7. Li, W., et al. Angiotensin-converting enzyme 2 is a functional receptor for the SARS coronavirus. Nature 426, 450-454 (2003).
8. Sui, J., et al. Potent neutralization of severe acute respiratory syndrome (SARS) coronavirus by a human mAb to S1 protein that blocks receptor association. Proc Natl Acad Sci USA 101, 2536-2541 (2004).
9. ter Meulen, J., et al. Human monoclonal antibody as prophylaxis for SARS coronavirus infection in ferrets. Lancet 363, 2139-2141 (2004).
10. ter Meulen, J., et al. Human monoclonal antibody combination against SARS coronavirus: synergy and coverage of escape mutants. PLoS Med 3, e237 (2006).
11. Zhu, Z., et al. Potent cross-reactive neutralization of SARS coronavirus isolates by human monoclonal antibodies. Proc Natl Acad Sci USA 104, 12123-12128 (2007).
12. Rockx, B., et al. Structural basis for potent cross-neutralizing human monoclonal antibody protection against lethal human and zoonotic severe acute respiratory syndrome coronavirus challenge. *J Virol* 82, 3220-3235 (2008).
13. Chen, Z., et al. Human neutralizing monoclonal antibody inhibition of Middle East respiratory syndrome coronavirus replication in the common marmoset. *J Infect Dis* 215, 1807-1815 (2017).
14. Choi, J. H., et al. Characterization of a human monoclonal antibody generated from a B-cell specific for a prefusion-stabilized spike protein of Middle East respiratory syndrome coronavirus. *PLoS One* 15, e0232757 (2020).
15. Niu, P., et al. Ultrapotent human neutralizing antibody repertoires against Middle East respiratory syndrome coronavirus from a recovered patient. *J Infect Dis* 218, 1249-1260 (2018).
16. Wang, L., et al. Importance of neutralizing monoclonal antibodies targeting multiple antigenic sites on the Middle East respiratory syndrome coronavirus spike glycoprotein to avoid neutralization escape. *J Virol* 92(2018).
17. Wang, N., et al. Structural definition of a neutralization-sensitive epitope on the MERS-CoV S1-NTD. *Cell Rep* 28, 3395-3405 e3396 (2019).
18. Zhang, S., et al. Structural definition of a unique neutralization epitope on the receptor-binding domain of MERS-CoV spike glycoprotein. *Cell Rep* 24, 441-452 (2018).
19. Corti, D., et al. Prophylactic and postexposure efficacy of a potent human monoclonal antibody against MERS coronavirus. *Proc Natl Acad Sci USA* 112, 10473-10478 (2015).
20. Jiang, L., et al. Potent neutralization of MERS-CoV by human neutralizing monoclonal antibodies to the viral spike glycoprotein. *Sci Transl Med* 6, 234ra259 (2014).
21. Tang, X. C., et al. Identification of human neutralizing antibodies against MERS-CoV and their role in virus adaptive evolution. *Proc Natl Acad Sci USA* 111, E2018-2026 (2014).
22. Ying, T., et al. Exceptionally potent neutralization of Middle East respiratory syndrome coronavirus by human monoclonal antibodies. *J Virol* 88, 7796-7805 (2014).
23. Jiang, S., Hillyer, C. & Du, L. Neutralizing antibodies against SARS-CoV-2 and other human coronaviruses. *Trends Immunol* 41, 355-359 (2020).
24. Valk, S. J., et al. Convalescent plasma or hyperimmune immunoglobulin for people with COVID-19: a rapid review. *Cochrane Database Syst Rev* 5, CD013600 (2020).
25. Zost, S. J., et al. Rapid isolation and profiling of a diverse panel of human monoclonal antibodies targeting the SARS-CoV-2 spike protein. *bioRxiv*, 2020.2005.2012.091462 (2020).
26. Yuan, M., et al. A highly conserved cryptic epitope in the receptor binding domains of SARS-CoV-2 and SARS-CoV. *Science* 368, 630-633 (2020).
27. Ianevski, A., He, L., Aittokallio, T. & Tang, J. SynergyFinder: a web application for analyzing drug combination dose-response matrix data. *Bioinformatics* 33, 2413-2415 (2017).
28. Lan, J., et al. Structure of the SARS-CoV-2 spike receptor-binding domain bound to the ACE2 receptor. *Nature* 581, 215-220 (2020).
29. Dinnon, K. H., et al. A mouse-adapted SARS-CoV-2 model for the evaluation of COVID-19 medical countermeasures. *bioRxiv*, 2020.2005.2006.081497 (2020).
30. Laha, S., et al. Characterizations of SARS-CoV-2 mutational profile, spike protein stability and viral transmission. *bioRxiv*, 2020.2005.2003.066266 (2020).

TABLE B

Neutralization $IC_{50}$, hACE2 blocking $IC_{50}$, and $EC_{50}$ values for binding to $S2P_{ecto}$ or $S_{RBD}$ antigens for mAb panel

| MAb | Neutralization $IC_{50}$, ng/mL | hACE2 blocking $IC_{50}$, ng/mL | $S2P_{ecto}$ binding $EC_{50}$, ng/mL | $S_{RBD}$ binding $EC_{50}$, ng/mL | SARS-CoV $S2P_{ecto}$ binding $EC_{50}$, ng/mL |
|---|---|---|---|---|---|
| COV2-2094 | 154 | 53 | 1.8 | 1.4 | 11.7 |
| COV2-2096 | 59 | 67 | 1.0 | 1.0 | — |
| COV2-2130 | 107 | 61 | 1.5 | 0.7 | — |
| COV2-2165 | 332 | 62 | 1.4 | 0.6 | — |
| COV2-2196 | 15 | 48 | 1.2 | 1.1 | — |
| COV2-3025 | 37 | 41 | 1.1 | 1.1 | — |
| rCR3022 | — | — | 10.2 | 1.1 | 5.2 |
| r2D22 | — | — | — | — | — |

TABLE C

Summary of electron microscopy data collection and statistics SARS-CoV-2 $S2P_{ecto}$ protein apo or in complex with human Fabs Structure of SARS-CoV-2 $S2P_{ecto}$ protein in complex with indicated Fab

| | | No Fab* | Fab COV2-2165 | Fab COV2-2196 | Fab COV2-2130 | Fab COV2-2196 + Fab COV2-2130 |
|---|---|---|---|---|---|---|
| Microscope setting | EMDB #: | EMD-21965 | EMD-21974 | EMD-21975 | EMD-21976 | EMD-21977 |
| | Microscope | TF-20 | TF-20 | TF-20 | TF-20 | TF-20 |
| | Voltage (kV) | 200 | 200 | 200 | 200 | 200 |
| | Detector | US-4000 CCD | US-4000 CCD | US-4000 CCD | US-4000 CCD | US-4000 CCD |
| | Magnification | 50,000x | 50,000x | 50,000x | 50,000x | 50,000x |

TABLE C-continued

Summary of electron microscopy data collection and statistics SARS-CoV-2 S2P$_{ecto}$ protein apo or in complex with human Fabs Structure of SARS-CoV-2 S2P$_{ecto}$ protein in complex with indicated Fab

|   |   | No Fab* | Fab COV2-2165 | Fab COV2-2196 | Fab COV2-2130 | Fab COV2-2196 + Fab COV2-2130 |
|---|---|---|---|---|---|---|
|   | Pixel size | 2.18 | 2.18 | 2.18 | 2.18 | 2.18 |
|   | Exposure (e−/Å2) | 25 | 25 | 25 | 30 | 38 |
|   | Defocus range (μm) | 1.5 to 1.8 | 1.5 to 1.8 | 1.5 to 1.8 | 1.5 to 1.8 | 1.5 to 1.8 |
|   | Micrographs, # | 122 | 83 | 190 | 550 | 466 |
|   | Particles, # | 3,836 | 3,705 | 5,471 | 10,000 | 9,434 |
| Data | Particles #, after 2D | 2,718 | 1,868 | 3,595 | 2,684 | 4,231 |
|   | Final particles, # | 2,188 | 1,057 | 2,737 | 1,385 | 3,018 |
|   | Symmetry | C1 | C1 | C1 | C1 | C1 |
| Model docking | CoV-2-S CC | PDB: 6VXX 0.895 | PDB: 6VYB 0.836 | PDB: 6VYB 0.828 | PDB: 6VXX 0.900 | PDB: 6VYB 0.8952 |
|   | Fab (PDB: 12E8) CC | n.a. | 0.916 | 0.905 | 0.91 | 0.8648/0.8929 |

*Previously reported, Zost et al., 2020 (reference 25).

Methods

Antibodies. The human antibodies studied in this paper were isolated from blood samples from two subjects in North America with previous laboratory-confirmed symptomatic SARS-CoV-2 infection that was acquired in China. The original clinical studies to obtain specimens after written informed consent were previously described[1] and had been approved by the Institutional Review Board of Vanderbilt University Medical Center and the Research Ethics Board of the University of Toronto. The subjects (a 56-year-old male and a 56-year-old female) are a married couple and residents of Wuhan, China who traveled to Toronto, Canada, where PBMCs were obtained by leukopheresis 50 days after symptom onset. The antibodies were isolated using diverse tools for isolation and cloning of single antigen-specific B cells and the antibody variable genes encoding monoclonal antibodies[1].

Cell culture. Vero E6 (CRL-1586, American Type Culture Collection (American Type Culture Collection, ATCC), Vero CCL81 (ATCC), HEK293 (ATCC), and HEK293T (ATCC) were maintained at 37° C. in 5% $CO_2$ in Dulbecco's minimal essential medium (DMEM) containing 10% (vol/vol) heat-inactivated fetal bovine serum (FBS), 10 mM HEPES pH 7.3, 1 mM sodium pyruvate, 1× non-essential amino acids, and 100 U/mL of penicillin-streptomycin. Vero-furin cells were obtained from T. Pierson (NIH) and have been described previously[2]. Expi293F cells (ThermoFisher Scientific, A1452) were maintained at 37° C. in 8% $CO_2$ in Expi293F Expression Medium (ThermoFisher Scientific, A1435102). ExpiCHO cells (ThermoFisher Scientific, A29127) were maintained at 37° C. in 8% $CO_2$ in ExpiCHO Expression Medium (ThermoFisher Scientific, A2910002). Mycoplasma testing of Expi293F and ExpiCHO cultures was performed on a monthly basis using a PCR-based mycoplasma detection kit (ATCC, 30-1012K).

Viruses. SARS-CoV-2 strain 2019 n-CoV/USA_WA1/2020 was obtained from the Centers for Disease Control and Prevention (a gift from Natalie Thornburg). Virus was passaged in Vero CCL81 cells and titrated by plaque assay on Vero E6 cells. All work with infectious SARS-CoV-2 was approved by the Washington University School of Medicine or UNC-Chapel Hill Institutional Biosafety Committees and conducted in approved BSL3 facilities using appropriate powered air purifying respirators and personal protective equipment.

Recombinant antigens and proteins. A gene encoding the ectodomain of a prefusion conformation-stabilized SARS-CoV-2 spike (S2P$_{ecto}$) protein was synthesized and cloned into a DNA plasmid expression vector for mammalian cells. A similarly designed S protein antigen with two prolines and removal of the furin cleavage site for stabilization of the prefusion form of S was reported previously[3]. Briefly, this gene includes the ectodomain of SARS-CoV-2 (to residue 1,208), a T4 fibritin trimerization domain, an AviTag site-specific biotinylation sequence, and a C-terminal 8x-His tag. To stabilize the construct in the prefusion conformation, we included substitutions K986P and V987P and mutated the furin cleavage site at residues 682-685 from RRAR to ASVG. This recombinant spike 2P-stabilized protein (designated here as S2P$_{ecto}$) was isolated by metal affinity chromatography on HisTrap Excel columns (GE Healthcare), and protein preparations were purified further by size-exclusion chromatography on a Superose 6 Increase 10/300 column (GE Healthcare). The presence of trimeric, prefusion conformation S protein was verified by negative-stain electron microscopy[1]. For electron microscopy with S and Fabs, we expressed a variant of S2P$_{ecto}$ lacking an AviTag but containing a C-terminal Twin-Strep-tag, similar to that described previously[3]. Expressed protein was isolated by metal affinity chromatography on HisTrap Excel columns (GE Healthcare), followed by further purification on a StrepTrap HP column (GE Healthcare) and size-exclusion chromatography on TSKgel G4000SW$_{XL}$ (TOSOH). To express the S$_{RBD}$ subdomain of SARS-CoV-2 S protein, residues 319-541 were cloned into a mammalian expression vector downstream of an IL-2 signal peptide and upstream of a thrombin cleavage site, an AviTag, and a 6x-His tag. RBD protein fused to mouse IgG1 Fc domain (designated RBD-mFc), was purchased from Sino Biological (40592-V05H). For epitope mapping by alanine scanning, SARS-CoV-2 RBD (residues 334-526) or RBD single mutation variants were cloned with an N-terminal CD33 leader sequence and C-terminal GSSG linker, AviTag, GSSG linker, and 8xHisTag. Spike proteins were expressed in FreeStyle 293 cells (Thermo Fisher) and isolated by affinity chromatography using a HisTrap column (GE Healthcare), followed by size exclusion chromatography with a Superdex200 column (GE Healthcare). Purified proteins were analyzed by SDS-PAGE to ensure purity and appropriate molecular weights.

Electron microscopy (EM) stain grid preparation, imaging and processing of SARS-CoV-2 S2P$_{ecto}$ protein or S2P$_{ecto}$/Fab complexes. To perform EM imaging, Fabs were produced by digesting recombinant chromatography-purified IgGs using resin-immobilized cysteine protease enzyme (FabALACTICA, Genovis). The digestion occurred in 100 mM sodium phosphate, 150 mM NaCl pH 7.2 for ~16 hrs at RT. In order to remove cleaved Fc and intact IgG, the digestion mix was incubated with CaptureSelect Fc resin (Genovis) for 30 min at RT in PBS buffer. If needed, the Fab was buffer exchanged into Tris buffer by centrifugation with a Zeba spin column (Thermo Scientific).

For screening and imaging of negatively-stained (NS) SARS-CoV-2 S2P$_{ecto}$ protein in complex with human Fabs, the proteins were incubated for ~1 hr and approximately 3 µL of the sample at concentrations of about 10 to 15 µg/mL was applied to a glow discharged grid with continuous carbon film on 400 square mesh copper EM grids (Electron Microscopy Sciences). The grids were stained with 0.75% uranyl formate (UF)[4]. Images were recorded on a Gatan US4000 4 k×4 k CCD camera using an FEI TF20 (TFS) transmission electron microscope operated at 200 keV and control with SerialEM[5]. All images were taken at 50,000× magnification with a pixel size of 2.18 Å/pix in low-dose mode at a defocus of 1.5 to 1.8 µm. Total dose for the micrographs was ~25 to 38 e⁻/Å². Image processing was performed using the cryoSPARC software package[6]. Images were imported, and particles were CTF estimated. The images then were denoised and picked with Topaz[7]. The particles were extracted with a box size of 256 pixels and binned to 128 pixels. 2D class averages were performed and good classes selected for ab-initio model and refinement without symmetry. For EM model docking of SARS-CoV-2 S2P$_{ecto}$ protein, the closed model (PDB: 6VXX) was used in Chimera[8] for docking to the EM map (see also Table C for details). For the SARS-CoV-2 S2P$_{ecto}$/Fab COV2-2165 and SARS-CoV-2 S2P$_{ecto}$/Fab COV2-2165 complexes, the open model of SARS-CoV-2 (PDB: 6VYB) and Fab (Fab: 12E8) was used in Chimera for docking to the EM maps (see also Table C for details). For the SARS-Cov-2 S2P$_{ecto}$/Fab COV2-2130 complex, the closed model and Fab (PDB: 12E8) were used in Chimera for docking to the EM map (see also Table C for details). All images were made with Chimera.

MAb production and purification. Sequences of mAbs that had been synthesized (Twist Bioscience) and cloned into an IgG1 monocistronic expression vector (designated as pTwist-mCis_G1) were used for mammalian cell culture mAb secretion. This vector contains an enhanced 2A sequence and GSG linker that allows simultaneous expression of mAb heavy and light chain genes from a single construct upon transfection[9]. We previously described microscale expression of mAbs in 1 mL ExpiCHO cultures in 96-well plates[1]. For larger scale mAb expression, we performed transfection (1 to 300 mL per antibody) of CHO cell cultures using the Gibco™ ExpiCHO™ Expression System and protocol for 50 mL mini bioreactor tubes (Corning) as described by the vendor. Culture supernatants were purified using HiTrap Mab Select SuRe (Cytiva, formerly GE Healthcare Life Sciences) on a 24-column parallel protein chromatography system (Protein BioSolutions). Purified mAbs were buffer-exchanged into PBS, concentrated using Amicon® Ultra-4 50 KDa Centrifugal Filter Units (Millipore Sigma) and stored at 4° C. until use.

ELISA binding assays. Wells of 96-well microtiter plates were coated with purified recombinant SARS-CoV-2 S protein or SARS-CoV-2 S$_{RBD}$ protein at 4° C. overnight. Plates were blocked with 2% non-fat dry milk and 2% normal goat serum in DPBS containing 0.05% Tween-20 (DPBS-T) for 1 hr. The bound antibodies were detected using goat anti-human IgG conjugated with HRP (horseradish peroxidase) (Southern Biotech) and TMB (3,3',5, 5'-tetramethylbenzidine) substrate (Thermo Fisher Scientific). Color development was monitored, 1N hydrochloric acid was added to stop the reaction, and the absorbance was measured at 450 nm using a spectrophotometer (Biotek). For dose-response assays, serial dilutions of purified mAbs were applied to the wells in triplicate, and mAb binding was detected as detailed above. Half-maximal effective concentration (EC$_{50}$) values for binding were determined using Prism v8.0 software (GraphPad) after log transformation of mAb concentration using sigmoidal dose-response nonlinear regression analysis.

RBD minimal ACE2-binding motif peptide binding ELISA. Wells of 384-well microtiter plates were coated with 1 µg/mL streptavidin at 4° C. overnight. Plates were blocked with 0.5% BSA in DPBS containing 0.05% Tween-20 (DPBS-T) for 1 hr. Plates were washed 4× with 1× PBST and 2 µg/mL biotinylated-ACE2 binding motif peptide (cat. #LT5578, from LifeTein, LLC) was added to bind streptavidin for 1 hr at RT. Purified mAbs were diluted in blocking buffer, added to the wells, and incubated for 1 hr at RT. The bound antibodies were detected using goat anti-human IgG conjugated with HRP (horseradish peroxidase) (cat. #2014-05, Southern Biotech) and TMB (3,3',5,5'-tetramethylbenzidine) substrate (ThermoFisher Scientific). Color development was monitored, 1N hydrochloric acid was added to stop the reaction, and the absorbance was measured at 450 nm using a spectrophotometer (Biotek). For dose-response assays, serial 3-fold dilutions starting at 10 µg/mL concentration of purified mAbs were applied to the wells in triplicate, and mAb binding was detected as detailed above.

Analysis of binding of antibodies to variant RBD proteins with alanine or arginine point mutations. Biolayer light interferometry (BLI) was performed using an Octet RED96 instrument (ForteBio; Pall Life Sciences) and wild-type RBD protein or a mutant RBD protein with a single amino acid change at defined positions to alanine or arginine. Binding of the RBD proteins were confirmed by first capturing octa-His-tagged RBD wild-type or mutant protein from a 10 µg/mL (≈200 nM) solution onto Penta-His biosensors for 300 sec. The biosensor tips then were submerged in binding buffer (PBS/0.2% Tween 20) for a 60 sec wash, followed by immersion in a solution containing 150 nM of mAb for 180 sec (association), followed by a subsequent immersion in binding buffer for 180 sec (dissociation). Response for each RBD mutant protein was normalized to that of the wild-type RBD protein.

Focus reduction neutralization test (FRNT). Serial dilutions of mAbs were incubated with 10² FFU of SARS-CoV-2 for 1 hr at 37° C. The mAb-virus complexes were added to Vero E6 cell culture monolayers in 96-well plates for 1 hr at 37° C. Subsequently, cells were overlaid with 1% (w/v) methylcellulose in Minimum Essential Medium (MEM) supplemented to contain 2% heat-inactivated FBS. Plates were fixed 30 hrs later by removing overlays and fixed with 4% PFA in PBS for 20 min at room temperature. The plates were incubated sequentially with 1 µg/mL of rCR3022 anti-S antibody[10] and horseradish-peroxidase (HRP)-conjugated goat anti-human IgG in PBS supplemented with 0.1% (w/v) saponin (Sigma) and 0.1% bovine serum albumin (BSA). SARS-CoV-2-infected cell foci were visualized using TrueBlue peroxidase substrate (KPL) and quantitated on an ImmunoSpot 5.0.37 Macro Analyzer (Cellular Technologies). Data were processed using Prism software version 8.0 (GraphPad).

Generation of S protein pseudotyped lentivirus. Suspension 293 cells were seeded and transfected with a third-generation HIV-based lentiviral vector expressing luciferase along with packaging plasmids encoding for the following: SARS-CoV-2 spike protein with a C-terminal 19 amino acid deletion, Rev, and Gag-pol. Medium was changed 16 to 20 hrs after transfection, and the supernatant containing virus was harvested 24 hrs later. Cell debris was removed by low-speed centrifugation, and the supernatant was passed through a 0.45 µm filter unit. The pseudovirus was pelleted by ultracentrifugation and resuspended in PBS for a 100-fold concentrated stock.

Pseudovirus neutralization assay. Serial dilutions of mAbs were prepared in a 384-well microtiter plate and pre-incubated with pseudovirus for 30 minutes at 37° C., to which 293 cells that stably express human ACE2 were added. The plate was returned to the 37° C. incubator, and then 48 hrs later luciferase activity measured on an EnVision 2105 Multimode Plate Reader (Perkin Elmer) using the Bright-Glo™ Luciferase Assay System (Promega), according to manufacturer's recommendations. Percent inhibition was calculated relative to pseudovirus-alone control. $IC_{50}$ values were determined by nonlinear regression using the Prism software version 8.1.0 (GraphPad). The average $IC_{50}$ value for each antibody was determined from a minimum of 3 independent experiments.

Measurement of synergistic neutralization by an antibody combination. Synergy was defined as higher neutralizing activity mediated by a cocktail of two mAbs when compared to that mediated by individual mAbs at the same total concentration of antibodies in vitro. To assess if two mAbs synergize in a cocktail to neutralize SARS-CoV-2, we used a previously reported approach to quantitate synergy[11]. To evaluate the significance of the beneficial effect from combining mAbs, the observed combination responses (dose-response matrix) were compared with the expected responses calculated by means of synergy scoring models[11]. Virus neutralization was measured in a conventional focus reduction neutralization test (FRNT) assay using wild-type SARS-CoV-2 and Vero E6 cell culture monolayers. Individual mAbs COV2-2196 and COV2-2130 were mixed at different concentrations to assess neutralizing activity of different ratios of mAbs in the cocktail. Specifically, each of seven-fold dilutions of mAb COV2-2130 (starting from 500 ng/mL) was mixed with each of the nine dilutions of mAb COV2-2196 (starting from 500 ng/mL) in a total volume of 50 µL of per each condition and then incubated with 50 µL of live SARS-CoV-2 in cell culture medium (RPMI-1640 medium supplemented with 2% FBS) before applying to confluent Vero E6 cells grown in 96-well plates. The control values included those for determining dose-response of the neutralizing activity measured separately for the individual mAb COV2-2196 or COV2-2130, which were assessed at the same doses as in the cocktail. Each measurement was performed in duplicate. We next calculated percent virus neutralization for each condition and then calculated the synergy score value, which defined interaction between these two mAbs in the cocktail. A synergy score of less than −10 indicates antagonism, a score from −10 to 10 indicates an additive effect, and a score greater than 10 indicates a synergistic effect[11].

MAb quantification. Quantification of purified mAbs was performed by UV spectrophotometry using a NanoDrop spectrophotometer and accounting for the extinction coefficient of human IgG.

Competition-binding analysis through biolayer interferometry. Anti-mouse IgG Fc capture biosensors (FortéBio 18-5089) on an Octet HTX biolayer interferometry instrument (ForteBio) were soaked for 10 minutes in 1× kinetics buffer (Molecular Devices 18-1105), followed by a baseline signal measurement for 60 seconds. Recombinant SARS-CoV-2 RBD fused to mouse IgG1 (RBD-mFc, Sino Biological 40592-V05H) was immobilized onto the biosensor tips for 180 seconds. After a wash step in 1× kinetics buffer for 30 seconds, the reference antibody (5 µg/mL) was incubated with the antigen-containing biosensor for 600 seconds. Reference antibodies included the SARS-CoV human mAb CR3022 and COV2-2196. After a wash step in 1× kinetics buffer for 30 seconds, the biosensor tips then were immersed into the second antibody (5 µg/mL) for 300 seconds. Maximal binding of each antibody was normalized to a buffer-only control. Self-to-self blocking was subtracted. Comparison between the maximal signal of each antibody was used to determine the percent binding of each antibody. A reduction in maximum signal to <33% of un-competed signal was considered full competition of binding for the second antibody in the presence of the reference antibody. A reduction in maximum signal to between 33 to 67% of un-competed was considered intermediate competition of binding for the second antibody in the presence of the reference antibody. Percent binding of the maximum signal >67% was considered absence of competition of binding for the second antibody in the presence of the reference antibody.

High-throughput ACE-2 binding inhibition analysis. Wells of 384-well microtiter plates were coated with purified recombinant SARS-CoV-2 $S2P_{ecto}$ protein at 4° C. overnight. Plates were blocked with 2% non-fat dry milk and 2% normal goat serum in DPBS-T for 1 hr. Purified mAbs from microscale expression were diluted two-fold in blocking buffer starting from 10 µg/mL in triplicate, added to the wells (20 µL/well), and incubated for 1 hr at ambient temperature. Recombinant human ACE2 with a C-terminal FLAG tag protein was added to wells at 2 µg/mL in a 5 µL/well volume (final 0.4 µg/mL concentration of ACE2) without washing of antibody and then incubated for 40 min at ambient temperature. Plates were washed, and bound ACE2 was detected using HRP-conjugated anti-FLAG antibody (Sigma) and TMB substrate. ACE2 binding without antibody served as a control. The signal obtained for binding of the ACE2 in the presence of each dilution of tested antibody was expressed as a percentage of the ACE2 binding without antibody after subtracting the background signal. Half-maximal inhibitory concentration ($IC_{50}$) values for inhibition by mAb of $S2P_{ecto}$ protein binding to ACE2 was determined after log transformation of antibody concentration using sigmoidal dose-response nonlinear regression analysis (Prism software, GraphPad Prism version 8.0).

ACE2 blocking assay using biolayer interferometry biosensor. Anti-mouse IgG biosensors on an Octet HTX biolayer interferometry instrument (ForteBio) were soaked for 10 minutes in 1× kinetics buffer, followed by a baseline signal measurement for 60 seconds. Recombinant SARS-CoV-2 RBD fused to mouse IgG1 (RBD-mFc, Sino Biological 40592-V05H) was immobilized onto the biosensor tips for 180 seconds. After a wash step in 1× kinetics buffer for 30 seconds, the antibody (5 μg/mL) was incubated with the antigen-coated biosensor for 600 seconds. After a wash step in 1× kinetics buffer for 30 seconds, the biosensor tips then were immersed into the ACE2 receptor (20 μg/mL) (Sigma-Aldrich SAE0064) for 300 seconds. Maximal binding of ACE2 was normalized to a buffer-only control. Percent binding of ACE2 in the presence of antibody was compared to ACE2 maximal binding. A reduction in maximal signal to <30% was considered ACE2 blocking.

High-throughput competition-binding analysis. Wells of 384-well microtiter plates were coated with purified recombinant SARS-CoV-2 S protein at 4° C. overnight. Plates were blocked with 2% BSA in DPBS containing 0.05% Tween-20 (DPBS-T) for 1 hr. Micro-scale purified unlabeled mAbs were diluted ten-fold in blocking buffer, added to the wells (20 μL/well) in quadruplicates, and incubated for 1 hr at ambient temperature. A biotinylated preparation of a recombinant mAb based on the variable gene sequence of the previously described mAb CR3022[12] and also newly identified mAbs COV2-2096, -2130, and -2196 that recognized distinct antigenic regions of the SARS-CoV-2 S protein were added to each of four wells with the respective mAb at 2.5 μg/mL in a 5 μL/well volume (final 0.5 μg/mL concentration of biotinylated mAb) without washing of unlabeled antibody and then incubated for 1 hr at ambient temperature. Plates were washed, and bound antibodies were detected using HRP-conjugated avidin (Sigma) and TMB substrate. The signal obtained for binding of the biotin-labeled reference antibody in the presence of the unlabeled tested antibody was expressed as a percentage of the binding of the reference antibody alone after subtracting the background signal. Tested mAbs were considered competing if their presence reduced the reference antibody binding to less than 41% of its maximal binding and non-competing if the signal was greater than 71%. A level of 40-70% was considered intermediate competition.

Binding analysis of mAbs to alanine or arginine RBD mutants. Biolayer light interferometry was performed using an Octet RED96 instrument (ForteBio; Pall Life Sciences). Binding was confirmed by first capturing octa-His-tagged RBD mutants 10 μg/mL (200 nM) onto Penta-His biosensors for 300 s. The biosensors then were submerged in binding buffer (PBS/0.2% TWEEN 20) for a wash for 60 sec followed by immersion in a solution containing 150 nM of mAbs for 180 sec (association), followed by a subsequent immersion in binding buffer for 180 sec (dissociation). Response for each RBD mutant was normalized to that of wild-type RBD.

Mouse experiments using human hACE2-transduced mice. Animal studies were carried out in accordance with the recommendations in the Guide for the Care and Use of Laboratory Animals of the National Institutes of Health. The protocols were approved by the Institutional Animal Care and Use Committee at the Washington University School of Medicine (assurance number A3381-01). Virus inoculations were performed under anesthesia that was induced and maintained with ketamine hydrochloride and xylazine, and all efforts were made to minimize animal suffering.

BALB/c mice were purchased from Jackson Laboratories (strain 000651). Female mice (10-11-week-old) were given a single intraperitoneal injection of 2 mg of anti-Ifnar1 mAb (MAR1-5A3[13], Leinco) one day before intranasal administration of $2.5\times10^8$ PFU of AdV-hACE2. Five days after AdV transduction, mice were inoculated with $4\times10^5$ PFU of SARS-CoV-2 by the intranasal route. Anti-SARS-CoV-2 human mAbs or isotype control mAbs were administered 24 hours prior to SARS-CoV-2 inoculation. Weights were monitored on a daily basis, and animals were sacrificed at days 5 or 7 post-infection, and tissues were harvested.

Measurement of viral burden. Tissues were weighed and homogenized with zirconia beads in a MagNA Lyser instrument (Roche Life Science) in 1 ml of DMEM media supplemented with 2% heat-inactivated FBS. Tissue homogenates were clarified by centrifugation at 10,000 rpm for 5 min and stored at ~80° C. RNA was extracted using MagMax mirVana Total RNA isolation kit (Thermo Scientific) and a Kingfisher Flex 96 well extraction machine (Thermo Scientific). TaqMan primers were designed to target a conserved region of the N gene using SARS-CoV-2 (MN908947) sequence as a guide (L Primer: ATGCTGCAATCGTGCTACAA; R primer: GACTGCCGCCTCTGCTC; probe: /56-FAM/TCAAGGAAC/ZEN/AACATTGCCAA/3IABkFQ/). To establish an RNA standard curve, we generated concatenated segments of the N gene in a gBlocks fragment (IDT) and cloned this into the PCR-II topo vector (Invitrogen). The vector was linearized, and in vitro T7-DNA-dependent RNA transcription was performed to generate materials for a quantitative standard curve.

Cytokine and chemokine mRNA measurements. RNA was isolated from lung homogenates at 7 dpi as described above. cDNA was synthesized from DNase-treated RNA using the High-Capacity cDNA Reverse Transcription kit (Thermo Scientific) with the addition of RNase inhibitor, following the manufacturer's protocol. Cytokine and chemokine expression was determined using TaqMan Fast Universal PCR master mix (Thermo Scientific) with commercial primers/probe sets specific for IFNγ(IDT: Mm.PT.58.41769240), IL-6 (Mm.PT.58.10005566), CXCL10 (Mm.PT.58.43575827), CCL2 (Mm.PT.58.42151692 and results were normalized to GAPDH (Mm.PT.39a.1) levels. Fold change was determined using the $2^{-\Delta\Delta Ct}$ method comparing anti-SARS-CoV-2 specific or isotype control mAb-treated mice to naïve controls.

Mouse experiments using wild-type mice. Animal studies were carried out in accordance with the recommendations in the Guide for the Care and Use of Laboratory Animals of the National Institutes of Health. The protocols were approved by the Institutional Animal Care and Use Committee at the UNC Chapel Hill School of Medicine (NIH/PHS Animal Welfare Assurance Number is D16-00256 (A3410-01)). Virus inoculations were performed under anesthesia that was induced and maintained with ketamine hydrochloride and xylazine, and all efforts were made to minimize animal suffering.

Mouse adapted SARS-CoV-2 (MA-SARS-CoV-2) virus. The virus was generated as described previously[14]. Virus was propagated in Vero E6 cells grown in DMEM with 10% Fetal Clone II and 1% Pen/Strep. Virus titer was determined by plaque assay. Briefly, virus was serial diluted and inoculated onto confluent monolayers of Vero E6 cells, followed by agarose overlay. Plaques were visualized on day 2 post-infection after staining with neutral red dye.

Wild-type mice. 12-month-old BALB/c mice from Envigo were used in experiments. Mice were acclimated in the BSL3 for at least 72 hours prior to start of experiments. At 6 hours prior to infection, mice were prophylactically treated with 200 μg of human monoclonal antibodies via intraperitoneal injection. The next day, mice were anesthetized with a mixture of ketamine and xylazine and intranasally infected with $10^5$ PFU of MA-SARS-CoV-2 diluted in PBS. Daily weight loss was measured, and at two days post-infection mice were euthanized by isoflurane overdose prior to tissue harvest.

Plaque assay of lung tissue homogenates. The lower lobe of the right lung was homogenized in 1 mL PBS using a MagnaLyser (Roche). Serial dilutions of virus were titered on Vero E6 cell culture monolayers, and virus plaques were visualized by neutral red staining at two days after inoculation. The limit of detection for the assay is 100 PFU per lung.

Quantification and statistical analysis. The descriptive statistics mean±SEM or mean±SD were determined for continuous variables as noted. Technical and biological replicates are described in the figure legends. In the mouse studies, analysis of weight change and viral burden in vivo were determined by two-way ANOVA and Mann-Whitney tests, respectively. Statistical analyses were performed using Prism v8.0 (GraphPad).

REFERENCES FOR ONLINE METHODS

1 Zost S J, G. P., Chen R E, Case J B, Reidy J X, Trivette A, Nargi R S, Sutton R E, Suryadevara N, Chen E C, Binshtein E, Shrihari S, Ostrowski M, Chu H Y, Didier J E, MacRenaris K W, Jones T, Day S, Myers L, Lee F E-H, Nguyen D C, Sanz I, Martinez D R, Baric R S, Thackray L B,. Diamond M S, Carnahan R H, Crowe J E Jr. Rapid isolation and profiling of a diverse panel of human monoclonal antibodies targeting the SARS-CoV-2 spike protein. bioRxiv 2020.05.12.091462; doi: https://doi.org/10.1101/2020.05.12.091462 (2020)

2 Mukherjee, S. et al. Enhancing dengue virus maturation using a stable furin over-expressing cell line. Virology 497, 33-40, doi:10.1016/j.virol.2016.06.022 (2016).

3 Wrapp, D. et al. Cryo-EM structure of the 2019-nCoV spike in the prefusion conformation. Science 367, 1260-1263, doi:10.1126/science.abb2507 (2020).

4 Ohi, M., Li, Y., Cheng, Y. & Walz, T. Negative staining and image classification—Powerful tools in modern electron microscopy. Biol Proced Online 6, 23-34, doi:10.1251/bpo70 (2004).

5 Mastronarde, D. N. Automated electron microscope tomography using robust prediction of specimen movements. J Struct Biol 152, 36-51, doi:10.1016/j.jsb.2005.07.007 (2005).

6 Punjani, A., Rubinstein, J. L., Fleet, D. J. & Brubaker, M. A. cryoSPARC: algorithms for rapid unsupervised cryo-EM structure determination. Nat Methods 14, 290-296, doi:10.1038/nmeth.4169 (2017).

7 Bepler, T., Noble, A. J., and Berger, B. Topaz-Denoise: general deep denoising models for cryoEM. bioRxiv. doi:10.1101/838920 (2019).

8 Pettersen, E. F. et al. UCSF Chimera—a visualization system for exploratory research and analysis. J Comput Chem 25, 1605-1612, doi:10.1002/jcc.20084 (2004).

9 Chng, J. et al. Cleavage efficient 2A peptides for high level monoclonal antibody expression in CHO cells. MAbs 7, 403-412, doi:10.1080/19420862.2015.1008351 (2015).

10 Yuan, M. et al. A highly conserved cryptic epitope in the receptor binding domains of SARS-CoV-2 and SARS-CoV. Science 368, 630-633, doi:10.1126/science.abb7269 (2020).

11 Ianevski, A., He, L., Aittokallio, T. & Tang, J. SynergyFinder: a web application for analyzing drug combination dose-response matrix data. Bioinformatics 33, 2413-2415, doi:10.1093/bioinformatics/btx162 (2017).

12 ter Meulen, J. et al. Human monoclonal antibody as prophylaxis for SARS coronavirus infection in ferrets. Lancet 363, 2139-2141, doi:10.1016/S0140-6736(04)16506-9 (2004).

13 Sheehan, K. C. et al. Blocking monoclonal antibodies specific for mouse IFN-alpha/beta receptor subunit 1 (IFNAR-1) from mice immunized by in vivo hydrodynamic transfection. J Interferon Cytokine Res 26, 804-819 (2006).

14 Dinnon K H, et al. A mouse-adapted SARS-CoV-2 model for the evaluation of COVID-19 medical countermeasures. bioRxiv 2020.05.06.081497; doi: https://doi.org/10.1101/2020.05.06.081497 (2020).

TABLE 1

NUCLEOTIDE SEQUENCES FOR ANTIBODY VARIABLE REGION

| Clone | SeqID | Chain | Variable Sequence Region |
|---|---|---|---|
| COV2-2165 | 1 | heavy | GAGGTGCAGCTGGTGGAGTCTGGGGGAGGCTTGGTCCAGCCTGGGGGGTCTCTGAGACTCTCCTGT GCAGCCTCTGGACTCACCGTCCGTAGCAACTACATGACCTGGGTCCGCCAGACTCCAGGGAAGGGG CTGGAATGGGTGTCAGTTATTTATAGCGGTGGTAGCACATTCTACGCAGACTCCGTGAAGGGCAGA TTCACCATCTCCAGAGACAATTCCAAGAACACCGTGTATCTTCAAATGAACAGCCTGAGAGCCGAG GACACGGCTGTGTATTACTGTGCGAGAGATCTCGTGACTTACGGTTTGGACGTCTGGGGCCAAGGG ACCACGGTCACCGTCTCCTCA |
|  | 2 | light | GACATCCAGTTGACCCAGTCTCCATCCTTCCTGTCTGCATCTGTAGGAGACAGAGTCACCATCACT TGCCGGGCCAGTCAGGGCATTAGCAATTATTTAGCCTGGTATCAGCAAAAACCAGGGACAGCCCCT AACCTCCTGATCTATGCTGCATCCACTTTGCAAAGTGGGGTCCCATCAAGGTTCAGCGGCAGTGGA TCTGGGACAGAATTCACTCTCACAATCAGCAGCCTGCAGCCTGAAGATTTTGCAACTTATTACTGT CAACTACTTAATAGTCACCCCCTCACCTTCGGCCAAGGGACACGACTGGAGATTAAA |
| COV2-2838 | 3 | heavy | CAAATGCAGCTGGTGCAGTCTGGGCCTGAGGTGAAGAAGCCTGGGACCTCAGTGAAGGTCTCCTGC AAGGCTTCTGGATTCACCTTTATGAGCTCTGCTGTGCAGTGGGTGCGACAGGCTCGTGGACAACGC CTTGAGTGGATAGGATGGATCGTCATTGGCAGTGGTAACACAAACTACGCACAGAAGTTCCAGGAA AGAGTCACCATTACCAGGGACATGTCCACAAGCACAGCCTACATGGAGCTGAGCAGCCTGAGATCC GAGGACACGGCCGTGTATTACTGTGCGGCCCCATATTGTAGTAGTATCAGCTGCAATGATGGTTTT GATATCTGGGGCCAAGGGACAATGGTCACCGTCTCTTCAG |

TABLE 1-continued

NUCLEOTIDE SEQUENCES FOR ANTIBODY VARIABLE REGION

| Clone | SeqID | Chain | Variable Sequence Region |
|---|---|---|---|
|  | 4 | light | GAAATTGTGTTGACGCAGTCTCCAGGCACCCTGTCTTTGTCTCCAGGGGAGAGAGCCACCCTCTCC<br>TGCAGGGCCAGTCAGAGTGTTAGCAGCAGCTACTTAGCCTGGTACCAGCAGAAACCTGGCCAGGCT<br>CCCAGGCTCCTCATCTATGGTGCATCCAGCAGGGCCACTGGCATCCCAGACAGGTTCAGTGGCAGT<br>GGGTCTGGGACAGACTTCACTCTCACCATCAGCAGACTGGAGCCTGAAGATTTTGCAGTGTATTAC<br>TGTCAGCACTATGGTAGCTCACGGGGTTGGACGTTCGGCCAAGGGACCAAGGTGGAAATCAAAC |
| COV2-2952 | 5 | heavy | GAGGTGCAGCTGGTGGAGTCTGGGGGAGGCTTGGTCCAGCCTGGGGGGTCTCTGAGACTCTCCTGT<br>GCAGCCTCTGGACTCACCGTCGTAGCAACTACATGACCTGGGTCCGCCAGACTCCAGGGAAGGGG<br>CTGGAATGGGTGTCAGTTATTTATAGCGGTGGTAGCACATTCTACGCAGACTCCGTGAAGGGCAGA<br>TTCACCATCTCCAGAGACAATTCCAAGAACACGGTGTATCTTCAAATGAACAGCCTGAGAGCCGAG<br>GACACGGCTGTGTATTACTGTGCGAGAGATCTCGTGACTTACGGTTTGGACGTCTGGGGCCAAGGG<br>ACCACGGTCACCGTCTCCTCA |
|  | 6 | light | GACATCCAGTTGACCCAGTCTCCATCCTTCCTGTCTGCATCTGTAGGAGACAGAGTCACCATCACT<br>TGCCGGGCCAGTCAGGGCATTAGCAATTATTTAGCCTGGTATCAGCAAAAACCAGGGACAGCCCCT<br>AACCTCCTGATCTATGCTGCATCCACTTTGCAAAGTGGGGTCCCATCAAGGTTCAGCGGCAGTGGA<br>TCTGGGACAGAATTCACTCTCACAATCAGCAGCCTGCAGCCTGAAGATTTTGCAACTTATTACTGT<br>CAACTACTTAATAGTCACCCCCTCACCTTCGGCCAAGGGACACGACTGGAGATTAAAC |
| COV2-2514 | 7 | heavy | GAGGTGCAGCTGGTGGAGTCTGGGGGAGGTGTGGTACGGCCTGGGGGTCCCTGAGACTCTCCTGT<br>GCAGCCTCTGGATTCATCTTTGATGATTATGACATGACCTGGGTCCGCCAAGCTCCAGGGAAGGGG<br>CTGGAGTGGGTCTCTGGTATTAATTGGAATGGTGGTAGCACAGGTTATGCAGACTCTGTGAAGGGC<br>CGATTCACCATCTCCAGAGACAACGCCAAGAACTCCCTGTATCTGCAAATGAACAGTCTGAGAGCC<br>GAGGACACGGCCTTGTATCACTGTGCAGTGATTATGTCTCCAATCCCCGTTATAGTGGCTACGAT<br>TGGGCGGGTGATGCTTTTGATATCTGGGGCCAAGGGACAATGGTCACCGTCTCTTCAG |
|  | 8 | light | TCTTCTGAGCTGACTCAGGACCCTGCTGTCTGTGCCTGTTGGGACAGCAGTCAGGATCACATGC<br>CTTGTCATCTATGATAAAAACAACCGGCCCTCAGGGATCCCAGACCGATTCTCTGGCTCCAGCTCA<br>GGAAACACAGCTTCCTTGACCATCACTGGGGCTCAGGCGGAAGATGAGGCTGACTATTACTGTAAC<br>TCCCGGGACAGCAGTGGTAACGCCGTGGTATTCGGCGGAGGGACCAAGCTGACCGTCCTAG |
| COV2-2391 | 9 | heavy | CAGGTGCAGCTGGTGCAGTCTGGGGCTGAGGTGAAGAAGCCTGGGGCCTCAGTGAAGGTCTCCTGC<br>AAGGCTTCTGGATACACCTTCGGCAGCTTTGATATCAACTGGGTGCGACAGGCCACTGGACAAGGG<br>CTTGAGTGGATGGGACGGATGAACTCTAACAGTGGGAACACAGCCTATGCACAGAAGTTCCAGGGC<br>AGAGTCACTATGACCAGGGACACCTCCACAAATACAGCCTACATGGAGTTGAGCAGCCTGAGATCT<br>GAGGACACGGCCATGTATTACTGTGCGAGAATGCGCAGTGGCTGGCCCACACATGGCCGCCCGGAT<br>GACTTCTGGGGCCGGGAACCCTGGTCACCGTCTCCTCAG |
|  | 10 | light | CAGTCTGTGCTGACTCAGGACACCCTCAGCGTCTGGGACCCCCGGGCAGAGGGTCACCATCTCTTGT<br>TCTGGAAGCAACTCCAATATCGGAAGTTATATATAAACTGGTACCAGCAGCTCCCAGGAACGGCC<br>CCCAAACTCCTCATTTATGGTAATGATCAGCGGACCTCAGGGGTCCCTGACCGATTCTCTGGCTCC<br>AAGTTTGGCACCTCGGCCTCCTGGCCATCAGTGGGCTCCAGTCTGAGGATGAAAATAATTATTAC<br>TGTGCAGTATGGGATGACAGCCTGAATGGCCTGGTATTCGGCGGAGGGACCAAACTGACCGTCCTAG |
| COV2-3025 | 11 | heavy | GAGGTGCAGCTGGTGCAGTCTGGGCCTGAGGTGAAGAAGCCTGGGACCTCAGTGAAGGTCTCCTGC<br>AAGGCTTCTGGATTCACCTTTATGAGCTCTGCTGTGCAGTGGGTGCGACAGGCTCGTGGACAACGC<br>CTTGAGTGGATAGGATGGATCGTCATTGGCAGTGGTAACACATACGCACAGAAGTTCCAGGAA<br>AGAGTCACCATTACCAGGGACATGTCCACAAGCACAGCCTACATGGAGTCTGAGCAGCCTGAGATCC<br>GAGGACACGGCCGTGTATTACTGTGCGGCCCCATATTGTAGTAGTATCAGCTGCAATGATGGTTTT<br>GATATCTGGGGCCAAGGGACAATGGTCACCGTCTCTTCA |
|  | 12 | light | GAAATTGTGTTGACGCAGTCTCCAGGCACCCTGTCTTTGTCTCCAGGGGAGAGAGTCACCCTCTCC<br>TGCAGGGCCAGTCAGAGTGTTAGCAGCAGCTACTTAGCCTGGTACCAGCAGAAACCTGGCCAGGCT<br>CCCAGGCTCCTCATCTATGGTGCATCCAGCAGGGCCACTGGCATCCCAGACAGGTTCAGTGGCAGT<br>GGGTCTGGGACAGACTTCACTCTCACCATCAGCAGACTGGAGCCTGAAGATTTTGCAGTGTATTAC<br>TGTCAGCACTATGGTAGCTCACGGGGTTGGACGTTCGGCCAAGGGACCAAGGTGGAAATCAAA |
| COV2-2196 | 13 | heavy | CAAATGCAGCTGGTGCAGTCTGGGCCTGAGGTGAAGAAGCCTGGGACCTCAGTGAAGGTCTCCTGC<br>AAGGCTTCTGGATTCACCTTTATGAGCTCTGCTGTGCAGTGGGTGCGACAGGCTCGTGGACAACGC<br>CTTGAGTGGATAGGATGGATCGTCATTGGCAGTGGTAACACAAACTACGCACAGAAGTTCCAGGAA<br>AGAGTCACCATTACCAGGGACATGTCCACAAGCACAGCCTACATGGAGCTGAGCAGCCTGAGATCC<br>GAGGACACGGCCGTGTATTACTGTGCGGCCCCATATTGTAGTAGTATCAGCTGCAATGATGGTTTT<br>GATATCTGGGGCCAAGGGACAATGGTCACCGTCTCTTCA |
|  | 14 | light | GAAATTGTGTTGACGCAGTCTCCAGGCACCCTGTCTTTGTCTCCAGGGGAGAGAGCCACCCTCTCC<br>TGCAGGGCCAGTCAGAGTGTTAGCAGCAGCTACTTAGCCTGGTACCAGCAGAAACCTGGCCAGGCT<br>CCCAGGCTCCTCATCTATGGTGCATCCAGCAGGGCCACTGGCATCCCAGACAGGTTCAGTGGCAGT<br>GGGTCTGGGACAGACTTCACTCTCACCATCAGCAGACTGGAGCCTGAAGATTTTGCAGTGTATTAC<br>TGTCAGCACTATGGTAGCTCACGGGGTTGGACGTTCGGCCAAGGGACCAAGGTGGAAATCAAA |
| COV2-2094 | 15 | heavy | GAGGTGCAGCTGGTGGAGTCTGGGGGAGGTGTGGTACGGCCTGGGGGTCCCTGAGACTCTCCTGT<br>GCAGCCTCTGGATTCATCTTTGATGATTATGACATGACCTGGGTCCGCCAAGCTCCAGGGAAGGGG<br>CTGGAGTGGGTCTCTGGTATTAATTGGAATGGTGGTAGCACAGGTTATGCAGACTCTGTGAAGGGC<br>CGATTCACCATCTCCAGAGACAACGCCAAGAACTCCCTGTATCTGCAAATGAACAGTCTGAGAGCC<br>GAGGACACGGCCTTGTATCACTGTGCAGTGATTATGTCTCCAATCCCCGTTATAGTGGCTACGAT<br>TGGGCGGGTGATGCTTTTGATATCTGGGGCCAAGGGACAATGGTCACCGTCTCTTCA |

TABLE 1-continued

NUCLEOTIDE SEQUENCES FOR ANTIBODY VARIABLE REGION

| Clone | SeqID | Chain | Variable Sequence Region |
|---|---|---|---|
| | 16 | light | TCTTCTGAGCTGACTCAGGACCCTGCTGTGTCTGTGGCCTTGGGACAGACAGTCAGGATCACATGC<br>CAAGGAGACAGCCTCAGAAGCTATTATGCAAGTTGGTACCAGCAGAAGCCAGGACAGGTCCCTATA<br>CTTGTCATCTATGATAAAAACAACCGGCCCTCAGGGATCCCAGACCGATTCTCTGGCTCCAGCTCA<br>GGAAACACAGCTTCCTTGACCATCACTGGGGCTCAGGCGGAAGATGAGGCTGACTATTACTGTAAC<br>TCCCGGGACAGCAGTGGTAACGCCGTGGTATTCGGCGGAGGGACCAAGCTGACCGTCCTA |
| COV2-2096 | 17 | heavy | CAGGTGCAGCTGGTGCAGTCTGGGGCTGAGGTGAAGAAGCCTGGGGCCTCAGTGAAGGTCTCCTGC<br>AAGGCTTCTGGATACACCTTCGGCAGCTTTGATATCAACTGGGTGCGACAGGCCACTGGACAAGGG<br>CTTGAGTGGATGGGACGGATGAACTCTAACAGTGGGAACACAGCCTATGCACAGAAGTTCCAGGGC<br>AGAGTCACTATGACCAGGGACACCTCCACAAATACAGCCTACATGGAGTTGAGCAGCCTGAGATCT<br>GAGGACACGGCCATGTATTACTGTGCGAGAATGCGCAGTGGCTGGCCCACACATGGCCGCCCGGAT<br>GACTTCTGGGGCCGGGGAACCCTGGTCACCGTCTCCTCA |
| | 18 | light | CAGTCTGTGCTGACTCAGGCACCCTCAGCGTCTGGGACCCCCGGGCAGAGGGTCACCATCTCTTGT<br>TCTGGAAGCAACTCCAATATCGGAAGTTATACTATAAACTGGTACCAGCAGCTCCCAGGAACGGCC<br>CCCAAACTCCTCATTTATGGTAATGATCAGCGGACCTCAGGGGTCCCTGACCGATTCTCTGGCTCC<br>AAGTTTGGCACCTCGGCCTCCCTGGCCATCAGTGGGCTCCAGTCTGAGGATGAAAATAATTATTAC<br>TGTGCAGTATGGGATGACAGCCTGAATGGCCTGGTATTCGGCGGAGGGACCAAACTGACCGTCCTA |
| COV2-2130 | 19 | heavy | GAGGTGCAGCTGGTGGAGTCTGGGGGAGGCTTGGTAAAGCCTGGGGGGTCCCTTAGACTCTCCTGT<br>GCAGCCTCTGGATTCACTTTCAGAGACGTCTGGATGAGCTGGGTCCGCCAGGCTCCAGGGAAGGGG<br>CTGGAGTGGGTTGGCCGTATTAAAAGCAAAATTGATGGTGGGACAACAGACTACGCTGCACCCGTG<br>AAAGGCAGATTCACCATCTCAAGAGATGATTCAAAAAACACGCTGTATCTGCAAATGAACAGCCTG<br>AAAACCGAGGACACAGCCGTGTATTACTGTACCACAGCGGGAAGCTATTACTATGATACTGTTGGT<br>CCAGGCCTCCCAGAGGGAAATTTGACTACTGGGGCCAGGGAACCCTGGTCACCGTCTCCTCA |
| | 20 | light | GACATCGTGATGACCCAGTCTCCAGACTCCCTGGCTGTGTCTCTGGGCGAGAGGGCCACCATCAAC<br>TGCAAGTCCAGCCAGAGTGTTTTATACAGCTCCAACAATAAGAACTACTTAGCTTGGTACCAGCAG<br>AAACCAGGACAGCCTCCTAAGCTGCTCATGTACTGGGCATCTACCCGGGAATCCGGGGTCCCTGAC<br>CGATTCAGTGGCAGCGGGTCTGGGACAGATTCACTCTCACCATCAGCAGCCTGCAGGCTGAAGAT<br>GTGGCAATTTATTACTGTCAGCAATATTATAGTACCCTCACTTTCGGCGGAGGGACCAAGGTGGAG<br>ATCAAA |

TABLE 2

PROTEIN SEQUENCES FOR ANTIBODY VARIABLE REGION

| Clone | SeqID | Chain | Variable Sequence Region |
|---|---|---|---|
| COV2-2165 | 21 | heavy | EVQLVESGGGLVQPGGSLRLSCAASGLTVRSNYMTWVRQTPGKGLEWVSVI<br>YSGGSTFYADSVKGRFTISRDNSKNTVYLQMNSLRAEDTAVYYCARDLVTY<br>GLDVWGQGTTVTVSS |
| | 22 | light | DIQLTQSPSFLSASVGDRVTITCRASQGISNYLAWYQQKPGTAPNLLIYAA<br>STLQSGVPSRFSGSGSGTEFTLTISSLQPEDFATYYCQLLNSHPLTFGQGT<br>RLEIK |
| COV2-2838 | 23 | heavy | QMQLVQSGPEVKKPGTSVKVSCKASGFTFMSSAVQWVRQARGQRLEWIGWI<br>VIGSGNTNYAQKFQERVTITRDMSTSTAYMELSSLRSEDTAVYYCAAPYCS<br>SISCNDGFDIWGQGTMVTVSS |
| | 24 | light | EIVLTQSPGTLSLSPGERATLSCRASQSVSSSYLAWYQQKPGQAPRLLIYG<br>ASSRATGIPDRFSGSGSGTDFTLTISRLEPEDFAVYYCQHYGSSRGWTFGQ<br>GTKVEIK |
| COV2-2952 | 25 | heavy | EVQLVESGGGLVQPGGSLRLSCAASGLTVRSNYMTWVRQTPGKGLEWVSVI<br>YSGGSTFYADSVKGRFTISRDNSKNTVYLQMNSLRAEDTAVYYCARDLVTY<br>GLDVWGQGTTVTVSS |
| | 26 | light | DIQLTQSPSFLSASVGDRVTITCRASQGISNYLAWYQQKPGTAPNLLIYAA<br>STLQSGVPSRFSGSGSGTEFTLTISSLQPEDFATYYCQLLNSHPLTFGQGT<br>RLEIK |
| COV2-2514 | 27 | heavy | EVQLVESGGGVVRPGGSLRLSCAASGFIFDDYDMTWVRQAPGKGLEWVSGI<br>NWNGGSTGYADSVKGRFTISRDNAKNSLYLQMNSLRAEDTALYHCAVIMSP<br>IPRYSGYDWAGDAFDIWGQGTMVTVSS |
| | 28 | light | SSELTQDPAVSVALGQTVRITCQGDSLRSYYASWYQQKPGQVPILVIYDKN<br>NRPSGIPDRFSGSSSGNTASLTITGAQAEDEADYYCNSRDSSGNAVVFGGG<br>TKLTVL |
| COV2-2391 | 29 | heavy | QVQLVQSGAEVKKPGASVKVSCKASGYTFGSFDINWVRQATGQGLEWMGRM<br>NSNSGNTAYAQKFQGRVTMTRDTSTNTAYMELSSLRSEDTAMYYCARMRSG<br>WPTHGRPDDFWGRGTLVTVSS |
| | 30 | light | QSVLTQAPSASGTPGQRVTISCSGSNSNIGSYTINWYQQLPGTAPKLLIYG<br>NDQRTSGVPDRFSGSKFGTSASLAISGLQSEDENNYYCAVWDDSLNGLVFG<br>GGTKLTVL |

TABLE 2-continued

PROTEIN SEQUENCES FOR ANTIBODY VARIABLE REGION

| Clone | SeqID | Chain | Variable Sequence Region |
|---|---|---|---|
| COV2-3025 | 31 | heavy | EVQLVQSGPEVKKPGTSVKVSCKASGFTFMSSAVQWVRQARGQRLEWIGWI VIGSGNTNYAQKFQERVTITRDMSTSTAYMELSSLRSEDTAVYYCAAPYCS SISCNDGFDIWGQGTMVTVSS |
|  | 32 | light | EIVLTQSPGTLSLSPGERVTLSCRASQSVSSSYLAWYQQKPGQAPRLLIYG ASSRATGIPDRFSGSGSGTDFTLTISRLEPEDFAVYYCQHYGSSRGWTFGQ GTKVEIK |
| COV2-2196 | 33 | heavy | QMQLVQSGPEVKKPGTSVKVSCKASGFTFMSSAVQWVRQARGQRLEWIGWI VIGSGNTNYAQKFQERVTITRDMSTSTAYMELSSLRSEDTAVYYCAAPYCS SISCNDGFDIWGQGTMVTVSS |
|  | 34 | light | EIVLTQSPGTLSLSPGERATLSCRASQSVSSSYLAWYQQKPGQAPRLLIYG ASSRATGIPDRFSGSGSGTDFTLTISRLEPEDFAVYYCQHYGSSRGWTFGQ GTKVEIK |
| COV2-2094 | 35 | heavy | EVQLVESGGGVVRPGGSLRLSCAASGFIFDDYDMTWVRQAPGKGLEWVSGI NWNGGSTGYADSVKGRFTISRDNAKNSLYLQMNSLRAEDTALYHCAVIMSP IPRYSGYDWAGDAFDIWGQGTMVTVSS |
|  | 36 | light | SSELTQDPAVSVALGQTVRITCQGDSLRSYYASWYQQKPGQVPILVIYDKN NRPSGIPDRFSGSSSGNTASLTITGAQAEDEADYYCNSRDSSGNAVVFGGG TKLTVL |
| COV2-2096 | 37 | heavy | QVQLVQSGAEVKKPGASVKVSCKASGYTFGSFDINWVRQATGQGLEWMGRM NSNSGNTAYAQKFQGRVTMTRDTSTNTAYMELSSLRSEDTAMYYCARMRSG WPTHGRPDDFWGRGTLVTVSS |
|  | 38 | light | QSVLTQAPSASGTPGQRVTISCSGSNSNIGSYTINWYQQLPGTAPKLLIYG NDQRTSGVPDRFSGSKFGTSASLAISGLQSEDENNYYCAVWDDSLNGLVFG GGTKLTVL |
| COV2-2130 | 39 | heavy | EVQLVESGGGLVKPGGSLRLSCAASGFTFRDVWMSWVRQAPGKGLEWVGRI KSKIDGGTTDYAAPVKGRFTISRDDSKNTLYLQMNSLKTEDTAVYYCTTAG SYYYDTVGPGLPEGKFDYWGQGTLVTVSS |
|  | 40 | light | DIVMTQSPDSLAVSLGERATINCKSSQSVLYSSNNKNYLAWYQQKPGQPPK LLMYWASTRESGVPDRFSGSGSGAEFTLTISSLQAEDVAIYYCQQYYSTLT FGGGTKVEIK |

TABLE 3

HEAVY CHAIN SEQUENCES

| Clone | CDRH1 | CDRH2 | CDRH3 |
|---|---|---|---|
| COV2-2165 | GLTVRSNY 41 | IYSGGST 42 | ARDLVTYGLDV 43 |
| COV2-2838 | GFTFMSSA 44 | IVIGSGNT 45 | AAPYCSSISCNDGFDI 46 |
| COV2-2952 | GLTVRSNY 47 | IYSGGST 48 | ARDLVTYGLDV 49 |
| COV2-2514 | GFIFDDYD 50 | INWNGGST 51 | AVIMSPIPRYSGYDWAGDAFDI 52 |
| COV2-2391 | GYTFGSFD 53 | MNSNSGNT 54 | ARMRSGWPTHGRPDDF 55 |
| COV2-3025 | GFTFMSSA 56 | IVIGSGNT 57 | AAPYCSSISCNDGFDI 58 |
| COV2-2196 | GFTFMSSA 59 | IVIGSGNT 60 | AAPYCSSISCNDGFDI 61 |
| COV2-2094 | GFIFDDYD 62 | INWNGGST 63 | AVIMSPIPRYSGYDWAGDAFDI 64 |

TABLE 3-continued

HEAVY CHAIN SEQUENCES

| Clone | CDRH1 | CDRH2 | CDRH3 |
|---|---|---|---|
| COV2-2096 | GYTFGSFD 65 | MNSNSGNT 66 | ARMRSGWPTHGRPDDF 67 |
| COV2-2130 | GFTFRDVW 68 | IKSKIDGGTT 69 | TTAGSYYYDTVGPGLPEGKFDY 70 |

TABLE 4

LIGHT CHAIN SEQUENCES

| Clone | CDRL1 | CDRL2 | CDRL3 |
|---|---|---|---|
| COV2-2165 | QGISNY 71 | AAS 72 | QLLNSHPLT 73 |
| COV2-2838 | QSVSSSY 74 | GAS 75 | QHYGSSRGWT 76 |
| COV2-2952 | QGISNY 77 | AAS 78 | QLLNSHPLT 79 |
| COV2-2514 | SLRSYY 80 | DKN 81 | NSRDSSGNAVV 82 |
| COV2-2391 | NSNIGSYT 83 | GND 84 | AVWDDSLNGLV 85 |
| COV2-3025 | QSVSSSY 86 | GAS 87 | QHYGSSRGWT 88 |
| COV2-2196 | QSVSSSY 89 | GAS 90 | QHYGSSRGWT 91 |
| COV2-2094 | SLRSYY 92 | DKN 93 | NSRDSSGNAVV 94 |
| COV2-2096 | NSNIGSYT 95 | GND 96 | AVWDDSLNGLV 97 |
| COV2-2130 | QSVLYSSNNKNY 98 | WAS 99 | QQYYSTLT 100 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, N.Y., 1988.
Abbondanzo et al., Am. J. Pediatr. Hematol. Oncol., 12(4), 480-489, 1990.
Allred et al., Arch. Surg., 125(1), 107-113, 1990.
Atherton et al., Biol. of Reproduction, 32, 155-171, 1985.
Barzon et al., Euro Surveill. 2016 Aug. 11; 21(32).
Beltramello et al., Cell Host Microbe 8, 271-283, 2010.
Brown et al., J. Immunol. Meth., 12; 130(1), :111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
De Jager et al., Semin. Nucl. Med. 23(2), 165-179, 1993.
Dholakia et al., J. Biol. Chem., 264, 20638-20642, 1989.
Diamond et al., J Virol 77, 2578-2586, 2003.
Doolittle and Ben-Zeev, Methods Mol. Biol., 109, :215-237, 1999.
Duffy et al., N. Engl. J. Med. 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., Somatic Cell Genet., 3:231-236, 1977.
Gornet et al., Semin Reprod Med. 2016 September; 34(5): 285-292. Epub 2016 Sep. 14.
Gulbis and Galand, Hum. Pathol. 24(12), 1271-1285, 1993.
Halfon et al., PLoS ONE 2010; 5 (5) e10569
Hessell et al., Nature 449, 101-4, 2007.
Khatoon et al., Ann. of Neurology, 26, 210-219, 1989.
King et al., J. Biol. Chem., 269, 10210-10218, 1989.
Kohler and Milstein, Eur. J Immunol., 6, 511-519, 1976.

Kohler and Milstein, *Nature,* 256, 495-497, 1975.
Kyte and Doolittle, *J. Mol. Biol.,* 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems,* Chapter 27, 1987.
O'Shannessy et al., *J. Immun. Meth.,* 99, 153-161, 1987.
Persic et al., *Gene* 187:1, 1997
Potter and Haley, *Meth. Enzymol.,* 91, 613-633, 1983.
Purpura et al., *Lancet Infect Dis.* 2016 October; 16(10): 1107-8. Epub 2016 Sep. 19.
Remington's Pharmaceutical Sciences, 15th Ed., 3:624-652, 1990.
Tang et al., *J Biol. Chem.,* 271:28324-28330, 1996.
Wawrzynczak & Thorpe, In: *Immunoconjugates, Antibody Conuugates In Radioimaging And Therapy Of Cancer,* Vogel (Ed.), NY, Oxford University Press, 28, 1987.
Yu et al., *J Immunol Methods* 336, 142-151, doi:10.1016/j.jim.2008.04.008, 2008.

What is claimed is:

1. An isolated antibody or antibody fragment that binds to a SARS-CoV-2 surface spike protein, wherein the antibody or fragment comprises
   (a) a CDRH1 comprising the amino acid sequence of SEQ ID NO:59, a CDRH2 comprising the amino acid sequence of SEQ ID NO:60, a CDRH3 comprising the amino acid sequence of SEQ ID NO:61, a CDRL1 comprising the amino acid sequence of SEQ ID NO:89, a CDRH2 comprising the amino acid sequence of SEQ ID NO:90, a CDRH3 comprising the amino acid sequence of SEQ ID NO:91;
   (b) a CDRH1 comprising the amino acid sequence of SEQ ID NO:68, a CDRH2 comprising the amino acid sequence of SEQ ID NO:69, a CDRH3 comprising the amino acid sequence of SEQ ID NO:70, a CDRL1 comprising the amino acid sequence of SEQ ID NO:98, a CDRH2 comprising the amino acid sequence of SEQ ID NO:99, a CDRH3 comprising the amino acid sequence of SEQ ID NO:100;
   (c) a CDRH1 comprising the amino acid sequence of SEQ ID NO:41, a CDRH2 comprising the amino acid sequence of SEQ ID NO:42, a CDRH3 comprising the amino acid sequence of SEQ ID NO:43, a CDRL1 comprising the amino acid sequence of SEQ ID NO:71, a CDRH2 comprising the amino acid sequence of SEQ ID NO:72, a CDRH3 comprising the amino acid sequence of SEQ ID NO:73;
   (d) a CDRH1 comprising the amino acid sequence of SEQ ID NO:44, a CDRH2 comprising the amino acid sequence of SEQ ID NO:45, a CDRH3 comprising the amino acid sequence of SEQ ID NO:46, a CDRL1 comprising the amino acid sequence of SEQ ID NO:74, a CDRH2 comprising the amino acid sequence of SEQ ID NO:75, a CDRH3 comprising the amino acid sequence of SEQ ID NO:76;
   (e) a CDRH1 comprising the amino acid sequence of SEQ ID NO:47, a CDRH2 comprising the amino acid sequence of SEQ ID NO:48, a CDRH3 comprising the amino acid sequence of SEQ ID NO:49, a CDRL1 comprising the amino acid sequence of SEQ ID NO:77, a CDRH2 comprising the amino acid sequence of SEQ ID NO:78, a CDRH3 comprising the amino acid sequence of SEQ ID NO:79;
   (f) a CDRH1 comprising the amino acid sequence of SEQ ID NO:50, a CDRH2 comprising the amino acid sequence of SEQ ID NO:51, a CDRH3 comprising the amino acid sequence of SEQ ID NO:52, a CDRL1 comprising the amino acid sequence of SEQ ID NO:80, a CDRH2 comprising the amino acid sequence of SEQ ID NO:81, a CDRH3 comprising the amino acid sequence of SEQ ID NO:82;
   (g) a CDRH1 comprising the amino acid sequence of SEQ ID NO:53, a CDRH2 comprising the amino acid sequence of SEQ ID NO:54, a CDRH3 comprising the amino acid sequence of SEQ ID NO:55, a CDRL1 comprising the amino acid sequence of SEQ ID NO:83, a CDRH2 comprising the amino acid sequence of SEQ ID NO:84, a CDRH3 comprising the amino acid sequence of SEQ ID NO:85;
   (h) a CDRH1 comprising the amino acid sequence of SEQ ID NO:56, a CDRH2 comprising the amino acid sequence of SEQ ID NO:57 a CDRH3 comprising the amino acid sequence of SEQ ID NO:58, a CDRL1 comprising the amino acid sequence of SEQ ID NO:86, a CDRH2 comprising the amino acid sequence of SEQ ID NO:87, a CDRH3 comprising the amino acid sequence of SEQ ID NO:88;
   (i) a CDRH1 comprising the amino acid sequence of SEQ ID NO:62, a CDRH2 comprising the amino acid sequence of SEQ ID NO:63 a CDRH3 comprising the amino acid sequence of SEQ ID NO:64, a CDRL1 comprising the amino acid sequence of SEQ ID NO:65, a CDRH2 comprising the amino acid sequence of SEQ ID NO:66, a CDRH3 comprising the amino acid sequence of SEQ ID NO:67; or
   (j) a CDRH1 comprising the amino acid sequence of SEQ ID NO:65, a CDRH2 comprising the amino acid sequence of SEQ ID NO:66, a CDRH3 comprising the amino acid sequence of SEQ ID NO:67, a CDRL1 comprising the amino acid sequence of SEQ ID NO:95, a CDRH2 comprising the amino acid sequence of SEQ ID NO:96, a CDRH3 comprising the amino acid sequence of SEQ ID NO:97.

2. The antibody or antibody fragment of claim 1, wherein the antibody or fragment comprises
   (a) a heavy chain variable sequence comprising the amino acid sequence of SEQ ID NO:33 and/or a light chain variable sequence comprising the amino acid sequence of SEQ ID NO:34;
   (b) a heavy chain variable sequence comprising the amino acid sequence of SEQ ID NO:39 and/or a light chain variable sequence comprising the amino acid sequence of SEQ ID NO:40;
   (c) a heavy chain variable sequence comprising the amino acid sequence of SEQ ID NO:21 and/or a light chain variable sequence comprising the amino acid sequence of SEQ ID NO:22;
   (d) a heavy chain variable sequence comprising the amino acid sequence of SEQ ID NO:23 and/or a light chain variable sequence comprising the amino acid sequence of SEQ ID NO:24;
   (e) a heavy chain variable sequence comprising the amino acid sequence of SEQ ID NO:25 and/or a light chain variable sequence comprising the amino acid sequence of SEQ ID NO:26;
   (f) a heavy chain variable sequence comprising the amino acid sequence of SEQ ID NO:27 and/or a light chain variable sequence comprising the amino acid sequence of SEQ ID NO:28;

(g) a heavy chain variable sequence comprising the amino acid sequence of SEQ ID NO:29 and/or a light chain variable sequence comprising the amino acid sequence of SEQ ID NO:30;
(h) a heavy chain variable sequence comprising the amino acid sequence of SEQ ID NO:31 and/or a light chain variable sequence comprising the amino acid sequence of SEQ ID NO:32;
(i) a heavy chain variable sequence comprising the amino acid sequence of SEQ ID NO:35 and/or a light chain variable sequence comprising the amino acid sequence of SEQ ID NO:36; or
(j) a heavy chain variable sequence comprising the amino acid sequence of SEQ ID NO:37 and/or a light chain variable sequence comprising the amino acid sequence of SEQ ID NO:38.

3. The antibody or antibody fragment of claim 1, wherein the antibody or fragment is monoclonal.

4. The antibody or antibody fragment of claim 1, wherein the antibody or fragment comprises a YTE mutation.

5. The antibody or antibody fragment of claim 1, wherein the antibody or fragment is an IgG.

6. The antibody or antibody fragment of claim 1, wherein the antibody or antibody fragment is able to bind RBD in the "up" and "down" conformations.

7. The antibody or antibody fragment of claim 1, wherein the antibody or antibody fragment is able to bind RBD in the "up" conformation and is not able to bind RBD in the "down" conformation.

8. The antibody or antibody fragment of claim 1, wherein the antibody or antibody fragment further comprises a detectable label.

9. A vaccine formulation comprising the antibody or antibody fragment of claim 1.

10. The vaccine formulation of claim 9, further comprising a second antibody or antibody fragment that binds to a SARS-CoV-2 surface spike protein.

11. A pharmaceutically acceptable composition or kit comprising a first antibody or antibody fragment that binds to a SARS-CoV-2 surface spike protein and a second antibody or antibody fragment that binds to a SAR-CoV-2 surface spike protein, wherein the first antibody or antibody fragment comprises a CDRH1 comprising the amino acid sequence of SEQ ID NO:59, a CDRH2 comprising the amino acid sequence of SEQ ID NO:60, a CDRH3 comprising the amino acid sequence of SEQ ID NO:61, a CDRL1 comprising the amino acid sequence of SEQ ID NO:89, a CDRH2 comprising the amino acid sequence of SEQ ID NO:90, a CDRH3 comprising the amino acid sequence of SEQ ID NO:91, and wherein the second antibody or antibody fragment comprises a CDRH1 comprising the amino acid sequence of SEQ ID NO:68, a CDRH2 comprising the amino acid sequence of SEQ ID NO:69, a CDRH3 comprising the amino acid sequence of SEQ ID NO:70, a CDRL1 comprising the amino acid sequence of SEQ ID NO:98, a CDRH2 comprising the amino acid sequence of SEQ ID NO:99, a CDRH3 comprising the amino acid sequence of SEQ ID NO:100.

12. The pharmaceutically acceptable composition of claim 11, wherein the first antibody or antibody fragment comprises a heavy chain variable sequence comprising the amino acid sequence of SEQ ID NO:33 and a light chain variable sequence comprising the amino acid sequence of SEQ ID NO:34, and wherein the second antibody or antibody fragment comprises a heavy chain variable sequence comprising the amino acid sequence of SEQ ID NO:39 and a light chain variable sequence comprising the amino acid sequence of SEQ ID NO:40.

13. The pharmaceutically acceptable composition of claim 12, wherein the first antibody comprises a YTE mutation, and wherein the second antibody comprises a YTE mutation.

14. The pharmaceutically acceptable composition of claim 13, wherein the first antibody is an IgG1, and wherein the second antibody is an IgG1.

15. The antibody or antibody fragment of claim 1, wherein the antibody or fragment is a recombinant IgG antibody or antibody fragment comprising an Fc portion, and wherein the Fc portion is a mutated Fc portion comprising a mutation selected from the group consisting of a mutation that alters FcR interactions, and a mutation that increases half-life and/or increase therapeutic efficacy, or a combination thereof.

16. The antibody or antibody fragment of claim 15, wherein the mutation of the mutated Fc portion is selected from the group consisting of LALA, LALA PG, N297, GASD/ALIE, DHS, YTE and LS, or a combination thereof.

17. An isolated antibody or antibody fragment that binds to a SARS-CoV-2 surface spike protein, wherein the antibody or fragment comprises a CDRH1 comprising the amino acid sequence of SEQ ID NO:59, a CDRH2 comprising the amino acid sequence of SEQ ID NO:60, a CDRH3 comprising the amino acid sequence of SEQ ID NO:61, a CDRL1 comprising the amino acid sequence of SEQ ID NO:89, a CDRH2 comprising the amino acid sequence of SEQ ID NO:90, a CDRH3 comprising the amino acid sequence of SEQ ID NO:91.

18. The antibody or antibody fragment of claim 17, wherein the antibody or fragment comprises a heavy chain variable sequence comprising the amino acid sequence of SEQ ID NO:33 and a light chain variable sequence comprising the amino acid sequence of SEQ ID NO:34.

19. The antibody or antibody fragment of claim 18, wherein the antibody is an IgG1.

20. The antibody or antibody fragment of claim 18, wherein the antibody comprises a YTE mutation.

21. The antibody or antibody fragment of claim 20, wherein the antibody is an IgG1.

22. An isolated antibody or antibody fragment that binds to a SARS-CoV-2 surface spike protein, wherein the antibody or fragment comprises a CDRH1 comprising the amino acid sequence of SEQ ID NO:68, a CDRH2 comprising the amino acid sequence of SEQ ID NO:69, a CDRH3 comprising the amino acid sequence of SEQ ID NO:70, a CDRL1 comprising the amino acid sequence of SEQ ID NO:98, a CDRH2 comprising the amino acid sequence of SEQ ID NO:99, a CDRH3 comprising the amino acid sequence of SEQ ID NO:100.

23. The antibody or antibody fragment of claim 22, wherein the antibody or fragment comprises a heavy chain variable sequence comprising the amino acid sequence of SEQ ID NO:39 and a light chain variable sequence comprising the amino acid sequence of SEQ ID NO:40.

24. The antibody or antibody fragment of claim 23, wherein the antibody is an IgG1.

25. The antibody or antibody fragment of claim 23, wherein the antibody comprises a YTE mutation.

26. The antibody or antibody fragment of claim 25, wherein the antibody is an IgG1.

* * * * *

UNITED STATES PATENT AND TRADEMARK OFFICE
CERTIFICATE OF CORRECTION

PATENT NO. : 11,345,741 B2
APPLICATION NO. : 17/212949
DATED : May 31, 2022
INVENTOR(S) : Crowe, Jr. et al.

It is certified that error appears in the above-identified patent and that said Letters Patent is hereby corrected as shown below:

In the Specification

In Column 6, Line 35, delete "of" before "A1-A3,".

In Column 9, Line 60, delete "aspet" and insert -- aspect --, therefor.

In Column 13, Line 56, delete "IC50<150" and insert -- $IC_{50}$<150 --, therefor.

In Column 17, Line 32, delete "a158-A167," and insert -- A158-A167, --, therefor.

In Column 22, Line 2, delete "B)" and insert -- 13B) --, therefor.

In Column 24, Line 18, delete "IC50" and insert -- $IC_{50}$ --, therefor.

In Column 24, Line 19, delete "IC50" and insert -- $IC_{50}$ --, therefor.

In Column 24, Line 26, delete "IC50" and insert -- $IC_{50}$ --, therefor.

In Column 24, Line 32, delete "IC50" and insert -- $IC_{50}$ --, therefor.

In Column 24, Line 38, delete "IC50" and insert -- $IC_{50}$ --, therefor.

In Column 24, Line 46, delete "IC50" and insert -- $IC_{50}$ --, therefor.

In Column 24, Line 50, delete "IC50" and insert -- $IC_{50}$ --, therefor.

In Column 26, Line 16, delete "2C)" and insert -- 23C) --, therefor.

In Column 26, Line 45, delete "FIG." and insert -- FIGS. --, therefor.

Signed and Sealed this
First Day of November, 2022

Katherine Kelly Vidal
*Director of the United States Patent and Trademark Office*

In Column 28, Line 42, delete "phylogenic" and insert -- phylogenetic --, therefor.

In Column 29, Line 12, delete "trasmission" and insert -- transmission --, therefor.

In Column 30, Line 2, delete "Centers" and insert -- Center --, therefor.

In Column 32, Line 35, delete "$V_{sub}H$" and insert -- $V_H$ --, therefor.

In Column 33, Lines 43-44, delete "carbodiimyde" and insert -- carbodiimide --, therefor.

In Column 33, Line 44, delete "bis-biazotized" and insert -- bis-diazotized --, therefor.

In Column 36, Line 12, delete "aor" and insert -- A or --, therefor.

In Column 37, Line 67, delete "(1999)," and insert -- (1999); --, therefor.

In Column 38, Line 12, delete "noncontiguous" and insert -- non-contiguous --, therefor.

In Column 38, Line 60, delete "to" and insert -- In --, therefor.

In Column 39, Line 28, delete "eptiope" and insert -- epitope --, therefor.

In Column 40, Line 21, delete "(1978)" and insert -- (1978). --, therefor.

In Column 40, Line 46, delete "Dr.," and insert -- Dr. --, therefor.

In Column 41, Line 66, delete "etc." and insert -- etc., --, therefor.

In Column 42, Line 15, delete "Fcgamma" and insert -- Fc gamma --, therefor.

In Column 42, Line 38, delete "Fcgamma" and insert -- Fc gamma --, therefor.

In Column 57, Line 16, delete "(scFv)" and insert -- (scFvs) --, therefor.

In Column 57, Line 54, delete "used" and insert -- used. --, therefor.

In Column 59, Line 48, delete "a" and insert -- α --, therefor.

In Column 62, Line 67, delete "sachette" and insert -- sachet --, therefor.

In Column 64, Line 14, delete "in in" and insert -- in --, therefor.

In Column 64, Line 49, delete "pertechnate" and insert -- pertechnetate --, therefor.

In Column 64, Line 53, delete "pertechnate," and insert -- pertechnetate, --, therefor.

In Column 64, Line 58, delete "ethylene diaminetetracetic" and insert -- ethylenediaminetetraacetic --, therefor.

In Column 64, Lines 65-66, delete "Renographin," and insert -- Renografin, --, therefor.

In Column 65, Line 36, delete "ethylenetriaminetetraacetic" and insert -- ethylenediaminetetraacetic --, therefor.

In Column 68, Line 21, delete "ELISAS" and insert -- ELISAs --, therefor.

In Column 71, Line 52, delete "Typically" and insert -- Typically, --, therefor.

In Column 75, Line 52, delete "Mab Select" and insert -- MabSelect --, therefor.

In Column 77, Line 67, delete "SJRP)" and insert -- 5JRP) --, therefor.

In Column 78, Line 3, delete "software'" and insert -- software$^{63}$ --, therefor.

In Column 78, Line 14, delete "pD" and insert -- pH --, therefor.

In Column 78, Line 38, delete "heat maps" and insert -- heatmaps --, therefor.

In Column 79, Line 20, delete "IVIES" and insert -- MES --, therefor.

In Column 81, Line 17, delete "Centers" and insert -- Center --, therefor.

In Column 81, Line 62, delete "ClustalO" and insert -- Clustal Omega --, therefor.

In Column 84, Line 10, delete "ClustalOmega," and insert -- Clustal Omega, --, therefor.

In Column 90, Line 42, delete "Cell182," and insert -- Cell 182, --, therefor.

In Column 94, under "TABLE A", Line 3, delete "IC50" and insert -- $IC_{50}$ --, therefor.

In Column 94, under "TABLE A", Line 6, delete "impedence)" and insert -- impedance) --, therefor.

In Column 94, under "TABLE A", Line 8, delete "IC50" and insert -- $IC_{50}$ --, therefor.

In Column 95, Line 33, delete "a" after "neutralizing".

In Column 95, Line 45, insert -- to -- before "S".

In Column 96, Line 46, delete "(FIG." and insert -- (FIGS. --, therefor.

In Column 96, Line 59, delete "(FIG." and insert -- (FIGS. --, therefor.

CERTIFICATE OF CORRECTION (continued)
U.S. Pat. No. 11,345,741 B2

In Column 99, Line 41, delete "HROO" and insert -- HR00 --, therefor.

In Column 104, Line 50, delete "G4000SW$_{XL}$" and insert -- G4000SWXL --, therefor.

In Column 111, Line 42, delete "(2020)" and insert -- (2020). --, therefor.

In Column 120, Line 63, delete "e10569" and insert -- e10569. --, therefor.

In Column 121, Line 8, delete "1997" and insert -- 1997. --, therefor.

In Column 122, Line 7, delete "Conuugates" and insert -- Conjugates --, therefor.

In the Claims

In Column 215, Claim 1, Line 23, delete "CDRH2" and insert -- CDRL2 --, therefor.

In Column 215, Claim 1, Line 24, delete "CDRH3" and insert -- CDRL3 --, therefor.

In Column 215, Claim 1, Line 31, delete "CDRH2" and insert -- CDRL2 --, therefor.

In Column 215, Claim 1, Line 32, delete "CDRH3" and insert -- CDRL3 --, therefor.

In Column 215, Claim 1, Line 39, delete "CDRH2" and insert -- CDRL2 --, therefor.

In Column 215, Claim 1, Line 40, delete "CDRH3" and insert -- CDRL3 --, therefor.

In Column 215, Claim 1, Line 47, delete "CDRH2" and insert -- CDRL2 --, therefor.

In Column 215, Claim 1, Line 48, delete "CDRH3" and insert -- CDRL3 --, therefor.

In Column 215, Claim 1, Line 55, delete "CDRH2" and insert -- CDRL2 --, therefor.

In Column 215, Claim 1, Line 56, delete "CDRH3" and insert -- CDRL3 --, therefor.

In Column 215, Claim 1, Line 63, delete "CDRH2" and insert -- CDRL2 --, therefor.

In Column 215, Claim 1, Line 64, delete "CDRH3" and insert -- CDRL3 --, therefor.

In Column 216, Claim 1, Line 16, delete "CDRH2" and insert -- CDRL2 --, therefor.

In Column 216, Claim 1, Line 17, delete "CDRH3" and insert -- CDRL3 --, therefor.

In Column 216, Claim 1, Line 24, delete "CDRH2" and insert -- CDRL2 --, therefor.

In Column 216, Claim 1, Line 25, delete "CDRH3" and insert -- CDRL3 --, therefor.

CERTIFICATE OF CORRECTION (continued)
U.S. Pat. No. 11,345,741 B2

In Column 216, Claim 1, Line 32, delete "CDRH2" and insert -- CDRL2 --, therefor.

In Column 216, Claim 1, Line 33, delete "CDRH3" and insert -- CDRL3 --, therefor.

In Column 216, Claim 1, Line 39, delete "CDRH2" and insert -- CDRL2 --, therefor.

In Column 216, Claim 1, Line 40, delete "CDRH3" and insert -- CDRL3 --, therefor.

In Column 217, Claim 11, Line 38, delete "or kit" after "composition".

In Column 217, Claim 11, Line 48, delete "CDRH2" and insert -- CDRL2 --, therefor.

In Column 217, Claim 11, Line 49, delete "CDRH3" and insert -- CDRL3 --, therefor.

In Column 217, Claim 11, Line 56, delete "CDRH2" and insert -- CDRL2 --, therefor.

In Column 217, Claim 11, Line 57, delete "CDRH3" and insert -- CDRL3 --, therefor.

In Column 218, Claim 17, Line 30, delete "CDRH2" and insert -- CDRL2 --, therefor.

In Column 218, Claim 17, Line 31, delete "CDRH3" and insert -- CDRL3 --, therefor.

In Column 218, Claim 22, Line 51, delete "CDRH2" and insert -- CDRL2 --, therefor.

In Column 218, Claim 22, Line 52, delete "CDRH3" and insert -- CDRL3 --, therefor.